United States Patent
Fairfax et al.

(10) Patent No.: US 7,307,094 B2
(45) Date of Patent: Dec. 11, 2007

(54) BENZOXAZOLE CARBOXAMIDES FOR TREATING CINV AND IBS-D

(75) Inventors: David J. Fairfax, Slingerlands, NY (US); Zhicai Yang, Schenectady, NY (US)

(73) Assignee: AMR Technology, Inc., Manchester, VT (US)

( * ) Notice: Subject to any disclaimer, the term of this patent is extended or adjusted under 35 U.S.C. 154(b) by 8 days.

(21) Appl. No.: 11/357,494

(22) Filed: Feb. 17, 2006

(65) Prior Publication Data

US 2006/0183769 A1     Aug. 17, 2006

Related U.S. Application Data

(60) Provisional application No. 60/653,821, filed on Feb. 17, 2005.

(51) Int. Cl.
*A61K 31/423* (2006.01)
*C07D 263/57* (2006.01)

(52) U.S. Cl. ........................ 514/375; 548/224
(58) Field of Classification Search ................ 540/477, 540/603; 546/126, 135; 514/304, 305, 214.03, 514/375; 548/224
See application file for complete search history.

(56) References Cited

U.S. PATENT DOCUMENTS

| 3,850,950 | A | 11/1974 | Amuller et al. | |
| 6,403,791 | B1 * | 6/2002 | Dyke et al. | 544/140 |
| 6,828,330 | B2 * | 12/2004 | Walker et al. | 514/305 |
| 2004/0132790 | A1 | 7/2004 | Xie et al. | |

FOREIGN PATENT DOCUMENTS

| WO | EP 0 507 637 A2 | 4/1992 |
| WO | WO 92/15593 | 9/1992 |
| WO | WO 9822460 A1 * | 5/1998 |
| WO | WO0158896 A1 * | 8/2001 |
| WO | WO 02/051821 A1 | 7/2002 |
| WO | WO 03/037896 A1 | 5/2003 |
| WO | WO 03037896 A1 * | 5/2003 |
| WO | WO 2004/016600 A1 | 2/2004 |

OTHER PUBLICATIONS

Lesch et al. Biol. Psychiatry 1998; vol. 44, pp. 179-192.*

PCT Notification of Transmittal of the International Search Report and the Written Opinion of the International Searching Authority, or the Declaration, dated Jul. 4, 2006, International Application No. PCT/US2006/005605, Applicant: AMR Technology, Inc.
Kumar et al., "Synthesis and Evaluation of Anticancer Benzoxazoles and Benzimidazoles related to UK-1", *Bioorganic & Medicinal Chemistry*, 10 (2002) 3997-4004.
Denny et al, "Structure-activity relationships for the mutagenic activity of tricyclic intercalatine agents in *Salmonella typhimurium*", *Mutation Research*, 232 (1990) 233-241.
Seshadri et al., "Synthesis of naphthoxazole derivatives by the application of the Vilsmeier-Haack reaction. Part II. 2-Hetarylnaphth[1,2-d]oxazole derivatives", *Dyes and Pigments*, 8(6) (1987), 405-16.
Kusumi et al, "Structures of novel antibiotics boxazomycins A, B and C", *Tennen Yuki Kagobutsu Toronkai Koen Yoshishu*, 28th (1986) 49-56 Coden: Tykyds.
Israili, Zafar H., "Clinical Pharmacology of Serotonin Receptor Type 3 (5-HT3) Antagonists", *Curr. Med. Chem*, 1, (2001), 171-199.

* cited by examiner

*Primary Examiner*—Kamal A. Saeed
*Assistant Examiner*—Karen Cheng
(74) *Attorney, Agent, or Firm*—Heslin Rothenberg Farley & Mesiti P.C.; Philip E. Hansen

(57) ABSTRACT

Compounds of formulae I and II:

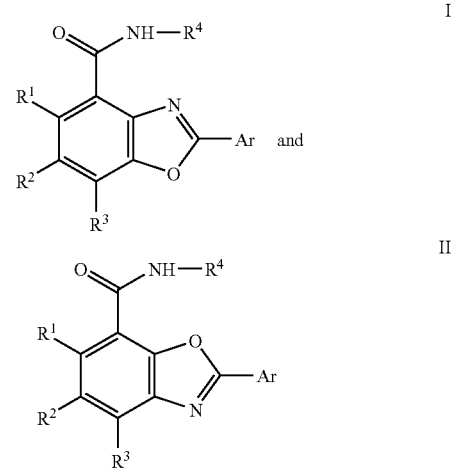

are disclosed as 5-HT$_3$ inhibitors. Those compounds that exhibit central activity are useful in treating CINV; those that inhibit peripheral receptors are useful to treat IBS-D.

22 Claims, No Drawings

BENZOXAZOLE CARBOXAMIDES FOR TREATING CINV AND IBS-D

CROSS-REFERENCE TO RELATED APPLICATIONS

This application claims the priority of U.S. provisional application 60/653,821, filed Feb. 17, 2005.

STATEMENT REGARDING FEDERALLY SPONSORED RESEARCH OR DEVELOPMENT

Not applicable

NAMES OF PARTIES TO A JOINT RESEARCH AGREEMENT

Not applicable

REFERENCE TO SEQUENCE LISTING

Not applicable

BACKGROUND OF THE INVENTION

1. Field of the Invention

The invention relates to a genus of benzoxazole carboxamides that are useful in treating chemotherapy-induced nausea and vomiting (CINV) and in treating diarrhea-predominant Irritable Bowel Syndrome (IBS-D).

2. Background

Nausea and vomiting caused by chemotherapy remain among the most distressing side effects for patients undergoing treatment for cancer. Depending upon the chemotherapy agents or regimens given, up to 90% of patients may suffer from some form of chemotherapy-induced nausea and vomiting (CINV). Symptoms from CINV can be severely debilitating and often result in patients refusing further courses of chemotherapy, with obviously unfavorable consequences as regards progression of the cancer. Furthermore, CINV is burdensome on the medical system, consuming time from the healthcare staff, who could otherwise attend to other patients or medical issues.

CINV is divided into two main categories: acute CINV and delayed CINV. Acute CINV occurs within the first 24 hours of treatment; delayed CINV occurs from 24 hours to 120 hours following treatment. Delayed CINV remains a highly under treated side effect in patients undergoing chemotherapy, as healthcare providers tend to underestimate the number of patients who suffer from delayed CINV. Furthermore, delayed CINV greatly impairs patients' ability to provide care to themselves once they have been discharged.

Compounds that inhibit central receptors are currently the most effective anti-emetics; they constitute the single greatest advance in the management of nausea and vomiting in patients with cancer. Blocking the 5-$HT_3$ signal in the CNS appears to prevent acute emesis. All approved 5-$HT_3$ inhibitors, except palonosetron (ALOXI™), are approved to prevent acute CINV. Palonosetron, which must be given intravenously, is the only 5-$HT_3$ inhibitor currently approved for the prevention of delayed CINV. This appears to be due to its long serum half-life. Therefore persons of skill in the art accept that 5-$HT_3$ inhibitors that have long serum half-lives will be effective therapeutic agents for both acute and delayed CINV; those that have short will be useful to treat acute CINV. In addition, the combination of palonosetron, a 5-$HT_3$ inhibitor, and aprepitant (EMEND®), a neurokinin antagonist, has been shown to be highly effective in preventing both acute and delayed CINV following a variety of moderately to highly emetogenic chemotherapy regimens in clinical trials. A large number of other 5-$HT_3$ inhibitors of the "setron" class have been described in clinical and preclinical use for CINV [see review article by Israili, *Curr. Med. Chem. CNS Agents* 1 171-199 (2001), which is incorporated herein by reference].

Irritable Bowel Syndrome (IBS) generally occurs in two types: diarrhea predominant (IBS-D) and constipation predominant (IBS-C). Diarrhea predominant Irritable Bowel Syndrome is a debilitating, though seldom fatal, disease. The typical sufferer of IBS-D exhibits primary symptoms including multiple and daily explosive diarrhea attacks and severe daily abdominal cramps. The most common secondary side effects include panic attacks, depression, withdrawal from social and family activities and malnutrition.

At present, compounds that inhibit peripheral 5-$HT_3$ receptors are the only effective treatment for IBS-D. The only drug currently approved for IBS-D is alosetron, which was introduced by Glaxo, withdrawn from the clinical trial by the FDA because it caused ischemic colitis, then reinstated by the FDA because the demand was so great for some treatment for IBS-D. In 2002, the US Food and Drug Administration approved alosetron hydrochloride (LOTRONEX®) tablets under restricted conditions for patients in whom the medical benefits outweigh the risks. The restrictions on the approval reflect the serious gastrointestinal adverse events that have been reported with the use of alosetron. A second peripheral 5-$HT_3$ inhibitor, cilanestron, was in clinical trials. Clearly there is a need for improved therapy for both CINV and IBS-D.

SUMMARY OF THE INVENTION

It has now been found that compounds of formulae I and II are potent and selective inhibitors of the 5-$HT_3$ receptor:

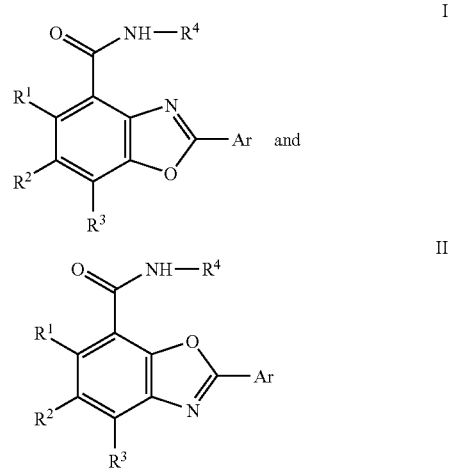

In these compounds $R^1$, $R^2$ and $R^3$ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;

$R^4$ is a residue chosen from:

(i) a saturated nitrogen heterocycle or methyl-substituted saturated nitrogen heterocycle, in which said nitrogen is tertiary, said heterocycle containing at least one 5 or 6-membered ring; and (ii) an imidazolylalkyl residue wherein the imidazole of said imidazolylalkyl is optionally substituted with up to three groups chosen from halogen, $(C_1-C_4)$alkyl, substituted $(C_1-C_4)$alkyl and $NH_2$; and Ar is chosen from the group consisting of (i) aryl;

(ii) heteroaryl;

(iii) substituted aryl;

(iv) substituted heteroaryl; and (v) dihydroheteroaryl.

Those members of the genus that are selective for central receptors are useful to treat CINV; those members of the genus that are selective for peripheral receptors are useful to treat IBS-D.

In another aspect, the invention relates to pharmaceutical compositions comprising a pharmaceutically acceptable carrier and a therapeutically effective amount of a compound of formula I or II. The compositions may comprise an additional antiemetic agent, particularly a neurokinin antagonist.

In another aspect, the invention relates to a method of treating a disorder arising from inappropriate activity of the serotonin type 3 receptor or dependent upon modulation of the serotonin type 3 receptor. The method comprises administering a therapeutically effective amount of a compound of formula I or II. Exemplary disorders arising from inappropriate activity of the serotonin type 3 receptor or dependent upon modulation of the serotonin type 3 receptor include emesis, particularly CINV, and IBS-D. Other such disorders include psychological disorders, obesity, substance abuse disorders, dementia associated with a neurodegenerative disease, cognition loss, pain, fibromyalgia syndrome and chronic fatigue syndrome (see US published application 2004/0204467). Serotonin type 3 receptor antagonists are also known to be useful for the prevention and treatment of bronchial asthma.

DETAILED DESCRIPTION OF THE INVENTION

Throughout this specification the substituents are defined when introduced and retain their definitions.

In a first aspect the invention relates to compounds of formula I and II

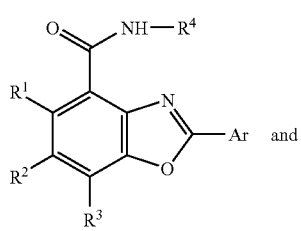

I

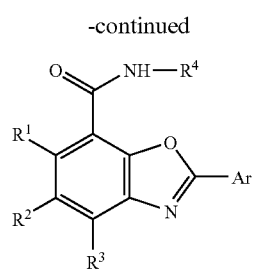

II

Two subgenera are:

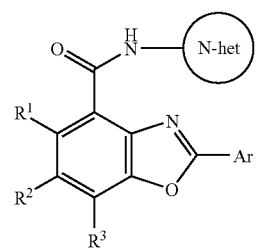

Ia

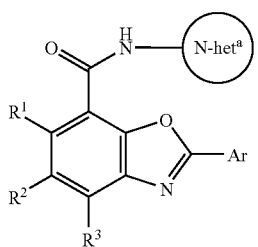

IIa

In these subgeneric compounds, $R^1$, $R^2$ and $R^3$ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;

represents a saturated nitrogen heterocycle or methyl-substituted saturated nitrogen heterocycle. In the heterocycle, any ring nitrogen is tertiary, and the heterocycle contains at least one 5 or 6-membered ring;

represents a saturated nitrogen heterocycle or methyl-substituted saturated nitrogen heterocycle. As before, the nitrogen is tertiary, but in structure II the heterocycle contains at least two 6-membered rings;

Ar is chosen from the group consisting of (i) aryl;

(ii) heteroaryl;

(iii) aryl substituted with from one to four substitutents chosen from lower alkoxy, phenoxy, trialkylsilylacetylenyl, anilino, lower alkynyl, lower alkyl, halogen, nitro, cyano, hydroxy, amino, methylenedioxy, alkylamino, dialkylamino, phenyl, heterocyclyl, methylheterocyclyl, methylenedioxy and acylamino;

(iv) heteroaryl substituted with one or two substitutents chosen from oxo, halogen, and alkyl; and (v) dihydroheteroaryl.

In two other subgenera, $R^4$ is imidazolylalkyl:

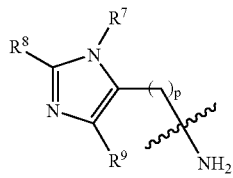

in which $R^7$, $R^8$ and $R^9$ are independently selected from hydrogen, halogen, amino, alkylamino, dialkylamino, acylamino, loweralkyl, fluoroloweralkyl and hydroxyloweralkyl; and p is an integer from 1 to 4.

Compounds falling within the foregoing parent genus and its subgenera are useful as $5\text{-HT}_3$ inhibitors. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a composition aspect, is all compounds of formulae I, Ia, II and IIa, except those that are in the public's possession.

Definitions

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a residue in which an aryl moiety is attached to the parent through an alkyl. Examples are benzyl, phenethyl and the like. Tolyl is not arylalkyl; tolyl is alkylaryl. Heteroarylalkyl means a heteroaryl residue attached to the parent via alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Nitrogen heterocycles are heterocycles containing at least one nitrogen. They may additionally include other heteroatoms and multiple nitrogens. Examples include quinuclidine, tropane, piperidine, piperazine, morpholine, quinoline and thiazole. It is to be noted that heteroaryl is a subset of heterocycle in which the heterocycle is aromatic. Dihydroheteroaryl are, as the name implies, heteraryl residues formally reduced by one mole of hydrogen. An examples of a dihydroheteroaryl residue is 2,3-dihydrobenzofuran.

Substituted alkyl, aryl, cycloalkyl, heterocyclyl etc. refer to alkyl, aryl, cycloalkyl, or heterocyclyl wherein up to four H atoms in each residue are replaced with halogen, haloalkyl, hydroxy, loweralkoxy, carboxy, alkoxycarbonyl (COOR), carboxamido (—CONR$_2$), sulfonamido (—SO$_2$NR$_2$), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. In the foregoing listing, R is hydrogen or alkyl.

The term "halogen" means fluorine, chlorine, bromine or iodine.

Some of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E or a mixture of the two in any proportion.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, chlorine and iodine include $^{3}H$, $^{14}C$, $^{35}S$, $^{18}F$, $^{36}Cl$ and $^{125}I$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds of the invention may be conveniently divided into two subgenera, the benzoxazole-4-carboxamides I and the benzoxazole-7-carboxamides II:

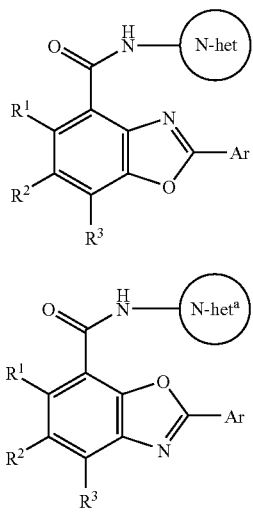

In these compounds,

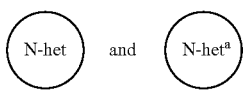

represent saturated nitrogen heterocycles or methyl-substituted saturated nitrogen heterocycles, in which the nitrogen is tertiary. In compounds of formula I, the heterocycle contains at least one 5 or 6-membered ring; in compounds of formula II the heterocycle contains two 6-membered rings. A nitrogen heterocycle (also referred to as a nitrogenous heterocycle) is a heterocycle containing at least one nitrogen in the ring; it may contain additional nitrogens, as well as other heteroatoms. In one embodiment,

or

is chosen from:

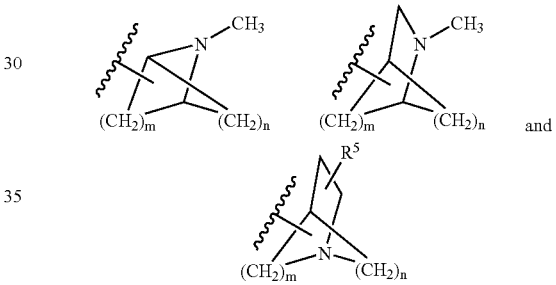

wherein m=1, 2, 3 or 4; n=0, 1, 2, 3 or 4; and $R^5$ is hydrogen or methyl. Nitrogenous heterocycles that appear in the examples include piperidine, methylpiperidine, quinuclidine, tropane, azabicyclo[3.3.1]nonane, methyl azabicyclo[3.3.1]nonane and 9-azabicyclo[3.3.1]nonan-3-one. Other nitrogenous heterocycles include:

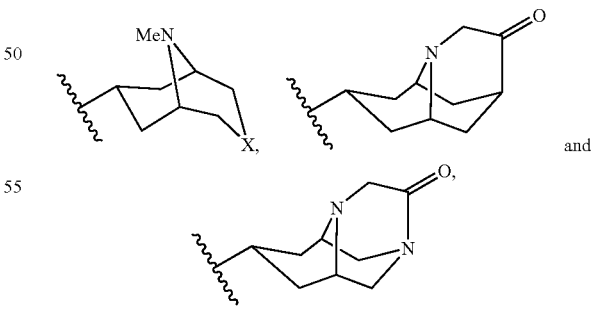

in which X is $NCH_3$, O, S, SO or $SO_2$.

In some embodiments $R^1$, $R^2$ and $R^3$ are hydrogen. In other embodiments one of $R^1$, $R^2$ and $R^3$ is halogen. In other embodiments, $R^1$ and $R^3$ are hydrogen and $R^2$ is chosen from amino, halogen, methoxy, hydroxy, acetylamino, and 4-morpholinyl.

In some embodiments Ar is chosen from the group consisting of phenyl and phenyl substituted with from 1 to 4 groups independently selected from ($C_1$ to $C_4$)alkyl, phenyl, phenoxy, halogen, ($C_1$ to $C_4$)alkoxy, amino, ($C_1$ to $C_4$)alkylamino, di($C_1$ to $C_4$)alkylamino [e.g. dimethylamino], anilino, heterocyclyl [e.g. morpholin-4-yl and pyridin-4-yl], methylheterocyclyl [e.g. 4-methylpiperazin1-yl], methylenedioxy, ($C_1$ to $C_4$)acylamino [e.g. acetylamino], ($C_1$ to $C_4$)alkynyl [e.g. propyn-1-yl] and nitro.

In other embodiments, Ar is chosen from the group consisting of heteroaryl, dihydroheteroaryl and substituted heteroaryl. Examples include compounds in which Ar is chosen from thiophene, cyclopenta[b]thiophene, furan, thiazole, isoxazole dihydrobenzofuran, benzofuran, pyridine benzothiophene, 3-pyridine-2-one, and their methylated and halogenated congeners. The term "methylated and halogenated congeners" refers to heteroaryl and dihydroheteroaryl substituted with from one to three methyls and/or halogens, for example, 3,5-dimethylisoxazol-4-yl; 4-methylthiazol-5-yl and 3-chlorothiophen-2-yl.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations" is incorporated herein by reference.

Generalized synthetic schemes are presented below:

SCHEME A

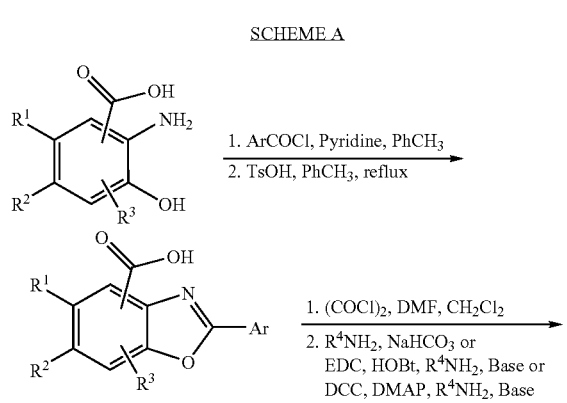

-continued

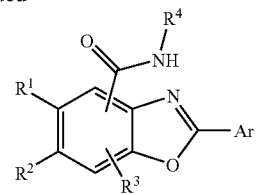

SCHEME B

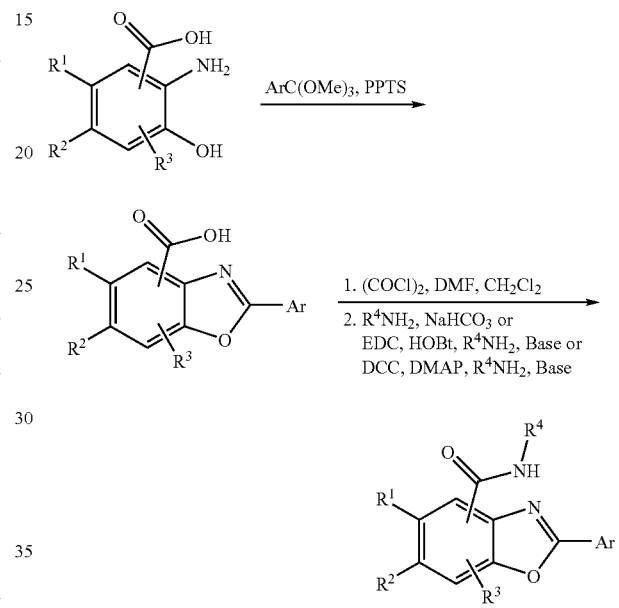

EXAMPLES

Exemplary syntheses are provided below.

Example 1

Preparation of N-[3-(2-Methylimidazol-1-yl)propyl]-2-phenylbenzoxazole-4-carboxamide

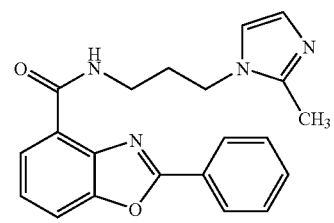

Step A: To a suspension of 3-hydroxyanthranilic acid (0.300 g, 1.96 mmol) in toluene (10 mL) was added benzoyl chloride (0.830 g, 5.90 mmol) followed by pyridine (0.545 g, 6.92 mmol) at room temperature. The resulting mixture was stirred at room temperature for 30 min then heated to 80° C. for 1 hr. After this time the reaction was cooled and poured into a mixture of ethyl acetate (50 mL) and 5% aqueous hydrochloric acid (50 mL). Subsequent separation of the layers, drying the organic over MgSO$_4$ and filtration afforded an orange solution. This solution was concentrated to an orange solid which was directly re-dissolved in xylenes (20 mL) and the solution treated with p-toluenesulfonic acid (0.800 g, 4.20 mmol). The reaction mixture was then heated to reflux for 6 hrs. After this time the reaction was cooled and poured into water (50 mL), the organic layer separated then washed with water (3×50 mL). The organic was dried over MgSO$_4$, filtered and concentrated to an orange/brown solid. Re-crystallization of this solid from ethyl acetate afforded 0.412 g (88% yield) of 2-phenylbenzoxazole-4-carboxylic acid as a light yellow solid: $^1$H NMR (300 MHz, CD$_3$OD) δ 11.58 (br s, 1H), 8.30 (m, 2H), 8.17 (dd, J=7.8, 0.8 Hz, 1H), 7.83 (dd, J=8.2, 0.8 Hz, 1H), 7.69-7.45 (m, 4H); MS (APCI) m/z 240 [M+H]$^+$.

Step B: A solution of 2-methylimidazole (0.820 g, 10.0 mmol) in DMF (10 mL) was cooled in an ice/water bath and sodium hydroxide (1.00 g, 25.0 mmol) added. The resulting mixture was stirred for 30 min, then 2-chloropropylamine hydrochloride (1.30 g, 10.0 mmol) added in one portion. The resulting suspension was then stirred for 16 h during which time the reaction slowly warmed to room temperature. After this time the mixture was poured into water (500 mL) and the mixture extracted with ether (3×100 mL). The combined ether extracts were dried over sodium bicarbonate, filtered and concentrated under reduced pressure to afford 0.726 g (52% yield) of 3-(2-methylimidazol-1-yl)propylamine as a yellow oil. $^1$H NMR (300 MHz, CD$_3$OD) δ 7.00 (d, J=1.4 Hz, 1H), 6.79 (d, J=1.4 Hz, 1H), 3.97 (t, J=7.3 Hz, 2H), 2.63 (t, J=7.1 Hz, 2H), 2.35 (s, 3H), 1.87 (m, 2H).

Step C: A 100-mL one-neck round-bottomed flask equipped with a magnetic stirrer was purged with nitrogen and charged with 2-phenylbenzoxazole-4-carboxylic acid (0.190 g, 0.79 mmol), DMF (0.588 g, 8.00 mmol) and anhydrous methylene chloride (15 mL). The resulting solution was treated with oxalyl chloride (1.46 g, 11.5 mmol) dropwise over 5 min and stirred at ambient temperature under nitrogen for 2 h. After this time, the reaction mixture was evaporated to a solid residue which was dissolved in anhydrous methylene chloride (15 mL). The resulting solution was treated with sodium bicarbonate (0.672 g, 8.00 mmol) and stirred at ambient temperature under nitrogen for 15 min. After this time, a solution of 3-(2-methylimidazol-1-yl)propylamine (0.332 g, 2.39 mmol) in anhydrous methylene chloride (5 mL) was added and the mixture stirred for a further 20 h. The reaction mixture was then diluted with methylene chloride (50 mL) and washed with 10% aqueous potassium carbonate (10 mL) followed by water (20 mL). The organic phase was dried over sodium sulfate, filtered and evaporated to a solid residue which was further purified by preparative HPLC to give 0.040 g (14% yield) of N-[3-(2-methylimidazol-1-yl)propyl]-2-phenylbenzoxazole-4-carboxamide as a white solid: mp 145-148° C.; $^1$H NMR (300 MHz, CD$_3$OD) δ 8.33 (m, 2H), 8.03 (dd, J=7.8, 0.9 Hz, 1H), 7.86 (dd, J=8.2, 0.9 Hz, 1H), 7.69-7.59 (m, 4H), 7.52 (t, J=8.0 Hz, 1H), 7.38 (d, J=2.1 Hz, 1H), 4.32 (t, J=7.1 Hz, 2H), 3.67 (t, J=7.1 Hz, 2H), 2.65 (s, 3H), 2.31 (m, 2H); MS (ESI) m/z 361 [M+H]$^+$.

Example 2

Preparation of N-[2-(2-Methylimidazol-1-yl)ethyl]-2-phenylbenzoxazole-4-carboxamide

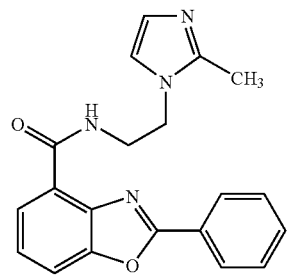

Step A: 2-(2-Methylimidazol-1-yl)ethylamine was prepared from 2-methylimidazole and 2-chloroethylamine hydrochloride using the method described in Step B of Example 1. This material was obtained as a light yellow oil in 47% yield. $^1$H NMR (300 MHz, CD$_3$OD) δ 6.95 (br s, 1H), 6.82 (br s, 1H), 4.90 (bs, 2H), 3.90 (t, J=6.9 Hz, 2H), 2.93 (t, J=6.9 Hz, 2H), 2.35 (s, 3H); MS (APCI) m/z 126 [M+H]$^+$.

Step B: N-[2-(2-Methylimidazol-1-yl)ethyl]-2-phenylbenzoxazole-4-carboxamide was prepared from 2-(2-methylimidazol-1-yl)ethylamine and 2-phenylbenzoxazole-4-carboxylic acid using the conditions described in Step C of Example 1. This compound was obtained in 35% yield as a white solid; mp 125-127° C.; $^1$H NMR (300 MHz, CD$_3$OD) δ 8.11 (dd, J=7.8, 1.0 Hz, 2H), 7.96 (d, J=7.8 Hz, 1H), 7.73 (d, J=8.2 Hz, 1H), 7.63-7.52 (m, 3H), 7.42 (t, J=8.0 Hz, 1H), 7.13 (s, 1H), 6.86 (s, 1H), 4.22 (t, J=5.8 Hz, 2H), 3.87 (t, J=6.0 Hz, 2H), 2.34 (s, 3H); MS (APCI) m/z 347 [M+H]$^+$ Example 4

Preparation of N-(1-Methylpiperidin-4-yl)-2-phenylbenzoxazole-4-carboxamide

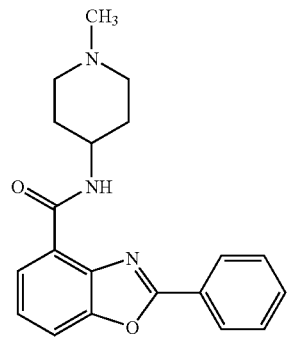

Step A: To a solution of 1-methyl-4-piperidone (1.84 g, 16.2 mmol) in MeOH (40 mL) was added a slurry of ammonium formate (10.2 g, 162 mmol) in water (4.4 mL) and the reaction stirred until all of the solids had dissolved. Palladium on carbon, (3.78 g, 10% Pd, 50% wet) was then added and the reaction stirred for 18 h at room temperature. After this time the mixture was filtered through a pad of celite and the filtrate concentrated under reduced pressure.

The resulting viscous clear oil was dissolved in EtOH (33 mL) and the solution treated with 37% hydrochloric acid (4.1 mL). After stirring at room temperature for 1 h, the solution was concentrated to a white solid which was re-crystallized from EtOH to afford 0.62 g (25% yield) of 4-amino-1-methylpiperidine dihydrochloride as a white solid: $^1$H NMR (300 MHz, DMSO-$d_6$) δ 10.95 (br s, 1H), 8.53 (br s, 3H), 3.42 (t, J=6.9 Hz, 3H), 3.23 (br s, 1H), 3.03 (t, J=11.7 Hz, 1H), 2.67 (s, 3H), 2.12 (m, 2H), 1.97 (m, 2H).

Step B: N-(1-Methylpiperidin-4-yl)-2-phenylbenzoxazole-4-carboxamide was prepared from 2-phenylbenzoxazole-4-carboxylic acid and 4-amino-1-methylpiperidine dihydrochloride using the conditions described for Step C in Example 1. This compound was obtained in 38% yield as a white solid; mp 126-128° C.; $^1$H NMR (300 MHz, CDCl$_3$) δ 9.26 (d, J=7.5 Hz, 1H), 8.25 (m, 2H), 8.19 (d, J=7.7 Hz, 1H), 7.70 (d, J=8.1 Hz, 1H), 7.63-7.53 (m, 3H), 7.46 (t, J=8.0 Hz, 1H), 4.20 (m, 1H), 2.86 (m, 2H), 2.37 (s, 3H), 2.33-2.13 (m, 4H), 1.85-1.73 (m, 2H); MS (APCI) m/z 336 [M+H]$^+$.

Example 5

Preparation of N-(9-Methyl-9-azabicyclo[3.3.1]non-3-yl)-2-phenylbenzoxazole-4-carboxamide

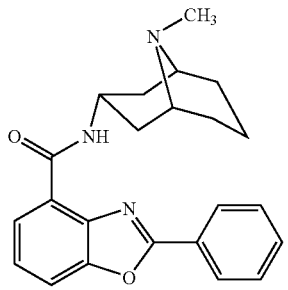

Step A: A mixture of 9-methyl-9-aza-bicyclo[3.3.1]nonan-3-one (0.658 g, 4.29 mmol) and hydroxylamine hydrochloride (0.312 g, 4.49 mmol) in methanol (6 mL) was stirred for 20 h at room temperature, during which time a white precipitate formed. This solid was collected by filtration, rinsed with additional methanol (2×10 mL), and dried under vacuum for 1 h to afford 0.672 g (76% yield) of 9-methyl-9-aza-bicyclo[3.3.1]nonan-3-one oxime hydrochloride as a white solid: $^1$H NMR (300 MHz, DMSO-$d_6$) d 10.82 (s, 1H), 3.71-3.52 (m, 2H), 3.34-3.23 (m, 1H), 3.12 (d, J=17.5 Hz, 1H), 2.90-2.79 (m, 3H), 2.73-2.55 (m, 1H), 2.42 (d, J=16.8 Hz, 1H), 2.27-2.05 (m, 2H), 1.87-1.42 (m, 4H); MS (ESI) m/z 169 [M+H]$^+$ Step B: A mixture of 9-methyl-9-aza-bicyclo[3.3.1]nonan-3-one oxime hydrochloride (0.670 g, 3.27 mmol), rhodium on carbon (0.610 g, 5% rhodium), methanol (18 mL), and concentrated ammonium hydroxide (8.0 mL, 120 mmol) was shaken under a 50 psi hydrogen atmosphere and warmed to 50° C. for 19 h. The mixture was then filtered through a pad of diatomaceous earth and the pad rinsed with additional methanol (3×20 mL). The filtrate was then concentrated to dryness, and residue was partitioned between 10% aqueous sodium carbonate (25 mL) and chloroform (25 mL). The layers were separated, and the aqueous layer was extracted with additional chloroform (2×25 mL). The combined organic extracts were dried over anhydrous potassium carbonate, filtered, and concentrated to afford 3-amino-9-methyl-9-azabicyclo[3.3.1]nonane (0.466 g, 92% yield) as a yellow oil: $^1$H NMR (500 MHz, CDCl$_3$) d 3.20 (m, 1H), 3.01 (d, J=11.1 Hz, 2H), 2.46 (s, 3H), 2.32-2.25 (m, 2H), 1.99-1.89 (m, 3H), 1.50-1.42 (m, 1H), 1.14-10.9 (m, 2H), 1.07 (br s, 2H), 0.98-0.91 (m, 2H); MS (ESI) m/z 155 [M+H]$^+$. This material was converted to the corresponding dihydrochloride salt in quantitative yield by treatment with excess 4M hydrogen chloride gas in dioxane: mp 232-235° C. $^1$H NMR (300 MHz, DMSO-$d_6$) δ 11.28 (br s, 1H), 10.31 (br s, 1H), 8.46 (br s, 2H), 3.85 (br s, 2H), 3.61 (br s, 1H), 3.07 (dd, J=18.1, 6.6 Hz, 1H), 2.96 (d, J=4.6 Hz, 2H), 2.76 (d, J=4.6 Hz, 1H), 2.46 (d, J=17.0 Hz, 1H), 2.30-2.18 (m, 2H), 2.02 (br d, J=7.8 Hz, 1H), 1.88-1.72 (m, 2H), 1.70-1.19 (m, 3H).

Step C: N-(9-Methyl-9-azabicyclo[3.3.1]non-3-yl)-2-phenylbenzoxazole-4-carboxamide was prepared from 3-amino-9-methyl-9-azabicyclo[3.3.1]nonane dihydrochloride and 2-phenylbenzoxazole-4-carboxylic acid using conditions similar to those described for Step C in Example 1. This compound was obtained in 40% yield as a white solid; mp 182-185° C.; $^1$H NMR (300 MHz, CDCl$_3$) δ 9.18 (d, J=6.5 Hz, 1H), 8.25 (m, 2H), 8.19 (dd, J=7.8, 0.9 Hz, 1H), 7.72 (dd, J=8.1, 1.0 Hz, 1H), 7.55-7.65 (m, 3H), 7.47 (t, J=8.0 Hz, 1H), 4.71-4.58 (m, 1H), 3.30 (m, 2H), 2.76 (m, 2H), 2.69 (s, 3H), 2.38-1.33 (m, 8H); MS (APCI) m/z 376 [M+H]$^+$ Example 6

Preparation of N-(8-Methyl-8-azabicyclo[3.2.1]oct-3-yl)-2-phenylbenzoxazole-4-carboxamide

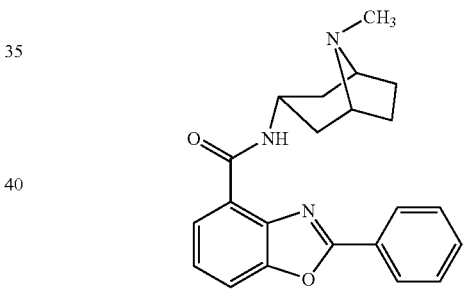

Step A: A 500-mL one-neck round-bottomed flask equipped with a magnetic stirrer was charged with 8-methyl-8-aza-bicyclo[3.2.1]octan-3-one (5.00 g, 35.9 mmol), hydroxylamine hydrochloride (7.08 g, 102 mmol) sodium acetate (39.0 g, 476 mmol) and ethanol (45 mL). After stirring at ambient temperature for 4 h, the reaction mixture was evaporated to a solid residue. This residue was triturated with ethyl acetate (200 mL) and filtered. Evaporation of the filtrate to dryness gave 5.08 g (93% yield) of 8-methyl-8-aza-bicyclo[3.2.1]octan-3-one oxime as a white solid: mp 140-142° C.; $^1$H NMR (300 MHz, CD$_3$OD) δ 3.76 (m, 2H), 3.33-3.23 (m, 2H), 2.75 (m, 1H), 2.69 (s, 3H), 2.46-2.14 (m, 4H), 1.88-1.66 (m, 2H); MS (APCI) m/z 155 [M+H]$^+$.

Step B: A 500-mL Parr hydrogenation vessel was purged with nitrogen and charged with platinum (IV) oxide (1.28 g, 5.64 mmol), 8-methyl-8-aza-bicyclo[3.2.1]octan-3-one oxime (4.00 g, 26.0 mmol), acetic acid (11 mL) and ethanol (110 mL). The bottle was evacuated, charged with hydrogen gas to a pressure of 50 psi and shaken for 24 h on a Parr hydrogenation apparatus. The hydrogen was then evacuated and nitrogen charged to the bottle. The reaction mixture was then mixed with Celite 521 (5.0 g), filtered, and the filtrate evaporated to a solid residue. This residue was dissolved in methanol (100 mL) and this solution treated with sodium carbonate (10 g). The resulting suspension was added diethyl ether (50 mL) and filtered. Evaporation of the filtrate to dryness afforded 3.64 g (100%) of 8-methyl-8-azabicyclo [3.2.1]oct-3-ylamine as a white solid: $^1$H NMR (300 MHz, CD$_3$OD) δ 5.18 (br s, 2H), 3.35 (br s, 2H), 3.21 (t, J=6.6 Hz, 1H), 2.40 (s, 3H), 2.26-2.00 (m, 6H), 1.68-1.58 (m, 2H).

Step C: N-(8-Methyl-8-azabicyclo[3.2.1]oct-3-yl)-2-phenylbenzoxazole-4-carboxamide was prepared from 3-amino-8-methyl-8-azabicyclo[3.2.1]octane and 2-phenylbenzoxazole-4-carboxylic acid using conditions similar to those described for Step C in Example 1. This compound was obtained in 25% yield as a white solid; mp 149-151° C.; $^1$H NMR (300 MHz, CDCl$_3$) δ 9.55 (d, J=7.6 Hz, 1H), 8.29 (m, 2H), 8.22 (dd, 1H, J=7.8, 1.0 Hz, 1H), 7.72 (dd, J=8.1, 1.0 Hz, 1H), 7.65-7.55 (m, 3H), 7.47 (t, J=8.0 Hz, 1H), 4.48 (q, 1H, J=7.2 Hz), 3.25 (br s, 2H), 2.43-2.24 (m, 9H), 1.87 (d, J=14.2 Hz, 2H); MS (APCI) m/z 362 [M+H]$^+$.

Example 7

Preparation of N-(9-Methyl-9-azabicyclo[3.3.1]non-3-yl)-6-chloro-2-phenylbenzoxazole-4-carboxamide

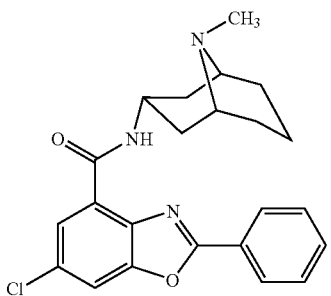

Step A: A 25-mL round bottomed flask equipped with a magnetic stirrer was charged with 2-amino-3-hydroxybenzoic acid (0.852 g, 5.59 mmol), acetic acid (0.4 mL) and diethyl ether (0.4 mL). After cooling to 0° C. sulfuryl chloride (0.754 g, 5.59 mmol) was added and the reaction stirred at ambient temperature for 4 h. Dilution with ether (15 mL), filtration and purification by preparative HPLC afforded 0.500 g (48% yield) of 2-amino-5-chloro-3-hydroxybenzoic acid as a white solid: $^1$H NMR (500 MHz, CD$_3$OD) δ 7.29 (d, J=9.5 Hz, 1H), 6.76 (d, 1H, J=9.5 Hz, 1H) MS (ESI) m/z 186 (M−H).

Step B: A 25-mL, round bottomed flask equipped with a magnetic stirrer was charged with 2-amino-5-chloro-3-hydroxybenzoic acid (0.931 g, 4.96 mmol), trimethyl orthobenzoate (7.23 g, 39.7 mmol), and pyridinium p-toluenesulfonate (0.062 g, 0.248 mmol). After stirring at 90° C. for 1 h, the reaction was diluted with hexanes (30 mL) filtered, and the filter cake dried in a vacuum oven at 40° C. to afford 0.455 g (33% yield) of 6-chloro-2-phenyl-benzoxazole-4-carboxylic acid as a brown solid: $^1$H NMR (500 MHz, DMSO-d$_6$) δ 8.24 (m, 3H), 7.84 (s, 1H), 7.65 (m, 3H); MS (ESI) m/z 272 (M−H).

Step C: A 15-mL, round bottomed flask equipped with a magnetic stirrer was purged with nitrogen and charged with 6-chloro-2-phenyl-benzoxazole-4-carboxylic acid (0.075 g, 0.274 mmol), 3-amino-9-methyl-9-azabicyclo[3.3.1]nonane dihydrochloride (0.063 g, 0.411 mmol) 1-ethyl-3-[3-(dimethylamino)propyl]carbodiimide hydrochloride (0.079 g, 0.411 mmol), 1-hydroxybenzotriazole (0.037 g, 0.274 mmol), diisopropylethylamine (0.141 g, 1.09 mmol), and DMF (1.0 mL). After stirring at ambient temperature for 18 h, the reaction was concentrated under reduced pressure and purified by preparative HPLC to afford 0.016 g (14% yield) of N-(9-methyl-9-azabicyclo[3.3.1]non-3-yl)-6-chloro-2-phenylbenzoxazole-4-carboxamide as an off-white solid: $^1$H NMR (500 MHz, CDCl$_3$) δ 8.95 (br s, 1H), 8.23 (d, J=6.9 Hz, 2H), 8.20 (d, J=2.0 Hz, 1H), 7.71 (d, J=2.0 Hz, 1H), 7.65-7.57 (m, 3H), 4.58 (q, J=7.1 Hz, 1H), 3.18 (br s, 2H), 2.58 (m, 5H), 2.25-2.02 (m, 3H), 1.55 (s, 3H), 1.23 (m, 3H); MS (APCI) m/z 409 [M+H]$^+$ Example 8

Preparation of N-(Piperidin-4-yl)-2-phenylbenzoxazole-4-carboxamide

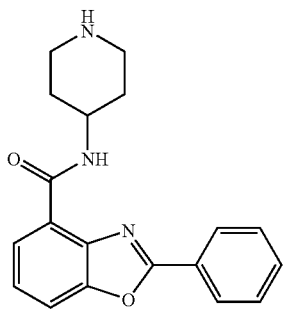

N-(1-tert-butyloxycarbonylpiperidin-4-yl)-2-phenylbenzoxazole-4-carboxamide was prepared from 4-amino-1-tert-butyloxycarbonylpiperidine and 2-phenylbenzoxazole-4-carboxylic acid using the coupling method described in Step C of Example 7. This crude material was immediately dissolved in a mixture of trifluoroacetic acid (1.0 mL) and water (0.05 mL) and the resulting solution stirred at ambient temperature for 0.5 hours. The reaction was then concentrated to dryness in vacuo. The resulting oil was purified using preparative HPLC to afford a 74% yield of N-(piperidin-4-yl)-2-phenylbenzoxazole-4-carboxamide as a white solid: mp 99-102° C.; $^1$H NMR (500 MHz, CD$_3$OD) δ 8.27 (dd, J=7.5, 2.0 Hz, 2H), 7.89 (dd, J=8.0, 1.0 Hz, 1H), 7.78 (d, J=8.0 Hz, 1H), 7.65-7.58 (m, 3H), 7.49 (t, J=8.0 Hz, 1H), 4.20-4.14 (m, 1H), 3.26 (d, J=13.0 Hz, 2H), 2.90 (t, J=12.0 Hz, 2H), 2.16 (d, J=12.5 Hz, 2H), 1.75 (q, J=12.5 Hz, 2H); MS (ESI) m/z 322 [M+H]$^+$.

Example 9

Preparation of N-(1-Azabicyclo[2.2.2]oct-3-yl)-2-phenylbenzoxazole-4-carboxamide

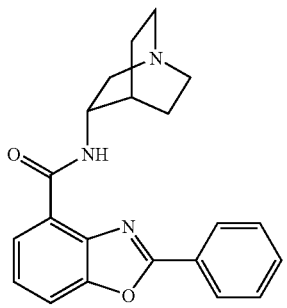

N-(1-Azabicyclo[2.2.2]oct-3-yl)-2-phenylbenzoxazole-4-carboxamide was prepared from 2-phenylbenzoxazole-4-carboxylic acid and 3-aminoquinuclidine dihydrochloride using the method outlined in Step C of Example 7. This compound was obtained in 51% yield as an off-white solid: mp 77-80° C.; ¹H NMR (500 MHz, CDCl₃) δ 9.58 (d, J=7.1 Hz, 1H), 8.24 (d, J=5.2 Hz, 2H), 8.19 (d, 1H, J=6.8 Hz, 1H), 7.72 (d, J=7.1 Hz, 1H), 7.61-7.49 (m, 3H), 7.48 (t, J=7.9 Hz, 1H), 4.31 (m, 1H), 3.51 (dd, J=7.1, 2.3 Hz, 1H), 3.10 (m, 2H), 2.91 (m, 2H), 2.83 (dd, J=10.1, 4.2 Hz, 1H), 2.16 (m, 1H), 2.05 (m, 1H), 1.65-1.43 (m, 3H); MS (APCI) m/z 348 [M+H]⁺

Example 10

Preparation of N-(1-Methyl-piperidin-4-yl)-6-chloro-2-phenylbenzoxazole-4-carboxamide

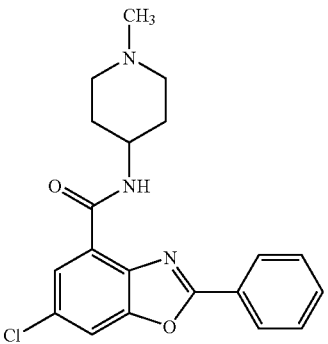

This material was prepared from 6-chloro-2-phenyl-benzoxazole-4-carboxylic acid and 4-amino-1-methylpiperdine using the method described in Step C of Example 7. This compound was obtained in 46% yield as a tan solid: mp 170-172° C.; ¹H NMR (300 MHz, CDCl₃) δ 9.14 (d, J=7.8 Hz, 1H), 8.23 (dd, J=6.6, 1.5 Hz, 2H), 8.18 (d, J=1.5 Hz, 1H), 7.71 (d, J=2.1 Hz, 1H), 7.65-7.54 (m, 3H), 4.19-4.13 (m, 1H), 2.87 (d, J=1.5 Hz, 2H), 2.37 (s, 3H), 2.32-2.26 (m, 2H), 2.17-2.13 (m, 2H), 1.84-1.72 (m, 2H); MS (ESI) m/z 370 [M+H]⁺

Example 11

Preparation of N-(Piperidin-4-yl)-6-chloro-2-phenylbenzoxazole-4-carboxamide

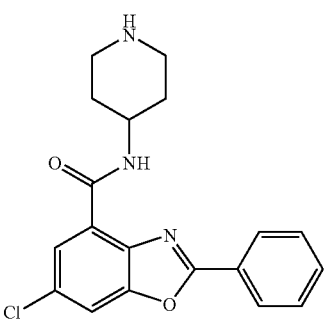

N-(1-tert-butyloxycarbonylpiperidin-4-yl)-6-chloro-2-phenylbenzoxazole-4-carboxamide was prepared from 4-amino-1-tert-butyloxycarbonylpiperidine and 2-phenyl-benzoxazole-4-carboxylic acid using the method described in Step C of Example 7. The crude product was immediately dissolved in a mixture of trifluoroacetic acid (1.0 mL) and water (0.05 mL) and the resulting solution stirred at ambient temperature for 0.5 hours. The reaction was then concentrated to dryness in vacuo. The resulting oil was purified using preparative HPLC to afford a 89% yield of N-(piperidin-4-yl)-6-chloro-2-phenylbenzoxazole-4-carboxamide as a white solid: mp 169-171° C.; ¹H NMR (500 MHz, CDCl₃) δ 9.12 (d, J=7.5 Hz, 1H), 8.24 (d, J=7.1 Hz, 2H), 8.18 (d, J=2.0 Hz, 1H), 7.71 (d, J=2.0 Hz, 1H), 7.64-7.56 (m, 3H), 4.43 (m, 1H), 3.19 (dt, J=5.1, 3.6 Hz, 2H), 2.87 (t, J=10.5 Hz, 2H), 2.06 (m, 2H), 1.63 (m, 2H); MS (APCI) m/z 357 [M+H]⁺.

Example 12

Preparation of N-(1-Azabicyclo[2.2.2]oct-3-yl)-6-chloro-2-phenylbenzoxazole-4-carboxamide

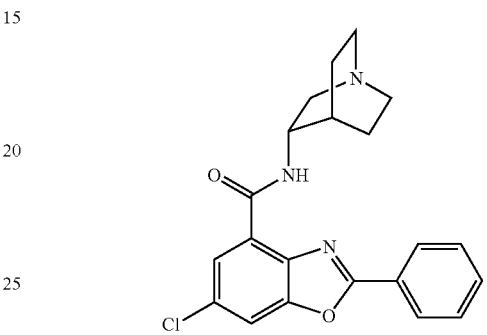

N-(1-Azabicyclo[2.2.2]oct-3-yl)-6-chloro-2-phenylbenzoxazole-4-carboxamide was prepared from 6-chloro-2-phenyl-benzoxazole-4-carboxylic acid and 3-aminoquinuclidine dihydrochloride using the method outlined in Step C of Example 7. This compound was obtained in 24% yield as a white solid: mp 180-183° C.; ¹H NMR (500 MHz, CDCl₃) δ 9.45 (d, J=7.3 Hz, 1H), 8.22 (d, J=5.0 Hz, 2H), 8.18 (d, J=2.0 Hz, 1H), 7.72 (d, J=2.0 Hz, 1H), 7.64-7.47 (m, 3H), 4.29 (m, 1H), 3.51 (dd, J=7.2, 2.1 Hz, 1H), 3.05 (m, 2H), 2.91 (m, 2H), 2.80 (dd, J=10.2, 4.0 Hz, 1H), 2.15 (m, 1H), 2.04 (m, 1H), 1.78-1.60 (m, 3H); MS (APCI) m/z 382 [M+H]⁺

Example 13

Preparation of N-(8-Methyl-8-azabicyclo[3.2.1]oct-3-yl)-6-chloro-2-phenylbenzoxazole-4-carboxamide

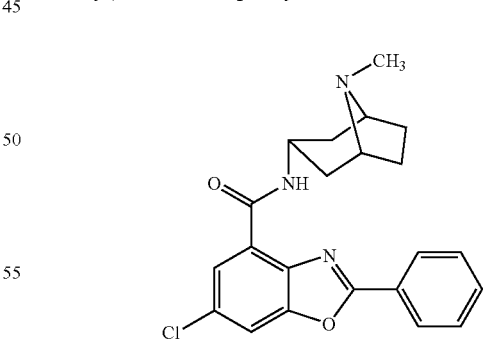

N-(8-Methyl-8-azabicyclo[3.2.1]oct-3-yl)-6-chloro-2-phenylbenzoxazole-4-carboxamide was prepared from 6-chloro-2-phenyl-benzoxazole-4-carboxylic acid and 3-amino-8-methyl-8-azabicyclo[3.2.1]octane using the method outlined in Step C of Example 7. This compound was obtained in 20% yield as a white solid: mp 187-190° C.; ¹H NMR (500 MHz, CDCl₃) δ 9.44 (d, J=7.5 Hz, 1H), 8.26 (d, J=7.1 Hz, 2H), 8.21 (d, J=2.0 Hz, 1H), 7.72 (d, J=2.0 Hz, 1H), 7.65-7.47 (m, 3H), 4.46 (q, J=7.2 Hz, 1H), 3.25 (br s, 1H), 2.38 (m, 5H), 2.26 (m, 4H), 1.84 (d, J=14.3 Hz, 2H), 2.15 (m, 1H), 2.04 (m, 1H), 1.78-1.60 (m, 3H); MS (APCI) m/z 397 [M+H]+

Example 14

Preparation of N-(1-Azabicyclo[2.2.2]oct-3-yl)-2-(4-chlorophenyl)benzoxazole-4-carboxamide

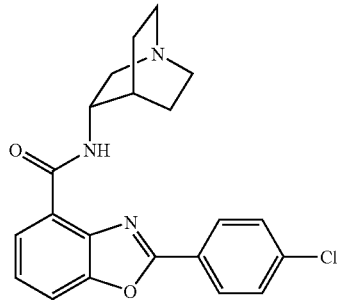

Step A: 2-(4-Chlorophenyl)benzoxazole-4-carboxylic acid was prepared from 3-hydroxyanthranilic acid and 4-chlorobenzoyl chloride using the method described in Step A of Example 1. This crude material (2.90 g, 10.6 mmol) was directly dissolved in DMF (40 mL), DIPEA (5.46 g, 42.4 mmol) and methyl iodide (5.93 g, 42.4 mmol) added and the reaction stirred at room temperature for 18 h. After this time the reaction was diluted with ethyl acetate (100 mL) and 2 N HCl (50 mL). The organic layer was separated and then washed with 2 N HCl (25 mL), water (50 mL) and brine (50 mL). The organic layer was then dried over sodium sulfate, filtered and concentrated to dryness to yield light yellow oil. This material was purified using silica gel chromatography to afford 0.532 g (30% yield) of methyl 2-(4-chlorophenyl)benzoxazole-4-carboxylate as a white solid: $^1$H NMR (300 MHz, CDCl$_3$) δ 8.28 (dd, J=6.9, 1.8 Hz, 2H), 8.04 (d, J=8.1 Hz, 1H), 7.78 (d, J=8.1 Hz, 1H), 7.52 (d, J=8.7 Hz, 2H), 7.43 (t, J=7.8 Hz, 1H), 4.06 (s, 3H); MS (ESI) m/z 288 [M+H]+

Step B: A 100 mL round bottom flask equipped with a magnetic stirrer was charged with methyl 2-(4-chlorophenyl)benzoxazole-4-carboxylate (0.50 g, 1.74 mmol), THF (10 mL), methanol (10 mL), lithium hydroxide (0.08 g, 3.48 mmol) and water (10 mL). The reaction was stirred at room temperature for 18 hours. After this time, the reaction was diluted with ethyl acetate (50 mL) then acidified to pH 4 with 2 N HCl. The aqueous layer was extracted with ethyl acetate (2×25 mL). The organic layers were then combined and washed with brine (1×25 mL), dried with sodium sulfate, filtered and concentrated to dryness in vacuo to yield 2-(4-chlorophenyl)benzoxazole-4-carboxylic acid (0.43 g, 90% yield) as a white solid: $^1$H NMR (500 MHz, CDCl$_3$) δ 11.53 (bs, 1H), 8.26 (d, J=8.5 Hz, 2H), 8.18 (d, J=8.0 Hz, 1H), 7.84 (d, J=8.0 Hz, 1H), 7.58 (d, J=8.5 Hz, 2H), 7.55 (t, J=8.0 Hz, 1H); MS (ESI) m/z 274 [M+H]+

Step C: A 25 mL round bottomed flask equipped with a reflux condenser was purged with nitrogen and charged with 2-(4-chlorophenyl)benzoxazole-4-carboxylic acid (0.050 g, 0.18 mmol) followed by thionyl chloride (5 mL). The resulting suspension was heated to reflux for 1 hr, after which time a light yellow solution was obtained. The reaction was then cooled and the thionyl chloride removed under reduced pressure affording an off-white solid. This solid was dissolved in methylene chloride (10 mL) and quinuclidine dihydrochloride (0.056 g, 0.27 mmol) added followed by the drop-wise addition of diisopropylethylamine (0.371 g, 2.87 mmol) over 5 min. After stirring at room temperature for 3 hrs the reaction was quenched by the addition of water (10 mL) and the organic layer separated. Subsequent washing of the organic layer with water (10 mL) followed by brine (10 mL), drying over MgSO$_4$, filtration and concentration afforded a tan solid. This solid was purified by preparative HPLC to afford 0.012 g (17% yield) of N-(1-azabicyclo[2.2.2]oct-3-yl)-2-(4-chlorophenyl)benzoxazole-4-carboxamide as an white solid: mp 194-196° C.; $^1$H NMR (500 MHz, DMSO-d$_6$) δ 9.13 (m, 1H), 8.23 (dd, J=6.7, 1.9 Hz, 2H), 8.03 (dd, J=8.2, 0.9 Hz, 1H), 7.97 (dd, J=7.7, 0.9 Hz, 1H), 7.78 (dd, J=6.7, 1.9 Hz, 2H), 7.58 (t, J=8.0 Hz, 1H), 4.09 (m, 1H), 3.28 (m, 1H), 2.85 (m, 2H), 2.75 (m, 2H), 2.63 (m, 1H), 2.08 (m, 1H), 1.99 (m, 1H), 1.65 (m, 2H), 1.57 (m, 1H); MS (ESI) m/z 382 [M+H]+.

Example 15

Preparation of N-(9-Methyl-9-azabicyclo[3.3.1]non-3-yl)-2-(4-chlorophenyl)benzoxazole-4-carboxamide

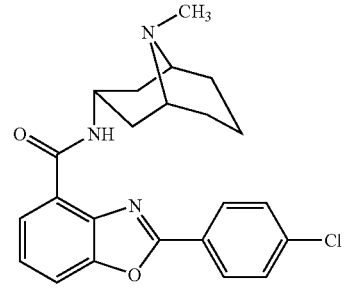

N-(9-Methyl-9-azabicyclo[3.3.1]non-3-yl)-2-(4-chlorophenyl)benzoxazole-4-carboxamide was prepared from 2-(4-chlorophenyl)benzoxazole-4-carboxylic acid and 3-amino-9-methyl-9-azabicyclo[3.3.1]nonane dihydrochloride using the method outlined in Step C of Example 14. This compound was obtained in 16% yield as a white solid: mp 185-187° C.; $^1$H NMR (500 MHz, DMSO-d$_6$) δ 8.72 (d, J=7.7 Hz, 1H), 8.27 (d, J=8.5 Hz, 2H), 7.99 (d, J=8.1 Hz, 1H), 7.98 (d, J=8.1 Hz, 1H), 7.76 (d, J=8.5 Hz, 2H), 7.56 (t, J=8.0 Hz, 1H), 4.01 (m, 1H), 3.02 (m, 2H), 2.44 (s, 3H), 2.41 (m, 2H), 2.09 (m, 1H), 1.97 (m, 2H), 1.47 (m, 3H), 1.00 (m, 2H); MS (ESI) m/z 410 [M+H]+

Example 16

Preparation of N-(1-Azabicyclo[2.2.2]oct-3-yl)-2-(4-methoxyphenyl)benzoxazole-4-carboxamide

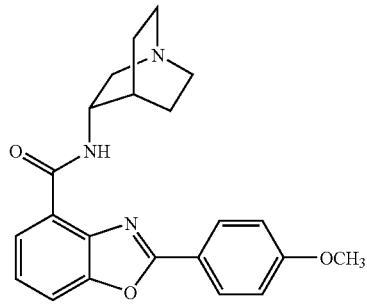

Step A: Methyl 2-(4-methoxyphenyl)benzoxazole-4-carboxylate was prepared from methyl 3-hydroxyanthranilate and 4-methoxybenzoyl chloride as described in Step A of Example 1. The product was obtained as an off-white solid in 18% yield. δ 8.29 (m, 2H), 8.01 (dd, J=7.8, 1.0 Hz, 1H), 7.74 (dd, J=8.1, 1.0 Hz, 1H), 7.37 (t, J=7.9 Hz, 1H), 7.03 (m, 2H), 4.06 (s, 3H); 3.91 (s, 3H); MS (ESI) m/z 284 [M+H]+.

Step B: 2-(4-Methoxyphenyl)benzoxazole-4-carboxylic acid was prepared via the lithium hydroxide mediated hydrolysis of methyl 2-(4-methoxyphenyl)benzoxazole-4-carboxylate as described in Step B of Example 14. This material was obtained in 92% yield as a white solid: δ 11.90 (br s, 1H), 8.25 (m, 2H), 8.13 (dd, J=7.8, 0.9 Hz, 1H), 7.79 (dd, J=7.8, 0.9 Hz, 1H), 7.48 (t, J=7.9 Hz, 1H), 7.08 (m, 2H), 3.93 (s, 3H); MS (ESI) m/z 270 [M+H]+

Step C: N-(1-Azabicyclo[2.2.2]oct-3-yl)-2-(4-methoxyphenyl)benzoxazole-4-carboxamide was prepared from 2-(4-methoxyphenyl)benzoxazole-4-carboxylic acid and 3-aminoquinuclidine dihydrochloride using the method outlined in Step C of Example 14. This compound was obtained in 5% yield as an off-white solid: mp 108-109° C.; $^1$H NMR (500 MHz, CD$_3$OD) δ 8.19 (dt, J=9.7, 2.8 Hz, 2H), 8.01 (dd, J=7.7, 0.9 Hz, 1H), 7.82 (dd, J=7.7, 0.9 Hz, 1H), 7.49 (t, J=8.0 Hz, 1H), 7.14 (dt, J=9.7, 2.8 Hz, 2H), 4.25 (m, 1H), 3.91 (s, 3H), 3.47 (m, 1H), 3.02 (m, 2H), 2.91 (m, 2H), 2.77 (m, 1H), 2.12 (m, 2H), 1.80 (m, 3H); MS (ESI) m/z 378 [M+H]+

Example 17

Preparation of N-(9-Methyl-9-azabicyclo[3.3.1]non-3-yl)-2-(4-methoxyphenyl)benzoxazole-4-carboxamide

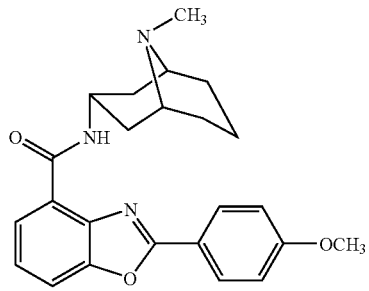

N-(9-Methyl-9-azabicyclo[3.3.1]non-3-yl)-2-(4-methoxyphenyl)benzoxazole-4-carboxamide was prepared from 2-(4-methoxyphenyl)benzoxazole-4-carboxylic acid and 3-amino-9-methyl-9-azabicyclo[3.3.1]nonane dihydrochloride using the method outlined in Step C of Example 14. This compound was obtained in 60% yield as a white solid: mp 103-105° C.; $^1$H NMR (500 MHz, CDCl$_3$) δ 9.07 (m, 1H), 8.19 (m, 3H), 7.66 (dd, J=8.0, 1.1 Hz, 1H), 7.41 (t, J=7.9 Hz, 1H), 7.07 (m, 2H), 4.60 (m, 1H), 3.92 (s, 3H), 3.11 (m, 2H), 2.66 (m, 2H), 2.54 (s, 3H), 2.13 (m, 1H), 2.03 (m, 2H), 1.53 (m, 3H), 1.17 (m, 2H); MS (ESI) m/z 406 [M+H]+

Example 18

Preparation of N-(9-Methyl-9-azabicyclo[3.3.1]non-3-yl)-2-(4-fluorophenyl)benzoxazole-4-carboxamide

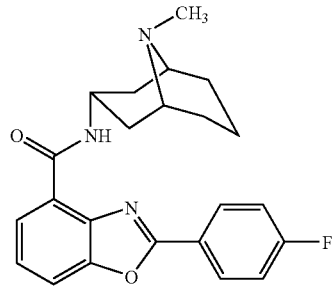

Step A: 2-(4-fluorophenyl)benzoxazole-4-carboxylic acid was prepared from 3-hydroxyanthranilic acid and 4-fluorobenzoyl chloride as described in Step A of Example 1. The crude product was dissolved in methylene chloride (20 mL) and the resulting solution treated with oxalyl chloride (1 mL) and DMF (0.05 mL). After stirring at room temperature for 6 h, the reaction was quenched by the addition of methanol (10 mL) and stirred at room temperature for a further 71 h. The reaction was then re-concentrated and the resulting solid purified by column chromatography to afford a 26% yield of methyl 2-(4-fluorophenyl)benzoxazole-4-carboxylate as a white solid: $^1$H NMR (500 MHz, CDCl$_3$) δ 8.36 (dd, J=14.7, 11.8 Hz, 2H), 8.03 (d, J=14.7 Hz, 1H), 7.78 (d, J=15.2 Hz, 1H), 7.42 (t, J=13.2 Hz, 1H), 7.18 (m, 2H), 4.06 (m, 3H).

Step B: 2-(4-Fluorophenyl)benzoxazole-4-carboxylic acid was prepared via the lithium hydroxide mediated hydrolysis of methyl 2-(4-fluorophenyl)benzoxazole-4-carboxylate as described in Step B of Example 14. This material was obtained in 60% yield as a white solid: $^1$H NMR (500 MHz, CDCl$_3$) δ 8.32 (dd, J=14.9, 11.8 Hz, 2H), 8.17 (d, J=13.1 Hz, 1H), 7.83 (d, J=13.6 Hz, 1H), 7.53 (t, J=13.4 Hz, 1H), 7.29 (m, 2H). MS (ESI) m/z 258 [M+H]+

Step C: N-(9-Methyl-9-azabicyclo[3.3.1]non-3-yl)-2-(4-fluorophenyl)benzoxazole-4-carboxamide was prepared from 2-(4-fluorophenyl)benzoxazole-4-carboxylic acid and 3-amino-9-methyl-9-azabicyclo[3.3.1]nonane dihydrochloride using the method outlined in Step C of Example 14. This compound was obtained in 60% yield as a white solid: mp 197-199° C.; $^1$H NMR (500 MHz, CDCl$_3$) δ 8.95 (m, 1H), 8.26 (m, 2H), 8.21 (dd, J=7.8, 1.0 Hz, 1H), 7.69 (dd, J=8.1, 1.0 Hz, 1H), 7.46 (t, J=7.9 Hz, 1H), 7.29 (m, 1H), 4.60 (m, 1H), 3.11 (m, 2H), 2.66 (m, 2H), 2.54 (s, 3H), 2.15 (m, 1H), 2.04 (m, 2H), 1.59 (m, 2H), 1.51 (m, 2H), 1.17 (m, 2H); MS (ESI) m/z 394 [M+H]+

Example 19

Preparation of N-(1-Azabicyclo[2.2.2]oct-3-yl)-2-(4-fluorophenyl)benzoxazole-4-carboxamide

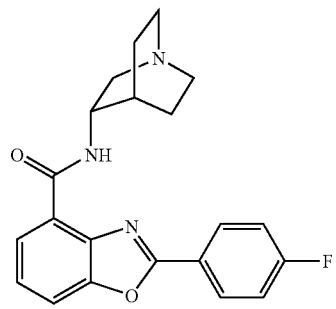

N-(1-Azabicyclo[2.2.2]oct-3-yl)-2-(4-fluorophenyl)benzoxazole-4-carboxamide was prepared from 2-(4-fluorophenyl)benzoxazole-4-carboxylic acid and 3-aminoquinuclidine dihydrochloride using the method outlined in Step C of Example 14. This compound was obtained in 8% yield as a white solid: mp 208-209° C.; $^1$H NMR (500 MHz, CD$_3$OD) δ 8.33 (m, 2H), 8.05 (m, 1H), 7.90 (dd, J=8.2, 0.9 Hz, 1H), 7.55 (m, 1H), 7.39 (m, 2H), 4.29 (m, 1H), 3.52 (m, 1H), 3.06 (m, 2H), 2.94 (m, 2H), 2.92 (m, 1H), 2.16 (m, 2H), 1.86 (m, 3H); MS (ESI) m/z 366 [M+H]+

Example 20

Preparation of N-(9-Methyl-9-azabicyclo[3.3.1]non-3-yl)-2-phenylbenzoxazole-7-carboxamide

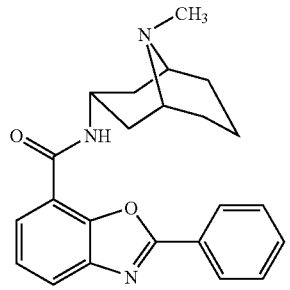

Step A: 2-Phenylbenzoxazole-7-carboxylic acid was prepared from 3-aminosalicylic acid and benzoyl chloride using a procedure identical to that described in Step A of Example 1. This material was obtained in 86% yield as an off-white solid: $^1$H NMR (500 MHz, CD$_3$OD) δ 8.30 (dd, J=7.2, 2.1 Hz, 2H), 7.98 (dd, J=12.9, 7.8 Hz, 2H), 7.60(m, 3H), 7.48 (t, J=7.8 Hz, 1H); MS (APCI) m/z 240 [M+H]$^+$ Step B: N-(9-Methyl-9-azabicyclo[3.3.1]non-3-yl)-2-phenylbenzoxazole-7-carboxamide was prepared from 2-phenylbenzoxazole-7-carboxylic acid and 3-amino-9-methyl-9-azabicyclo[3.3.1]nonane dihydrochloride using the method outlined in Step C of Example 7. This compound was obtained in 43% yield and obtained as an off-white solid: mp 208-210° C.; $^1$H NMR (500 MHz, CDCl$_3$) δ 8.95 (br s, 1H), 8.23 (d, J=6.9 Hz, 2H), 8.20(d, J=2.0 Hz, 1H), 7.71 (d, J=2.0 Hz, 1H), 7.57-7.65 (m, 3H), 4.58 (q, J=7.1 Hz, 1H), 3.18 (br s, 2H), 2.58 (m, 5H), 2.02-2.25 (m, 3H), 1.55 (s, 3H), 1.23 (m, 3H); MS (APCI) m/z 411 [M+H]$^+$

Example 21

Preparation of N-(1-Methylpiperidin-4-yl)-2-phenyl-benzoxazole-7-carboxamide

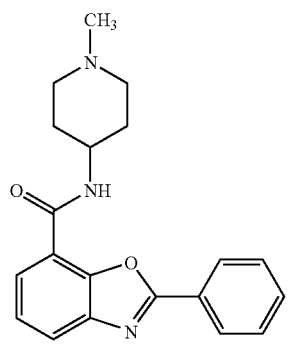

N-(1-Methylpiperidin-4-yl)-2-phenylbenzoxazole-7-carboxamide was prepared from 2-phenylbenzoxazole-7-carboxylic acid and 4-amino-1-methylpiperidine using the method outlined in Step C of Example 7. This compound was obtained in 58% yield and obtained as a white solid: mp 209-210° C.; $^1$H NMR (300 MHz, CDCl$_3$) δ 8.22 (m, 1H), 8.21 (dd, J=5.7, 1.8 Hz, 1H), 8.10 (dd, J=8.1, 0.9 Hz, 1H), 7.91 (dd, J=9.9, 1.2 Hz, 1H), 7.64-7.54 (m, 3H), 7.48 (t, J=7.8, 1H), 4.26-4.17 (m, 1H), 2.93 (d, J=11.4 Hz, 2H), 2.46 (s, 3H), 2.30 (t, J=11.1 Hz, 2H), 2.22-2.17 (m, 2H), 1.85-1.73 (m, 2H); MS (ESI) m/z 336 [M+H]$^+$

Example 22

Preparation of N-(Piperidin-4-yl)-2-phenylbenzoxazole-7-carboxamide

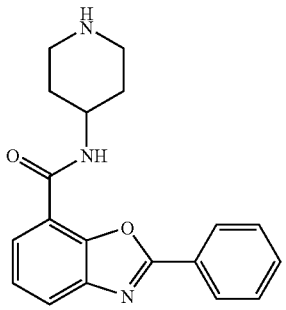

N-(1-tert-butyloxycarbonylpiperidin-4-yl)-2-phenylbenzoxazole-7-carboxamide was prepared from 4-amino-1-tert-butyloxycarbonylpiperidine using the coupling method described in Step C of Example 7. This crude material was immediately dissolved in trifluoroacetic acid (1.0 mL) and water (0.05 mL) and the resulting solution stirred at ambient temperature for 0.5 hours. The reaction was then concentrated to dryness in vacuo. The resulting oil was purified using preparative HPLC to afford a 51% yield of N-(1-tert-butyloxycarbonylpiperidin-4-yl)-2-phenylbenzoxazole-7-carboxamide as a white solid: mp 191-193° C.; $^1$H NMR (500 MHz, CD$_3$OD) δ 8.27 (m, 1H), 8.26 (dd, J=8.5, 2.0 Hz, 1H), 7.89 (d, J=7.5 Hz, 1H), 7.78 (d, J=7.5 Hz, 1H), 7.64-7.58 (m, 3H), 7.48 (t, J=8.0 Hz, 1H), 4.14-4.06 (m, 1H), 3.13 (d, J=13.0 Hz, 2H), 2.75 (t, J=12.5 Hz, 2H), 2.08 (d, J=12.0 Hz, 2H), 1.64 (q, J=8.5 Hz, 2H); MS (ESI) m/z 320 [M+H]$^+$

Example 23

Preparation of N-(1-Azabicyclo[2.2.2]oct-3-yl)-2-phenylbenzoxazole-7-carboxamide

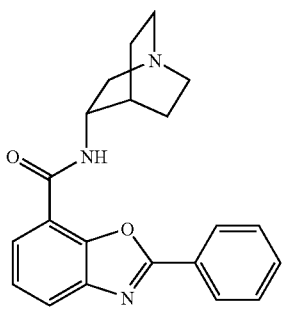

N-(1-Azabicyclo[2.2.2]oct-3-yl)-2-phenylbenzoxazole-7-carboxamide was prepared from 2-phenylbenzoxazole-7-carboxylic acid and 3-aminoquinuclidine dihydrochloride using the method outlined in Step C of Example 7. This compound was obtained in 57% yield as a white solid: mp 179-180° C.; ¹H NMR (300 MHz, CDCl₃) δ 8.21 (dd, J=7.5, 2.1 Hz, 2H), 8.10 (dd, J=7.8, 1.2 Hz, 1H), 7.92 (dd, J=7.8, 1.2 Hz, 1H), 7.61-7.54 (m, 3H), 7.51-7.46 (m, 2H), 4.38-4.33 (m, 1H), 3.63-3.54 (m, 1H), 3.13-3.05 (m, 2H), 2.23 (q, J=3.0 Hz, 1H), 2.00-1.90 (m, 1H), 1.84-1.73 (m, 2H), 1.71-1.64 (m, 1H); MS (ESI) m/z 348[M+H]⁺.

Example 24

Preparation of N-(8-Methyl-8-azabicyclo[3.2.1]oct-3-yl)-2-phenylbenzoxazole-7-carboxamide

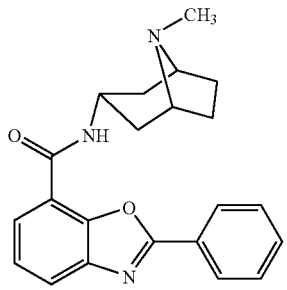

N-(8-Methyl-8-azabicyclo[3.2.1]oct-3-yl)-2-phenylbenzoxazole-7-carboxamide was prepared from 3-amino-8-methyl-8-azabicyclo[3.2.1]octane and 2-phenylbenzoxazole-7-carboxylic acid using conditions similar to those described for Step C in Example 7. This compound was obtained in 57% yield as a white solid: mp 164-166° C.; ¹H NMR (300 MHz, CH₃OD) δ 8.25 (dd, J=8.1, 1.8 Hz, 2H), 7.90 (dd, J=8.1, 1.2 Hz, 1H), 7.80 (d, J=7.5 Hz, 1H), 7.64-7.58 (m, 3H), 7.50 (t, J=7.8 Hz, 1H), 4.25 (t, J=5.0 Hz, 1H), 3.63 (br s, 2H), 2.63 (s, 3H), 2.53-2.35 (m, 6H), 2.22-2.17 (m, 2H); MS (ESI) m/z 362 [M+H]⁺.

Example 25

Preparation of N-(1-Azabicyclo[2.2.2]oct-3-yl)-5-chloro-2-phenyl-benzoxazole-7-carboxamide

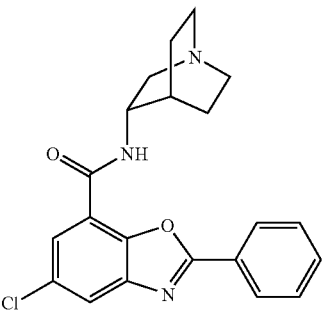

Step A: A 250-mL single-neck round bottomed flask equipped with a magnetic stirrer was charged with methyl 4-chlorosalicylate (25.0 g, 134 mmol) followed by concentrated sulfuric acid (73 mL) and the resulting suspension cooled to 0° C. using an ice bath. Concentrated nitric acid (6.20 mL, 147 mmol) was then added and the reaction stirred for 1 h at 0° C. After this time, the reaction was poured into ice and the resulting precipitate collected by vacuum filtration. The filter cake was washed with water (20 mL) and then re-crystallized from hot ethanol (100 mL) to afford methyl 4-chloro-3-nitrosalicylate in 52% yield (16.0 g) as white solid: ¹H NMR (300 MHz, CDCl₃) δ 8.15 (d, J=2.7 Hz, 1H), 8.11 (d, J=2.7 Hz, 1H), 4.03 (s, 3H); MS (ESI) m/z 232 [M+H]⁺.

Step B: A 100-mL single-neck round bottomed flask equipped with a magnetic stirrer and reflux condenser was charged with methyl 4-chloro-3-nitrosalicylate (1.00 g, 4.32 mmol), glacial acetic acid (23 mL) and methanol (18 mL). The stirred solution was then treated with 325 mesh iron powder (2.41 g, 43.2 mmol) and heated at reflux for 30 min. After this time, the reaction was cooled to room temperature and filtered through a pad of celite 521. The pad was rinsed with methanol (10 mL) and the filtrates combined and partitioned between ethyl acetate (100 mL) and saturated aqueous sodium bicarbonate (50 mL). The organic layer was separated and washed with water (2×100 mL) then dried over sodium sulfate. The suspension was filtered and the filtrate treated with decolorizing carbon (0.50 g) and warmed to reflux. The suspension was then re-filtered hot through a pad of celite 521 and the resulting filtrate concentrated to dryness under reduced pressure to afford methyl 3-amino-4-chlorosalicylate in 81% yield (0.70 g) as white solid: ¹H NMR (300 MHz, CDCl₃) δ 7.19 (d, J=2.7 Hz, 1H), 6.82 (d, J=2.1 Hz, 1H), 3.95 (br s, 2H), 3.94 (s, 3H); MS (ESI) m/z 202 [M+H]⁺.

Step C: Methyl 5-chloro-2-phenylbenzoxazole-7-carboxylate was prepared from methyl 3-amino-4-chlorosalicylate and trimethyl orthobenzoate as described in Step B of Example 7. This material was obtained as white needles in 99% yield. ¹H NMR (300 MHz, CDCl₃) δ 8.30 (dd, J=8.1, 2.1 Hz, 2H), 7.94 (dd, J=13.8, 2.1 Hz, 2H), 7.59-7.55 (m, 3H), 4.07 (s, 3H); MS (ESI) m/z 288 [M+H]⁺

Step D: 5-Chloro-2-phenylbenzoxazole-7-carboxylic acid was prepared from methyl 5-chloro-2-phenyl-benzoxazole-7-carboxylate via lithium hydroxide mediated hydrolysis as described in Step B of Example 14. This material was obtained as a white solid in 82% yield. ¹H NMR (300 MHz, DMSO-d₆) δ 13.84 (br s, 1H), 8.22-8.19 (m, 3H), 7.85 (d, J=2.1 Hz, 1H), 7.70-7.63 (m, 3H), 4.07 (s, 3H); MS (ESI) m/z 274 [M+H]⁺.

Step E: N-(1-Azabicyclo[2.2.2]oct-3-yl)-5-chloro-2-phenylbenzoxazole-7-carboxamide was prepared from 5-chloro-2-phenyl-benzoxazole-7-carboxylic acid and 3-aminoquinuclidine dihydrochloride using the method outlined in Step C of Example 7. This compound was obtained in 56% yield as a white solid: mp 283-285° C.; ¹H NMR (300 MHz, CH₃OD) δ 8.22 (dd, J=8.1, 1.5 Hz, 2H), 7.86 (d, J=2.1 Hz, 1H), 7.70 (d, J=2.1 Hz, 1H), 7.64-7.56 (m, 3H), 4.27-4.24 (m, 1H), 3.50-3.42 (m, 1H), 3.12-2.86 (m, 5H), 2.17 (q, J=3.0 Hz, 1H), 2.11-2.06 (m, 1H), 1.85-1.73 (m, 2H), 1.74-1.67 (m, 1H); MS (ESI) m/z 382[M+H]⁺.

Example 26

Preparation of N-(9-Methyl-9-azabicyclo[3.3.1]non-3-yl)-5-chloro-2-phenyl-benzoxazole-7-carboxamide

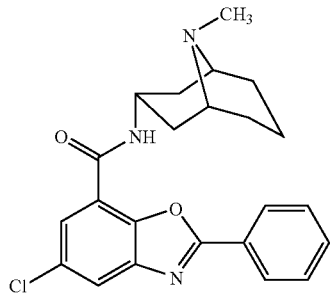

N-(9-Methyl-9-azabicyclo[3.3.1]non-3-yl)-5-chloro-2-phenyl-benzoxazole-7-carboxamide was prepared from 5-chloro-2-phenyl-benzoxazole-7-carboxylic acid and 3-amino-9-methyl-9-azabicyclo[3.3.1]nonane dihydrochloride using the method outlined in Step C of Example 7. This compound was obtained in 49% yield as a white solid: mp 199-201° C.; $^1$H NMR (300 MHz, CDCl$_3$) δ 8.19 (dd, J=7.5, 2.1 Hz, 2H), 8.05 (d, J=2.1 Hz, 1H), 7.85 (d, J=2.1 Hz, 1H), 7.66-7.55 (m, 3H), 6.84 (d, J=7.8 Hz, 1H), 4.65-4.56 (m, 1H), 3.15 (d, J=10.5 Hz, 2H), 2.71-2.60 (m, 2H), 2.53 (s, 3H), 2.17-2.10 (m, 1H), 2.03 (d, J=6.6 Hz, 3H), 1.78 (br s, 1H), 1.60-1.52 (m, 1H), 1.41 (t, J=10.8 Hz, 2H), 1.16-1.10 (m, 2H); MS (ESI) m/z 410 [M+H]$^+$.

Example 27

Preparation of N-(1-Azabicyclo[2.2.2]oct-3-yl)-2-(4-fluorophenyl)benzoxazole-7-carboxamide

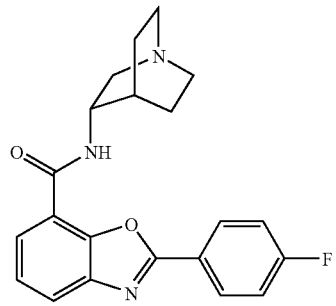

Step A: Methyl 2-(4-fluorophenyl)benzoxazole-7-carboxylate was prepared from 3-aminosalicyclic acid and 4-fluorobenzoyl chloride in 28% yield using the procedure described in Step A in Example 14. $^1$H NMR (500 MHz, CDCl$_3$) δ 8.32 (dd, J=14.9, 9.0 Hz, 2H), 7.98 (dd J=14.9, 9.0 Hz, 2H), 7.43 (t, J=13.1 Hz, 1H), 7.26 (m, 2H), 4.06 (s, 3H); MS (ESI) m/z 272 [M+H]$^+$ Step B: 2-(4-Fluorophenyl)benzoxazole-7-carboxylic acid was prepared via the lithium hydroxide mediated hydrolysis of methyl 2-(4-fluorophenyl)benzoxazole-7-carboxylate as described in Step B of Example 14. This material was obtained in quantitative yield as a white solid: $^1$H NMR (500 MHz, DMSO-d$_6$) δ 8.25 (dd, J=14.8, 8.9 Hz, 2H), 8.07 (dd, J=13.1, 1.6 Hz, 1H), 7.92 (dd, J=13.1, 1.6 Hz, 1H), 7.51 (m, 3H); MS (ESI) m/z 258 [M+H]$^+$.

Step C: A solution of 2-(4-fluorophenyl)benzoxazole-7-carboxylic acid (0.100 g, 0.39 mmol) in acetonitrile (10 mL) was treated with DCC (0.089 g, 0.43 mmol) and the mixture stirred at room temperature for 1 h. After this time a thick granular precipitate had formed. 3-Aminoquinuclidine dihydrochloride (0.086 g, 0.43 mmol) and DMAP (0.010 g, 0.08 mmol) were then added to the reaction followed by the dropwise addition of triethylamine (0.101 g, 1.00 mmol) over 15 min. The reaction was then stirred at room temperature overnight. Subsequent concentration of the reaction mixture and purification of the resulting solid residue by column chromatography afforded 0.100 g (70% yield) of N-(1-azabicyclo[2.2.2]oct-3-yl)-2-(4-fluorophenyl)benzoxazole-7-carboxamide as a white solid: mp 185-187° C.; $^1$H NMR (500 MHz, DMSO-d$_6$) δ 8.46 (d, J=6.7 Hz, 1H), 8.24 (m, 2H), 7.95 (m, 1H), 7.70 (m, 1H), 7.51 (m, 3H), 4.06 (m, 1H), 3.21 (m, 1H), 2.92 (m, 1H), 2.74 (m, 4H), 1.96 (m, 2H), 1.64 (m, 2H), 1.44 (m, 1H); MS (ESI) m/z 366 [M+H]$^+$.

Example 28

Preparation of N-(9-Methyl-9-azabicyclo[3.3.1]non-3-yl)-2-(4-fluorophenyl)benzoxazole-7-carboxamide

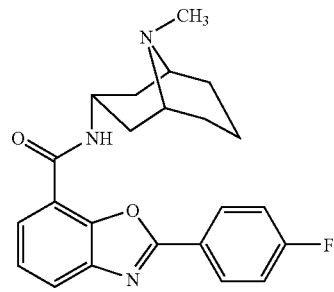

N-(9-Methyl-9-azabicyclo[3.3.1]non-3-yl)-2-(4-fluorophenyl)benzoxazole-7-carboxamide was prepared from 2-(4-fluorophenyl)benzoxazole-7-carboxylic acid and 3-amino-9-methyl-9-azabicyclo[3.3.1]nonane dihydrochloride using the method outlined in Step C of Example 14. This compound was obtained in 15% yield as an off-white solid: mp 229-231° C.; $^1$H NMR (500 MHz, DMSO-d$_6$) δ 8.26 (m, 2H), 8.20 (d, J=8.3 Hz, 1H), 7.94 (dd, J=1.0, 7.9 Hz, 1H), 7.71 (dd, J=1.0, 7.6 Hz, 1H), 7.50 (m, 3H), 4.39 (m, 1H), 3.02 (m, 2H), 2.43 (s, 3H), 2.32 (m, 2H), 2.08 (m, 1H), 1.93 (m, 2H), 1.48 (m, 3H), 0.96 (m, 2H); MS (ESI) m/z 394 [M+H]$^+$.

Example 29

Preparation of N-(1-Azabicyclo[2.2.2]oct-3-yl)-2-(4-methoxyphenyl)benzoxazole-7-carboxamide Step A: Methyl 2-(4-methoxyphenyl)benzoxazole-7-carboxylate was prepared from methyl 3-aminosalicylate and 4-methoxybenzoyl chloride as described in Step A of Example 1. The crude material was suspended in thionyl chloride (15 mL) and the mixture heated to reflux overnight. After this time the reaction was cooled and concentrated to a dark oil. This oil was treated with methanol and the solution stirred at room temperature for 1 h. Subsequent concentration afforded a dark brown solid which was purified by column chromatography to afford a 24% yield of methyl 2-(4-methoxyphenyl)benzoxazole-7-carboxylate as a yellow solid: $^1$H NMR (500 MHz, DMSO-d$_6$) δ 8.19 (d, J=8.7 Hz, 2H), 8.04 (d, J=7.8 Hz, 1H), 7.91 (d, J=7.8 Hz, 1H), 7.51 (t, J=7.8 Hz, 1H), 7.20 (d, J=8.7 Hz, 2H), 3.99 (s, 3H); 3.88 (s, 3H); MS (ESI) m/z 284 [M+H]$^+$.

Step B: Methyl 2-(4-methoxyphenyl)benzoxazole-7-carboxylate was hydrolyzed to 2-(4-methoxyphenyl)benzoxazole-7-carboxylic acid using lithium hydroxide as described in Step B of Example 14. This material was obtained in 65% yield as an off-white solid $^1$H NMR (500 MHz, DMSO-d$_6$) δ 8.15 (d, J=8.7 Hz, 2H), 8.01 (d, J=7.8 Hz, 1H), 7.88 (d, J=7.8 Hz, 1H), 7.49 (t, J=7.8 Hz, 1H), 7.20 (d, J=8.7 Hz, 2H), 3.99 (s, 3H); 3.83 (s, 3H); MS (ESI) m/z 270 [M+H]$^+$.

Step C: N-(1-Azabicyclo[2.2.2]oct-3-yl)-2-(4-methoxyphenyl)benzoxazole-7-carboxamide was prepared from 2-(4-methoxyphenyl)benzoxazole-7-carboxylic acid and 3-aminoquinuclidine dihydrochloride using the method outlined in Step C of Example 14. This compound was obtained in 24% yield as a white solid: mp 166-167° C.; $^1$H NMR (500 MHz, CD$_3$OD) δ 8.20 (dd, J=7.0, 2.0 Hz, 2H), 7.86 (d, J=7.9 Hz, 1H), 7.84 (d, J=7.9 Hz, 1H), 7.49 (t, J=7.9 Hz, 1H), 7.14 (dd, J=1.9, 7.0 Hz, 2H), 4.26 (m, 1H), 3.91 (s, 3H), 3.42 (m, 1H), 3.02 (m, 1H), 2.92 (m, 3H), 2.83 (m, 1H), 2.16 (d, J=3.1 Hz, 1H), 2.07 (m, 1H), 1.84 (m, 2H), 1.68 (m, 1H); MS (ESI) m/z 378 [M+H]$^+$.

Example 30

Preparation of N-(9-Methyl-9-azabicyclo[3.3.1]non-3-yl)-2-(4-methoxyphenyl)benzoxazole-7-carboxamide

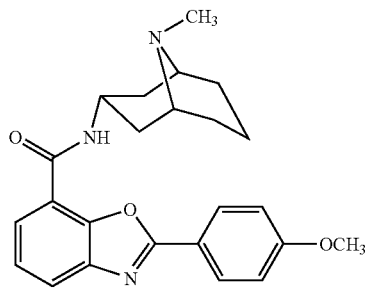

N-(9-Methyl-9-azabicyclo[3.3.1]non-3-yl)-2-(4-methoxyphenyl)benzoxazole-7-carboxamide was prepared from 2-(4-methoxyphenyl)benzoxazole-7-carboxylic acid and 3-amino-9-methyl-9-azabicyclo[3.3.1]nonane dihydrochloride using the method outlined in Step C of Example 14. This compound was obtained in 36% yield as a off-white solid: mp 160-162° C.; $^1$H NMR (500 MHz, CD$_3$OD) δ 8.22 (dt, J=9.7, 2.8 Hz, 2H), 7.82 (dd, J=7.9, 1.0 Hz, 1H), 7.72 (dd, J=7.7, 1.0 Hz, 1H), 7.46 (t, J=7.8 Hz, 1H), 7.14 (dt, J=9.7, 2.8 Hz, 2H), 4.61 (m, 1H), 3.90 (s, 3H), 3.16 (m, 2H), 2.59 (m, 2H), 2.55 (s, 3H), 2.14 (m, 1H), 2.08 (m, 2H), 1.61 (m, 3H), 1.99 (m, 2H); MS (ESI) m/z 406 [M+H]$^+$.

Example 31

Preparation of N-(1-Azabicyclo[2.2.2]oct-3-yl)-2-(4-chlorophenyl)benzoxazole-7-carboxamide

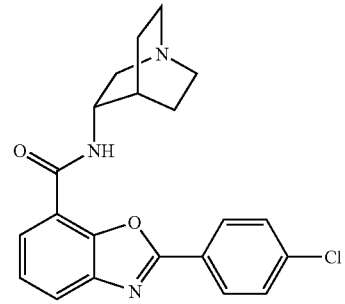

Step A: Methyl 2-(4-chlorophenyl)benzoxazole-7-carboxylate was prepared from 3-hydroxysalicylic acid and 4-chlorobenzoyl chloride using the method described in Step A of Example 14 in 45% overall yield. This material was obtained as a white solid: $^1$H NMR (300 MHz, CDCl$_3$) δ 8.25 (dd, J=6.6, 1.8 Hz, 2H), 8.04 (d, J=8.1 Hz, 1H), 7.78 (d, J=8.1 Hz, 1H), 7.52 (d, J=8.7 Hz, 2H), 7.43 (t, J=7.8 Hz, 1H), 4.06 (s, 3H); MS (ESI) m/z 288 [M+H]$^+$.

Step B: Methyl 2-(4-chlorophenyl)benzoxazole-7-carboxylate was converted to 2-(4-chlorophenyl)benzoxazole-7-carboxylic acid by lithium hydroxide mediated hydrolysis using the procedure described in Step B of Example 14. This material was obtained in 84% yield as a white solid: $^1$H NMR (500 MHz, DMSO-d$_6$) δ 13.49 (br s, 1H), 8.20 (d, J=8.5 Hz, 2H), 8.07 (d, J=8.0 Hz, 1H), 7.95 (d, J=7.5 Hz, 1H), 7.72 (d, J=8.5 Hz, 2H), 7.53 (t, J=7.5 Hz, 1H); MS (ESI) m/z 274 [M+H]$^+$.

Step C: N-(1-Azabicyclo[2.2.2]oct-3-yl)-2-(4-chlorophenyl)benzoxazole-7-carboxamide was prepared from 2-(4-chlorophenyl)benzoxazole-7-carboxylic acid and 3-aminoquinuclidine dihydrochloride using the method outlined in Step C of Example 14. This compound was obtained in 55% yield as a off-white solid: mp 181-183° C.; $^1$H NMR (500 MHz, CDCl$_3$) δ 8.14 (d, J=8.6 Hz, 2H), 8.11 (dd, J=1.0, 11.1 Hz, 2H), 7.92 (dd, J=1.0, 7.9 Hz, 1H), 7.56 (d, J=8.6 Hz, 2H), 7.50 (t, J=7.8 Hz, 1H), 7.32 (d, J=7.1 Hz, 1H), 4.31 (m, 1H), 3.57 (dd, J=9.4, 14.4 Hz, 1H), 3.01 (t, J=7.9 Hz, 2H), 2.92 (m, 2H), 2.74 (m, 1H), 2.17 (m, 1H), 1.91 (m, 1H), 1.78 (m, 2H), 1.63 (m, 4H); MS (ESI) m/z 382 [M+H]$^+$.

Example 32

Preparation of N-(9-Methyl-9-azabicyclo[3.3.1]non-3-yl)-2-(4-chlorophenyl)benzoxazole-7-carboxamide

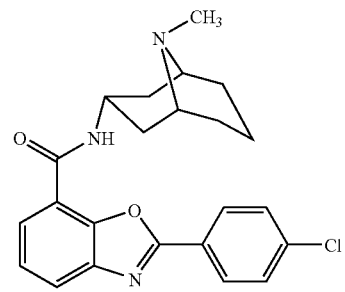

N-(9-Methyl-9-azabicyclo[3.3.1]non-3-yl)-2-(4-chlorophenyl)benzoxazole-7-carboxamide was prepared from 2-(4-chlorophenyl)benzoxazole-7-carboxylic acid and 3-amino-9-methyl-9-azabicyclo[3.3.1]nonane dihydrochloride using the method outlined in Step C of Example 14. This compound was obtained in 43% yield as an off-white solid: mp 193-196° C.; $^1$H NMR (500 MHz, DMSO-$d_6$) δ 8.14 (d, J=8.4 Hz, 2H), 8.06 (d, J=7.7 Hz, 1H), 7.88 (d, J=7.7 Hz, 1H), 7.55 (d, J=8.4 Hz, 2H), 7.46 (t, J=7.8 Hz, 1H); 6.88 (d, J=6.6 Hz, 1H), 4.62 (m, 1H), 3.19 (d, J=10.0 Hz, 2H), 2.84-2.60 (m, 2H), 2.56 (s, 3H), 2.08 (m, 3H), 1.60 (m, 1H), 1.50 (t, J=11.4 Hz, 2H), 1.30-1.15 (m, 2H); MS (ESI) m/z 410 [M+H]$^+$.

Example 35

Preparation of N-(1-Azabicyclo[2.2.2]oct-3-yl)-2-(3-methoxyphenyl)benzoxazole-4-carboxamide

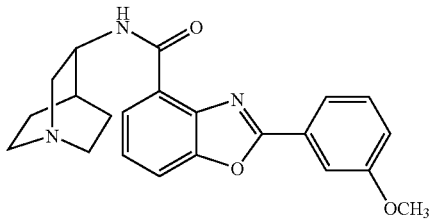

Step A: To a suspension of 2-amino-3-hydroxybenzoic acid (100 mg, 0.65 mmol) in dichloromethane (15 mL) was added pyridine (0.32 ml, 3.92 mmol) followed by m-anisoyl chloride (0.35 mL, 2.61 mmol) at room temperature. The resulting reaction mixture was stirred at room temperature for 15 min and DMAP (8 mg, 0.07 mmol) was added, then the reaction mixture was stirred at room temperature overnight. The reaction was quenched with aqueous 1 N HCl (30 mL) until the solution reached pH 1. The solution was stirred for 30 min. The aqueous layer was extracted with ethyl acetate. The organic layers were washed with brine, dried over Na$_2$SO$_4$, filtered and concentrated. The product was dissolved in toluene (10 mL) and the solution treated with p-toluenesulfonic acid monohydrate (274 mg, 1.44 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to a yellow solid. The crude product was purified by column chromatography (silica gel, 9:1 to 2:1, ethyl acetate/methanol) to afford the desired product (61 mg, 24%): MS (ESI+) m/z 270 (M+H).

Step B: A mixture of 2-(2-methoxyphenyl)benzoxazole-4-carboxylic acid from Step A (59 mg, 0.22 mmol), 3-aminoquinuclidine dihydrochloride (51 mg, 0.26 mmol), 1-ethyl-3-(3-dimethylaminopropyl)carbodiimide hydrochloride (84 mg, 0.44 mmol) and 1-hydroxybenzotriazole (59 mg, 0.44 mmol) in DMF (10 mL) was stirred for 10 min at room temperature, then DIPEA (0.14 mL, 0.88 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-2-(3-methoxyphenyl)benzoxazole-4-carboxamide (38 mg, 46%) as a white solid: $^1$H NMR (500 MHz, CDCl$_3$) δ 9.60 (d, J=7.5 Hz, 1H), 8.20 (dd, J=7.5, 1.0 Hz, 1H), 7.86-7.82 (m, 1H), 7.78-7.75 (m, 1H), 7.72 (dd, J=8.0, 1.0 Hz, 2H), 7.48 (t, J=16.0 Hz, 2H), 7.15 (dd, J=8.5, 2.5 Hz, 1H), 4.36-4.28 (m, 1H), 3.56-3.48 (m, 1H), 3.10 (s, 3H), 3.15-2.98 (m, 2H), 2.96-2.87 (m, 2H), 2.86-2.79 (m, 1H), 2.20-2.05 (m, 2H), 1.80-1.60 (m, 2H); MS (ESI+) m/z 378 (M+H); HPLC>99% (AUC), $t_R$=12.48 min.

Example 36

Preparation of (S)-N-(1-Azabicyclo[2.2.2]oct-3-yl)-2-(2-hydroxyphenyl)benzoxazole-4-carboxamide Hydrochloride

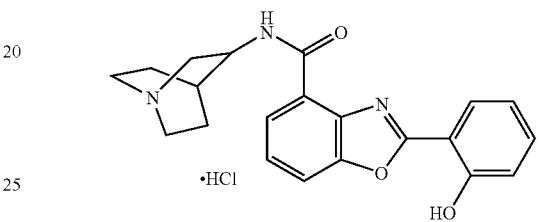

(S)-Enantiomer

Step A: A mixture of 2-(2-methoxyphenyl)benzoxazole-4-carboxylic acid (160 mg, 0.59 mmol) and 48% hydrobromic acid (10 mL) was heated to reflux overnight. The reaction mixture was cooled to room temperature and the solid was filtered and washed with diethyl ether to afford the desired product (154 mg, 81%) as a brown solid: $^1$H NMR (500 MHz, DMSO-$d_6$) δ 13.08 (br s, 1H), 8.06 (dd, J=7.8, 1.8 Hz, 1H), 8.04 (dd, J=8.0, 1.1 Hz, 1H), 7.91 (dd, J=7.8, 1.0 Hz, 1H), 7.67-7.61 (m, 2H), 7.51 (t, J=7.9 Hz, 1H), 7.32-7.28 (m, 1H), 7.19-7.14 (m, 1H); MS (ESI+) m/z 256 (M+H).

Step B: A mixture of 2-(2-hydroxyphenyl)benzoxazole-4-carboxylic acid (50 mg, 0.2 mmol), 1-ethyl-3-(3-dimethylaminopropyl)carbodiimide hydrochloride (75 mg, 0.4 mmol), 1-hydroxybenzotriazole (57 mg, 0.4 mmol) and (S)-(−)-3-aminoquinuclidine dihydrochloride (39 mg, 0.2 mmol) in DMF (5 mL) was stirred at room temperature for 10 min, then triethylamine (0.08 mL, 0.6 mmol) was added. The resulting reaction mixture was stirred at room temperature for 12 h. The reaction mixture was diluted with ethyl acetate (50 mL), and then treated with a saturated solution of sodium bicarbonate. The organic layer was isolated and the aqueous layer was further extracted with ethyl acetate (2×50 mL). The combined organics were washed with water (2×25 mL), brine (2×25 mL), dried (Na$_2$SO$_4$), filtered and concentrated. The crude material was purified by semi-preparative HPLC to afford the desired product (49 mg, 68%) as a light yellow solid: $^1$H NMR (500 MHz, CDCl$_3$) δ 10.43 (s, 1H), 8.37 (d, J=6.7 Hz, 1H), 8.22 (dd, J=7.8, 1.0 Hz, 1H), 8.10 (dd, J=7.9, 1.6 Hz, 1H), 7.77 (dd, J=8.1, 0.9 Hz, 1H), 7.55-7.50 (m, 2H), 7.16 (dd, J=8.6, 0.6 Hz, 1H), 7.08 (t, J=7.0 Hz, 1H), 4.40-4.30 (m, 1H), 3.63-3.55 (m, 1H), 3.22-3.20 (m, 1H), 3.07-2.90 (m, 3H), 2.87-2.80 (m, 1H), 2.22-2.17 (m, 1H), 2.02-1.92 (m, 1H), 1.85-1.78 (m, 2H), 1.73-1.65 (m, 1H); MS (ESI+) m/z 364 (M+H).

Step C: To a solution of (S)-N-(1-azabicyclo[2.2.2]oct-3-yl)-2-(2-hydroxyphenyl)benzoxazole-4-carboxamide (46 mg, 0.12 mmol) in methanol (1.0 mL) was added a solution of HCl in diethyl ether (1 N, 0.13 mL, 0.13 mmol) at room temperature slowly. The reaction mixture was diluted with diethyl ether. The resulting solid was filtered and washed with diethyl ether to afford (S)-N-(1-azabicyclo[2.2.2]oct-3-yl)-2-(2-hydroxyphenyl)benzoxazole-4-carboxamide hydrochloride (36 mg, 72%) as a white solid: $^1$H NMR (500 MHz, DMSO-$d_6$) δ 10.93 (s, 1H), 10.07 (br s, 1H), 9.29 (d, J=6.5 Hz, 1H), 8.08 (dd, J=7.8, 1.6 Hz, 1H), 8.03 (dd, J=8.1, 0.9 Hz, 1H), 7.90 (dd, J=7.7, 0.8 Hz, 1H), 7.59-7.51 (m, 2H), 7.19 (d, J=8.3 Hz, 1H), 7.12-7.06 (m, 1H), 4.50-4.42 (m, 1H), 3.80-3.70 (m, 1H), 3.40-3.20 (m, 5H), 2.35-2.25 (m, 2H), 2.00-1.95 (m, 2H), 1.95-1.85 (m, 1H); MS (ESI+) m/z 364 (M+H); HPLC>99% (AUC), $t_R$=11.64 min.

Example 37

Preparation of N-(9-Methyl-9-azabicyclo[3.3.1]non-3-yl)-2-(2-hydroxyphenyl)benzoxazole-4-carboxamide Hydrochloride

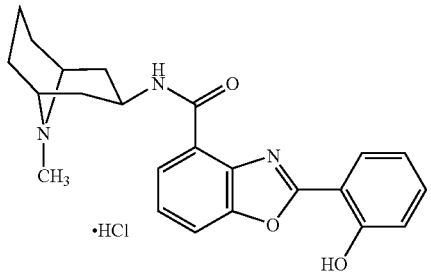

Step A: A mixture of 2-(2-hydroxyphenyl)benzoxazole-4-carboxylic acid (96 mg, 0.37 mmol), 1-ethyl-3-(3-dimethylaminopropyl)carbodiimide hydrochloride (143 mg, 0.75 mmol), 1-hydroxybenzotriazole (102 mg, 0.75 mmol) and 3-amino-9-methyl-9-azabicyclo[3.3.1]nonane dihydrochloride (85 mg, 0.37 mmol) in DMF (5 mL) was stirred at room temperature for 10 min, then triethylamine (0.15 mL, 1.12 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with water (2×50 mL) and brine (2×50 mL), dried (Na$_2$SO$_4$), filtered and concentrated. The crude material was purified by column chromatography (silica gel, 90:9:1 dichloromethane/methanol/concentrated ammonium hydroxide) and recrystallization from acetonitrile to afford the desired product (70 mg, 48%) as a white solid: $^1$H NMR (500 MHz, CDCl$_3$) δ 10.54 (s, 1H), 8.21 (dd, J=7.8, 1.1 Hz, 1H), 8.09 (dd, J=8.1, 1.6 Hz, 1H), 7.80-7.77 (m, 1H), 7.75 (dd, J=8.1, 0.9 Hz, 1H), 7.57-7.50 (m, 2H), 7.17 (dd, J=8.6, 0.6 Hz, 1H), 7.10-7.05 (m, 1H), 4.70-4.60 (m, 1H), 3.25-3.15 (m, 2H), 2.73-2.69 (m, 2H), 2.56 (s, 3H), 2.15-1.95 (m, 2H), 1.65-1.45 (m, 4H), 1.25-1.10 (m, 2H); MS (ESI+) m/z 392 (M+H).

Step B: To a solution of N-(9-methyl-9-azabicyclo[3.3.1]non-3-yl)-2-(2-hydroxyphenyl)benzoxazole-4-carboxamide (66 mg, 0.17 mmol) in methanol (1.0 mL) was added a solution of HCl in diethyl ether (1 N, 0.18 mL, 0.18 mmol) at room temperature slowly. The reaction mixture was diluted with diethyl ether. The resulting solid was filtered and washed with diethyl ether to afford N-(9-methyl-9-azabicyclo[3.3.1]non-3-yl)-2-(2-hydroxyphenyl)benzoxazole-4-carboxamide hydrochloride (39 mg, 54%) as a white solid: $^1$H NMR (500 MHz, CDCl$_3$) δ 12.30 (br s, 0.5H), 12.01 (br s, 0.5H), 8.30-8.10 (m, 2H), 7.90-7.75 (m, 1H), 7.58-7.50 (m, 2H), 7.18-7.12 (m, 2H), 4.95-4.85 (m, 0.5H), 4.70-4.60 (m, 0.5H), 3.70-3.55 (m, 2H), 3.25-3.15 (m, 1H), 3.00-2.75 (m, 5H), 2.50-2.00 (m, 5H), 1.90-1.50 (m, 4H); MS (ESI+) m/z 392 (M+H); HPLC 96.7% (AUC), $t_R$=12.44 min.

Example 38

Preparation of N-(9-Methyl-9-azabicyclo[3.3.1]non-3-yl)-2-(2-bromophenyl)benzoxazole-4-carboxamide Hydrochloride

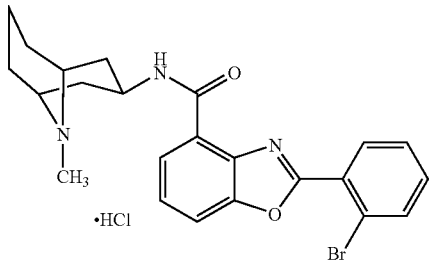

Step A: To a suspension of 2-amino-3-hydroxybenzoic acid hydrobromide (2.0 g, 8.5 mmol) in dichloromethane (50 mL) was added triethyamine (4.77 mL, 34.2 mmol) followed by 2-bromobenzoyl chloride (1.12 mL, 8.54 mmol) at room temperature. The resulting reaction mixture was stirred at room temperature overnight. The reaction was quenched with aqueous 2 N HCl (50 mL). The reaction mixture was extracted with dichloromethane. The combined organic layers were dried over Na$_2$SO$_4$, filtered and concentrated to a brown solid. The crude was dissolved in toluene (10 mL) and the solution was treated with p-toluenesulfonic acid monohydrate (2.45 g, 12.8 mmol). The resulting reaction mixture was then heated at 90° C. under nitrogen for 4 h. The reaction was cooled to room temperature, poured into water and extracted with dichloromethane (400 mL). The organic layer was separated, washed with water and brine, dried over Na$_2$SO$_4$, filtered and concentrated to a brown solid. The crude product was purified by recrystallization from methanol to afford the desired product (1.51 g, 55%) as a brown solid: $^1$H NMR (500 MHz, DMSO-$d_6$) δ 13.08 (br s, 1H), 8.06 (dd, J=7.8, 1.8 Hz, 1H), 8.04 (dd, J=8.0, 1.1 Hz, 1H), 7.91 (dd, J=7.8, 1.0 Hz, 1H), 7.67-7.61 (m, 1H), 7.51 (t, J=7.9 Hz, 1H), 7.32-7.28 (m, 1H), 7.19-7.14 (m, 1H); MS (ESI+) m/z 319 (M+H).

Step B: A mixture of the 2-(2-bromophenyl)benzoxazole-4-carboxylic acid (1.00 g, 3.14 mmol), 3-amino-9-methyl-9-azabicyclo[3.3.1]nonane dihydrochloride (1.07 g, 4.72 mmol), 1-ethyl-3-(3-dimethylaminopropyl)carbodiimide hydrochloride (1.20 g, 6.28 mmol), 1-hydroxybenzotriazole (0.85 g, 6.3 mmol) and DMF (20 mL) was stirred under nitrogen at room temperature for 10 min, and then triethylamine (1.75 mL, 12.6 mmol) was added. The resulting reaction mixture was stirred at room temperature overnight, then quenched with a saturated solution of sodium bicarbonate and extracted with methylene chloride. The combined organic layers were washed with brine, dried (Na$_2$SO$_4$), filtered and concentrated. The crude material was purified by column chromatography (silica gel, 90:9:1 dichloromethane/methanol/concentrated ammonium hydroxide) to afford the desired amide (910 mg, 64%) as an off-white solid: $^1$H NMR (500 MHz, CDCl$_3$) δ 9.73 (d, J=7.2 Hz, 1H), 8.25 (dd, J=8.1, 1.8 Hz, 1H), 8.21 (dd, J=7.8, 1.0 Hz, 1H), 7.85 (dd, J=9.2, 1.0 Hz, 1H), 7.73 (d, J=8.2 Hz, 1H), 7.55-7.50 (m, 2H), 7.45-7.40 (m, 1H), 4.67-4.53 (m, 1H), 3.23-3.15 (m, 2H), 2.72-2.50 (m, 5H), 2.15-1.95 (m, 3H), 1.62-1.53 (m, 3H), 1.21-1.15 (m, 2H); MS (ESI+) m/z 455 (M+H).

Step C: To a solution of the amide from Step B (50 mg, 0.11 mmol) in dichloromethane (1.0 mL) was added a solution of HCl in diethyl ether (1 N, 0.11 mL, 0.11 mmol) at 0° C. slowly. The reaction mixture was diluted with diethyl ether. The resulting solid was filtered and washed with diethyl ether to afford N-(9-methyl-9-azabicyclo[3.3.1] non-3-yl)-2-(2-bromophenyl)benzoxazole-4-carboxamide hydrochloride (56 mg, 96%) as a white solid: $^1$H NMR (500 MHz, CDCl$_3$) δ 12.15 (br s, 0.5H), 11.78 (br s, 0.5H), 9.48 (d, J=5.8 Hz, 1H), 8.22 (dd, J=7.8, 0.8 Hz, 0.5H), 8.18 (dd, J=7.8, 0.8 Hz, 0.5H), 8.15-8.12 (m, 1H), 7.86-7.76 (m, 2H), 7.61-7.51 (m, 2H), 7.50-7.41 (m, 1H), 4.93-4.84 (m, 0.5H), 4.70-4.60 (m, 0.5H), 3.63-3.55 (m, 2H), 2.98-2.90 (m, 3H), 2.83-2.75 (m, 2H), 2.55-2.45 (m, 1H), 2.20-2.05 (m, 2H), 1.95-1.90 (m, 2H), 1.80-1.70 (m, 3H); MS (ESI+) m/z 455 (M+H); HPLC>99% (AUC), $t_R$=12.72 min.

Example 39

Preparation of N-(9-Methyl-9-azabicyclo[3.3.1]non-3-yl)-2-(2-aminophenyl)benzoxazole-4-carboxamide Dihydrochloride

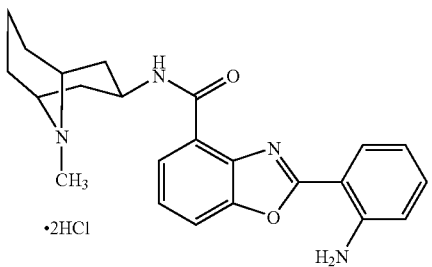

Step A: A dry flask was charged with N-(9-methyl-9-azabicyclo[3.3.1]non-3-yl)-2-(2-bromophenyl)benzoxazole-4-carboxamide (300 mg, 0.7 mmol), tert-butyl carbamate (115 mg, 0.990 mmol), Pd(OAc)$_2$ (15 mg, 0.07 mmol), xantphos (57 mg, 0.10 mmol) and cesium carbonate (300 mg, 0.92 mmol) and 1,4-dioxane (5 mL). The mixture was degassed with argon. The resulting reaction mixture was heated at 100° C. for 12 h. The reaction mixture was cooled to room temperature, and then diluted with methylene chloride and water. The reaction mixture was extracted with methylene chloride (2×50 mL). The combined organic layers were washed with brine, dried (Na$_2$SO$_4$) and concentrated under reduced pressure. The crude material was purified by column chromatography (silica gel, 90:9:1 dichloromethane/methanol/concentrated ammonium hydroxide) to afford the desired carbamate (229 mg, 71%) as a light yellow solid: $^1$H NMR (500 MHz, CDCl$_3$) δ 9.85 (br s, 1H), 8.43 (d, J=8.5 Hz, 1H), 8.22 (dd, J=8.7, 0.9 Hz, 1H), 8.17 (d, J=7.3 Hz, 1H), 8.12 (dd, J=7.9, 1.5 Hz, 1H), 7.73 (dd, J=8.1, 1.0 Hz, 1H), 7.58-7.54 (m, 1H), 7.50 (t, J=7.9 Hz, 1H), 7.21-7.15 (m, 1H), 4.57-4.52 (m, 1H), 3.12-3.08 (m, 1H), 2.62-2.58 (m, 2H), 2.52 (s, 3H), 2.15-1.95 (m, 3H), 1.65-1.50 (m, 13H), 1.10-1.05 (m, 2H); MS (ESI+) m/z 491 (M+H).

Step B: To a solution of the carbamate from Step A (225 mg, 0.460 mmol) in methylene chloride (1 mL) was added HCl in 1,4-dioxane (4.0 N, 0.34 mL, 1.37 mmol) at 0° C. The reaction mixture was allowed to warm to room temperature and stirred for 4 h. The resulting precipitate was isolated by filtration, washed with diethyl ether and dried under high vacuum to afford N-(9-methyl-9-azabicyclo[3.3.1]non-3-yl)-2-(2-aminophenyl)benzoxazole-4-carboxamide dihydrochloride (53 mg, 25%) as an off-white solid: $^1$H NMR (500 MHz, DMSO-d$_6$) δ 10.30 (br s, 0.2H), 9.44 (br s, 0.8H), 8.71 (d, J=5.4 Hz, 0.2H), 8.57 (d, J=7.6 Hz, 0.8H), 8.00-7.94 (m, 2H), 7.90-7.82 (m, 1H), 7.55-7.47 (m, 1H), 7.38-7.30 (m, 1H), 7.00-6.93 (m, 1H), 6.75-6.62 (m, 1H), 4.75-4.35 (m, 4H), 3.70-3.65 (m, 1.6H), 3.60-3.55 (m, 0.4H), 2.90-2.80 (m, 3H), 2.75-2.60 (m, 3H), 2.20-2.05 (m, 3H), 1.90-1.80 (m, 2H), 1.60-1.50 (m, 2H); MS (ESI+) m/z 391 (M+H); HPLC>99% (AUC), $t_R$=12.28 min.

Example 40

Preparation of N-(9-Methyl-9-azabicyclo[3.3.1]non-3-yl)-2-(biphenyl-2-yl)benzoxazole-4-carboxamide Hydrochloride

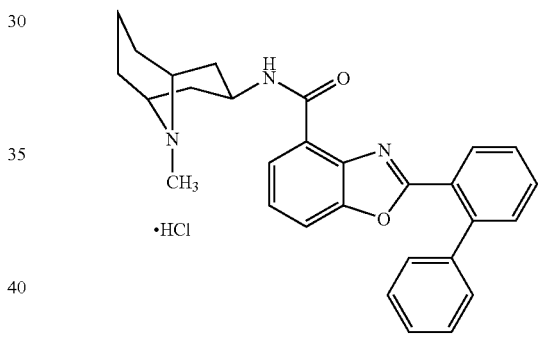

Step A: A mixture of N-(9-methyl-9-azabicyclo[3.3.1] non-3-yl)-2-(2-bromophenyl)benzoxazole-4-carboxamide (100 mg, 0.22 mmol), phenylboronic acid (40 mg, 0.33 mmol), and aqueous 2 M Na$_2$CO$_3$ (1.5 mL) in toluene (4 mL) was degassed with argon for 15 min. To the mixture was added Pd(PPh$_3$)$_4$ (25 mg, 0.022 mmol), and the resulting reaction mixture was heated at 80° C. for 12 h. The reaction mixture was cooled to room temperature, filtered through a microfilter and the filtrate was concentrated to give an off-white solid. The crude material was purified by preparative TLC (90:9:1 methylene chloride/methanol/concentrated ammonium hydroxide) to afford the desired amide (94 mg, 94%) as a white solid: $^1$H NMR (500 MHz, CDCl$_3$) δ 8.56 (br s, 1H), 8.16 (d, J=7.6 Hz, 1H), 8.09 (d, J=7.6 Hz, 1H), 7.65-7.61 (m, 1H), 7.58-7.47 (m, 3H), 7.39 (t, J=8.0 Hz, 1H), 7.38-7.28 (m, 5H), 4.52-4.43 (m, 1H), 3.20-3.05 (m, 2H), 2.65-2.40 (m, 5H), 2.15-1.95 (m, 3H), 1.62-1.53 (m, 2H), 1.21-1.15 (m, 2H); MS (ESI+) m/z 452 (M+H).

Step B: To a solution of the amide from Step A (82 mg, 0.18 mmol) in dichloromethane (1.0 mL) was added a solution of HCl in diethyl ether (1 N, 0.20 mL, 0.20 mmol) at 0° C. slowly. The reaction mixture was diluted with diethyl ether. The resulting solid was filtered and washed with diethyl ether to afford N-(9-methyl-9-azabicyclo[3.3.1]

non-3-yl)-2-(biphenyl-2-yl)benzoxazole-4-carboxamide hydrochloride (56 mg, 96%) as a white solid: $^1$H NMR (500 MHz, DMSO-d$_6$) δ 9.83 (br s, 0.2H), 9.17 (br s, 0.8H), 8.95 (d, J=5.6 Hz, 0.2H), 8.43 (d, J=5.6 Hz, 0.8H), 8.20-8.10 (m, 1H), 7.98-7.92 (m, 1H), 7.85 (d, J=8.1 Hz, 1H), 7.80-7.75 (m, 1H), 7.65-7.60 (m, 1H), 7.55-7.50 (m, 1H), 7.40-7.35 (m, 5H), 4.55-4.47 (m, 0.8H), 4.35-4.25 (m, 0.2H), 3.70-3.65 (m, 1.6H), 3.60-3.55 (m, 0.4H), 2.90-2.80 (m, 3H), 2.70-2.60 (m, 1H), 2.47-2.40 (m, 2H), 2.20-2.00 (m, 3H), 1.90-1.80 (m, 3H), 1.60-1.47 (m, 2H); MS (ESI+) m/z 452 (M+H); HPLC>99% (AUC), t$_R$=12.97 min.

Example 41

Preparation of N-(9-Methyl-9-azabicyclo[3.3.1]non-3-yl)-2-(2-pyridine-4-yl)phenylbenzoxazole-4-carboxamide Dihydrochloride

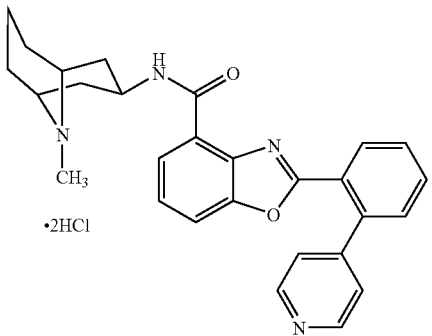

Step A: A mixture of N-(9-methyl-9-azabicyclo[3.3.1]non-3-yl)-2-(2-bromophenyl)benzoxazole-4-carboxamide (100 mg, 0.22 mmol), 4-pyridine boronic acid (40 mg, 0.33 mmol), and aqueous 2 M Na$_2$CO$_3$ (1.5 mL) in toluene (4 mL) was degassed with argon for 15 min. To the mixture was added Pd(PPh$_3$)$_4$ (25 mg, 0.022 mmol), and the resulting reaction mixture was heated at 80° C. for 12 h. The reaction mixture was cooled to room temperature, filtered through a microfilter and the filtrate was concentrated to give an off-white solid. The crude material was purified by preparative TLC (90:9:1 methylene chloride/methanol/concentrated ammonium hydroxide) to afford the desired amide (63 mg, 63%) as an off-white solid: $^1$H NMR (500 MHz, CDCl$_3$) δ 8.63 (br s, 2H), 8.16 (d, J=7.6 Hz, 2H), 7.72-7.61 (m, 2H), 7.58-7.50 (m, 2H), 7.39 (t, J=8.0 Hz, 1H), 7.38-7.28 (m, 3H), 4.52-4.43 (m, 1H), 3.20-3.05 (m, 2H), 2.70-2.40 (m, 5H), 2.15-1.95 (m, 3H), 1.62-1.53 (m, 4H), 1.21-1.15 (m, 2H); MS (ESI+) m/z 453 (M+H).

Step B: To a solution of the amide from Step A (63 mg, 0.14 mmol) in methanol (1.0 mL) was added a solution of HCl in diethyl ether (1 N, 0.42 mL, 0.42 mmol) at 0° C. slowly. The reaction mixture was diluted with diethyl ether. The resulting solid was filtered and washed with diethyl ether to afford N-(9-methyl-9-azabicyclo[3.3.1]non-3-yl)-2-(2-pyridine-4-yl)phenylbenzoxazole-4-carboxamide dihydrochloride (53 mg, 72%) as a white solid: $^1$H NMR (500 MHz, DMSO-d$_6$) δ 10.44 (br s, 0.2H), 9.63 (br s, 0.8H), 8.85-8.81 (m, 2H), 8.32-8.05 (m, 2H), 7.98-7.70 (m, 8H), 7.56 (d, J=8.1 Hz, 1H), 7.40-7.36 (m, 1H), 4.55-4.47 (m, 0.8H), 4.35-4.25 (m, 0.2H), 3.75-3.65 (m, 1.6H), 3.63-3.57 (m, 0.4H), 2.90-2.80 (m, 3H), 2.47-2.40 (m, 2H), 2.22-2.00 (m, 3H), 1.80-1.47 (m, 5H); MS (ESI+) m/z 453 (M+H); HPLC>99% (AUC), t$_R$=11.91 min Example 42

Preparation of N-(1-Azabicyclo[2.2.2]oct-3-yl)-2-p-tolylbenzoxazole-4-carboxamide

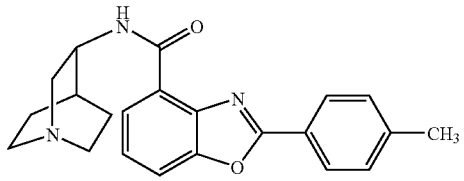

Step A: To a suspension of 2-amino-3-hydroxy benzoic acid (100 mg, 0.65 mmol) in dichloromethane (15 mL) was added pyridine (0.32 mL, 3.92 mmol) followed by 4-methylbenzoyl chloride (0.34 mL, 2.61 mmol) at room temperature. The resulting reaction mixture was stirred at room temperature for 15 min then DMAP (8 mg, 0.07 mmol) was added and the reaction mixture was stirred at room temperature overnight. The reaction was quenched with aqueous 1 N HCl (30 mL) until the solution reached pH 1. The solution was stirred for 30 min. The aqueous layer was extracted with ethyl acetate. The organic layers were washed with brine, dried over Na$_2$SO$_4$, filtered and concentrated to give an orange solid. The product was directly re-dissolved in toluene (10 mL) and the solution treated with p-toluenesulfonic acid monohydrate (311 mg, 1.63 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to give an orange solid. The crude product was purified by column chromatography (silica gel, 9:1 to 2:1, ethyl acetate/methanol) to afford the desired product (128 mg, 46%) as a pale orange solid: MS (ESI+) m/z 254 (M+H).

Step B: A mixture of 2-p-tolylbenzoxazole-4-carboxylic acid from Step A (62 mg, 0.24 mmol), 3-aminoquinuclidine dihydrochloride (58 mg, 0.29 mmol), 1-ethyl-3-(3-dimethylaminopropyl)carbodiimide hydrochloride (94 mg, 0.49 mmol) and 1-hydroxybenzotriazole (66 mg, 0.49 mmol) in DMF (5 mL) was stirred for 10 min at room temperature, then DIPEA (0.16 mL, 0.98 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-2-p-tolylbenzoxazole-4-carboxamide (57 mg, 66%) as a white solid: $^1$H NMR (500 MHz, CDCl$_3$) δ 9.61 (d, J=7.0 Hz, 1H), 8.18 (dd, J=8.0, 1.0 Hz, 1H), 8.13 (d, J=8.0 Hz, 2H), 7.70 (dd, J=8.5, 1.0 Hz, 1H), 7.45 (t, J=8.0 Hz, 1H), 7.37 (d, J=8.5 Hz, 2H), 4.35-4.30 (m, 1H), 3.55-3.50 (m, 1H), 3.15-2.99 (m, 2H), 2.95-2.89 (m, 2H), 2.88-2.81 (m, 1H), 2.48 (s, 3H), 2.19-2.15 (m, 1H), 2.13-2.05 (m, 1H), 1.81-1.75 (m, 2H) 1.68-1.60 (m, 1H); MS (ESI+) m/z 362 (M+H); HPLC 98.4% (AUC), t$_R$=12.90 min.

Example 43

Preparation of N-(9-Methyl-9-azabicyclo[3.3.1]non-3-yl)-2-p-tolylbenzoxazole-4-carboxamide

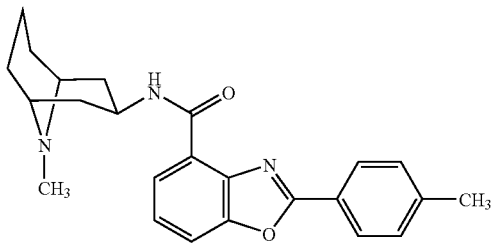

A mixture of 2-p-tolylbenzoxazole-4-carboxylic acid (62 mg, 0.24 mmol), 3-amino-9-methyl-9-azabicyclo[3.3.1]nonane dihydrochloride (66 mg, 0.29 mmol), 1-ethyl-3-(3-dimethylaminopropyl)carbodiimide hydrochloride (94 mg, 0.49 mmol) and 1-hydroxybenzotriazole (66 mg, 0.49 mmol) in DMF (5 mL) was stirred for 10 min at room temperature, then DIPEA (0.16 mL, 0.98 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-2-p-tolylbenzoxazole-4-carboxamide (25 mg, 27%) as a white solid: $^1$H NMR (500 MHz, CDCl$_3$) δ 9.10 (d, J=7.0 Hz, 1H), 8.20 (dd, J=7.5, 0.5 Hz, 1H), 8.14 (d, J=8.5 Hz, 2H), 7.68 (dd, J=8.0, 1.0 Hz, 1H), 7.45 (t, J=7.0 Hz, 1H), 7.39 (d, J=8.0 Hz, 2H), 4.64-4.55 (m, 1H), 3.17-3.11 (m, 2H), 2.70-2.60 (m, 2H) 2.56 (s, 3H), 2.48 (s, 3H), 2.08-1.98 (m, 2H), 1.75-1.50 (m, 3H), 1.25-1.17 (m, 3H); MS (ESI+) m/z 390 (M+H); HPLC>99% (AUC), $t_R$=13.37 min.

Example 44

Preparation of N-(1-Azabicyclo[2.2.2]oct-3-yl)-2-(4-nitrophenyl)benzoxazole-4-carboxamide

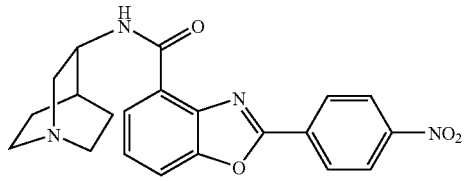

Step A: To a suspension of 2-amino-3-hydroxybenzoic acid (300 mg, 1.96 mmol) in dichloromethane (40 mL) was added pyridine (0.95 mL, 11.8 mmol) followed by 4-nitrobenzoyl chloride (1.45 g, 7.84 mmol) at room temperature. The resulting reaction mixture was stirred at room temperature for 15 min then DMAP (24 mg, 0.20 mmol) was added and the reaction mixture was stirred at room temperature overnight. The reaction was quenched with aqueous 1 N HCl (30 mL) until the solution reached pH 1. The solution was stirred for 30 min. The aqueous layer was extracted with ethyl acetate. The organic layers were washed with brine, dried over Na$_2$SO$_4$, filtered and concentrated to give a yellow solid. The product was directly re-dissolved in toluene (30 mL) and the solution treated with p-toluenesulfonic acid monohydrate (618 mg, 1.63 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to give an orange solid. The crude product was purified by column chromatography (silica gel, 9:1 to 2:1 ethyl acetate/methanol) to afford the desired product (628 mg, quantitative) as a pale orange solid: MS (ESI+) m/z 285 (M+H).

Step B: A mixture of 2-(4-nitrophenyl)benzoxazole-4-carboxylic acid from Step A (311 mg, 1.09 mmol), 3-aminoquinuclidine dihydrochloride (261 mg, 1.31 mmol), 1-ethyl-3-(3-dimethylaminopropyl)carbodiimide hydrochloride (265 mg, 2.19 mmol) and 1-hydroxybenzotriazole (296 mg, 2.19 mmol) in DMF (5 mL) was stirred for 10 min at room temperature, then DIPEA (0.72 mL, 4.38 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-2-(4-nitrophenyl)benzoxazole-4-carboxamide (31 mg, 7%) as a yellow solid: $^1$H NMR (500 MHz, CDCl$_3$) δ 9.35 (d, J=7.0 Hz, 1H), 8.47-8.40 (m, 4H), 8.24 (dd, J=7.5, 1.0 Hz, 1H), 7.79 (dd, J=8.0, 0.5 Hz, 1H), 7.57 (t, J=8.0 Hz, 1H), 4.34-4.30 (m, 1H), 3.56-3.51 (m, 1H), 3.12-2.86 (m, 4H), 2.85-2.77 (m, 1H), 2.19-2.14 (m, 1H), 1.82-1.74 (m, 2H), 1.71-1.58 (m, 2H); MS (ESI+) m/z 393 (M+H); HPLC>99% (AUC), $t_R$=12.18 min.

Example 45

Preparation of N-(1-Azabicyclo[2.2.2]oct-3-yl)-2-(4-aminophenyl)benzoxazole-4-carboxamide

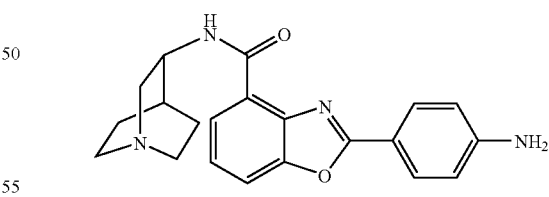

To a solution of N-(1-azabicyclo[2.2.2]oct-3-yl)-2-(4-nitrophenyl)benzoxazole-4-carboxamide (24 mg 0.06 mmol) in ethanol was added tin(II) chloride (116 mg, 0.61 mmol). The reaction mixture was then heated to reflux for 4 h. The reaction was cooled down to room temperature, then concentrated. The residue was dissolved in ethyl acetate (10 mL). The resulting solution was washed with 1 N NaOH (12 mL), water and brine, dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo

[2.2.2]oct-3-yl)-2-(4-aminophenyl)benzoxazole-4-carboxamide (7 mg, 2%) as a yellow solid: $^1$H NMR (500 MHz, CDCl$_3$) δ 9.68 (d, J=6.5 Hz, 1H), 8.13 (d, J=8.0 Hz, 1H), 8.02 (d, J=8.5 Hz, 2H), 7.65 (d, J=8.0 Hz, 1H), 7.39 (t, J=8.0 Hz, 1H), 6.79 (d, J=8.5 Hz, 2H), 4.40-4.36 (m, 1H), 4.19-4.16 (m, 3H), 3.20-2.90 (m, 5H), 2.30-0.80 (m, 5H); MS (ESI+) m/z 363 (M+H); HPLC 96.0% (AUC), t$_R$=12.35 min.

Example 46

Preparation of N-(1-Azabicyclo[2.2.2]oct-3-yl)-2-(4-acetylaminophenyl)benzoxazole-4-carboxamide

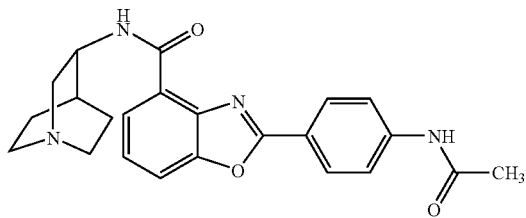

Step A: To a solution of N-(1-azabicyclo[2.2.2]oct-3-yl)-2-(4-aminophenyl)benzoxazole-4-carboxamide (22 mg, 0.06 mmol) in dichloromethane was added acetic anhydride (10 μL, 0.12 mmol), pyridine (15 μL, 0.18 mmol) and DMAP (1.5 mg, 0.01 mmol). The reaction mixture was stirred at room temperature for 3 h. Acetic anhydride (2 equiv) and pyridine (3 equiv) were re-filled and the reaction was stirred at room temperature for an additional 1.5 h. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) and then recrystallized from acetonitrile to afford N-(1-azabicyclo[2.2.2]oct-3-yl)-2-(4-acetylaminophenyl)benzoxazole-4-carboxamide (11 mg, 44%) as a white solid: $^1$H NMR (500 MHz, CDCl$_3$) δ 9.59-9.58 (m, 1H), 8.17-8.16 (m, 3H), 7.77-7.69 (m, 4H), 7.46-7.43 (m, 1H), 7.39 (t, J=8.0 Hz, 1H), 4.40-4.33 (m, 1H), 2.26 (s, 3H), 3.58-3.53 (m, 1H), 3.19-2.88 (m, 3H), 2.13-1.70 (m, 6H); MS (ESI+) m/z 405 (M+H); HPLC 97.3% (AUC), t$_R$=13.85 min.

Example 47

Preparation of N-(1-Azabicyclo[2.2.2]oct-3-yl)-2-(4-dimethylaminophenyl)benzoxazole-4-carboxamide

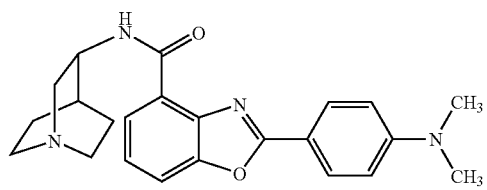

Step A: To a suspension of 2-amino-3-hydroxybenzoic acid hydrobromide (152 mg, 0.65 mmol) in dichloromethane (15 mL) was added pyridine (0.42 ml, 5.2 mmol) followed by 4-dimethylaminobenzoyl chloride (358 mg, 1.95 mmol). The resulting reaction mixture was stirred at room temperature for 15 min and DMAP (40 mg, 0.33 mmol) was added, then the reaction mixture was stirred at room temperature overnight. The reaction was quenched with aqueous 1 N HCl (30 mL) until the solution reached pH 1. The solution was stirred for 30 min. The aqueous layer was extracted with ethyl acetate. The organic layers were washed with brine, dried over Na$_2$SO$_4$, filtered and concentrated. The amide product was dissolved in toluene (10 mL) and the solution was treated with p-toluenesulfonic acid monohydrate (200 mg, 1.05 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to a pale yellow solid. The crude product was purified by column chromatography (silica gel, 9:1 to 2:1 ethyl acetate/methanol) to afford the desired product (94 mg, 48%): MS (ESI+) m/z 283 (M+H).

Step B: A mixture of 2-(4-dimethylaminophenyl)benzoxazole-4-carboxylic acid from Step A (47 mg, 0.12 mmol), (±)-3-aminoquinuclidine dihydrochloride (40 mg, 0.20 mmol), 1-ethyl-3-(3-dimethylaminopropyl)carbodiimide hydrochloride (45 mg, 0.23 mmol) and 1-hydroxybenzotriazole (63 mg, 0.47 mmol) in DMF (5 mL) was stirred for 10 min at room temperature, then DIPEA (0.14 mL, 0.83 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) and recrystallized from acetonitrile and ethyl acetate to afford N-(1-azabicyclo[2.2.2]oct-3-yl)-2-(4-dimethylaminophenyl)benzoxazole-4-carboxamide (40 mg, 60%) as an off-white solid: $^1$H NMR (500 MHz, CDCl$_3$) δ 9.74 (d, J=6.5 Hz, 1H), 8.13-8.04 (m, 3H), 7.63 (d, J=8.0 Hz, 1H), 7.36 (t, J=8.0 Hz, 1H), 6.79 (d, J=9.0 Hz, 2H), 4.35-4.27 (m, 1H), 3.51 (t, J=12.0 Hz, 1H), 3.11 (s, 6H), 2.96-2.82 (m, 3H), 2.22-2.11 (m, 2H), 1.80-1.50 (m, 5H); MS (ESI+) m/z 391 (M+H); HPLC>99% (AUC), t$_R$=14.65 min.

Example 48

Preparation of N-(9-Methyl-9-azabicyclo[3.3.1]non-3-yl)-2-(4-dimethylaminophenyl)benzoxazole-4-carboxamide

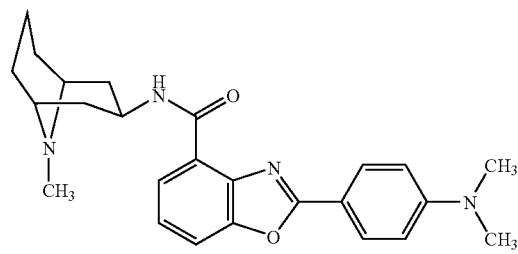

A mixture of 2-(4-dimethylaminophenyl)benzoxazole-4-carboxylic acid (78 mg, 0.32 mmol), 3-amino-9-methyl-9-azabicyclo[3.3.1]nonane dihydrochloride (86 mg, 0.38 mmol), 1-ethyl-3-(3-dimethylaminopropyl)carbodiimide hydrochloride (86 mg, 0.45 mmol) and 1-hydroxybenzotriazole (122 mg, 0.90 mmol) in DMF (5 mL) was stirred for 10 min at room temperature, then DIPEA (0.26 mL, 1.6 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) and recrystallized from acetonitrile to afford N-(9-methyl-9-azabicyclo[3.3.1]non-3-yl)-2-(4-dimethylaminophenyl)benzoxazole-4-carboxamide (51 mg, 41%) as a yellow solid: $^1$H NMR (500 MHz, $CDCl_3$) δ 9.21 (d, J=7.0 Hz, 1H), 8.15-8.09 (m, 3H), 7.61 (d, J=8.0 Hz, 1H), 7.35 (t, J=8.0 Hz, 1H), 6.80 (d, J=9.0 Hz, 2H), 4.61-4.54 (m, 1H), 3.10-3.15 (m, 8H), 2.68-2.62 (m, 2H), 2.55 (s, 3H), 2.05-1.96 (m, 2H), 1.59-1.49 (m, 4H), 1.22-1.19 (m, 1H); MS (ESI+) m/z 419 (M+H); HPLC 93.1% (AUC), $t_R$=16.55 mm.

Example 49

Preparation of N-(9-Methyl-9-azabicyclo[3.3.1]non-3-yl)-2-(2-dimethylaminophenyl)benzoxazole-4-carboxamide

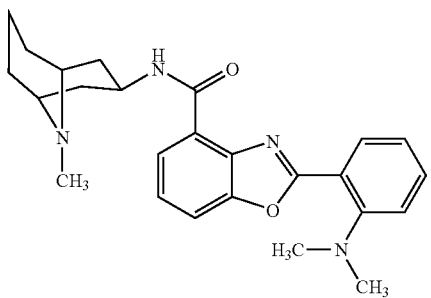

Step A: To an ice-cooled solution of 2-dimethylaminobenzoic acid (354 mg, 2.14 mmol) in dichloromethane (15 mL) was added oxalyl chloride (0.18 mL, 2.14 mmol) dropwise, then the reaction mixture was stirred at room temperature for 1 h. 2-Amino-3-hydroxybenzoic acid hydrobromide (0.50 g, 2.14 mmol) was added into the reaction mixture followed by triethylamine (1.2 mL, 8.6 mmol). The resulting reaction mixture was stirred at room temperature for 12 h, then diluted with dichloromethane, washed with brine, dried ($Na_2SO_4$), filtered and concentrated. The crude product was dissolved in toluene (15 mL) and the solution was treated with p-toluenesulfonic acid monohydrate (610 mg, 3.21 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated. The crude product was purified by column chromatography (silica gel, 9:1 to 3:1 ethyl acetate/methanol) to afford the desired product (0.64 g, quantitative) as a yellow solid: $^1$H NMR (500 MHz, DMSO-$d_6$) δ 7.92-7.78 (m, 3H), 7.52-7.48 (m, 1H), 7.43 (t, J=7.5 Hz, 1H), 7.16-7.08 (m, 1H), 7.05-6.96 (m, 1H), 2.82 (s, 1H), 2.70 (s, 6H); MS (ESI+) m/z 283 (M+H).

Step B: A mixture of benzoxazole carboxylic acid from Step A (100 mg, 0.35 mmol), 3-amino-9-methyl-9-azabicyclo[3.3.1]nonane dihydrochloride (80 mg, 0.35 mmol), 1-ethyl-3-(3-dimethylaminopropyl)carbodiimide hydrochloride (134 mg, 0.70 mmol) and 1-hydroxybenzotriazole (95 mg, 0.70 mmol) in DMF (1 mL) was stirred for 5 min at room temperature, then triethylamine (0.19 mL, 1.4 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) followed by recrystallization from ethyl acetate to afford N-(9-methyl-9-azabicyclo[3.3.1]non-3-yl)-2-(2-dimethylaminophenyl)benzoxazole-4-carboxamide (50 mg, 34%) as a yellow solid: $^1$H NMR (500 MHz, $CDCl_3$) δ 9.13 (d, J=7.5 Hz, 1H), 8.20 (dd, J=8.0, 1.0 Hz, 1H), 8.05 (dd, J=7.5, 1.5 Hz, 1H), 7.69 (dd, J=8.0, 1.0 Hz, 1H), 7.50-7.42 (m, 2H), 7.14 (d, J=7.5 Hz, 1H), 7.05 (t, J=8.0 Hz, 1H), 4.64-4.55 (m, 1H), 3.12 (d, J=10.5 Hz, 2H), 2.88 (s, 6H), 2.65-2.58 (m, 2H), 2.53 (s, 3H), 2.12-1.95 (m, 3H), 1.60-1.52 (m, 1H), 1.44 (t, J=10.5 Hz, 2H), 1.09 (d, J=12.5 Hz, 2H); MS (ESI+) m/z 419 (M+H); HPLC>99% (AUC), $t_R$=13.95 min.

Example 50

Preparation of (S)-N-(1-Azabicyclo[2.2.2]oct-3-yl)-2-(2-dimethylaminophenyl)benzoxazole-4-carboxamide

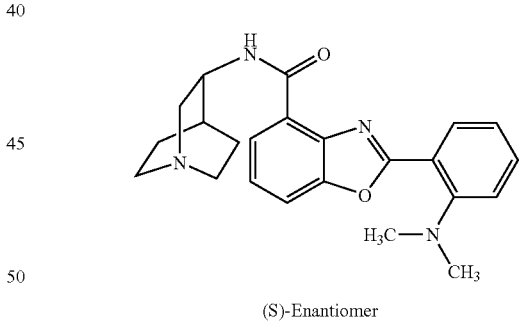

(S)-Enantiomer

A mixture of 2-(2-(dimethylamino)phenyl)benzo[d]oxazole-4-carboxylic acid (100 mg, 0.35 mmol), (S)-(−)-3-aminoquinuclidine dihydrochloride (70 mg, 0.35 mmol), 1-ethyl-3-(3-dimethylaminopropyl)carbodiimide hydrochloride (134 mg, 0.70 mmol) and 1-hydroxybenzotriazole (95 mg, 0.70 mmol) in DMF (1 mL) was stirred for 5 min at room temperature, then triethylamine (0.19 mL, 1.4 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)-N-(1-azabicyclo[2.2.2]oct-3-yl)-2-(2-dimethylaminophenyl)benzoxazole-4-carboxamide (46 mg, 34%) as a yellow solid: $^1$H NMR (500 MHz, CDCl$_3$) δ 9.60 (d, J=7.0 Hz, 1H), 8.19 (dd, J=7.5, 1.0 Hz, 1H), 7.99 (dd, J=8.0, 2.0 Hz, 1H), 7.71 (dd, J=8.0, 1.0 Hz, 1H), 7.49-7.42 (m, 2H), 7.13 (d, J=8.5 Hz, 1H), 7.03 (t, J=8.5 Hz, 1H), 4.28-4.26 (m, 1H), 3.49 (ddd, J=11.5, 9.5, 2.0 Hz, 1H), 3.10-2.85 (m, 4H), 2.85 (s, 6H), 2.77 (dd, J=14.0, 4.5 Hz, 1H), 2.15-2.11 (m, 1H), 2.04-1.98 (m, 1H), 1.78-1.70 (m, 2H), 1.60-1.51 (m, 1H); MS (ESI+) m/z 391 (M+H); HPLC>99% (AUC), $t_R$=12.81 min.

Example 51

Preparation of N-(9-Methyl-9-azabicyclo[3.3.1]non-3-yl)-6-chloro-2-(2-dimethylaminophenyl)benzoxazole-4-carboxamide

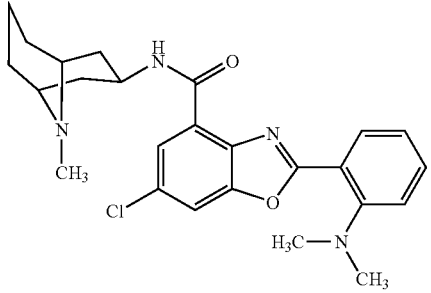

Step A: To an ice-cooled solution of 2-dimethylaminobenzoic acid (439 mg, 2.66 mmol) in dichloromethane (15 mL) was added oxalyl chloride (0.23 mL, 2.66 mmol) dropwise, then the reaction mixture was stirred at room temperature for 1 h. 2-Amino-5-chloro-3-hydroxybenzoic acid (0.50 g, 2.66 mmol) was added into the reaction mixture followed by triethylamine (1.1 mL, 8.0 mmol). The resulting reaction mixture was stirred at room temperature for 12 h, then diluted with dichloromethane, washed with brine, dried (Na$_2$SO$_4$), filtered and concentrated. The crude product was dissolved in toluene (18 mL) and the solution was treated with p-toluenesulfonic acid monohydrate (506 mg, 2.66 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated. The crude product was purified by column chromatography (silica gel, 9:1 to 3:1 ethyl acetate/methanol) to afford the desired product (0.57 g, 68%) as a brown solid: $^1$H NMR (500 MHz, DMSO-d$_6$) δ 7.92 (d, J=7.5 Hz, 1H), 7.81 (d, J=7.5 Hz, 1H), 7.67-7.57 (m, 2H), 7.35-7.28 (m, 1H), 6.99 (t, J=7.5 Hz, 1H), 2.77 (s, 1H), 2.69 (s, 6H); MS (ESI+) m/z 317 (M+H).

Step B: A mixture of benzoxazole carboxylic acid from Step A (100 mg, 0.32 mmol), 3-amino-9-methyl-9-azabicyclo[3.3.1]nonane dihydrochloride (73 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred for 5 min at room temperature, then triethylamine (0.17 mL, 1.3 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford N-(9-methyl-9-azabicyclo[3.3.1]non-3-yl)-6-chloro-2-(2-dimethylaminophenyl)benzoxazole-4-carboxamide (33 mg, 23%) as a yellow solid: $^1$H NMR (500 MHz, CDCl$_3$) δ 9.01 (d, J=7.5 Hz, 1H), 8.18 (d, J=2.0 Hz, 1H), 8.03 (dd, J=8.0, 2.0 Hz, 1H), 7.68 (d, J=1.5 Hz, 1H), 7.50-7.46 (m, 1H), 7.14 (d, J=8.0 Hz, 1H), 7.05 (t, J=8.0 Hz, 1H), 4.63-4.53 (m, 1H), 3.12 (d, J=11.0 Hz, 2H), 2.88 (s, 6H), 2.65-2.57 (m, 2H), 2.52 (s, 3H), 2.08-1.95 (m, 3H), 1.60-1.54 (m, 1H), 1.42 (td, J=13.5, 3.0 Hz, 2H), 1.07 (d, J=12.5 Hz, 2H); MS (ESI+) m/z 453 (M+H); HPLC>99% (AUC), $t_R$=13.42 min.

Example 52

Preparation of (S)-N-(1-Azabicyclo[2.2.2]oct-3-yl)-6-chloro-2-(2-dimethylaminophenyl)benzoxazole-4-carboxamide

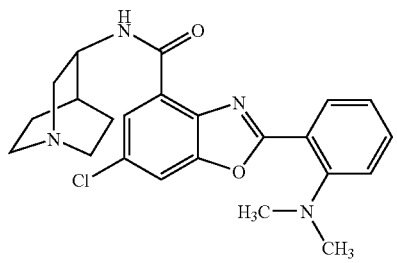

(S)-Enantiomer

A mixture of 2-(2-(dimethylamino)phenyl)benzo[d]oxazole-4-carboxylic acid (100 mg, 0.32 mmol), (S)-(−)-3-aminoquinuclidine dihydrochloride (64 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred for 5 min at room temperature, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford the (S)-N-(1-azabicyclo[2.2.2]oct-3-yl)-6-chloro-2-(2-dimethylaminophenyl)benzoxazole-4-carboxamide (43 mg, 32%) as a yellow solid: $^1$H NMR (500 MHz, CDCl$_3$) δ 9.47 (d, J=7.5 Hz, 1H), 8.17 (d, J=2.0 Hz, 1H), 7.97 (dd, J=8.0, 1.5 Hz, 1H), 7.71 (d, J=2.0 Hz, 1H), 7.50-7.46 (m, 1H), 7.13 (d, J=8.5 Hz, 1H), 7.02 (t, J=8.0 Hz, 1H), 4.28-4.25 (m, 1H), 3.49 (ddd, J=11.5, 9.5, 2.0 Hz, 1H), 3.08-2.84 (m, 4H), 2.84 (s, 6H), 2.76 (dd, J=14.0, 4.5 Hz, 1H), 2.13-2.10 (m, 1H), 1.99-1.94 (m, 1H), 1.76-1.68 (m, 2H), 1.58-1.52 (m, 1H); MS (ESI+) m/z 425 (M+H); HPLC>99% (AUC), $t_R$=13.47 min.

Example 53

Preparation of N-(1-Azabicyclo[2.2.2]oct-3-yl)-2-(4-cyanophenyl)benzoxazole-4-carboxamide

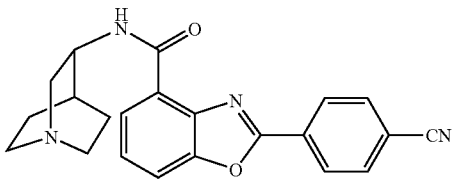

Step A: To a suspension of 2-amino-3-hydroxybenzoic acid (200 mg, 0.85 mmol) in dichloromethane (30 mL) was added pyridine (0.55 mL, 6.84 mmol) followed by 4-cyanobenzoyl chloride (566 mg, 3.42 mmol) at room temperature. The resulting reaction mixture was stirred at room temperature for 15 min then DMAP (11 mg, 0.09 mmol) was added and the reaction mixture was stirred at room temperature overnight. The reaction was quenched with aqueous 1 N HCl (30 mL) until the solution reached pH 1. The solution was stirred for 30 min. The aqueous layer was extracted with ethyl acetate. The organic layers were washed with brine, dried over $Na_2SO_4$, filtered and concentrated to give an orange solid. The product was dissolved in toluene (15 mL) and the solution treated with p-toluenesulfonic acid monohydrate (331 mg, 1.74 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to an orange solid. The crude product was purified by column chromatography (silica gel, 9:1 to 2:1 ethyl acetate/methanol) to afford the desired product (577 mg, quantitative) as a pale orange solid: MS (ESI+) m/z 265 (M+H).

Step B: A mixture of 2-(4-cyanophenyl)benzoxazole-4-carboxylic acid from Step A (289 mg, 1.09 mmol), 3-aminoquinuclidine dihydrochloride (261 mg, 1.31 mmol), 1-ethyl-3-(3-dimethylaminopropyl)carbodiimide hydrochloride (418 mg, 2.19 mmol) and 1-hydroxybenzotriazole (296 mg, 2.19 mmol) in DMF (15 mL) was stirred for 10 min at room temperature, then DIPEA (0.90 mL, 5.47 mmol) was added. The resulting reaction mixture was stirred at room temperature overnight. The mixture was diluted with ethyl acetate and then washed with a saturated solution of sodium bicarbonate. The aqueous layer was further extracted with ethyl acetate. The combined organics were dried ($Na_2SO_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-2-(4-cyanophenyl)benzoxazole-4-carboxamide (7 mg, 2%) as a white solid: $^1$H NMR (500 MHz, CDCl$_3$) δ 9.35 (d, J=7.5 Hz, 1H), 8.35 (d, J=8.5 Hz, 2H), 8.25 (d, J=7.5, Hz, 1H), 7.88 (d, J=8.5, Hz, 2H), 7.77 (d, J=7.5 Hz, 1H), 7.56 (t, J=8.0 Hz, 1H), 4.36-4.26 (m, 1H), 3.58-3.47 (m, 1H), 3.12-3.00 (m, 2H), 2.97-2.89 (m, 2H), 2.86-2.79 (m, 1H), 2.30-2.00 (m, 2H), 1.82-1.75 (m, 3H); MS (ESI+) m/z 373 (M+H); HPLC 94.3% (AUC), $t_R$=12.18 min.

Example 54

Preparation of N-(1-Azabicyclo[2.2.2]oct-3-yl)-2-(4-iodophenyl)benzoxazole-4-carboxamide

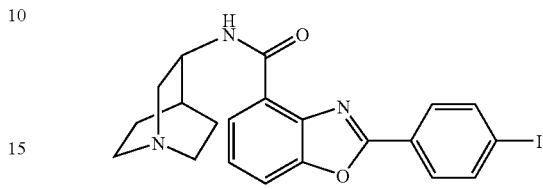

Step A: To a solution of methyl 3-hydroxyanthranilate (550 mg, 3.29 mmol) in methylene chloride (20 mL) was added 4-iodobenzoyl chloride (2.63 g, 9.87 mmol) followed by pyridine (1.06 mL, 13.2 mmol) and DMAP (40 mg, 0.33 mmol) at room temperature. The resulting mixture was stirred under nitrogen at room temperature overnight and then the reaction mixture was quenched with a saturated solution of sodium bicarbonate (100 mL) with stirring at room temperature for 30 min. The organic layer was separated and the aqueous layer was extracted with methylene chloride. The combined organic layers were washed with brine, dried over sodium sulfate, filtered and concentrated in vacuo. The residue was dissolved in toluene (20 mL) and the solution was treated with p-toluenesulfonic acid monohydrate (600 mg, 3.16 mmol). The reaction mixture was then heated at reflux under nitrogen overnight. The reaction mixture was cooled to room temperature, diluted with ethyl acetate, washed with a saturated solution of sodium bicarbonate and brine, dried over sodium sulfate, filtered and concentrated. The crude material was purified by column chromatography (silica gel, 4:1 hexanes/ethyl acetate) to afford the methyl ester (274 mg, 23%) as an off-white solid: $^1$H NMR (300 MHz, CDCl$_3$) δ 8.10 (dt, J=8.5, 2.0 Hz, 2H), 8.07 (dd, J=8.0, 1.0 Hz, 1H), 7.92 (dt, J=8.5, 2.0 Hz, 2H), 7.81 (dd, J=8.0, 1.0 Hz, 1H), 7.47 (t, J=8.0 Hz, 1H), 4.09 (s, 3H); MS (ESI+) m/z 380 (M+H).

Step B: To a solution of the methyl ester from Step A (0.4 g, 1.05 mmol) in THF (5 mL) was added 1 N NaOH (3 mL, 3 mmol), and then the reaction mixture was stirred at room temperature for 12 h. The reaction mixture was acidified with 1 N HCl (pH=1), then extracted with methylene chloride. The combined organic layers were dried ($Na_2SO_4$), filtered and concentrated to provide the carboxylic acid (0.4 g, quantitative) as an off-white solid: $^1$H NMR (500 MHz, CDCl$_3$) δ 11.00 (br s, 1H), 8.18 (dd, J=8.0, 1.0 Hz, 1H), 8.01 (dt, J=8.5, 2.0 Hz, 2H), 7.96 (dt, J=8.5, 2.0 Hz, 2H), 7.84 (dd, J=8.0, 1.0 Hz, 1H), 7.55 (t, J=8.0 Hz, 1H); MS (ESI+) m/z 366 (M+H).

Step C: A mixture of the carboxylic acid from Step B (190 mg, 0.52 mmol), (±)-3-aminoquinuclidine dihydrochloride (124 mg, 0.624 mmol), 1-ethyl-3-(3-dimethylaminopropyl)carbodiimide hydrochloride (199 mg, 1.04 mmol) and 1-hydroxybenzotriazole (140 mg, 1.04 mmol) in DMF (10 mL) was stirred under nitrogen at room temperature for 10 min, and then triethylamine (0.29 mL, 2.08 mmol) was added. The resulting reaction mixture was stirred at room temperature overnight, and then was quenched with a saturated solution of sodium bicarbonate, extracted with methylene chloride. The combined organic layers were dried ($Na_2SO_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-(4-iodophenyl)benzoxazole-4-carboxamide (150 mg, 61%) as a white solid: $^1$H NMR (500 MHz, CDCl$_3$) δ 9.47 (d, J=7.0 Hz, 1H), 8.20 (dd, J=8.0, 1.0 Hz, 1H), 7.94 (s, 4H), 7.72 (dd, J=8.0, 1.0 Hz, 1H), 7.49 (t, J=8.0 Hz, 1H), 4.36-4.29 (m, 1H), 3.53 (ddd, J=14.0, 9.5, 2.0 Hz, 1H), 3.12-2.82 (m, 5H), 2.18-2.02 (m, 2H), 1.80-1.65 (m, 3H); MS (ESI+) m/z 474 (M+H); HPLC>99% (AUC), $t_R$=13.35 min.

Example 55

Preparation of N-(1-Azabicyclo[2.2.2]oct-3-yl)-2-(4-trimethylsilylethynylphenyl)benzoxazole-4-carboxamide

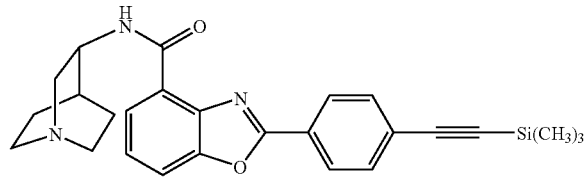

To a solution of N-(1-azabicyclo[2.2.2]oct-3-yl)-2-(4-iodophenyl)benzoxazole-4-carboxamide (50 mg, 0.11 mmol) in DMF (1 mL) and triethylamine (1 mL), (trimethylsilyl)acetylene (0.045 mL, 0.33 mmol) was added at room temperature followed by copper(I) iodide (4.2 mg, 0.022 mmol) and bis(triphenylphosphine)dichloropalladium(II) (7.7 mg, 0.011 mmol). The resulting mixture was stirred under nitrogen at room temperature for 1 h, and then was quenched with water, extracted with methylene chloride. The combined organic layers were washed with water and brine, dried (Na$_2$SO$_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-(4-trimethylsilylethynylphenyl)benzoxazole-4-carboxamide (44 mg, 94%) as a light yellow solid: $^1$H NMR (500 MHz, CDCl$_3$) δ 9.51 (d, J=7.0 Hz, 1H), 8.20 (dd, J=8.0, 1.0 Hz, 1H), 8.17 (d, J=8.0 Hz, 2H), 7.72 (dd, J=8.0, 1.0 Hz, 1H), 7.64 (d, J=8.0 Hz, 2H), 7.49 (t, J=8.0 Hz, 1H), 4.32-4.29 (m, 1H), 3.52 (ddd, J=14.0, 9.5, 2.0 Hz, 1H), 3.12-2.76 (m, 5H), 2.18-2.02 (m, 2H), 1.80-1.62 (m, 3H), 0.29 (s, 9H); MS (ESI+) m/z 444 (M+H); HPLC>99% (AUC), $t_R$=14.91 min.

Example 56

Preparation of N-(1-Azabicyclo[2.2.2]oct-3-yl)-2-(4-propyn-1-ylphenyl)benzoxazole-4-carboxamide

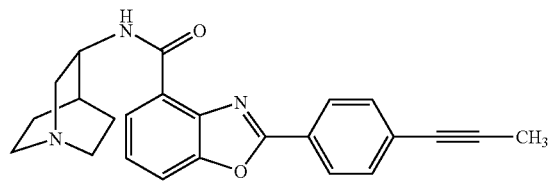

Zinc chloride (1.0 M in ether, 0.33 mL, 0.33 mmol) was added dropwise to a solution of 1-propynylmagnesium bromide in THF (0.5 M in THF, 0.66 mL, 0.33 mmol) at room temperature and the mixture was stirred under nitrogen for 10 min. N-(1-Azabicyclo[2.2.2]oct-3-yl)benzoxazole-4-carboxamide (50 mg, 0.11 mmol) in DMF (2 mL) was added followed by bis(triphenylphosphine)dichloropalladium(II) (7.7 mg, 0.011 mmol). The resulting mixture was stirred under nitrogen at room temperature for 2 h, and then was quenched with saturated ammonium chloride, extracted with methylene chloride. The combined organic layers were washed with water and brine, dried (Na$_2$SO$_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-(4-propyn-1-ylphenyl)benzoxazole-4-carboxamide (36 mg, 88%) as a light yellow solid: $^1$H NMR (300 MHz, CDCl$_3$) δ 9.56 (d, J=7.0 Hz, 1H), 8.23 (dd, J=8.0, 1.0 Hz, 1H), 8.17 (d, J=8.4 Hz, 2H), 7.73 (dd, J=8.0, 1.0 Hz, 1H), 7.58 (d, J=8.4 Hz, 2H), 7.49 (t, J=8.0 Hz, 1H), 4.35-4.29 (m, 1H), 3.54 (ddd, J=14.0, 9.5, 2.0 Hz, 1H), 3.16-2.82 (m, 5H), 2.20-2.03 (m, 2H), 2.14 (s, 3H), 1.80-1.60 (m, 3H); MS (ESI+) m/z 386 (M+H); HPLC>99% (AUC), $t_R$=13.24 min.

Example 57

Preparation of N-(1-Azabicyclo[2.2.2]oct-3-yl)-2-(4-ethynylphenyl)benzoxazole-4-carboxamide

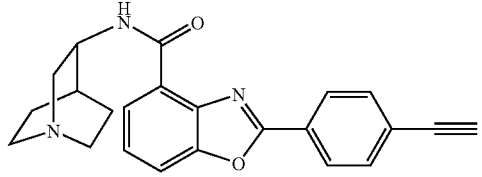

A mixture of N-(1-azabicyclo[2.2.2]oct-3-yl)-2-(4-trimethylsilylethynylphenyl)benzoxazole-4-carboxamide (20 mg, 0.045 mmol), potassium carbonate (20 mg, 0.14 mmol) and methanol (1 mL) was stirred at room temperature for 2 h, and then was diluted with ethyl acetate, washed with water and brine, dried (Na$_2$SO$_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-(4-ethynylphenyl)benzoxazole-4-carboxamide (14 mg, 84%) as a white solid: $^1$H NMR (500 MHz, CDCl$_3$) δ 9.49 (d, J=7.0 Hz, 1H), 8.22-8.18 (m, 3H), 7.73 (dd, J=8.0, 1.0 Hz, 1H), 7.68 (d, J=8.5 Hz, 2H), 7.48 (t, J=8.0 Hz, 1H), 4.35-4.31 (m, 1H), 3.53 (ddd, J=14.0, 9.5, 2.0 Hz, 1H), 3.30 (s, 1H), 3.15-2.82 (m, 5H), 2.20-2.03 (m, 2H), 1.80-1.62 (m, 3H); MS (ESI+) m/z 372 (M+H); HPLC>99% (AUC), $t_R$=12.77 min.

Example 58

Preparation of N-(1-Azabicyclo[2.2.2]oct-3-yl)-2-biphenyl-4-ylbenzoxazole-4-carboxamide

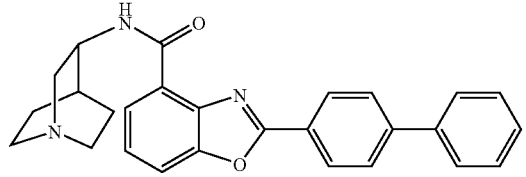

To a mixture of N-(1-azabicyclo[2.2.2]oct-3-yl)-2-(4-iodophenyl)benzoxazole-4-carboxamide (30 mg, 0.063 mmol), phenylboronic acid (12 mg, 0.098 mmol), 2 M Na$_2$CO$_3$ (2 mL) and toluene (2 mL) was deoxygenated with nitrogen for 10 min, and then tetrakis(triphenylphosphine) palladium(0) (7.3 mg, 0.0063 mmol) was added. The resulting mixture was heated at 80° C. under nitrogen overnight, and then was cooled to room temperature, quenched with saturated sodium bicarbonate, extracted with methylene chloride. The combined organic layers were washed with brine, dried (Na$_2$SO$_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-biphenyl-4-ylbenzoxazole-4-carboxamide (21 mg, 78%) as a light yellow solid: $^1$H NMR (500 MHz, CDCl$_3$) δ 9.60 (d, J=7.0 Hz, 1H), 8.31 (d, J=8.0 Hz, 2H), 8.21 (d, J=7.5 Hz, 1H), 7.80 (d, J=8.0 Hz, 2H), 7.74 (d, J=7.5 Hz, 1H), 7.69-7.67 (m, 2H), 7.52-7.42 (m, 4H), 4.36-4.30 (m, 1H), 3.53 (ddd, J=14.0, 9.5, 2.0 Hz, 1H), 3.17-2.84 (m, 5H), 2.19-2.10 (m, 2H), 1.80-1.63 (m, 3H); MS (ESI+) m/z 424 (M+H); HPLC 96.3% (AUC), t$_R$=14.01 min.

Example 59

Preparation of N-(1-Azabicyclo[2.2.2]oct-3-yl)-2-(4-phenoxyphenyl)benzoxazole-4-carboxamide

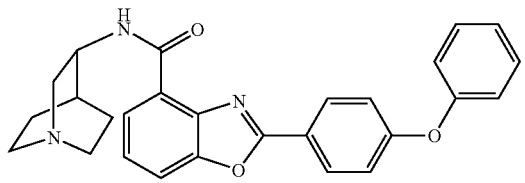

A mixture of N-(1-azabicyclo[2.2.2]oct-3-yl)-2-(4-iodophenyl)benzoxazole-4-carboxamide (35 mg, 0.074 mmol), phenol (14 mg, 0.15 mmol), copper(I) bromide (2 mg, 0.014 mmol), cesium carbonate (49 mg, 0.15 mmol) and pyridine (1 mL) was heated at 130° C. under nitrogen overnight, and then was cooled to room temperature, quenched with saturated sodium bicarbonate, extracted with methylene chloride. The combined organic layers were washed with brine, dried (Na$_2$SO$_4$), filtered and concentrated. The crude material was purified by semi-preparative HPLC to afford N-(1-azabicyclo[2.2.2]oct-3-yl)-2-(4-phenoxyphenyl)benzoxazole-4-carboxamide (16 mg, 50%) as a light yellow solid: $^1$H NMR (500 MHz, CDCl$_3$) δ 9.66 (d, J=7.0 Hz, 1H), 8.20-8.17 (m, 3H), 7.70 (dd, J=8.0, 1.0 Hz, 1H), 7.47-7.42 (m, 3H), 7.23 (t, J=8.0 Hz, 1H), 7.14-7.11 (m, 4H), 4.35-4.28 (m, 1H), 3.52 (ddd, J=14.0, 9.5, 2.0 Hz, 1H), 3.09-2.81 (m, 5H), 2.17-2.07 (m, 2H), 1.80-1.62 (m, 3H); MS (ESI+) m/z 440 (M+H); HPLC>99% (AUC), t$_R$=13.81 min.

Example 60

Preparation of N-(1-Azabicyclo[2.2.2]oct-3-yl)-2-(4-phenylaminophenyl) benzoxazole-4-carboxamide

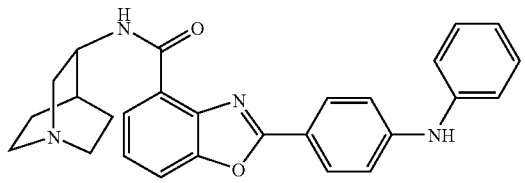

A mixture of N-(1-azabicyclo[2.2.2]oct-3-yl)-2-(4-iodophenyl)benzoxazole-4-carboxamide (27 mg, 0.057 mmol), aniline (10.4 μL, 0.114 mmol), palladium acetate (1.3 mg, 0.0057 mmol), racemic BINAP (10.6 mg, 0.017 mmol) and toluene (2 mL) was stirred under nitrogen at room temperature for 30 min. Cesium carbonate (37 mg, 0.11 mmol) was added and the mixture was heated at 110° C. under nitrogen for 5 h. The mixture was cooled to room temperature, quenched with saturated aqueous sodium bicarbonate, extracted with methylene chloride. The combined organic layers were washed with brine, dried (Na$_2$SO$_4$), filtered and concentrated. The crude material was purified by semi-preparative HPLC to afford N-(1-azabicyclo[2.2.2]oct-3-yl)-2-(4-phenylaminophenyl)benzoxazole-4-carboxamide (21 mg, 84%) as a light yellow solid: $^1$H NMR (500 MHz, CDCl$_3$) δ 9.66 (d, J=7.5 Hz, 1H), 8.15 (dd, J=8.0, 1.0 Hz, 1H), 8.09 (dd, J=7.5, 2.0 Hz, 2H), 7.66 (dd, J=8.0, 1.0 Hz, 1H), 7.41-7.36 (m, 3H), 7.22 (d, J=7.5 Hz, 2H), 7.12-7.10 (m, 3H), 6.15 (s, 1H), 4.32-4.28 (m, 1H), 3.52 (ddd, J=14.0, 9.5, 2.0 Hz, 1H), 3.10-2.81 (m, 5H), 2.17-2.06 (m, 2H), 1.78-1.64 (m, 3H); MS (ESI+) m/z 439 (M+H); HPLC>99% (AUC), t$_R$=14.32 min.

Example 61

Preparation of N-(9-Methyl-9-azabicyclo[3.3.1]non-3-yl)-2-benzo[1,3]dioxol-5-ylbenzoxazole-4-carboxamide

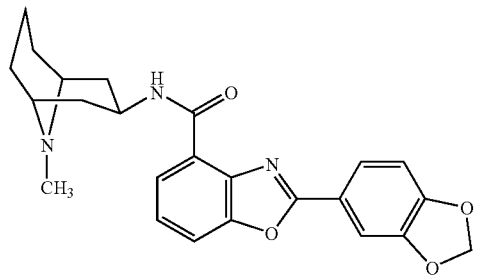

Step A: To a suspension of 2-amino-3-hydroxybenzoic acid (152 mg, 0.65 mmol) in dichloromethane (15 mL) was added pyridine (0.42 mL, 5.2 mmol) followed by piperonyloyl chloride (310 mg, 1.95 mmol). The resulting reaction mixture was stirred at room temperature for 15 min, then DMAP (16 mg, 0.13 mmol) was added and the reaction mixture was stirred at room temperature overnight. The reaction was quenched with aqueous 1 N HCl (20 mL) until the solution reached pH 1. The solution was stirred for 30 min. The aqueous layer was extracted with ethyl acetate. The organic layers were washed with brine and dried over Na$_2$SO$_4$, filtered and concentrated to a yellow solid. The product was directly re-dissolved in toluene (10 mL) and the solution was treated with p-toluenesulfonic acid monohydrate (177 mg, 0.93 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to a yellow solid. The crude product was purified by column chromatography (silica gel, 9:1 to 2:1 ethyl acetate/methanol) to afford the desired product (82 mg, 46%) as a pale orange solid: $^1$H NMR (500 MHz, CD$_3$OD) δ 7.90 (dd, J=7.5, 1.0 Hz, 1H), 7.63-7.58 (m, 2H), 7.54 (d, J=1.5 Hz, 1H), 7.39 (t, J=8.0 Hz, 1H), 6.72 (d, J=8.5 Hz, 1H), 5.97 (s, 2H); MS (ESI+) m/z 284 (M+H).

Step B: A mixture of 2-benzo[1,3]dioxol-5-ylbenzoxazole-4-carboxylic acid from Step A (82 mg, 0.29 mmol), 3-amino-9-methyl-9-azabicyclo[3.3.1]nonane dihydrochloride (80 mg, 0.35 mmol), 1-ethyl-3-(3-dimethylaminopropyl)carbodiimide hydrochloride (78 mg, 0.58 mmol) and 1-hydroxybenzotriazole (111 mg, 0.82 mmol) in DMF (5 mL) was stirred for 10 min at room temperature, then DIPEA (0.19 mL, 1.45 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-2-benzo[1,3]dioxol-5-ylbenzoxazole-4-carboxamide (84 mg, 69%) as a white solid: $^1$H NMR (500 MHz, CDCl$_3$) δ 9.01 (d, J=7.0 Hz, 1H), 8.19 (dd, J=7.5, 1.0 Hz, 1H), 7.84 (dd, J=8.0, 1.5 Hz, 1H), 7.67-7.64 (m, 2H), 7.42 (t, J=8.0 Hz, 1H), 6.99 (d, J=8.0 Hz, 1H), 6.12 (s, 2H), 4.63-4.54 (m, 1H), 3.16-3.11 (m, 2H), 2.68-2.61 (m, 2H), 2.55 (s, 3H), 2.19-2.00 (m, 3H), 1.61-1.48 (m, 4H), 1.21-1.18 (m, 1H); MS (ESI+) m/z 420 (M+H); HPLC 98.2% (AUC), t$_R$=13.15 min.

Example 62

Preparation of (S)-N-(1-Azabicyclo[2.2.2]oct-3-yl)-2-benzo[1,3]dioxol-5-yl-benzoxazole-4-carboxamide

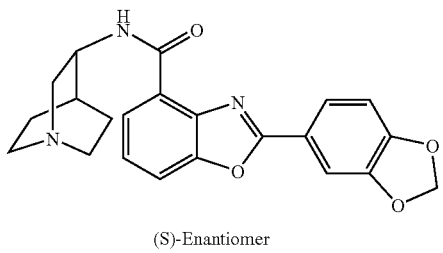

(S)-Enantiomer

A mixture of 2-benzo[1,3]dioxol-5-yl-benzoxazole-4-carboxylic acid (29 mg, 0.10 mmol), (S)-3-aminoquinuclidine dihydrochloride (24 mg, 0.12 mmol), 1-ethyl-3-(3-dimethylaminopropyl)carbodiimide hydrochloride (38 mg, 0.20 mmol) and 1-hydroxybenzotriazole (27 mg, 0.20 mmol) in DMF (5 mL) was stirred for 10 min at room temperature, then DIPEA (66 µL, 0.40 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-benzo[1,3]dioxol-5-yl-benzoxazole-4-carboxamide (17 mg, 42%) as a white solid: $^1$H NMR (500 MHz, CDCl$_3$) δ 9.54 (d, J=7.0 Hz, 1H), 8.17 (dd, J=7.5, 1.0 Hz, 1H), 7.82 (dd, J=8.0, 1.5 Hz, 1H), 7.68 (dd, J=8.0, 1.0 Hz, 1H), 7.64 (d, J=1.5 Hz, 1H), 7.44 (t, J=8.0 Hz, 1H), 6.98 (d, J=8.5 Hz, 1H), 6.11 (s, 2H), 4.33-4.29 (m, 1H), 3.56-3.48 (m, 1H), 3.13-2.99 (m, 2H), 2.95-2.88 (m, 2H), 2.85-2.79 (m, 1H), 2.18-2.13 (m, 1H), 1.80-1.59 (m, 4H); MS (ESI+) m/z 392 (M+H); HPLC 97.4% (AUC), t$_R$=12.51 min.

Example 63

Preparation of N-(1-Azabicyclo[2.2.2]oct-3-yl)-2-benzofuran-5-ylbenzoxazole-4-carboxamide

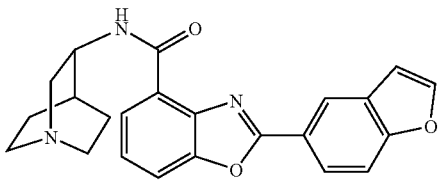

Step A: To a suspension of 3-hydroxyanthranilic acid (70 mg, 0.46 mmol) in methylene chloride (4 mL) was added 1-benzofuran-5-carbonyl chloride (250 mg, 1.38 mmol) followed by pyridine (0.15 mL, 1.83 mmol) and DMAP (6 mg, 0.049 mmol) at room temperature. The resulting mixture was stirred under nitrogen at room temperature overnight and then the reaction mixture was quenched with 2 N HCl (40 mL), extracted with methylene chloride. The combined organic layers were washed with brine, dried over sodium sulfate, filtered and concentrated in vacuo. The residue was dissolved in toluene (10 mL) and the resulting solution was treated with p-toluenesulfonic acid monohydrate (87 mg, 0.46 mmol). The reaction mixture was then heated at reflux under nitrogen overnight. The reaction mixture was cooled to room temperature, diluted with ethyl acetate, washed with water and brine, dried over sodium sulfate, filtered and concentrated. The crude material was purified by column chromatography (silica gel, 9:1 to 3:1 ethyl acetate/methanol) to afford the carboxylic acid (76 mg, 60%) as a white solid: $^1$H NMR (300 MHz, CDCl$_3$) δ 11.50 (br s, 1H), 8.60 (d, J=1.2 Hz, 1H), 8.28 (dd, J=8.4, 1.5 Hz, 1H), 8.16 (dd, J=7.8, 1.2 Hz, 1H), 7.84 (dd, J=8.4, 1.2 Hz, 1H), 7.77 (d, J=2.4 Hz, 1H), 7.70 (d, J=7.8 Hz, 1H), 7.51 (t, J=8.4 Hz, 1H), 6.94 (dd, J=2.4, 1.2 Hz, 1H); MS (ESI+) m/z 280 (M+H).

Step B: A mixture of the carboxylic acid from Step A (76 mg, 0.27 mmol), (±)-3-aminoquinuclidine dihydrochloride (65 mg, 0.33 mmol), 1-ethyl-3-(3-dimethylaminopropyl) carbodiimide hydrochloride (103 mg, 0.54 mmol) and 1-hydroxybenzotriazole (73 mg, 0.54 mmol) in DMF (5 mL) was stirred under nitrogen at room temperature for 10 min, and then triethylamine (0.15 mL, 1.08 mmol) was added. The resulting reaction mixture was stirred at room temperature for 15 h, and then was quenched with a saturated solution of sodium bicarbonate, extracted with methylene chloride. The combined organic layers were dried (Na$_2$SO$_4$), filtered and concentrated. The crude material was purified by column chromatography (silica gel, 90:10:1 ethyl acetate/methanol/concentrated ammonium hydroxide) to afford N-(1-azabicyclo[2.2.2]oct-3-yl)-2-benzofuran-5-ylbenzoxazole-4-carboxamide (77 mg, 73%) as a white solid: $^1$H NMR (300 MHz, CDCl$_3$) δ 9.62 (d, J=7.2 Hz, 1H), 8.51 (d, J=1.5 Hz, 1H), 8.21 (dd, J=8.4, 1.5 Hz, 1H), 8.19 (dd, J=7.8, 1.2 Hz, 1H), 7.76 (d, J=2.4 Hz, 1H), 7.73 (dd, J=8.4, 1.2 Hz, 1H), 7.68 (d, J=8.7 Hz, 1H), 7.46 (t, J=8.1 Hz, 1H), 6.93 (dd, J=2.4, 1.2 Hz, 1H), 4.38-4.32 (m, 1H), 3.55 (ddd, J=14.1, 9.3, 2.1 Hz, 1H), 3.21-2.86 (m, 5H), 2.25-2.09 (m, 2H), 1.83-1.67 (m, 3H); MS (ESI+) m/z 388 (M+H); HPLC>99% (AUC), $t_R$=12.89 min.

Example 64

Preparation of N-(1-Azabicyclo[2.2.2]oct-3-yl)-2-(2, 3-dihydrobenzofuran-5-yl)benzoxazole-4-carboxamide

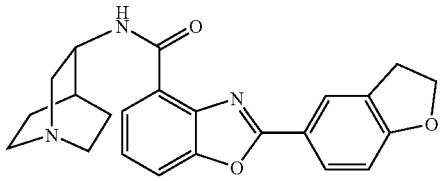

A mixture of N-(1-azabicyclo[2.2.2]oct-3-yl)-2-benzofuran-5-ylbenzoxazole-4-carboxamide (30 mg, 0.077 mmol), 10% palladium on carbon (10 mg), and methanol (1 mL) was treated with hydrogen (50 psi) for 24 h on a parr-shaker apparatus, and then the mixture was filtered through a microfilter and washed with methanol. The filtrate was concentrated and the crude material was purified by semi-preparative HPLC to afford N-(1-azabicyclo[2.2.2]oct-3-yl)-2-(2,3-dihydrobenzofuran-5-yl)benzoxazole-4-carboxamide (8 mg, 26%) as a white solid: $^1$H NMR (500 MHz, CDCl$_3$) δ 9.60 (d, J=7.0 Hz, 1H), 8.15 (dd, J=7.5, 1.5 Hz, 1H), 8.05 (s, 1H), 8.04 (dd, J=8.5, 1.5 Hz, 1H), 7.66 (dd, J=8.5, 1.0 Hz, 1H), 7.42 (t, J=8.0 Hz, 1H), 6.94 (d, J=8.5 Hz, 1H), 4.72 (t, J=8.5 Hz, 2H), 4.36-4.30 (m, 1H), 3.54 (ddd, J=14.0, 9.5, 2.0 Hz, 1H), 3.34 (t, J=8.5 Hz, 2H), 3.16-2.86 (m, 5H), 2.22-2.09 (m, 2H), 1.83-1.65 (m, 3H); MS (ESI+) m/z 390 (M+H); HPLC>99% (AUC), $t_R$=12.67 min.

Example 65

Preparation of N-(9-Methyl-9-azabicyclo[3.3.1]non-3-yl)-2-(2,4-dimethoxyphenyl)benzoxazole-4-carboxamide

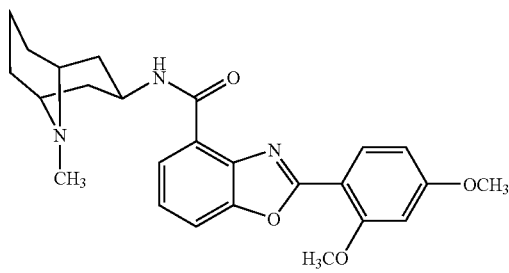

Step A: To a mixture of 2-amino-3-hydroxybenzoic acid hydrobromide (0.50 g, 2.14 mmol) and 2,4-dimethoxybenzoyl chloride (0.43 g, 2.14 mmol) in dichloromethane (15 mL) was added triethylamine (1.2 mL, 8.6 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried (Na$_2$SO$_4$), filtered and concentrated. The crude product was dissolved in toluene (12 mL) and the solution was treated with p-toluenesulfonic acid monohydrate (348 mg, 1.83 mmol). The reaction mixture was then heated to reflux overnight. The reaction was cooled down to room temperature, poured into water and extracted with ethyl acetate. The organic layer was separated then washed with water, brine, dried (Na$_2$SO$_4$), filtered and concentrated. The crude product was purified by column chromatography (silica gel, 9:1 to 3:1 ethyl acetate/methanol) to afford the desired product (0.69 g, quantitative) as a brown solid: $^1$H NMR (500 MHz, DMSO-d$_6$) δ 7.87 (d, J=7.5 Hz, 2H), 7.73 (d, J=7.5 Hz, 1H), 7.37 (t, J=7.5 Hz, 1H), 6.70-6.53 (m, 2H), 3.88 (s, 3H), 3.82 (s, 3H); MS (ESI+) m/z 300 (M+H).

Step B: A mixture of benzoxazole carboxylic acid from Step A (100 mg, 0.33 mmol), 3-amino-9-methyl-9-azabicyclo[3.3.1]nonane dihydrochloride (75 mg, 0.33 mmol), 1-ethyl-3-(3-dimethylaminopropyl)carbodiimide hydrochloride (126 mg, 0.66 mmol) and 1-hydroxybenzotriazole (89 mg, 0.66 mmol) in DMF (1.5 mL) was stirred at room temperature for 5 min, then triethylamine (0.18 mL, 1.32 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford N-(9-methyl-9-azabicyclo[3.3.1]non-3-yl)-2-(2,4-dimethoxyphenyl)benzoxazole-4-carboxamide (80 mg, 56%) as an off-white solid: $^1$H NMR (500 MHz, CDCl$_3$) δ 9.25 (d, J=7.0 Hz, 1H), 8.18-8.13 (m, 2H), 7.65 (dd, J=8.0, 1.0 Hz, 1H), 7.40 (t, J=8.0 Hz, 1H), 6.67 (dd, J=9.0, 2.5 Hz, 1H), 6.62 (d, J=1.0 Hz, 1H), 4.64-4.57 (m, 1H), 4.02 (s, 3H), 3.92 (s, 3H), 3.13 (d, J=10.0 Hz, 2H), 2.69-2.62 (m, 2H), 2.54 (s, 3H), 2.14-1.97 (m, 3H), 1.62-1.55 (m, 1H), 1.49 (t, J=12.0 Hz, 2H), 1.12 (d, J=12.0 Hz, 2H); MS (ESI+) m/z 436 (M+H); HPLC 96.6% (AUC), $t_R$=13.35 min.

Example 66

Preparation of (S)-N-(1-Azabicyclo[2.2.2]oct-3-yl)-2-(2,4-dimethoxyphenyl)benzoxazole-4-carboxamide

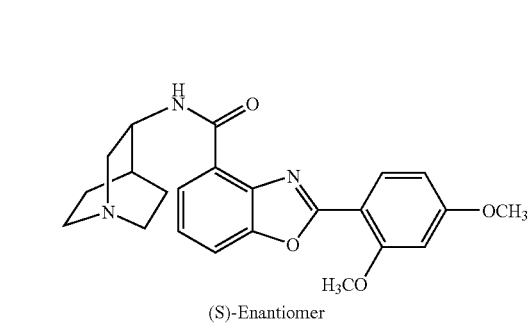

(S)-Enantiomer

A mixture of 2-(2,4-dimethoxyphenyl)benzo[d]oxazole-4-carboxylic acid (100 mg, 0.33 mmol), (S)-(−)-3-aminoquinuclidine dihydrochloride (66 mg, 0.33 mmol), 1-ethyl-3-(3-dimethylaminopropyl)carbodiimide hydrochloride (126 mg, 0.66 mmol) and 1-hydroxybenzotriazole (89 mg, 0.66 mmol) in DMF (1.5 mL) was stirred at room temperature for 5 min, then triethylamine (0.18 mL, 1.32 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)-N-(1-azabicyclo[2.2.2]oct-3-yl)-2-(2,4-dimethoxyphenyl)benzoxazole-4-carboxamide (61 mg, 46%) as a white solid: $^1$H NMR (500 MHz, $CDCl_3$) δ 9.68 (d, J=7.0 Hz, 1H), 8.16 (d, J=7.5 Hz, 1H), 8.11 (d, J=8.5 Hz, 1H), 7.68 (d, J=8.0 Hz, 1H), 7.41 (t, J=8.0 Hz, 1H), 6.68-6.65 (m, 2H), 4.32-4.26 (m, 1H), 4.00 (s, 3H), 3.92 (s, 3H), 3.50 (ddd, J=11.5, 9.5, 2.0 Hz, 1H), 3.10-2.86 (m, 4H), 2.83 (dd, J=14.5, 4.5 Hz, 1H), 2.22-2.17 (m, 1H), 2.10-1.98 (m, 1H), 1.78-1.70 (m, 2H), 1.60-1.51 (m, 1H); MS (ESI+) m/z 408 (M+H); HPLC 96.1% (AUC), $t_R$=12.82 min.

Example 67

Preparation of N-(9-Methyl-9-azabicyclo[3.3.1]non-3-yl)-2-(2,4-dichlorophenyl)benzoxazole-4-carboxamide

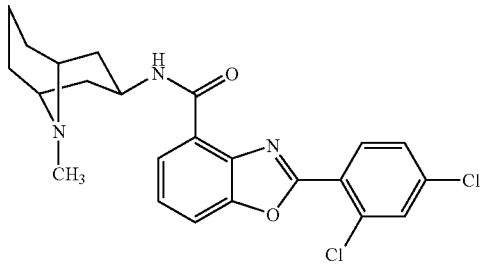

Step A: To a mixture of 2-amino-3-hydroxybenzoic acid hydrobromide (0.50 g, 2.14 mmol) and 2,4-dichlorobenzoyl chloride (0.30 mL, 2.14 mmol) in dichloromethane (15 mL) was added triethylamine (1.2 mL, 8.6 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (13 mL) and the solution was treated with p-toluenesulfonic acid monohydrate (373 mg, 1.96 mmol). The reaction mixture was then heated to reflux overnight. The reaction was cooled down to room temperature, poured into water and extracted with ethyl acetate. The organic layer was separated then washed with water, brine, dried ($Na_2SO_4$), filtered and concentrated. The crude product was purified by column chromatography (silica gel, 9:1 to 3:1 ethyl acetate/methanol) to afford the desired product (0.34 g, 56%) as an off-white solid: $^1$H NMR (500 MHz, DMSO-$d_6$) δ 7.92-7.78 (m, 3H), 7.65-7.55 (m, 1H), 7.51-7.42 (m, 2H); MS (ESI+) m/z 308 (M+H).

Step B: A mixture of benzoxazole carboxylic acid from Step A (100 mg, 0.32 mmol), 3-amino-9-methyl-9-azabicyclo[3.3.1]nonane dihydrochloride (73 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford N-(9-methyl-9-azabicyclo[3.3.1]non-3-yl)-2-(2,4-dichlorophenyl)benzoxazole-4-carboxamide (63 mg, 44%) as a white solid: $^1$H NMR (500 MHz, $CDCl_3$) δ 9.08 (d, J=7.5 Hz, 1H), 8.24 (dd, J=7.5, 1.0 Hz, 1H), 8.20 (d, J=8.5 Hz, 1H), 7.72 (dd, J=8.0, 1.0 Hz, 1H), 7.66 (d, J=2.0 Hz, 1H), 7.52 (t, J=8.0 Hz, 1H), 7.48 (dd, J=8.5, 2.0 Hz, 1H), 4.64-4.57 (m, 1H), 3.12 (d, J=10.0 Hz, 2H), 2.69-2.62 (m, 2H), 2.53 (s, 3H), 2.14-1.97 (m, 3H), 1.62-1.55 (m, 1H), 1.43 (t, J=12.0 Hz, 2H), 1.09 (d, J=12.0 Hz, 2H); MS (ESI+) m/z 444 (M+H); HPLC 98.7% (AUC), $t_R$=14.42 min.

Example 68

Preparation of (S)-N-(1-Azabicyclo[2.2.2]oct-3-yl)-2-(2,4-dichlorophenyl)benzoxazole-4-carboxamide

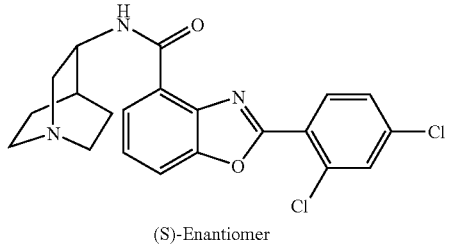

(S)-Enantiomer

A mixture of 2-(2,4-dichlorophenyl)benzo[d]oxazole-4-carboxylic acid (100 mg, 0.32 mmol), (S)-(−)-3-aminoquinuclidine dihydrochloride (64 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)-N-(1-azabicyclo[2.2.2]oct-3-yl)-2-(2,4-dichlorophenyl)benzoxazole-4-carboxamide (63 mg, 47%) as a white solid: $^1$H NMR (500 MHz, $CDCl_3$) δ 9.40 (d, J=7.0 Hz, 1H), 8.25 (dd, J=7.5, 1.0 Hz, 1H), 8.17 (d, J=8.5 Hz, 1H), 7.75 (dd, J=8.0, 1.0 Hz, 1H), 7.65 (d, J=2.0 Hz, 1H), 7.54 (t, J=8.0 Hz, 1H), 7.47 (dd, J=8.5, 2.0 Hz, 1H), 4.32-4.26 (m, 1H), 3.50 (ddd, J=11.5, 9.5, 2.0 Hz, 1H), 3.10-2.72 (m, 5H), 2.15-2.10 (m, 1H), 2.02-1.95 (m, 1H), 1.82-1.70 (m, 2H), 1.60-1.51 (m, 1H); MS (ESI+) m/z 416 (M+H); HPLC>99% (AUC), $t_R$=13.23 min.

Example 69

Preparation of (S)-N-(1-Azabicyclo[2.2.2]oct-3-yl)-2-(4-chloro-2-methoxyphenyl)benzoxazole-4-carboxamide

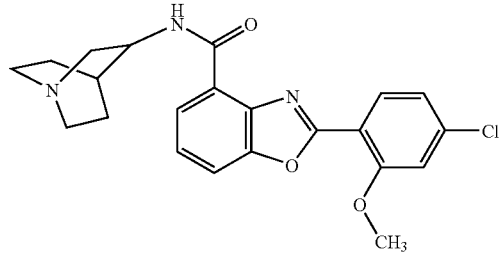

(S)-Enantiomer

Step A: To an ice-cold suspension of 4-chloro-2-methoxybenzoic acid (400 mg, 2.14 mmol) in dichloromethane (10 mL) was added oxalyl chloride (0.18 mL, 2.14 mmol) dropwise. After the ice-water bath was removed, the mixture was stirred for 1 h. To the above solution was added 2-amino-3-hydroxybenzoic acid hydrobromide (0.50 g, 2.14 mmol) followed by the addition of triethylamine (1.19 mL, 8.56 mmol). The resulting reaction mixture was stirred at room temperature overnight. The reaction was quenched with water (50 mL). The reaction mixture was extracted with dichloromethane. The aqueous layer was extracted with dichloromethane (2×50 mL). The combined organic layers were dried over $Na_2SO_4$, filtrated and concentrated to afford a yellow solid. The crude was dissolved in toluene (5 mL) and the solution was treated with p-toluenesulfonic acid monohydrate (258 mg, 1.36 mmol). The reaction mixture was then heated at 95° C. under nitrogen for 5 h. The reaction was cooled down to room temperature, poured into water and extracted with dichloromethane. The organic layer was separated, washed with water, brine, dried over $Na_2SO_4$, filtered and concentrated to a yellow solid. The crude material was purified by recrystallization from methanol to afford the desired product (198 mg, 48%) as an off-white solid: $^1H$ NMR (500 MHz, DMSO-$d_6$) δ 13.06 (s, 1H), 8.09 (d, J=8.4 Hz, 1H), 8.03 (dd, J=8.1, 0.7 Hz, 1H), 7.92 (dd, J=7.8, 0.7 Hz, 1H), 7.52 (t, J=7.9 Hz, 1H), 7.41 (d, J=1.8 Hz, 1H), 7.25 (dd, J=8.4, 1.9 Hz, 1H), 3.98 (s, 3H); MS (ESI+) m/z 304 (M+H).

Step B: A mixture of 2-(4-chloro-2-methoxyphenyl)benzoxazole-4-carboxylic acid (95 mg, 0.31 mmol), 1-ethyl-3-(3-dimethylaminopropyl)carbodiimide hydrochloride (119 mg, 0.62 mmol), 1-hydroxybenzotriazole (76 mg, 0.62 mmol) and (S)-(−)-3-aminoquinuclidine dihydrochloride (78 mg, 0.39 mmol) in DMF (3 mL) was stirred at room temperature for 10 min, then triethylamine (0.20 mL, 1.4 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried ($Na_2SO_4$), filtered and concentrated. The crude material was purified by column chromatography (silica gel, 90:9:1 dichloromethane/methanol/concentrated ammonium hydroxide) to afford (S)-N-(1-azabicyclo[2.2.2]oct-3-yl)-2-(4-chloro-2-methoxyphenyl)benzoxazole-4-carboxamide (69 mg, 54%) as a white solid: $^1H$ NMR (500 MHz, CDCl$_3$) δ 9.59 (d, J=7.0 Hz, 1H), 8.19 (dd, J=7.8, 1.0 Hz, 1H), 8.08 (d, J=8.2 Hz, 1H), 7.83 (dd, J=8.2, 1.0 Hz, 1H), 7.47 (t, J=7.9 Hz, 1H), 7.15-7.10 (m, 2H), 4.40-4.22 (m, 1H), 4.02 (s, 3H), 3.55-3.50 (m, 1H), 3.20-2.75 (m, 5H), 2.23-2.19 (m, 1H), 2.10-2.00 (m, 1H), 1.80-1.75 (m, 2H), 1.60-1.50 (m, 1H); MS (ESI+) m/z 412 (M+H); HPLC>99% (AUC), $t_R$=13.78 min.

Example 70

Preparation of N-(9-Methyl-9-azabicyclo[3.3.1]non-3-yl)-2-(4-chloro-2-methoxyphenyl)benzoxazole-4-carboxamide

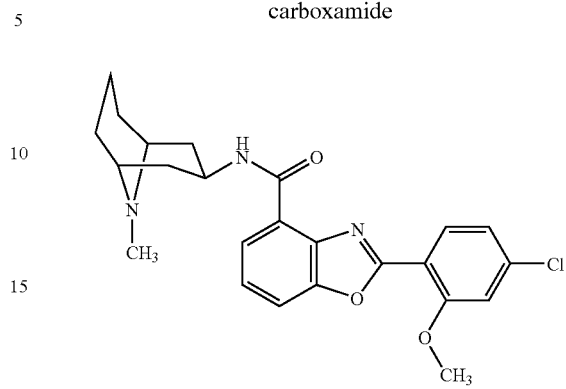

A mixture of 2-(4-chloro-2-methoxyphenyl)benzoxazole-4-carboxylic acid (95 mg, 0.31 mmol), 1-ethyl-3-(3-dimethylaminopropyl)carbodiimide hydrochloride (119 mg, 0.62 mmol), 1-hydroxybenzotriazole (76 mg, 0.62 mmol) and 3-amino-9-methyl-9-azabicyclo[3.3.1]nonane dihydrochloride (89 mg, 0.39 mmol) in DMF (3 mL) was stirred at room temperature for 10 min, then triethylamine (0.18 mL, 1.25 mmol) was added. The resulting reaction mixture was stirred at room temperature overnight. The mixture was diluted with dichloromethane and then washed with a saturated solution of sodium bicarbonate. The aqueous layer was further extracted with dichloromethane (3×50 mL). The combined organic layers were washed with water (3×50 mL), brine (3×50 mL), dried ($Na_2SO_4$), filtered and concentrated. The crude material was purified by column chromatography (silica gel, 90:9:1 dichloromethane/methanol/concentrated ammonium hydroxide) to afford N-(9-methyl-9-azabicyclo[3.3.1]non-3-yl)-2-(4-chloro-2-methoxyphenyl)benzoxazole-4-carboxamide (102 mg, 67%) as a light yellow solid: $^1H$ NMR (500 MHz, CDCl$_3$) δ 9.17 (br s, 1H), 8.20 (dd, J=7.7, 0.8 Hz, 1H), 8.11 (d, J=8.4 Hz, 1H), 7.69 (dd, J=7.3, 0.9 Hz, 1H), 7.45 (t, J=4.0 Hz, 1H), 7.16-7.10 (m, 2H), 4.67-4.56 (m, 1H), 4.04 (s, 3H), 3.10-3.02 (m, 2H), 2.70-2.60 (m, 5H), 2.57 (s, 3H), 2.20-2.00 (m, 3H), 1.20-1.10 (m, 2H); MS (ESI+) m/z 440 (M+H); HPLC 98.7% (AUC), $t_R$=14.10 min.

Example 71

Preparation of (S)-N-(1-Azabicyclo[2.2.2]oct-3-yl)-2-(4-methoxy-2-methylphenyl)benzoxazole-4-carboxamide

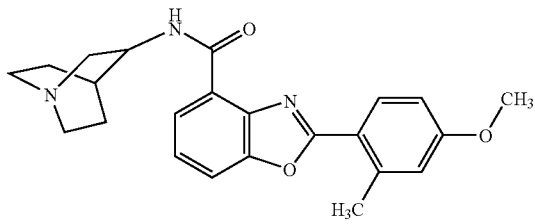

(S)-Enantiomer

Step A: To an ice-cold suspension of 4-methoxy-2-methylbenzoic acid (356 mg, 2.14 mmol) in dichloromethane (10 mL) was added oxalyl chloride (0.18 mL, 2.14 mmol) dropwise, then the ice-water bath was removed and the mixture was stirred for 1 h. To the above solution was added 2-amino-3-hydroxybenzoic acid hydrobromide (0.50 g, 2.14 mmol) followed by the addition of triethylamine (1.19 mL, 8.56 mmol). The resulting reaction mixture was stirred at room temperature overnight. The reaction was quenched with water (50 mL). The reaction mixture was extracted with dichloromethane. The aqueous layer was extracted with dichloromethane (2×50 mL). The combined organic layers were dried over $Na_2SO_4$, filtered and concentrated to afford a yellow solid. The crude was dissolved in toluene (5 mL) and the solution was treated with p-toluenesulfonic acid monohydrate (258 mg, 1.36 mmol). The reaction mixture was then heated at 95° C. under nitrogen for 5 h. The reaction was cooled down to room temperature, poured into water and extracted with dichloromethane. The organic layer was separated, washed with water, brine, dried over $Na_2SO_4$, filtered and concentrated to a yellow solid. The crude product was purified by column chromatography (silica gel, 9:1 to 3:2 ethyl acetate/methanol) to afford the desired product (204 mg, 34%) as a yellow solid: $^1$H NMR (500 MHz, DMSO-$d_6$) δ 13.06 (s, 1H), 8.25-8.10 (m, 1H), 7.82-7.75 (m, 2H), 7.37 (t, J=7.9 Hz, 1H), 7.41 (dd, J=8.0, 1.3 Hz, 1H), 7.10-6.95 (m, 1H), 3.85 (s, 3H), 3.13 (s, 3H); MS (ESI+) m/z 283 (M+H).

Step B: A mixture of 2-(4-methoxy-2-methylphenyl)benzoxazole-4-carboxylic acid (100 mg, 0.35 mmol), 1-ethyl-3-(3-dimethylaminopropyl)carbodiimide hydrochloride (134 mg, 0.70 mmol), 1-hydroxybenzotriazole (95 mg, 0.70 mmol) and (S)-(−)-3-aminoquinuclidine dihydrochloride (87 mg, 0.44 mmol) in DMF (3 mL) was stirred at room temperature for 10 min, then triethylamine (0.20 mL, 1.4 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried ($Na_2SO_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-(4-methoxy-2-methylphenyl)benzoxazole-4-carboxamide (41 mg, 30%) as an off-white solid: $^1$H NMR (500 MHz, CDCl$_3$) δ 9.46 (d, J=7.0 Hz, 1H), 8.20-8.15 (m, 2H), 7.72 (dd, J=7.1, 1.0 Hz, 1H), 7.45 (t, J=7.9 Hz, 1H), 6.95-6.90 (m, 2H), 4.51-4.42 (m, 1H), 3.91 (s, 3H), 3.70-3.63 (m, 1H), 3.22-3.00 (m, 4H), 2.98-2.90 (m, 1H), 2.86 (s, 3H), 2.35-2.30 (m, 1H), 2.20-2.10 (m, 1H), 2.00-1.95 (m, 2H), 1.75-1.70 (m, 1H); MS (ESI+) m/z 392 (M+H); HPLC 96.6% (AUC), $t_R$=13.19 min.

Example 72

Preparation of N-(9-Methyl-9-azabicyclo[3.3.1]non-3-yl)-2-(4-methoxy-2-methylphenyl)benzoxazole-4-carboxamide

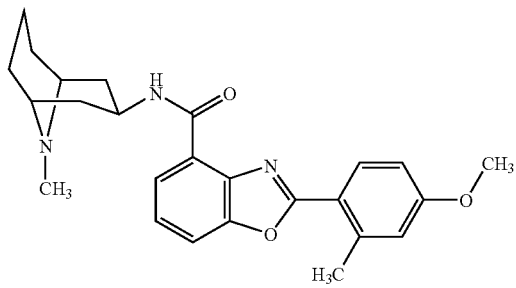

A mixture of 2-(4-methoxy-2-methylphenyl)benzoxazole-4-carboxylic acid (100 mg, 0.35 mmol), 1-ethyl-3-(3-dimethylaminopropyl)carbodiimide hydrochloride (134 mg, 0.70 mmol), 1-hydroxybenzotriazole (95 mg, 0.70 mmol) and 3-amino-9-methyl-9-azabicyclo[3.3.1]nonane dihydrochloride (99 mg, 0.44 mmol) in DMF (3 mL) was stirred at room temperature for 10 min, then triethylamine (0.20 mL, 1.40 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with water (2×50 mL), brine (2×50 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford N-(9-methyl-9-azabicyclo[3.3.1]non-3-yl)-2-(4-methoxy-2-methylphenyl)benzoxazole-4-carboxamide (24 mg, 16%) as a light yellow solid: $^1$H NMR (500 MHz, CDCl$_3$) δ 9.11 (d, J=7.2 Hz, 1H), 8.22-8.16 (m, 2H), 7.67 (dd, J=8.8, 0.8 Hz, 1H), 7.43 (t, J=7.9 Hz, 1H), 6.94-6.90 (m, 2H), 4.66-4.60 (m, 1H), 3.90 (s, 3H), 3.15-3.10 (m, 2H), 2.89 (s, 3H), 2.66-2.58 (m, 2H), 2.55 (s, 3H), 2.10-1.90 (m, 3H), 1.58-1.42 (m, 3H), 1.20-1.05 (m, 2H); MS (ESI+) m/z 420 (M+H); HPLC>99% (AUC), $t_R$=13.54 min.

Example 73

Preparation of (S)-N-(1-Azabicyclo[2.2.2]oct-3-yl)-2-(4-chloro-2-methylphenyl)benzoxazole-4-carboxamide

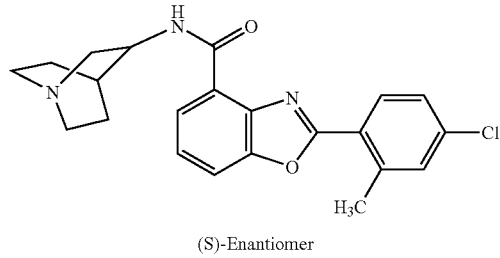

(S)-Enantiomer

Step A: To an ice-cold suspension of 4-chloro-2-methylbenzoic acid (426 mg, 2.50 mmol) in dichloromethane (15 mL) was added oxalyl chloride (0.21 mL, 2.50 mmol) dropwise. Then the ice-water bath was removed and the mixture was stirred for 1 h. To the above solution was added 2-amino-3-hydroxybenzoic acid hydrobromide (0.58 g, 2.50 mmol) followed by the addition of triethylamine (1.4 mL, 8.56 mmol). The resulting reaction mixture was stirred at room temperature overnight. The reaction was quenched with water (50 mL). The reaction mixture was extracted with dichloromethane. The aqueous layer was extracted with dichloromethane (2×50 mL). The combined organic layers were washed with water, brine, dried over $Na_2SO_4$, filttered and concentrated to afford a yellow solid. The crude was dissolved in toluene (5 mL) and the solution was treated with p-toluenesulfonic acid monohydrate (342 mg, 1.80 mmol). The reaction mixture was then heated at 95° C. under nitrogen for 5 h. The reaction was cooled down to room temperature, poured into water and extracted with dichloromethane. The organic layer was separated, washed with water, brine, dried over $Na_2SO_4$, filtered and concentrated to a yellow solid. The crude material was purified by recrystallization from methanol to afford the desired product (127 mg, 24%) as a yellow solid: $^1$H NMR (500 MHz, DMSO-$d_6$)

δ 8.12 (d, J=7.5 Hz, 1H), 7.85-7.80 (m, 2H), 7.63-7.60 (m, 1H), 7.45-7.40 (m, 2H); MS (ESI+) m/z 288 (M+H).

Step B: A mixture of 2-(4-chloro-2-methylphenyl)benzoxazole-4-carboxylic acid (59 mg, 0.21 mmol), 1-ethyl-3-(3-dimethylaminopropyl)carbodiimide hydrochloride (79 mg, 0.41 mmol), 1-hydroxybenzotriazole (55 mg, 0.41 mmol) and (S)-(−)-3-aminoquinuclidine dihydrochloride (51 mg, 0.26 mmol) in DMF (2 mL) was stirred at room temperature for 10 min, then triethylamine (0.11 mL, 0.82 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried (Na$_2$SO$_4$), filtered and concentrated. The crude material was purified by preparative TLC (silica gel, 90:9:1 dichloromethane/methanol/concentrated ammonium hydroxide) to afford (S)-N-(1-azabicyclo[2.2.2]oct-3-yl)-2-(4-chloro-2-methylphenyl)benzoxazole-4-carboxamide (16 mg, 19%) as a light yellow solid: $^1$H NMR (500 MHz, CDCl$_3$) δ 9.47 (d, J=7.0 Hz, 1H), 8.29 (d, J=1.7 Hz, 1H), 8.20-8.10 (m, 2H), 7.83 (d, J=1.7 Hz, 1H), 7.06 (d, J=8.8 Hz, 2H), 4.45-4.35 (m, 1H), 3.93 (s, 3H), 3.55-3.45 (m, 1H), 3.15-3.00 (m, 2H), 2.95-2.90 (m, 2H), 2.85-2.75 (m, 1H), 2.20-2.15 (m, 1H), 2.10-2.00 (m, 1H), 1.80-1.75 (m, 2H), 1.70-1.55 (m, 1H); MS (ESI+) m/z 396 (M+H); HPLC 99.0% (AUC), t$_R$=14.57 min.

Example 74

Preparation of N-(9-Methyl-9-azabicyclo[3.3.1]non-3-yl)-2-(4-chloro-2-methylphenyl)benzoxazole-4-carboxamide

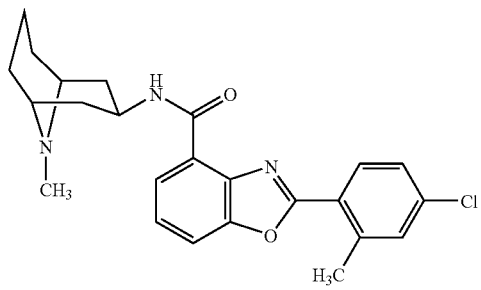

A mixture of 2-(4-chloro-2-methylphenyl)benzoxazole-4-carboxylic acid (59 mg, 0.21 mmol), 1-ethyl-3-(3-dimethylaminopropyl)carbodiimide hydrochloride (79 mg, 0.41 mmol), 1-hydroxybenzotriazole (55 mg, 0.41 mmol) and 3-amino-9-methyl-9-azabicyclo[3.3.1]nonane dihydrochloride (72 mg, 0.26 mmol) in DMF (3 mL) was stirred at room temperature for 10 min, then triethylamine (0.11 mL, 0.82 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×20 mL). The combined organic layers were washed with water (2×20 mL), brine (2×20 mL), dried (Na$_2$SO$_4$), filtered and concentrated. The crude material was purified by preparative TLC (silica gel, 90:9:1 dichloromethane/methanol/concentrated ammonium hydroxide) to afford N-(9-methyl-9-azabicyclo[3.3.1]non-3-yl)-2-(4-chloro-2-methylphenyl)benzoxazole-4-carboxamide (19 mg, 22%) as a light yellow solid: $^1$H NMR (500 MHz, CDCl$_3$) δ 9.01 (br s, 1H), 8.22 (dd, J=7.8, 1.0 Hz, 1H), 8.18 (d, J=8.4 Hz, 1H), 7.71 (dd, J=8.1, 0.9 Hz, 1H), 7.49 (t, J=7.9 Hz, 1H), 7.43-7.36 (m, 2H), 4.67-4.60 (m, 1H), 3.25-3.15 (m, 2H), 2.88 (s, 3H), 2.70-2.55 (m, 2H), 2.48 (s, 3H), 2.10-2.00 (m, 3H), 1.65-1.40 (m, 3H), 1.20-1.10 (m, 2H); MS (ESI+) m/z 424 (M+H); HPLC 98.4% (AUC), t$_R$=13.82 min.

Example 75

Preparation of N-(9-Methyl-9-azabicyclo[3.3.1]non-3-yl)-2-(2,6-dimethylphenyl)benzoxazole-4-carboxamide

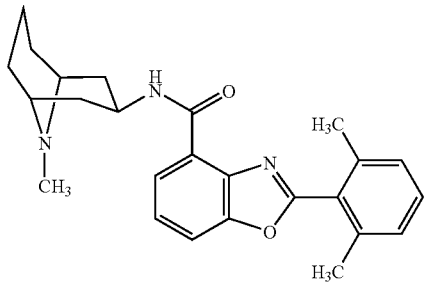

Step A: To a solution of 2,6-dimethylbenzoic acid (192 mg, 1.28 mmol) in dichloromethane (8 mL) was added oxalyl chloride (0.33 mL, 3.85 mmol) slowly. The reaction was stirred at room temperature for 2 h. The solvent was evaporated and the solid was directly redissolved in dichloromethane (8 mL). 2-amino-3-hydroxybenzoic acid hydrobromide (314 mg, 1.34 mmol) was added, followed by triethylamine (0.75 mL, 5.4 mmol). The resulting reaction mixture was stirred at room temperature overnight. The reaction was quenched with aqueous 2 N HCl (25 mL) until the solution reached pH 1. The aqueous layer was extracted with dichloromethane. The organic layers were washed with brine and dried over Na$_2$SO$_4$, filtered and concentrated. The residue was directly re-dissolved in toluene (7 mL) and the solution was treated with p-toluenesulfonic acid monohydrate (312 mg, 1.64 mmol). The reaction mixture was then heated to reflux for 1.5 h. The reaction was cooled down to room temperature and the toluene was evaporated. The reaction mixture was poured into water and extracted with ethyl acetate. The organic layer was separated, then washed with water, brine, dried over Na$_2$SO$_4$, filtered and concentrated to a yellow solid. The crude product was purified by column chromatography (silica gel, 9:1 to 2:1 ethyl acetate/methanol) to afford the desired product (101 mg, 35%) as a yellow solid: $^1$H NMR (500 MHz, CD$_3$OD) δ 7.95-7.86 (m, 1H), 7.79 (d, J=8.0 Hz, 1H), 7.48 (t, J=7.5 Hz, 1H), 7.30-7.24 (m, 1H), 7.14-6.98 (m, 2H), 3.34 (s, 3H), 3.31 (s, 3H); MS (ESI+) m/z 268 (M+H).

Step B: A mixture of 2-(2,6-dimethylphenyl)benzoxazole-4-carboxylic acid from Step A (44 mg, 0.17 mmol), 3-amino-9-methyl-9-azabicyclo[3.3.1]nonane dihydrochloride (45 mg, 0.20 mmol), 1-ethyl-3-(3-dimethylaminopropyl)carbodiimide hydrochloride (65 mg, 0.34 mmol) and 1-hydroxybenzotriazole (46 mg, 0.34 mmol) in DMF (2 mL) was stirred at room temperature for 10 min, then triethylamine (0.12 mL, 0.85 mmol) was added. The resulting reaction mixture was stirred at room temperature overnight. The mixture was diluted with dichoromethane (30 mL), and then washed with a saturated solution of sodium bicarbonate. The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) and semi-preparative HPLC to afford N-(9-methyl-9-azabicyclo[3.3.1]non-3-yl-2-(2,6-dimethylphenyl)benzoxazole-4-carboxamide (11 mg, 16%) as an off-white solid: $^1$H NMR (500 MHz, CDCl$_3$) δ 8.99 (s, 1H), 8.25 (d, J=7.5 Hz, 1H), 7.72 (d, J=8.0 Hz, 1H), 7.50 (t, J=8.0 Hz, 1H), 7.38 (t, J=7.5 Hz, 1H), 7.22 (d, J=8.0 Hz, 2H), 4.63-4.56 (m, 1H), 3.18-3.11 (m, 2H), 2.63-2.53 (m, 5H), 2.41 (s, 6H), 2.10-1.92 (m, 3H), 1.56-1.38 (m, 3H), 1.18-1.02 (m, 2H); MS (ESI+) m/z 404 (M+H); HPLC>99% (AUC), t$_R$=13.13 min.

Example 76

Preparation of (S)-N-(1-Azabicyclo[2.2.2]oct-3-yl)-2-(2,6-dichlorophenyl)benzoxazole-4-carboxamide

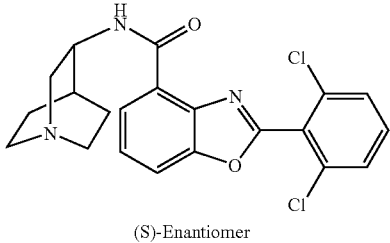

(S)-Enantiomer

Step A: To a suspension of 2-amino-3-hydroxybenzoic acid hydrobromide (350 mg, 1.50 mmol) in dichloromethane (8 mL) was added 2,6-dichlorobenzoyl chloride (0.21 mL, 1.50 mmol). The resulting reaction mixture was stirred at room temperature for 10 min, then triethylamine (0.83 mL, 6.00 mmol) was added and the reaction mixture was stirred at room temperature overnight. The reaction was diluted in dichloromethane (30 mL) and quenched with aqueous 2 N HCl (10 mL) until the solution reached pH 1. The aqueous layer was further extracted with dichloromethane (2×30 mL). The organic layers were washed with water and brine, dried over Na$_2$SO$_4$, filtered and concentrated. The residue was directly re-dissolved in toluene (8 mL) and the solution was treated with p-toluenesulfonic acid monohydrate (253 mg, 1.33 mmol). The reaction mixture was then heated to reflux overnight. The reaction was cooled down to room temperature and the toluene was evaporated. The reaction mixture was poured into water and extracted with ethyl acetate. The organic layer was separated, then washed with water, brine, dried over Na$_2$SO$_4$, filtered and concentrated to an orange solid. The crude product was purified by column chromatography (silica gel, 9:1 to 3:1 ethyl acetate/methanol) to afford the desired product (194 mg, 70%) as a pale orange solid: $^1$H NMR (300 MHz, DMSO-d$_6$) δ 7.87-7.38 (m, 6H); MS (ESI+) m/z 308 (M+H).

Step B: A mixture of 2-(2,6-dichlorophenyl)benzoxazole-4-carboxylic acid from Step A (73 mg, 0.24 mmol), (S)-3-aminoquinuclidine dihydrochloride (58 mg, 0.29 mmol), 1-ethyl-3-(3-dimethylaminopropyl)carbodiimide hydrochloride (92 mg, 0.48 mmol) and 1-hydroxybenzotriazole (65 mg, 0.48 mmol) in DMF (2.5 mL) was stirred at room temperature for 10 min, then triethylamine (0.17 mL, 1.20 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) and recrystallization from acetonitrile to afford (S)-N-(1-azabicyclo[2.2.2]oct-3-yl)-2-(2,6-dichlorophenyl)benzoxazole-4-carboxamide (31 mg, 31%) as white needles: $^1$H NMR (500 MHz, CDCl$_3$) δ 9.38 (d, J=6.5 Hz, 1H), 8.27 (d, J=7.5 Hz, 1H), 7.78 (d, J=8.0 Hz, 1H), 7.59-7.46 (m, 4H), 4.33-4.25 (m, 1H), 3.47 (t, J=11.0 Hz, 1H), 3.02-2.85 (m, 4H), 2.81-2.74 (m, 1H), 2.11 (s, 1H), 1.99-1.90 (m, 1H), 1.78-1.69 (m, 2H), 1.56-1.46 (m, 1H); MS (ESI+) m/z 416 (M+H); HPLC>99% (AUC), t$_R$=12.19 min.

Example 77

Preparation of N-(9-Methyl-9-azabicyclo[3.3.1]non-3-yl)-2-(2,6-dichlorophenyl)benzoxazole-4-carboxamide

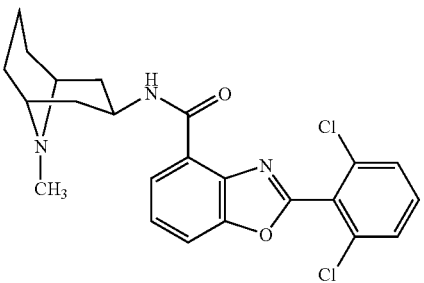

A mixture of 2-(2,6-dichlorophenyl)benzoxazole-4-carboxylic acid (71 mg, 0.23 mmol), 3-amino-9-methyl-9-azabicyclo[3.3.1]nonane dihydrochloride (64 mg, 0.28 mmol), 1-ethyl-3-(3-dimethylaminopropyl)carbodiimide hydrochloride (88 mg, 0.46 mmol) and 1-hydroxybenzotriazole (62 mg, 0.46 mmol) in DMF (2 mL) was stirred at room temperature for 10 min, then triethylamine (0.16 mL, 1.16 mmol) was added. The resulting reaction mixture was stirred at room temperature overnight. The mixture was diluted with dichloromethane (30 mL), and then washed with a saturated solution of sodium bicarbonate (10 mL). The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) and recrystallization from acetonitrile to afford N-(9-methyl-9-azabicyclo[3.3.1]non-3-yl)-2-(2,6-dichlorophenyl)benzoxazole-4-carboxamide (39 mg, 38%) as off-white crystals: $^1$H NMR (500 MHz, CDCl$_3$) δ 8.85 (s, 1H), 8.29 (d, J=7.5 Hz, 1H), 7.76 (d, J=7.5 Hz, 1H), 7.57-7.46 (m, 4H), 4.62-4.54 (m, 1H), 3.14-3.06 (m, 2H), 2.53 (s, 3H), 2.05-1.92 (m, 3H), 1.65-1.40 (m, 5H), 1.16-1.05 (m, 2H); MS (ESI+) m/z 444 (M+H); HPLC>99% (AUC), t$_R$=12.70 min.

Example 78

Preparation of N-(1-Azabicyclo[2.2.2]oct-3-yl)-6-chloro-2-p-tolylbenzoxazole-4-carboxamide

Step A: To a 60 mL of aqueous solution of KOH (2.68 g, 47.8 mmol) was added ether (200 mL) followed by the addition of 1-methyl-3-nitro-1-nitrosoguanidine (5.28 g, 35.9 mmol) slowly at 0° C. The ethereal layer was isolated and added into a solution of 2-amino-3-methoxybenzoic acid (2.0 g, 11.9 mmol) in acetone (20 mL). The reaction mixture was quenched with 2 mL of acetic acid and concentrated under reduced pressure. The residue was dissolved into ether and washed with saturated solution of NaHCO$_3$, brine, dried over Na$_2$SO$_4$, filtered and concentrated to a light orange solid (2.16 g, 99%): $^1$H NMR (300 MHz, CDCl$_3$) δ 7.47 (dd, J=8.2, 1.0 Hz, 1H), 6.85 (dd, J=7.8, 1.2 Hz, 1H), 6.58 (t, J=8.4 Hz, 1H), 6.00 (br s, 2H), 3.87 (s, 6H).

Step B: To a solution of methyl ester from Step A (2.16 g, 11.9 mmol) in DMF (15 mL) was added N-chlorosuccinimide (1.60 g, 11.9 mmol). The resulting mixture was stirred and heated at 50° C. for 2 h. The reaction mixture was cooled to room temperature, then diluted with ether and water. The aqueous layer was isolated and extracted with ether (2×100 mL). The combined organic layers were washed with water (2×100 mL), brine (100 mL), dried over Na$_2$SO$_4$, filtered and concentrated to afford 2-amino-5-chloro-3-methoxybenzoate (2.36 g, 92%) as a brown solid: $^1$H NMR (300 MHz, CDCl$_3$) δ 7.45 (d, J=2.2 Hz, 1H), 6.79 (d, J=2.2 Hz, 1H), 6.00 (br s, 2H), 3.87 (s, 6H).

Step C: A mixture of 2-amino-5-chloro-3-methoxybenzoate (2.76 g, 12.8 mmol), 48% aqueous solution of hydrobromic acid (25 mL) and glacial acetic acid (1 mL) was heated to reflux for 48 h. The reaction mixture was cooled down to room temperature, treated with saturated solution of Na$_2$CO$_3$ to pH~6, concentrated and purified by column chromatography (silica gel, 90:10 dichloromethane/methanol) to afford 2-amino-5-chloro-3-hydroxybenzoic acid (0.84 g, 35%) as a light brown solid: MS (ESI+) m/z 188 (M+H).

Step D: To a suspension of 2-amino-5-chloro-3-hydroxybenzoic acid (100 mg, 0.53 mmol) in dichloromethane (10 mL) was added pyridine (0.17 mL, 2.13 mmol) followed by p-tolyl chloride (246 mg, 1.6 mmol) at room temperature. The resulting reaction mixture was stirred at room temperature for 20 min, then DMAP (7 mg, 0.05 mmol) was added. The reaction mixture was stirred at room temperature overnight, then quenched with aqueous 2 N HCl (50 mL). The reaction was extracted with ethyl acetate, then the organic layer was washed with brine, dried over Na$_2$SO$_4$, filtered and concentrated to a yellow solid. The crude was dissolved in toluene (10 mL) and the solution was treated with p-toluenesulfonic acid monohydrate (146 mg, 0.77 mmol). The reaction mixture was then heated to reflux under nitrogen overnight. The reaction was cooled down to room temperature, poured into water and extracted with ethyl acetate. The organic layer was separated then washed with water, brine, dried over Na$_2$SO$_4$, filtered and concentrated to give a yellow solid. The crude product was purified by column chromatography (silica gel, 9:1 to 3:1, ethyl acetate/methanol) to afford the desired product (90 mg, 60%) as a yellow solid: MS (ESI+) m/z 288 (M+H).

Step E: A mixture of 6-chloro-2-p-tolylbenzoxazole-4-carboxylic acid from Step D (45 mg, 0.16 mmol), 1-ethyl-3-(3-dimethylaminopropyl)carbodiimide hydrochloride (60 mg, 0.31 mmol), 1-hydroxybenzotriazole (43 mg, 0.31 mmol) and 3-aminoquinuclidine dihydrochloride (37 mg, 0.19 mmol) in DMF (5 mL) was stirred 10 min at room temperature, then triethylamine (0.07 mL, 0.63 mmol) was added to the reaction mixture. The resulting reaction mixture was stirred at room temperature for 12 h. The mixture was diluted with ethyl acetate (20 mL), and then washed with a saturated solution of sodium bicarbonate. The aqueous layer was further extracted with ethyl acetate (2×25 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-6-chloro-2-p-tolylbenzoxazole-4-carboxamide (18 mg, 29%) as a white solid: $^1$H NMR (500 MHz, CDCl$_3$) δ 9.48 (d, J=7.3 Hz, 1H), 8.16 (d, J=1.9 Hz, 1H), 8.10 (d, J=8.2 Hz, 2H), 7.69 (d, J=1.9 Hz, 1H), 7.37 (d, J=8.0 Hz, 2H), 4.32-4.25 (m, 1H), 3.55-3.45 (m, 1H), 3.12-3.00 (m, 2H), 2.95-2.85 (m, 2H), 2.82 (dd, J=14.3, 3.8 Hz, 1H), 2.48 (s, 3H), 2.20-2.00 (m, 2H), 1.80-1.70 (m, 3H); MS (ESI+) m/z 396 (M+H); HPLC>99% (AUC), t$_R$=13.30 min.

Example 79

Preparation of N-(9-Methyl-9-azabicyclo[3.3.1]non-3-yl)-6-chloro-2-p-tolylbenzoxazole-4-carboxamide

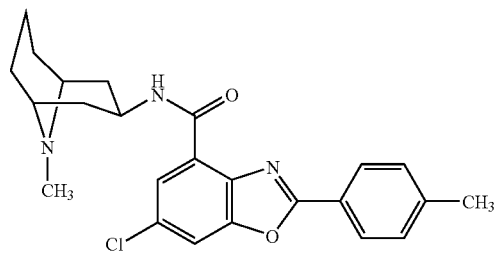

A mixture of 6-chloro-2-p-tolylbenzoxazole-4-carboxylic acid (45 mg, 0.16 mmol), 3-amino-9-methyl-9-azabicyclo[3.3.1]nonane dihydrochloride (43 mg, 0.19 mmol), 1-ethyl-3-(3-dimethylaminopropyl)carbodiimide hydrochloride (60 mg, 0.31 mmol) and 1-hydroxybenzotriazole (43 mg, 0.31 mmol) in DMF (5 mL) was stirred for 10 min at room temperature, then triethylamine (0.07 mL, 0.63 mmol) was added. The resulting reaction mixture was stirred at room temperature for 12 h. The mixture was diluted with ethyl acetate (20 mL), and then washed with a saturated solution of sodium bicarbonate. The aqueous layer was further extracted with ethyl acetate (2×22 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-6-chloro-2-p-tolylbenzoxazole-4-carboxamide (18 mg, 26%) as a white solid: $^1$H NMR (500 MHz, CDCl$_3$) δ 8.94 (d, J=7.3 Hz, 1H), 8.18 (d, J=1.9 Hz, 1H), 8.11 (d, J=8.2 Hz, 2H), 7.67 (d, J=1.9 Hz, 1H), 7.39 (d, J=8.0 Hz, 2H), 4.63-4.50 (m, 1H), 3.12 (d, J=10.4 Hz, 2H), 2.70-2.57 (m, 2H), 2.54 (s, 3H), 2.48 (s, 3H), 2.20-1.90 (m, 2H), 1.65-1.52 (m, 2H), 1.51-1.48 (m, 2H), 1.20-1.10 (m, 2H); MS (ESI+) m/z 424 (M+H); HPLC 95.0% (AUC), t$_R$=13.80 min.

Example 80

Preparation of N-(1-Azabicyclo[2.2.2]oct-3-yl)-6-chloro-2-(4-methoxyphenyl)benzoxazole-4-carboxamide

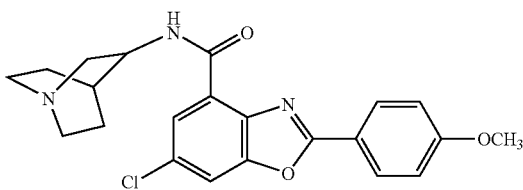

Step A: To a suspension of 2-amino-5-chloro-3-hydroxybenzoic acid (200 mg, 1.07 mmol) in dichloromethane (20 mL) was added pyridine (0.35 mL, 4.28 mmol) followed by p-anisoyl chloride (548 mg, 3.21 mmol) at room temperature. The resulting reaction mixture was stirred at room temperature for 20 min, then DMAP (13 mg, 0.10 mmol) was added and the reaction mixture was stirred at room temperature overnight. The reaction was quenched with aqueous 2 N HCl (50 mL). The reaction mixture was extracted with ethyl acetate, and the organic layer was washed with brine, dried over $Na_2SO_4$, filtered and concentrated to give a yellow solid. The crude was dissolved in toluene (10 mL) and the solution treated with p-toluenesulfonic acid monohydrate (319 mg, 1.68 mmol). The reaction mixture was then heated to reflux under nitrogen overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 3:1 ethyl acetate/methanol) to afford the desired product (89 mg, 26%) as an off-white solid: MS (ESI+) m/z 304 (M+H).

Step B: A mixture of 6-chloro-2-(4-methoxyphenyl)-benzoxazole-4-carboxylic acid from Step A (42 mg, 0.14 mmol), 1-ethyl-3-(3-dimethylaminopropyl)carbodiimide hydrochloride (53 mg, 0.28 mmol), 1-hydroxybenzotriazole (37 mg, 0.28 mmol) and 3-aminoquinuclidine dihydrochloride (33 mg, 0.17 mmol) in DMF (4 mL) was stirred for 10 min at room temperature, then triethylamine (0.08 mL, 0.55 mmol) was added. The resulting reaction mixture was stirred at room temperature for 12 h. The mixture was diluted with ethyl acetate and then washed with a saturated solution of sodium bicarbonate. The aqueous layer was further extracted with ethyl acetate (2×50 mL). The combined organic layers were dried ($Na_2SO_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-6-chloro-2-(4-methoxyphenyl)benzoxazole-4-carboxamide (14 mg, 25%) as a white solid: $^1$H NMR (500 MHz, $CDCl_3$) δ 9.48 (d, J=7.3 Hz, 1H), 8.18-8.10 (m, 3H), 7.68 (d, J=1.9 Hz, 1H), 7.07 (d, J=8.9 Hz, 2H), 4.40-4.32 (m, 1H), 3.93 (s, 3H), 3.60-3.50 (m, 1H), 3.20-3.05 (m, 2H), 3.00-2.95 (m, 2H), 2.87 (dd, J=14.1, 3.5 Hz, 1H), 2.20 (q, J=3.1 Hz, 1H), 215-2.00 (m, 1H), 1.85-1.80 (m, 2H), 1.74-1.57(m, 1H); MS (ESI+) m/z 412 (M+H); HPLC>99% (AUC), $t_R$=13.09 min.

Example 81

Preparation of N-(9-Methyl-9-azabicyclo[3.3.1]non-3-yl)-6-chloro-2-(4-methoxyphenyl)benzoxazole-4-carboxamide

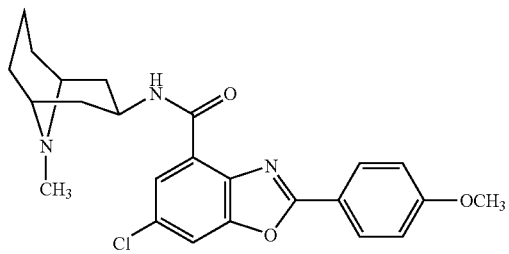

A mixture of 6-chloro-2-(4-methoxyphenyl)benzoxazole carboxylic acid (42 mg, 0.14 mmol), 1-ethyl-3-(3-dimethylaminopropyl)carbodiimide hydrochloride (60 mg, 0.31 mmol), 1-hydroxybenzotriazole (43 mg, 0.31 mmol) and 3-amino-9-methyl-9-azabicyclo[3.3.1]nonane dihydrochloride (43 mg, 0.19 mmol) in DMF (4 mL) was stirred for 10 min at room temperature, then triethylamine (0.08 mL, 0.55 mmol) was added. The resulting reaction mixture was stirred at room temperature for 18 h. The mixture was diluted with ethyl acetate and then washed with a saturated solution of sodium bicarbonate. The aqueous layer was further extracted with ethyl acetate (2×50 mL). The combined organic layers were washed with brine, dried ($Na_2SO_4$), filtered and concentrated. The crude material was purified by preparative TLC (silica gel, 90:9:1 ethyl acetate/methanol/concentrated ammonium hydroxide) to afford N-(9-methyl-9-azabicyclo[3.3.1]non-3-yl)-6-chloro-2-(4-methoxyphenyl)benzoxazole-4-carboxamide (11 mg, 18%) as a white solid: $^1$H NMR (500 MHz, $CDCl_3$) δ 8.98 (br s, 1H), 8.20-8.15 (m, 3H), 7.66 (d, J=1.8 Hz, 1H), 7.08 (d, J=8.7 Hz, 2H), 4.60-4.45 (m, 1H), 3.93 (s, 3H), 3.35-3.05 (m, 2H), 2.70-2.50 (m, 6H), 2.20-1.90 (m, 3H), 1.70-1.45 (m, 3H), 1.35-1.10 (m, 1H); MS (ESI+) m/z 440 (M+H); HPLC 97.8% (AUC), $t_R$=13.65 min.

Example 82

Preparation of N-(1-Azabicyclo[2.2.2]oct-3-yl)-6-bromo-2-phenylbenzoxazole-4-carboxamide

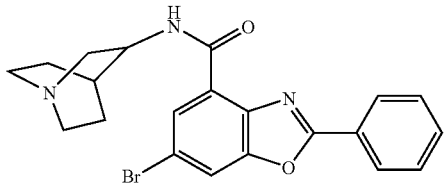

Step A: To a solution of 2-amino-3-methoxybenzoate (1.62 g, 8.97 mmol) in DMF (15 mL) was added N-bromosuccinimide (1.76 g, 9.87 mmol). The resulting mixture was stirred at room temperature for 2 h. The reaction mixture was diluted with ether and water. The aqueous layer was isolated and extracted with ether (2×100 mL). The combined organic layers were washed with water (2×100 mL), brine, dried over $Na_2SO_4$, filtered and concentrated to afford a brown solid. The crude material was purified by column chromatography (silica gel, 95:5 hexanes/ethyl acetate) to afford the desired product (2.08 g, 89%) as a light orange solid: $^1$H NMR (300 MHz, $CDCl_3$) δ 7.60 (d, J=2.1 Hz, 1H), 6.90 (d, J=2.1 Hz, 1H), 6.03 (br s, 2H), 3.86 (s, 6H); MS (ESI+) m/z 259 (M+H).

Step B: A mixture of 2-amino-5-bromo-3-methoxybenzoate (2.08 g, 8.03 mmol), 48% aqueous solution of hydrobromic acid (20 mL) and glacial acetic acid (0.75 mL) was heated to reflux for 18 h. The reaction mixture was cooled down to room temperature. A light brown solid was precipitated and the solid was filtered, washed with diethyl ether and hexanes to afford the desired compound (0.92 g, 51%) as a light brown solid: MS (ESI+) m/z 232 (M+H).

Step C: To a suspension of 2-amino-5-bromo-3-hydroxybenzoic acid hydrobromide (312 mg, 1.0 mmol) in dichloromethane (10 mL) was added pyridine (0.49 mL, 6.0 mmol) followed by benzoyl chloride (420 mg, 3.0 mmol) at room temperature. The resulting reaction mixture was stirred at room temperature for 20 min then DMAP (24 mg, 0.20 mmol) was added, and the reaction mixture was stirred room temperature overnight. The reaction was quenched with aqueous 2 N HCl (50 mL), then extracted with dichloromethane (2×100 mL). The combined organic layers were dried over Na$_2$SO$_4$, filtered and concentrated to a yellow solid. The crude was dissolved in toluene (10 mL) and the solution was treated with p-toluenesulfonic acid monohydrate (350 mg, 1.84 mmol). The reaction mixture was then heated to reflux under nitrogen for 22 h. The reaction was cooled down to room temperature, poured into water and extracted with ethyl acetate. The organic layer was separated then washed with water, brine, dried over Na$_2$SO$_4$, filtered and concentrated to a yellow solid. The crude product was purified by column chromatography (silica gel, 9:1 to 3:1 ethyl acetate/methanol) to afford the desired product (169 mg, 43%) as a yellow solid: MS (ESI+) m/z 317 (M+H).

Step D: A mixture of 6-bromo-2-phenylbenzoxazole-4-carboxylic acid from Step C (82 mg, 0.26 mmol), 1-ethyl-3-(3-dimethylaminopropyl)carbodiimide hydrochloride (99 mg, 0.52 mmol), 1-hydroxybenzotriazole (70 mg, 0.52 mmol) and 3-aminoquinuclidine dihydrochloride (62 mg, 0.31 mmol) in DMF (5 mL) was stirred for 10 min at room temperature, then triethylamine (0.10 mL, 1.03 mmol) was added. The resulting reaction mixture was stirred at room temperature for 12 h. The mixture was diluted with ethyl acetate (50 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(1-azabicyclo[2.2.2]oct-3-yl)-6-bromo-2-phenylbenzoxazole-4-carboxamide (61 mg, 55%) as a white solid: $^1$H NMR (500 MHz, CDCl$_3$) δ 9.45 (d, J=7.3 Hz, 1H), 8.32 (d, J=1.9 Hz, 1H), 8.25-8.15 (m, 2H), 7.89 (d, J=1.8 Hz, 1H), 7.65-7.52 (m, 3H), 4.40-4.25 (m, 1H), 3.60-3.45 (m, 1H), 3.18-3.12 (m, 2H), 2.90-2.80 (m, 2H), 2.83 (dd, J=14.3, 3.9 Hz, 1H), 2.22-2.15 (m, 1H), 2.10-2.00 (m, 2H), 1.85-1.60 (m, 2H); MS (ESI+) m/z 426 (M+H); HPLC 98.1% (AUC), t$_R$=12.98 min.

Example 83

Preparation of N-(9-Methyl-9-azabicyclo[3.3.1]non-3-yl)-6-bromo-2-phenylbenzoxazole-4-carboxamide

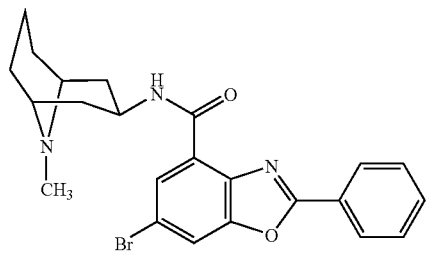

A mixture of 6-bromo-2-phenylbenzoxazole-4-carboxylic acid (82 mg, 0.26 mmol), 1-ethyl-3-(3-dimethylaminopropyl)carbodiimide hydrochloride (99 mg, 0.52 mmol), 1-hydroxybenzotriazole (70 mg, 0.52 mmol) and 3-amino-9-methyl-9-azabicyclo[3.3.1]nonane (48 mg, 0.31 mmol) in DMF (5 mL) was stirred for 10 min at room temperature, then triethylamine (0.10 mL, 1.03 mmol) was added. The resulting reaction mixture was stirred at room temperature overnight. The mixture was diluted with diethyl ether (50 mL) and then washed with a saturated solution of sodium bicarbonate. The aqueous layer was further extracted with ethyl acetate (2×50 mL). The combined organics were dried (Na$_2$SO$_4$), filtered and concentrated under reduced pressure. During the concentration, a white solid was crashed out. The solid was isolated, washed with ether and dried under high vacuum to afford N-(9-methyl-9-azabicyclo[3.3.1]non-3-yl)-6-bromo-2-phenylbenzoxazole-4-carboxamide (40 mg, 34%) as a white solid: $^1$H NMR (500 MHz, CDCl$_3$) δ 8.89 (d, J=7.3 Hz, 1H), 8.34 (d, J=1.8 Hz, 1H), 8.25-8.20 (m, 2H), 7.86 (d, J=1.8 Hz, 1H), 7.65-7.55 (m, 3H), 4.60-4.52 (m, 1H), 3.12 (d, J=10.8 Hz, 2H), 2.70-2.60 (m, 2H), 2.54 (s, 3H), 2.20-1.95 (m, 2H), 1.62-1.52 (m, 2H), 1.50-1.45 (m, 2H), 1.20-1.10 (m, 2H); MS (ESI+) m/z 454 (M+H); HPLC>99% (AUC), t$_R$=13.52 min.

Example 84

Preparation of N-(1-Azabicyclo[2.2.2]oct-3-yl)-6-bromo-2-p-tolylbenzoxazole-4-carboxamide

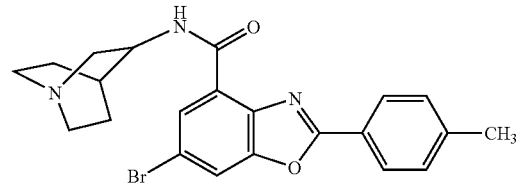

Step A: To a suspension of 2-amino-5-bromo-3-hydroxybenzoic acid hydrobromide (290 mg, 0.93 mmol) in dichloromethane (10 mL) was added pyridine (0.46 mL, 5.60 mmol) followed by p-tolyl chloride (431 mg, 2.80 mmol) at room temperature. The resulting reaction mixture was stirred at room temperature for 20 min and then DMAP (22 mg, 0.19 mmol) was added to the reaction mixture. The resulting reaction mixture was stirred at room temperature overnight. The reaction was quenched with water (50 mL), then extracted with dichloromethane (2×50 mL). The combined organic layers were dried over Na$_2$SO$_4$, filtrated and concentrated to afforded a pinkish solid, which was dissolved in toluene (10 mL) and the solution treated with p-toluenesulfonic acid monohydrate (333 mg, 1.76 mmol). The reaction mixture was then heated to reflux under nitrogen for 22 h. The reaction was cooled down to room temperature, poured into water and extracted with ethyl acetate. The organic layer was separated, washed with water, brine, dried over Na$_2$SO$_4$, filtered and concentrated to a yellow solid. The crude product was purified by column chromatography (silica gel, 9:1 to 3:1 ethyl acetate/methanol) to afford the desired product (173 mg, 56%) as a yellow solid: MS (ESI+) m/z 332 (M+H).

Step B: A mixture of 6-bromo-2-p-tolylbenzoxazole-4-carboxylic acid (85 mg, 0.26 mmol), 1-ethyl-3-(3-dimethylaminopropyl)carbodiimide hydrochloride (60 mg, 0.31 mmol), 1-hydroxybenzotriazole (60 mg, 0.31 mmol) and 3-aminoquinuclidine dihydrochloride (61 mg, 0.31 mmol) in DMF (5 mL) was stirred 10 min at room temperature, then triethylamine (0.12 mL, 1.02 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×25 mL). The combined organic layers were dried (Na$_2$SO$_4$), filtered and concentrated under reduced pressure. The crude material was purified by column chromatography (silica gel, 90:9:1 ethyl acetate/methanol/concentrated ammonium hydroxide) to afford N-(1-azabicyclo[2.2.2]oct-3-yl)-6-bromo-2-p-tolylbenzoxazole-4-carboxamide (60 mg, 54%) as a white solid: $^1$H NMR (500 MHz, CDCl$_3$) δ 9.48 (d, J=7.3 Hz, 1H), 8.30 (d, J=1.8 Hz, 1H), 8.10 (d, J=8.3 Hz, 2H), 7.85 (d, J=1.8 Hz, 1H), 7.37 (d, J=8.0 Hz, 2H), 4.35-4.25 (m, 1H), 3.60-3.45 (m, 1H), 3.15-3.00 (m, 2H), 2.95-2.82 (m, 2H), 2.80 (dd, J=14.2, 4.1 Hz, 1H), 2.48 (s, 3H), 2.14 (q, J=3.1 Hz, 1H), 2.10-2.00 (m, 1H), 1.80-1.60 (m, 3H); MS (ESI+) m/z 440 (M+H); HPLC 98.6% (AUC), $t_R$=13.51 min.

Example 85

Preparation of N-(9-Methyl-9-azabicyclo[3.3.1]non-3-yl)-6-bromo-2-p-tolylbenzoxazole-4-carboxamide

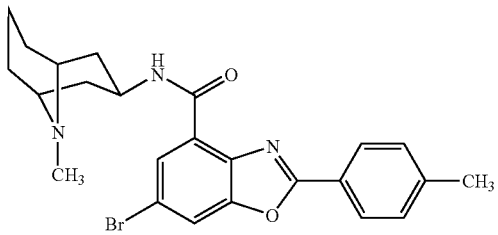

Step A: To a suspension of 2-amino-5-bromo-3-hydroxybenzoic acid hydrobromide (290 mg, 0.93 mmol) in dichloromethane (10 mL) was added pyridine (0.46 mL, 5.60 mmol) followed by p-toluoyl chloride (431 mg, 2.80 mmol) at room temperature. The resulting reaction mixture was stirred at room temperature for 20 min and then DMAP (22 mg, 0.19 mmol) was added to the reaction mixture. The resulting reaction mixture was stirred at room temperature overnight. The reaction was quenched with water (50 mL). The organic layer was separated and the aqueous layer was extracted with dichloromethane (2×50 mL). The combined organic layers were dried over Na$_2$SO$_4$, filtrated and concentrated to afford a pinkish solid. The crude was dissolved in toluene (10 mL) and the solution was treated with p-toluenesulfonic acid monohydrate (333 mg, 1.76 mmol). The reaction mixture was then heated to reflux under nitrogen for 22 h. The reaction was cooled down to room temperature, poured into water and extracted with ethyl acetate. The combined organic layers were washed with water, brine, dried over Na$_2$SO$_4$, filtered and concentrated to a yellow solid. The crude product was purified by column chromatography (silica gel, 9:1 to 3:1 ethyl acetate/methanol) to afford the desired product (173 mg, 56%) as a yellow solid: MS (ESI+) m/z 332 (M+H).

Step B: A mixture of 6-bromo-2-p-tolylbenzoxazole-4-carboxylic acid (85 mg, 0.26 mmol), 3-amino-9-methyl-9-azabicyclo[3.3.1]nonane dihydrochloride (85 mg, 0.31 mmol), 1-hydroxybenzotriazole (69 mg, 0.51 mmol) and 1-ethyl-3-(3-dimethylaminopropyl)carbodiimide hydrochloride (98 mg, 0.51 mmol) in DMF (5 mL) was stirred for 10 min at room temperature, then triethylamine (0.12 mL, 1.02 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organic layers were dried (Na$_2$SO$_4$), filtered and concentrated under reduced pressure. The crude material was purified by column chromatography (silica gel, 90:9:1 ethyl acetate/methanol/concentrated ammonium hydroxide) followed by recrystallization from acetonitrile to afford N-(9-methyl-9-azabicyclo[3.3.1]non-3-yl)-6-bromo-2-p-tolylbenzoxazole-4-carboxamide (30 mg, 25%) as a white solid: $^1$H NMR (300 MHz, CDCl$_3$) δ 8.94 (d, J=7.3 Hz, 1H), 8.33 (d, J=1.8 Hz, 1H), 8.12 (d, J=8.2 Hz, 2H), 7.83 (d, J=1.9 Hz, 1H), 7.39 (d, J=8.0 Hz, 2H), 4.63-4.50 (m, 1H), 3.12 (d, J=10.6 Hz, 2H), 2.70-2.55 (m, 2H), 2.54 (s, 3H), 2.48 (s, 3H), 2.20-1.95 (m, 2H), 1.65-1.45 (m, 4H), 1.20-1.10 (m, 2H); MS (ESI+) m/z 468 (M+H); HPLC 98.4% (AUC), $t_R$=14.06 min.

Example 86

Preparation of N-(1-Azabicyclo[2.2.2]oct-3-yl)-6-bromo-2-(4-methoxyphenyl)benzoxazole-4-carboxamide

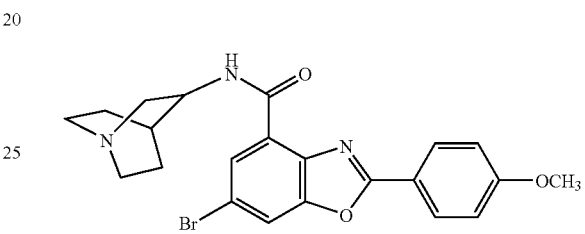

Step A: To a suspension of 2-amino-5-bromo-3-hydroxybenzoic acid (311 mg, 1.00 mmol) in dichloromethane (10 mL) was added pyridine (0.48 mL, 6.00 mmol) followed by p-anisoyl chloride (512 mg, 3.00 mmol) at room temperature. The resulting reaction mixture was stirred at room temperature for 20 min, then DMAP (24 mg, 0.20 mmol) was added and the reaction mixture was stirred at room temperature overnight. The reaction was quenched with aqueous 2 N HCl (50 mL). The reaction mixture was extracted with ethyl acetate, and the organic layer was washed with brine, dried over Na$_2$SO$_4$, filtered and concentrated to give a yellow solid. The crude was dissolved in toluene (10 mL) and the solution was treated with p-toluenesulfonic acid monohydrate (328 mg, 1.72 mmol). The reaction mixture was then heated to reflux under nitrogen overnight. The reaction was cooled down to room temperature, poured into water and extracted with ethyl acetate. The combined organic layers were washed with water, brine, dried over Na$_2$SO$_4$, filtered and concentrated to give a yellow solid. The crude product was purified by column chromatography (silica gel, 9:1 to 3:1 ethyl acetate/methanol) to afford the desired product (172 mg, 49%) as an off-white solid: MS (ESI+) m/z 348 (M+H).

Step B: A mixture of 6-bromo-2-(4-methoxyphenyl)benzoxazole-4-carboxylic acid from Step A (86 mg, 0.25 mmol), 1-ethyl-3-(3-dimethylaminopropyl)carbodiimide hydrochloride (94 mg, 0.49 mmol), 1-hydroxybenzotriazole (67 mg, 0.49 mmol) and (±)-3-aminoquinuclidine dihydrochloride (59 mg, 0.30 mmol) in DMF (5 mL) was stirred 10 min at room temperature, then triethylamine (0.10 mL, 0.99 mmol) was added. The resulting reaction mixture was stirred at room temperature for 12 h. The mixture was diluted with ethyl acetate and then washed with a saturated solution of sodium bicarbonate. The aqueous layer was further extracted with ethyl acetate (2×100 mL). The combined organic layers were dried (Na$_2$SO$_4$) and concentrated. The crude material was purified by column chromatography (silica gel, 90:9:1 ethyl acetate/methanol/concentrated ammonium hydroxide) to afford N-(1-azabicyclo[2.2.2]oct-3-yl)-6-bromo-2-(4-methoxyphenyl)benzoxazole-4-carboxamide (56 mg, 50%) as a white solid: $^1$H NMR (500 MHz, CDCl$_3$) δ 9.47 (d, J=7.0 Hz, 1H), 8.29 (d, J=1.7 Hz, 1H), 8.20-8.10 (m, 2H), 7.83 (d, J=1.7 Hz, 1H), 7.06 (d, J=8.8 Hz, 2H), 4.45-4.35 (m, 1H), 3.93 (s, 3H), 3.55-3.45 (m, 1H), 3.15-3.00 (m, 2H), 2.95-2.90 (m, 2H), 2.85-2.75 (m, 1H), 2.20-2.15 (m, 1H), 2.10-2.00 (m, 1H), 1.80-1.75 (m, 2H), 1.70-1.55 (m, 1H); MS (ESI+) m/z 456 (M+H); HPLC 96.9% (AUC), t$_R$=14.64 min.

Example 87

Preparation of N-(9-Methyl-9-azabicyclo[3.3.1]non-3-yl)-6-bromo-2-(4-methoxyphenyl)benzoxazole-4-carboxamide

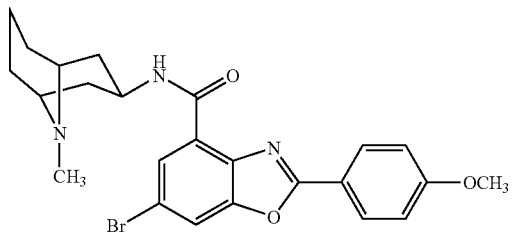

A mixture of 6-bromo-2-(4-methoxyphenyl)benzoxazole carboxylic acid (86 mg, 0.25 mmol), 1-ethyl-3-(3-dimethylaminopropyl)carbodiimide hydrochloride (94 mg, 0.49 mmol), 1-hydroxybenzotriazole (67 mg, 0.49 mmol) and 3-amino-9-methyl-9-azabicyclo[3.3.1]nonane dihydrochloride (67 mg, 0.30 mmol) in DMF (5 mL) was stirred for 10 min at room temperature, then triethylamine (0.100 mL, 0.99 mmol) was added. The resulting reaction mixture was stirred at room temperature for 18 h. The mixture was diluted with ethyl acetate and then washed with a saturated solution of sodium bicarbonate. The aqueous layer was further extracted with ethyl acetate (2×100 mL). The combined organic layers were washed with brine (2×100 mL), dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-6-bromo-2-(4-methoxyphenyl)benzoxazole-4-carboxamide (32 mg, 27%) as a white solid: $^1$H NMR (500 MHz, CDCl$_3$) δ 8.99 (br s, 1H), 8.30 (d, J=1.8 Hz, 1H), 8.17 (d, J=8.8 Hz, 2H), 7.81 (d, J=1.8 Hz, 1H), 7.10-7.05 (m, 2H), 4.60-4.55 (m, 1H), 3.93 (s, 3H), 3.25-3.15 (m, 2H), 2.70-2.55 (m, 5H), 2.40-2.00 (m, 3H), 1.70-1.20 (m, 5H); MS (ESI+) m/z 484 (M+H); HPLC>99% (AUC), t$_R$=15.30 min.

Example 88

Preparation of N-(9-Methyl-9-azabicyclo[3.3.1]non-3-yl)-6-amino-2-phenylbenzoxazole-4-carboxamide Dihydrochloride

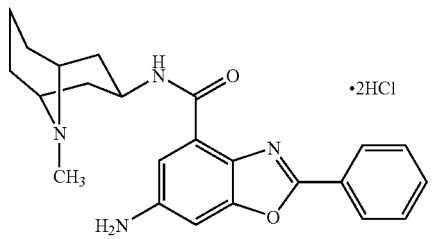

Step A: A dry flask was charged with N-(9-methyl-9-azabicyclo[3.3.1]non-3-yl)-6-bromo-2-phenylbenzoxazole-4-carboxamide (454 mg, 1.00 mmol), tert-butyl carbamate (176 mg, 1.50 mmol), Pd(OAc)$_2$ (22 mg, 0.10 mmol), xantphos (87 mg, 0.15 mmol) and cesium carbonate (489 mg, 1.50 mmol) and 1,4-dioxane (10 mL). The mixture was degassed with argon. The resulting reaction mixture was heated at 100° C. for 12 h. The reaction mixture was cooled to room temperature, and then diluted with methylene chloride and water. The reaction mixture was extracted with methylene chloride (2×50 mL). The combined organic layers were washed with brine, dried (Na$_2$SO$_4$) and concentrated under reduced pressure. The crude material was purified by column chromatography (silica gel, 90:9:1 methylene chloride/methanol/concentrated ammonium hydroxide) to afford the carbamate (228 mg, 70%) as an off-white solid: $^1$H NMR (500 MHz, CDCl$_3$) δ 9.09 (br s, 1H), 8.40 (s, 1H), 8.25-8.15 (m, 2H), 7.68 (d, J=1.9 Hz, 1H), 7.65-7.54 (m, 3H), 7.26 (s, 1H), 6.76 (s, 1H), 4.60-4.55 (m, 1H), 3.40-3.20 (m, 2H), 2.90-2.65 (m, 6H), 2.15-2.00 (m, 3H), 1.80-1.70 (m, 3H), 1.58 (s, 9H); MS (ESI+) m/z 491 (M+H).

Step B: To a solution of the carbamate from Step A (220 mg, 0.47 mmol) in methylene chloride (4 mL) was added TFA (2 mL) at 0° C. The reaction mixture was allowed to warm to room temperature and stirred for 2 h. The reaction mixture was concentrated under reduced pressure. The residue was dissolved in methanol and methylene chloride, and the solution was diluted with diethyl ether. The resulting precipitate was isolated by filtration, dissolved in methylene chloride and treated with aqueous 10% Na$_2$CO$_3$. The aqueous layer was extracted with methylene chloride (3×50 mL). The combined organic layers were washed with brine, dried (Na$_2$SO$_4$) and concentrated under reduced pressure to afford a yellow solid. The crude material was purified by preparative TLC (90:9:1 methylene chloride/methanol/concentrated ammonium hydroxide) to afford the desired product (121 mg, 73%) as a light yellow solid: $^1$H NMR (500 MHz, CDCl$_3$) δ 9.09 (br s, 1H), 8.40 (s, 1H), 8.25-8.15 (m, 2H), 7.68 (d, J=1.9 Hz, 1H), 7.65-7.54 (m, 3H), 7.26 (s, 1H), 6.76 (s, 1H), 4.60-4.55 (m, 1H), 3.40-3.20 (m, 2H), 2.90-2.65 (m, 6H), 2.15-2.00 (m, 3H), 1.80-1.70 (m, 4H); MS (ESI+) m/z 391 (M+1).

Step C: To a solution of the amide from Step B (120 mg, 0.31 mmol) in methanol (1.0 mL) was added a solution of HCl in diethyl ether (1 N, 0.93 mL, 0.93 mmol) at room temperature slowly. The reaction mixture was diluted with diethyl ether. The resulting solid was filtered and washed with diethyl ether to afford N-(9-methyl-9-azabicyclo[3.3.1]non-6-amino-2-phenylbenzoxazole-4-carboxamide dihydrochloride (54 mg, 38%) as a yellow solid: $^1$H NMR (500 MHz, DMSO-d$_6$) δ 10.48 (br s, 0.4H), 9.69 (br s, 0.6H), 9.16 (d, J=5.8 Hz, 0.6H), 8.88 (d, J=6.9 Hz, 0.4H), 8.23-8.15 (m, 2H), 7.70-7.60 (m, 3H), 7.55-7.50 (m, 1H), 7.36 (s, 1H), 4.90-4.35 (m, 4H), 3.70-3.65 (m, 1.4H), 3.60-3.55 (m, 0.6H), 2.90-2.80 (m, 4H), 2.75-2.60 (m, 2H), 2.40-2.10 (m, 3H), 1.95-1.82 (m, 2H), 1.60-1.50 (m, 2H); MS (ESI+) m/z 391 (M+H); HPLC>99% (AUC), t$_R$=11.49 min.

Example 89

Preparation of N-(1-Azabicyclo[2.2.2]oct-3-yl)-5-bromo-2-phenylbenzoxazole-4-carboxamide

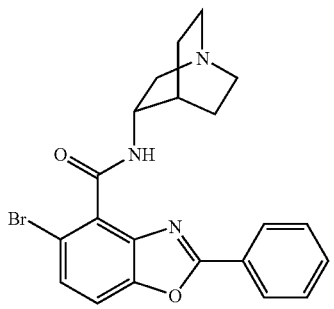

Step A: To a mixture of 3-methoxy-2-nitrobenzoic acid (2.5 g, 12.7 mmol) and silver sulfate (2.0 g, 6.4 mmol) in concd sulfuric acid (50 mL) was added bromine (2.03 g, 12.7 mmol), then the reaction mixture was stirred at room temperature in the dark for 2 h. Water was then added, and the resulting precipitate was collected. The solid was dissolved in acetone and the residue was filtered off. The filtrate was dried (MgSO$_4$), filtered and concentrated to afford the brominated product (2.64 g, 75%) as an off-white solid: $^1$H NMR (500 MHz, DMSO-d$_6$) δ 14.50 (br s, 1H), 7.92 (d, J=9.0 Hz, 1H), 7.42 (d, J=9.0 Hz, 1H), 3.93 (s, 3H).

Step B: A mixture of the brominated product from Step A (1.3 g, 4.71 mmol) in hydrobromic acid (48% in H$_2$O, 7 mL) and glacial acetic acid (0.6 mL) was refluxed for 12 h. After cooled to room temperature, the reaction mixture was neutralized by the addition of 6 N NaOH and the aqueous layer was extracted with dichloromethane. The combined organics were dried (Na$_2$SO$_4$), filtered and concentrated. The crude material was purified by column chromatography (silica gel, 9:1 to 3:1 ethyl acetate/methanol) to afford the desired product (1.6 g, quantitative) as a brown solid: $^1$H NMR (300 MHz, DMSO-d$_6$) δ 11.5 (br s, 1H), 7.40 (d, J=8.7 Hz, 1H), 6.85 (d, J=8.7 Hz, 1H), 3.72 (s, 1H); MS (ESI−) m/z 260 (M−H).

Step C: To a solution of 2-nitro-6-bromo-3-hydroxybenzoic acid from Step B (1.23 g, 4.71 mmol) in THF (110 mL) was added a solution of sodium hydrosulfite (4.80 g, 23.6 mmol) in water (60 mL), then the resulting reaction mixture was warmed to 60° C. for 0.5 h. After cooled to room temperature, the organic layer was separated and the aqueous layer was extracted with ethyl acetate (2×80 mL). The combined organics were washed with brine, dried (Na$_2$SO$_4$), filtered and concentrated. The crude material was purified by column chromatography (silica gel, 9:1 to 3:1 ethyl acetate/methanol) to afford amino acid (0.51 g, 47%) as a brown solid: $^1$H NMR (500 MHz, DMSO-d$_6$) δ 6.56 (d, J=8.5 Hz, 1H), 6.53 (d, J=8.5 Hz, 1H), 3.75 (s, 1H), 2.01 (s, 3H); MS (ESI+) m/z 232 (M+H).

Step D: To a suspension of 2-amino-6-bromo-3-hydroxybenzoic acid (500 mg, 2.15 mmol) in dichloromethane (15 mL) was added pyridine (1.1 mL, 12.9 mmol) followed by benzoyl chloride (0.75 mL, 6.45 mmol) at room temperature. The resulting reaction mixture was stirred at room temperature for 10 min, then DMAP (52 mg, 0.43 mmol) was added and the reaction mixture was stirred at room temperature overnight. The reaction was quenched with aqueous 2 N HCl and the solution was stirred for 30 min. The aqueous layer was extracted with dichloromethane. The organic layers were washed with brine and dried over Na$_2$SO$_4$, filtered and concentrated to give a brown solid. The crude product was dissolved in toluene (15 mL) and the solution was treated with p-toluenesulfonic acid monohydrate (409 mg, 2.15 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated. The crude product was purified by column chromatography (silica gel, 9:1 to 3:1 ethyl acetate/methanol) to afford the desired product (0.30 g, 44%) as a brown solid: $^1$H NMR (500 MHz, DMSO-d$_6$) δ 12.5 (br s, 1H), 8.17 (dd, J=7.5, 2.0 Hz, 2H), 7.68-7.61 (m, 3H), 7.52-7.45 (m, 2H); MS (ESI+) m/z 318 (M+H).

Step E: A mixture of phenylbenzoxazole carboxylic acid from Step D (180 mg, 0.56 mmol), (±)-3-aminoquinuclidine dihydrochloride (134 mg, 0.67 mmol), 1-ethyl-3-(3-dimethylaminopropyl)carbodiimide hydrochloride (215 mg, 1.12 mmol) and 1-hydroxybenzotriazole (151 mg, 1.12 mmol) in DMF (2.5 mL) was stirred for 5 min at room temperature, then triethylamine (0.31 mL, 2.24 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) followed by recrystallization from ethyl acetate to afford N-(1-azabicyclo[2.2.2]oct-3-yl)-5-bromo-2-phenylbenzoxazole-4-carboxamide (20 mg, 8%) as an off-white solid: $^1$H NMR (500 MHz, CDCl$_3$) δ 8.25 (d, J=5.5 Hz, 1H), 8.24-8.21 (m, 2H), 7.68 (d, J=8.5 Hz, 1H), 7.62-7.54 (m, 3H), 7.52 (d, J=8.5 Hz, 1H), 4.38-4.28 (m, 1H), 3.53 (ddd, J=11.5, 9.5, 2.0 Hz, 1H), 3.10-2.85 (m, 4H), 2.80 (dd, J=14.0, 4.5 Hz, 1H), 2.21 (dt, J=6.0, 3.0 Hz, 1H), 2.10-2.02 (m, 1H), 1.79-1.74 (m, 2H), 1.64-1.61 (m, 1H); MS (ESI+) m/z 426 (M+H); HPLC 98.4% (AUC), t$_R$=11.29 min.

Example 90

Preparation of N-(9-Methyl-9-azabicyclo[3.3.1]non-3-yl)-5-bromo-2-phenylbenzoxazole-4-carboxamide

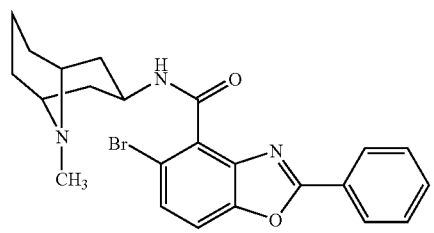

A mixture of 5-bromo-2-phenylbenzo[d]oxazole-4-carboxylic acid (180 mg, 0.56 mmol), 3-amino-9-methyl-9-azabicyclo[3.3.1]nonane dihydrochloride (152 mg, 0.67 mmol), 1-ethyl-3-(3-dimethylaminopropyl)carbodiimide hydrochloride (215 mg, 1.12 mmol) and 1-hydroxybenzotriazole (151 mg, 1.12 mmol) in DMF (2.5 mL) was stirred for 5 min at room temperature, then triethylamine (0.31 mL, 2.24 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford N-(9-methyl-9-azabicyclo[3.3.1]non-3-yl)-5-bromo-2-phenylbenzoxazole-4-carboxamide (31 mg, 12%) as a white solid: $^1$H NMR (500 MHz, CDCl$_3$) δ 8.25-8.23 (m, 2H), 7.62 (d, J=8.5 Hz, 1H), 7.60-7.53 (m, 3H), 7.48 (d, J=8.5 Hz, 1H), 7.12 (br s, 1H), 4.69-4.63 (m, 1H), 3.13 (d, J=10.0 Hz, 2H), 2.67 (td, J=12.5, 7.0 Hz, 2H), 2.54 (s, 3H), 2.05-1.93 (m, 3H), 1.60-1.52 (m, 1H), 1.43 (t, J=11.0 Hz, 2H), 1.15-1.10 (m, 2H); MS (ESI+) m/z 454 (M+H); HPLC 98.4% (AUC), t$_R$=11.89 min.

Example 91

Preparation of N-(9-Methyl-9-azabicyclo[3.3.1]non-3-yl)-7-bromo-2-phenylbenzoxazole-4-carboxamide

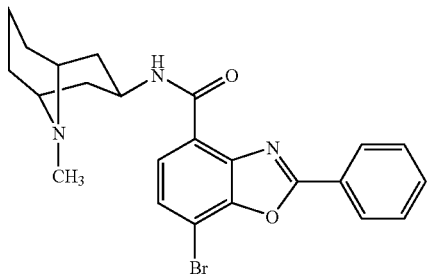

Step A: To a suspension of 3-hydroxy-2-nitrobenzoic acid (2.0 g, 10.9 mmol) in acetic acid (4 mL) was added a solution of bromine (0.59 mL, 11.4 mmol) in acetic acid (3 mL) dropwise via a addition funnel over 0.5 h, then the reaction mixture was stirred in the dark at 60° C. for 12 h. After cooled to room temperature, the reaction mixture was concentrated to give the desired product as a yellow solid (contained 30% of di-brominated products). The crude product was dissolved in THF (90 mL) and a solution of sodium hydrosulfite (11.2 g, 54.5 mmol) in water (50 mL) was added. The reaction mixture was stirred at 60° C. for 40 min. After the reaction mixture was cooled to room temperature, the aqueous layer was separated and extracted with ethyl acetate. The combined organics were dried (Na$_2$SO$_4$), filtered and concentrated. The crude material was purified by column chromatography (silica gel, 4:1 ethyl acetate/hexane to 3:1 ethyl acetate/methanol) to afford the desired product (1.17 g, 46%) as a pale-brown solid (contained 20% isomer): $^1$H NMR (500 MHz, DMSO-d$_6$) δ 9.20 (br s, 1H), 7.21 (d, J=8.5 Hz, 1H), 6.65 (d, J=8.5 Hz, 1H), 3.32 (s, 3H).

Step B: To a suspension of 2-amino-4-bromo-3-hydroxybenzoic acid (1.16 g, 5.00 mmol) in dichloromethane (40 mL) was added pyridine (2.4 mL, 30 mmol) followed by benzoyl chloride (1.7 mL, 15 mmol) at room temperature. The resulting reaction mixture was stirred at room temperature for 10 min, then DMAP (122 mg, 1.0 mmol) was added and the reaction mixture was stirred at room temperature overnight. The reaction was quenched with aqueous 2 N HCl and the solution was stirred for 30 min. The aqueous layer was extracted with dichloromethane. The organic layers were washed with brine and dried over Na$_2$SO$_4$, filtered and concentrated to give a brown solid. The crude product was dissolved in toluene (35 mL) and the solution was treated with p-toluenesulfonic acid monohydrate (950 mg, 5.0 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated. The crude product was purified by column chromatography (silica gel, 9:1 to 3:1 ethyl acetate/methanol) to afford the desired product (0.75 g, 47%) as a pale-brown solid: $^1$H NMR (500 MHz, DMSO-d$_6$) δ 13.50 (br s, 1H), 8.25-8.20 (m, 2H), 7.86-7.80 (m, 2H), 7.68-7.58 (m, 3H); MS (ESI+) m/z 318 (M+H).

Step C: A mixture of phenylbenzoxazole carboxylic acid from Step B (200 mg, 0.62 mmol), 3-amino-9-methyl-9-azabicyclo[3.3.1]nonane dihydrochloride (100 mg, 0.62 mmol), 1-ethyl-3-(3-dimethylaminopropyl)carbodiimide hydrochloride (237 mg, 1.24 mmol) and 1-hydroxybenzotriazole (167 mg, 1.24 mmol) in DMF (2.5 mL) was stirred for 5 min at room temperature, then triethylamine (0.34 mL, 2.48 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) followed by semi-preparative HPLC to afford N-(9-methyl-9-azabicyclo[3.3.1]non-3-yl)-7-bromo-2-phenylbenzoxazole-4-carboxamide (44 mg, 16%) as a white solid: $^1$H NMR (500 MHz, CDCl$_3$) δ 8.86 (d, J=7.5 Hz, 1H), 8.30-8.28 (m, 2H), 8.10 (d, J=8.5 Hz, 1H), 7.68-7.57 (m, 4H), 4.61-4.55 (m, 1H), 3.12 (d, J=10.5 Hz, 2H), 2.67-2.60 (m, 2H), 2.54 (s, 3H), 2.23-1.98 (m, 3H), 1.63-1.58 (m, 1H), 1.49 (t, J=10.5 Hz, 2H), 1.21-1.14 (m, 2H); MS (ESI+) m/z 454 (M+H); HPLC>99% (AUC), t$_R$=13.56 min.

Example 92

Preparation of N-(1-Azabicyclo[2.2.2]oct-3-yl)-7-bromo-2-phenylbenzoxazole-4-carboxamide

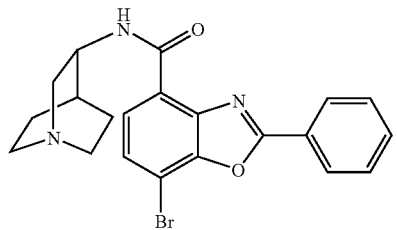

A mixture of 7-bromo-2-phenylbenzo[d]oxazole-4-carboxylic acid (200 mg, 0.62 mmol), (±)-3-aminoquinuclidine dihydrochloride (148 mg, 0.74 mmol), 1-ethyl-3-(3-dimethylaminopropyl)carbodiimide hydrochloride (237 mg, 1.24 mmol) and 1-hydroxybenzotriazole (167 mg, 1.24 mmol) in DMF (2.5 mL) was stirred 5 min at room temperature, then triethylamine (0.34 mL, 2.48 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) followed by semi-preparative HPLC to afford N-(1-azabicyclo[2.2.2]oct-3-yl)-7-bromo-2-phenylbenzoxazole-4-carboxamide (34 mg, 13%) as a white solid: $^1$H NMR (500 MHz, $CDCl_3$) δ 9.41 (d, J=7.0 Hz, 1H), 8.29-8.26 (m, 2H), 8.09 (d, J=8.5 Hz, 1H), 7.66-7.57 (m, 4H), 4.31-4.27 (m, 1H), 3.51 (ddd, J=11.5, 9.5, 2.0 Hz, 1H), 3.15-2.85 (m, 4H), 2.81 (dd, J=14.0, 4.0 Hz, 1H), 2.17-2.14 (m, 1H), 2.07-2.02 (m, 1H), 1.79-1.61 (m, 3H); MS (ESI+) m/z 426 (M+H); HPLC>99% (AUC), $t_R$=13.09 min.

Example 93

Preparation of N-(1-Azabicyclo[2.2.2]oct-3-yl)-6-iodo-2-phenylbenzoxazole-4-carboxamide

Step A: To a solution of methyl 2-amino-3-methoxybenzoate (2.00 g, 11.0 mmol) in ethanol (25 mL) was added silver sulfate (3.61 g, 11.6 mmol). To the above mixture was added iodine (2.94 g, 11.6 mmol). The resulting mixture was stirred at room temperature for 3 h. The reaction mixture was diluted with methylene chloride and water. The aqueous layer was separated and extracted with methylene chloride (2×100 mL). The combined organic layers were washed with a saturated solution of sodium hydrogen sulfite (2×100 mL), brine, dried over $Na_2SO_4$, filtered and concentrated to afford a dark brown solid. The crude material was purified by column chromatography (silica gel, 95:5 hexanes/ethyl acetate) to afford the desired product (2.49 g, 74%) as an off-white solid: $^1$H NMR (300 MHz, $CDCl_3$) δ 7.60 (d, J=2.1 Hz, 1H), 6.90 (d, J=2.1 Hz, 1H), 6.03 (br s, 2H), 3.86 (s, 6H); MS (ESI+) m/z 308 (M+H).

Step B: To a mixture of methyl 2-amino-5-iodo-3-methoxybenzoate from Step A (307 mg, 1.00 mmol) in methylene chloride (2.5 mL) was added a solution of boron tribromide (2.2 mL, 1.0 M in $CH_2Cl_2$, 2.2 mmol) slowly at −78° C. and stirred at −78° C. for 30 min, then at 0° C. for 1 h and at room temperature for 10 h. The reaction was quenched with methanol and concentrated to afford the desired product (0.31 g, quantitative) as a brown solid: $^1$H NMR (300 MHz, DMSO-$d_6$) δ 10.10 (br s, 1H), 7.48 (d, J=2.0 Hz, 1H), 7.03 (d, J=2.0 Hz, 1H), 4.80 (br s, 3H); MS (ESI+) m/z 280 (M+H).

Step C: To a suspension of 2-amino-5-iodo-3-hydroxybenzoic acid (300 mg, 1.0 mmol) in dichloromethane (10 mL) was added pyridine (0.25 mL, 3.0 mmol) followed by benzoyl chloride (428 mg, 3.1 mmol) at room temperature. The resulting reaction mixture was stirred at room temperature for 20 min then DMAP (25 mg, 0.20 mmol) was added, and the reaction mixture was stirred at room temperature overnight. The reaction was quenched with aqueous 2 N HCl (50 mL). The reaction mixture was extracted with dichloromethane. The combined organic layers were dried over $Na_2SO_4$, filtered and concentrated to give a yellow solid. The crude was dissolved in toluene (10 mL) and the solution was treated with p-toluenesulfonic acid monohydrate (298 mg, 1.57 mmol). The reaction mixture was then heated to reflux under nitrogen for 24 h. The reaction was cooled down to room temperature, poured into water and extracted with ethyl acetate. The organic layer was separated then washed with water, brine, dried over $Na_2SO_4$, filtered and concentrated to give a yellow solid. The crude product was purified by column chromatography (silica gel, 9:1 to 3:1 ethyl acetate/methanol) to afford the desired product (158 mg, 42%) as an off-white solid: $^1$H NMR (500 MHz, DMSO-$d_6$) δ 8.49 (d, J=1.6 Hz, 1H), 8.25-8.20 (m, 2H), 8.16 (d, J=1.6 Hz, 1H), 7.70-7.60 (m, 3H); MS (ESI+) m/z 366 (M+H).

Step D: A mixture of 6-iodo-2-phenylbenzoxazole-4-carboxylic acid from Step C (75 mg, 0.21 mmol), 1-ethyl-3-(3-dimethylaminopropyl)carbodiimide hydrochloride (78 mg, 0.41 mmol), 1-hydroxybenzotriazole (55 mg, 0.41 mmol) and (±)-3-aminoquinuclidine dihydrochloride (50 mg, 0.25 mmol) in DMF (5 mL) was stirred for 10 min at room temperature, then triethylamine (0.08 mL, 0.82 mmol) was added. The resulting reaction mixture was stirred at room temperature for 12 h. The mixture was diluted with ethyl acetate (50 mL), and then washed with a saturated solution of sodium bicarbonate. The aqueous layer was further extracted with ethyl acetate (3×50 mL). The combined organics were dried ($Na_2SO_4$), filtered and concentrated. The crude material was purified by column chromatography (silica gel, 90:9:1 methylene chloride/methanol/concentrated ammonium hydroxide) to afford N-(1-azabicyclo[2.2.2]oct-3-yl)-6-iodo-2-phenylbenzoxazole-4-carboxamide (52 mg, 53%) as an off-white solid: $^1$H NMR (500 MHz, $CDCl_3$) δ 9.44 (d, J=7.1 Hz, 1H), 8.49 (d, J=1.5 Hz, 1H), 8.25-8.15 (m, 2H), 8.08 (d, J=1.6 Hz, 1H), 7.65-7.52 (m, 3H), 4.35-4.30 (m, 1H), 3.60-3.50 (m, 1H), 3.16-3.05 (m, 2H), 3.00-2.90 (m, 2H), 2.85 (dd, J=14.2, 3.5 Hz, 1H), 2.22-2.17 (m, 1H), 2.12-2.05 (m, 1H), 1.85-1.78 (m, 2H), 1.75-1.63 (m, 1H); MS (ESI+) m/z 474 (M+H); HPLC>99% (AUC), $t_R$=13.41 mm.

Example 94

Preparation of N-(9-Methyl-9-azabicyclo[3.3.1]non-3-yl)-6-iodo-2-phenylbenzoxazole-4-carboxamide

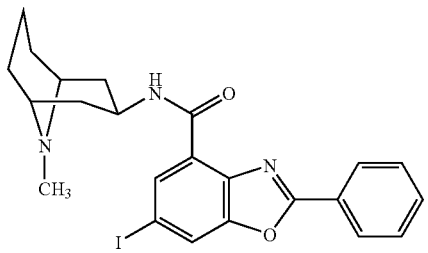

A mixture of 6-iodo-2-phenylbenzoxazole-4-carboxylic acid (75 mg, 0.21 mmol), 1-ethyl-3-(3-dimethylaminopropyl)carbodiimide hydrochloride (78 mg, 0.41 mmol), 1-hydroxybenzotriazole (55 mg, 0.41 mmol) and 3-amino-9-methyl-9-azabicyclo[3.3.1]nonane dihydrochloride (69 mg, 0.25 mmol) in DMF (5 mL) was stirred 10 min at room temperature, then triethylamine (0.10 mL, 0.82 mmol) was added. The resulting reaction mixture was stirred at room temperature overnight. The mixture was diluted with diethyl ether (50 mL) and then washed with a saturated solution of sodium bicarbonate. The aqueous layer was further extracted with ethyl acetate (2×50 mL). The combined organics were dried ($Na_2SO_4$), filtered and concentrated under reduced pressure. The crude material was purified by column chromatography (silica gel, 90:9:1 methylene chloride/methanol/concentrated ammonium hydroxide) followed by recrystallization from acetonitrile to afford N-(9-methyl-9-azabicyclo[3.3.1]non-3-yl)-6-iodo-2-phenylbenzoxazole-4-carboxamide (64 mg, 63%) as a light yellow solid: $^1$H NMR (500 MHz, CDCl$_3$) δ 8.91 (br s, 1H), 8.52 (d, J=1.6 Hz, 1H), 8.25-8.20 (m, 2H), 8.06 (d, J=1.5 Hz, 1H), 7.65-7.55 (m, 3H), 4.65-4.52 (m, 1H), 3.32-3.10 (m, 2H), 2.70-2.50 (m, 5H), 2.20-1.20 (m, 2H), 1.65-1.45 (m, 4H), 1.25-1.10 (m, 2H); MS (ESI+) m/z 502 (M+H); HPLC>99% (AUC), $t_R$=13.83 min.

Example 95

Preparation of N-(1-Azabicyclo[2.2.2]oct-3-yl)-6-morpholine-2-phenylbenzoxazole-4-carboxamide

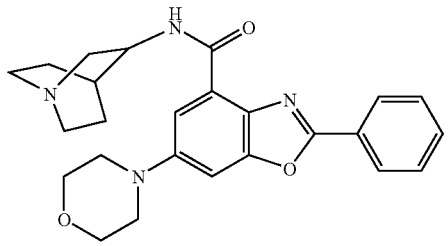

A reaction tube was charged with N-(1-azabicyclo[2.2.2]oct-3-yl)-6-bromo-2-phenylbenzoxazole-4-carboxamide (50 mg, 0.12 mmol), morpholine (0.10 mL, 1.15 mmol), Pd(OAc)$_2$ (7.0 mg, 0.03 mmol), xantphos (25 mg, 0.04 mmol) and cesium carbonate (54 mg, 0.16 mmol) in DMF (0.1 mL). The reaction tube was exposed to microwave irradiation for 14 min at 130° C. The reaction tube was thereafter cooled to room temperature and reaction mixture was extracted with methylene chloride. The combined organic layers were washed with water, brine, dried over sodium sulfate and concentrated to give a yellow solid. The crude was purified by semi-preparative HPLC to afford N-(1-azabicyclo[2.2.2]oct-3-yl)-6-morpholine-2-phenyl-benzoxazole-4-carboxamide (7 mg, 34%) as a light yellow solid: $^1$H NMR (500 MHz, CDCl$_3$) δ 9.55 (d, J=7.3 Hz, 1H), 8.20-8.15 (m, 2H), 7.82 (d, J=2.4 Hz, 1H), 7.57-7.52 (m, 3H), 7.19 (d, J=2.4 Hz, 1H), 4.35-4.27 (m, 1H), 3.91 (t, J=4.7 Hz, 4H), 3.57-3.50 (m, 1H), 3.29 (t, J=4.8 Hz, 4H), 3.15-3.00 (m, 2H), 2.95-2.90 (m, 2H), 2.85 (dd, J=14.1, 3.9 Hz, 1H), 2.17-2.14 (m, 1H), 2.13-2.03 (m, 1H), 1.80-1.73 (m, 2H), 1.70-1.60 (m, 1H); MS (ESI+) m/z 433 (M+H); HPLC 97.5% (AUC), $t_R$=20.59 min.

Example 96

Preparation of N-(1-Azabicyclo[2.2.2]oct-3-yl)-6-amino-2-phenylbenzoxazole-4-carboxamide

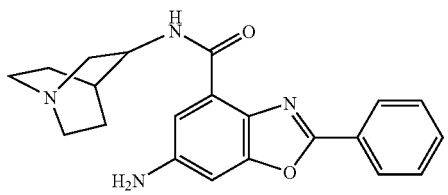

Step A: A dry flask was charged with N-(1-azabicyclo[2.2.2]oct-3-yl)-6-bromo-2-phenylbenzoxazole-4-carboxamide (300 mg, 0.70 mmol), tert-butyl carbamate (124 mg, 1.06 mmol), Pd(OAc)$_2$ (16 mg, 0.07 mmol), xantphos (61 mg, 0.11 mmol) and cesium carbonate (321 mg, 0.99 mmol) in 1,4-dioxane (3 mL). The mixture was degassed with argon. The resulting reaction mixture was heated at 100° C. for 12 h. The reaction mixture was cooled to room temperature, diluted with methylene chloride and water. The reaction mixture was extracted with methylene chloride (2×50 mL). The combined organic layers were washed with brine, dried (Na$_2$SO$_4$) and concentrated under reduced pressure. The crude material was purified by column chromatography (silica gel, 90:9:1 methylene chloride/methanol/concentrated ammonium hydroxide) to afford the compound (228 mg, 70%) as an off-white solid: $^1$H NMR (500 MHz, CDCl$_3$) δ 9.51 (d, J=7.3 Hz, 1H), 8.41 (s, 1H), 8.19 (dd, J=8.2, 1.3 Hz, 2H), 7.67 (d, J=1.9 Hz, 1H), 7.70-7.54 (m, 3H), 6.80 (s, 1H), 4.45-4.30 (m, 1H), 3.55-3.47 (m, 1H), 3.15-2.98 (m, 2H), 2.95-2.87 (m, 2H), 2.82 (dd, J=14.1, 3.9 Hz, 1H), 2.17-2.14 (m, 1H), 2.12-2.03 (m, 1H), 1.80-1.73 (m, 2H), 1.65-1.60 (m, 1H), 1.58 (s, 9H); MS (ESI+) m/z 463 (M+H).

Step B: To a solution of carbamate obtained in Step A (220 mg, 0.47 mmol) in methylene chloride (4 mL) was added TFA (2 mL) at 0° C. The reaction mixture was allowed to warm to room temperature and stirred for 2 h. The reaction mixture was concentrated under reduced pressure. The solid was dissolved in methanol and methylene chloride, and then diethyl ether was added. The resulting precipitate was isolated by filtration, dissolved in methylene chloride and treated with 10% Na$_2$CO$_3$. The aqueous layer was extracted with methylene chloride (3×50 mL). The combined organic layers were washed with brine, dried (Na$_2$SO$_4$) and concentrated under reduced pressure to afford a yellow solid. The solid was further purified by recrystallization from ethyl acetate to afford N-(1-azabicyclo[2.2.2]oct-3-yl)-6-amino-2-phenylbenzoxazole-4-carboxamide (115 mg, 67%) as a yellow solid: $^1$H NMR (500 MHz, CDCl$_3$) δ 9.55 (d, J=7.4 Hz, 1H), 8.19-8.15 (m, 2H), 7.55-7.50 (m, 4H), 6.97 (d, J=2.0 Hz, 1H), 4.30-4.24 (m, 1H), 3.99 (br s, 2H), 3.52-3.45 (m, 1H), 3.13-2.98 (m, 2H), 2.95-2.87 (m, 2H), 2.82 (dd, J=14.3, 4.0 Hz, 1H), 2.15-2.12 (m, 1H), 2.10-2.05 (m, 1H), 1.77-1.72 (m, 2H), 1.65-1.60 (m, 1H); MS (ESI+) m/z 363 (M+H); HPLC 98.3% (AUC), $t_R$=20.00 min.

Example 97

Preparation of N-(1-Azabicyclo[2.2.2]oct-3-yl)-6-acetylamino-2-phenylbenzoxazole-4-carboxamide

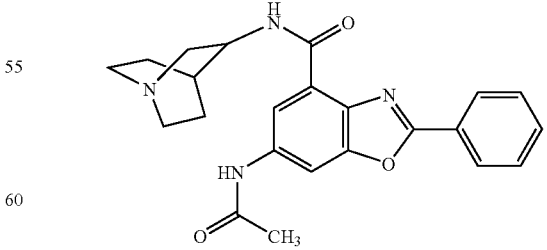

To a solution of N-(1-azabicyclo[2.2.2]oct-3-yl)-6-amino-2-phenylbenzoxazole-4-carboxamide (35 mg, 0.09 mmol) in methylene chloride (1 mL) was added pyridine (11 μL, 0.14 mmol) and acetic anhydride (11 μL, 0.10 mmol) at 0° C. and stirred for 30 min, then allowed to warm to room temperature for 1 h. The reaction mixture was quenched with saturated solution of sodium bicarbonate and concentrated under reduced pressure. The crude was purified by semi-preparative HPLC to afford N-(1-azabicyclo[2.2.2]oct-3-yl)-6-acetylamino-2-phenylbenzoxazole-4-carboxamide (13 mg, 44%) as a light yellow solid: $^1$H NMR (500 MHz, CDCl$_3$) δ 9.58 (d, J=7.4 Hz, 1H), 8.73 (d, J=1.9 Hz, 1H), 8.20 (d, J=6.8 Hz, 1H), 8.13 (s, 1H), 7.81 (d, J=1.7 Hz, 1H), 7.55-7.50 (m, 4H), 4.35-4.27 (m, 1H), 3.57-3.48 (m, 1H), 3.16-3.03 (m, 2H), 2.97-2.82 (m, 2H), 2.27 (s, 3H), 2.17-2.05 (m, 2H), 1.85-1.60 (m, 3H); MS (ESI+) m/z 405 (M+H); HPLC>99% (AUC), $t_R$=23.81 min.

Example 98

Preparation of (S)-N-(1-Azabicyclo[2.2.2]oct-3-yl)-6-methoxy-2-phenylbenzoxazole-4-carboxamide

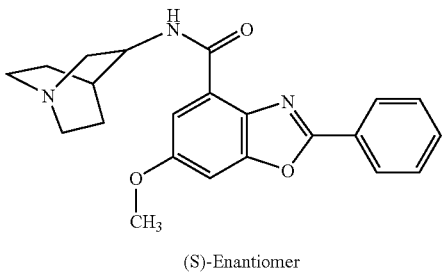

(S)-Enantiomer

Step A: To a suspension of 6-bromo-2-phenylbenzoaxazole-4-carboxylic acid (480 mg, 1.51 mmol) in a mixture of toluene and methanol (10 mL) was added trimethylsilyldiazomethane (1.51 mL, 2.0 M in ether, 3.01 mmol) at room temperature. The resulting reaction mixture was stirred at room temperature for 10 min. The reaction was quenched with aqueous acetic acid (0.25 mL) and concentrated to remove solvents. The reaction mixture was extracted with dichloromethane. The organic layer was washed with brine, dried over Na$_2$SO$_4$, filtered and concentrated to afford the desired product (485 mg, 96%) as an off-white solid: $^1$H NMR (500 MHz, CDCl$_3$) δ 8.34-8.30 (m, 2H), 8.15 (d, J=1.9 Hz, 1H), 7.93 (d, J=1.8 Hz, 1H), 7.10-6.95 (m, 3H), 4.06 (s, 3H); MS (ESI+) m/z 333 (M+H).

Step B: A mixture of 6-bromo-2-phenylbenzoaxazole-4-carboxylic acid methyl ester from Step A (485 mg, 1.46 mmol), bis(pinacolato)diboron (463 mg, 1.83 mmol), potassium acetate (429 mg, 4.38 mmol) in DMF (5 mL) was degassed and refilled with argon, then PdCl$_2$(dppf) (119 mL, 0.15 mmol) was added. The resulting reaction mixture was degassed, refilled with argon and then heated at 80° C. for 10 h. The mixture was diluted with ethyl acetate and then washed with water. The aqueous layer was further extracted with ethyl acetate (2×100 mL). The combined organic layers were dried (Na$_2$SO$_4$), filtered and concentrated to afford the desired product (553 mg, quantitative) as a brown solid: $^1$H NMR (500 MHz, CDCl$_3$) δ 8.46 (d, J=0.9 Hz, 1H), 8.38-8.34 (m, 2H), 7.93 (d, J=0.9 Hz, 1H), 7.56-7.50 (m, 3H), 4.06 (s, 3H), 1.38 (s, 12H); MS (ESI+) m/z 380 (M+H).

Step C: To a vigorously stirred solution of sodium hydroxide (80 mg, 2.19 mmol) in 8 mL of water was added boronate obtained from Step B (553 mg, 1.46 mmol) at 0° C. followed by sodium bicarbonate (491 mg, 5.84 mmol) and acetone (2.5 mL) and then the mixture was stirred for 5 min. To the above solution was added oxone (1.35 g, 2.19 mmol) and then the mixture was stirred at 0° C. for 20 min. The reaction was quenched with 10% NaHSO$_4$ solution and pH was adjusted to 7 by addition of 1 N HCl. The reaction was extracted with ethyl acetate (2×100 mL), and the combined organic layers were washed with brine, dried over Na$_2$SO$_4$ and concentrated under reduced pressure to afford the desired product (590 mg, quantitative) as a brown solid: $^1$H NMR (300 MHz, CDCl$_3$) δ 8.30-8.20 (m, 2H), 7.60-7.45 (m, 5H), 7.33-7.25 (m, 1H), 4.05 (s, 3H); MS (ESI+) m/z 270 (M+H).

Step D: To a stirred solution of compound obtained in Step C (400 mg, 1.4 mmol) in DMF (6 mL) was added cesium carbonate (2.4 g, 7.4 mmol) and methyl iodide (1.05 g, 7.4 mmol) at room temperature. The resulting reaction mixture was stirred at room temperature for 10 h. The reaction mixture was extracted with ethyl acetate (3×100 mL). The combined organic layers were washed with water (4×50 mL), brine (2×50 mL), dried over Na$_2$SO$_4$, filtered and concentrated. The crude material was purified by column chromatography (silica gel, 8:2 hexanes/ethyl acetate) to afford the desired product (156 mg, 37%) as a brown solid: $^1$H NMR (500 MHz, CDCl$_3$) δ 8.32-8.28 (m, 2H), 8.62 (d, J=2.5 Hz, 1H), 7.55-7.50 (m, 3H), 7.32 (d, J=2.5 Hz, 1H), 4.07 (s, 3H), 3.93 (s, 3H); MS (ESI+) m/z 284 (M+H).

Step E: A mixture of the compound obtained in step D (156 mg, 0.55 mmol) and lithium hydroxide monohydrate (35 mg, 0.83 mmol) in a mixture of tetrahydrofuran/methanol/water (2:1:1, 4 mL) was heated at 100° C. for 2 h. The reaction mixture was concentrated to dryness and treated with 2 N HCl to adjust the pH to 4. The reaction mixture was extracted with ethyl acetate (2×50 mL), and the combined organic layers were washed with brine, dried over Na$_2$SO$_4$, filtered and concentrated to afford the desired product (131 mg, 89%) as a light brown solid: $^1$H NMR (500 MHz, DMSO-d$_6$) δ 13.17 (br s, 1H), 8.20-8.17 (m, 2H), 7.70 (d, J=2.5 Hz, 1H), 7.64-7.60 (m, 3H), 7.45 (d, J=2.5 Hz, 1H), 7.10-6.95 (m, 3H), 3.90 (s, 3H); MS (ESI+) m/z 270 (M+H).

Step F: A mixture of 6-methoxy-2-phenylbenzoxazole-4-carboxylic acid (50 mg, 0.18 mmol), 1-ethyl-3-(3-dimethylaminopropyl)carbodiimide hydrochloride (71 mg, 0.37 mmol), 1-hydroxybenzotriazole (50 mg, 0.37 mmol) and (S)-(−)-3-aminoquinuclidine dihydrochloride (46 mg, 0.23 mmol) in DMF (3 mL) was stirred at room temperature for 10 min, then triethylamine (0.10 mL, 0.72 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried (Na$_2$SO$_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-6-methoxy-2-phenylbenzoxazole-4-carboxamide (55 mg, 76%) as a white solid: $^1$H NMR (500 MHz, CDCl$_3$) δ 9.56 (d, J=7.2 Hz, 1H), 8.21-8.17 (m, 2H), 7.79 (d, J=2.5 Hz, 1H), 7.60-7.52 (m, 3H), 7.26-7.24 (m, 1H), 4.34-4.30 (m, 1H), 3.94 (s, 3H), 3.56-3.51 (m, 1H), 3.16-3.05 (m, 2H), 2.95-2.84 (m, 3H), 2.20-2.18 (m, 1H), 2.15-2.03 (m, 1H), 1.82-1.76 (m, 2H), 1.70-1.55 (m, 1H); MS (ESI+) m/z 378 (M+H); HPLC>99% (AUC), $t_R$=12.90 min.

87

Example 99

Preparation of N-(9-Methyl-9-azabicyclo[3.3.1]non-3-yl)-6-methoxy-2-phenylbenzoxazole-4-carboxamide

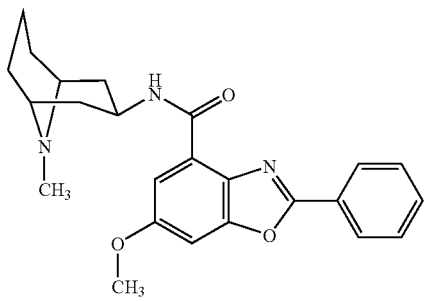

A mixture of 6-methoxy-2-phenylbenzoxazole-4-carboxylic acid (100 mg, 0.35 mmol), 1-ethyl-3-(3-dimethylaminopropyl)carbodiimide hydrochloride (134 mg, 0.70 mmol), 1-hydroxybenzotriazole (95 mg, 0.70 mmol) and 3-amino-9-methyl-9-azabicyclo[3.3.1]nonane dihydrochloride (99 mg, 0.44 mmol) in DMF (3 mL) was stirred at room temperature for 10 min, then triethylamine (0.20 mL, 1.40 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with water (2×50 mL), brine (2×50 mL), dried (Na$_2$SO$_4$), filtered and concentrated. The crude material was purified by column chromatography (silica gel, 90:9:1 dichloromethane/methanol/concentrated ammonium hydroxide) and recrystallization from acetonitrile to afford N-(9-methyl-9-azabicyclo[3.3.1]non-3-yl)-6-methoxy-2-phenylbenzoxazole-4-carboxamide (24 mg, 16%) as a light yellow solid: $^1$H NMR (500 MHz, CDCl$_3$) δ 9.08 (br s, 1H), 8.21-8.19 (m, 2H), 7.81 (d, J=2.5 Hz, 1H), 7.59-7.54 (m, 3H), 7.23 (d, J=2.5 Hz, 1H), 4.65-4.55 (m, 1H), 3.93 (s, 3H), 3.25-3.10 (m, 2H), 2.70-2.55 (m, 5H), 2.27-2.00 (m, 3H), 1.65-1.55 (m, 3H), 1.35-1.20 (m, 2H); MS (ESI+) m/z 406 (M+H); HPLC>99% (AUC), $t_R$=13.14 min.

Example 100

Preparation of (S)-N-(1-Azabicyclo[2.2.2]oct-3-yl)-6-hydroxy-2-phenylbenzoxazole-4-carboxamide

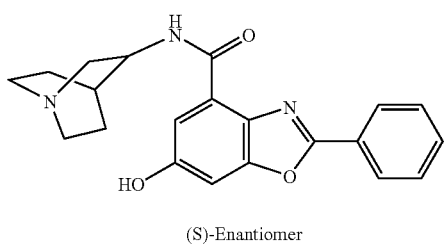

(S)-Enantiomer

Step A: A mixture of 6-hydroxy-2-phenylbenzo[d]oxazole-4-carboxylic acid (190 mg, 0.71 mmol) and lithium hydroxide monohydrate (45 mg, 1.07 mmol) in a mixture of tetrahydrofuran/methanol/water (2:1:1, 4 mL) was heated at 100° C. for 1 h. The reaction mixture was concentrated to dryness and treated with 2 N HCl to adjust the pH to 4. The reaction mixture was extracted with ethyl acetate (25 mL) and the combined organic layers were washed with water (25 mL), brine (25 mL), dried over Na$_2$SO$_4$, filtered and concentrated to afford the desired product (107 mg, 57%) as a light brown solid: $^1$H NMR (500 MHz, DMSO-d$_6$) δ 13.05 (br s, 1H), 10.18 (s, 1H), 8.20-8.16 (m, 2H), 7.65-7.50 (m, 3H), 7.40-7.32 (m, 2H); MS (ESI+) m/z 256 (M+H).

Step B: A mixture of 6-hydroxy-2-phenylbenzoxazole-4-carboxylic acid (104 mg, 0.35 mmol), 1-ethyl-3-(3-dimethylaminopropyl)carbodiimide hydrochloride (134 mg, 0.70 mmol), 1-hydroxybenzotriazole (95 mg, 0.70 mmol) and (S)-(–)-3-aminoquinuclidine dihydrochloride (87 mg, 0.44 mmol) in DMF (3 mL) was stirred at room temperature for 10 min, then triethylamine (0.20 mL, 1.4 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried (Na$_2$SO$_4$), filtered and concentrated. The crude material was purified by column chromatography (silica gel, 90:9:1 ethyl acetate/methanol/concentrated ammonium hydroxide) and recrystallization from acetonitrile to afford (S)-N-(1-azabicyclo[2.2.2]oct-3-yl)-6-hydroxy-2-phenylbenzoxazole-4-carboxamide (29 mg, 30%) as a white solid: $^1$H NMR (500 MHz, CDCl$_3$) δ 10.22 (br s, 1H), 9.29 (d, J=7.4 Hz, 1H), 8.17-8.13 (m, 2H), 7.67-7.63 (m, 3H), 7.46 (d, J=2.3 Hz, 1H), 7.32 (d, J=2.3 Hz, 1H), 4.09-4.06 (m, 1H), 3.30-3.27 (m, 1H), 2.90-2.86 (m, 2H), 2.77-2.72 (m, 2H), 2.62-2.59 (m, 1H), 1.99-1.94 (m, 2H), 1.69-1.63 (m, 3H); MS (ESI+) m/z 364 (M+H); HPLC>99% (AUC), $t_R$=11.90 min.

Example 101

Preparation of (S)-N-(1-Azabicyclo[2.2.2]oct-3-yl)-6-fluoro-2-phenylbenzoxazole-4-carboxamide

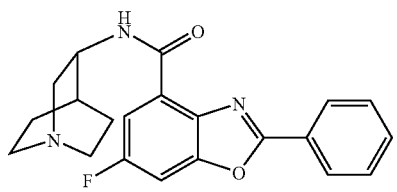

Step A: Iodine (3.6 g, 14.2 mmol) was added to a mixture of methyl 2-amino-5-fluorobenzoate (2.4 g, 14.2 mmol), silver sulfate (4.42 g, 14.2 mmol) and ethanol (30 mL) at room temperature. The mixture was stirred under nitrogen for 1 h, and then quenched with a saturated solution of sodium bicarbonate, extracted with ethyl acetate. The combined organic layers were washed with brine, dried (Na$_2$SO$_4$), filtered and concentrated. The crude material was purified by column chromatography (silica gel, 90:10 hexanes/ethyl acetate) to afford iodide (3.9 g, 93%) as a light yellow solid: $^1$H NMR (300 MHz, CDCl$_3$) δ 7.66-7.58 (m, 2H), 6.21 (br s, 2H), 3.89 (s, 3H); $^{19}$F NMR (282 MHz, CDCl$_3$) δ –127.87; MS (ESI+) m/z 296 (M+H).

Step B: A mixture of the iodide from Step A (500 mg, 1.69 mmol), bis(pinacolato)diboron (515 mg, 2.03 mmol), potassium acetate (497 mg, 5.07 mmol), and toluene (10 mL) was degassed with nitrogen for 15 min. PdCl$_2$(dppf) (277 mg, 0.34 mmol) was added. The mixture was heated at 100° C. under nitrogen for 24 h and then cooled to room temperature, quenched with a saturated solution of sodium bicarbonate, extracted with ethyl acetate. The combined organic layers were washed with brine, dried (Na$_2$SO$_4$), filtered and concentrated. The crude material was purified by column chromatography (silica gel, 90:10 hexanes/ethyl acetate) to afford borate (264 mg, 53%) as a light yellow solid: $^1$H NMR (300 MHz, CDCl$_3$) δ 7.64 (dd, J=9.6, 3.3 Hz, 1H), 7.52 (dd, J=8.1, 3.3 Hz, 1H), 6.88 (br s, 2H), 3.85 (s, 3H), 1.35 (s, 12H); $^{19}$F NMR (282 MHz, CDCl$_3$) δ −131.16; MS (ESI+) m/z 296 (M+H).

Step C: Benzoyl chloride (88 μL, 0.76 mmol) was added to a solution of the amine from Step B (180 mg, 0.61 mmol) in methylene chloride (2 mL) at room temperature, followed by triethylamine (0.17 mL, 1.22 mmol). The mixture was stirred under nitrogen overnight and then quenched with a saturated solution of sodium bicarbonate, extracted with methylene chloride. The combined organic layers were washed with brine, dried (Na$_2$SO$_4$), filtered and concentrated. The crude material was purified by column chromatography (silica gel, 50:50 hexanes/ethyl acetate) to afford amide (150 mg, 62%) as a white solid: $^1$H NMR (500 MHz, CDCl$_3$) δ 13.10 (br s, 1H), 8.08-8.06 (m, 2H), 7.71-7.58 (m, 5H), 4.01 (s, 3H), 1.40 (s, 12H); MS (ESI+) m/z 400 (M+H).

Step D: To a solution of sodium hydroxide (22 mg, 0.56 mmol) and sodium bicarbonate (126 mg, 1.50 mmol) in water (5 mL), was added oxone (364 mg, 0.564 mmol) at 0° C., followed by the borate from Step C (150 mg, 0.376 mmol) in acetone (3 mL). The mixture was allowed to warm to room temperature and stirred for 30 min, and then quenched with water, extracted with methylene chloride. The combined organic layers were washed with brine, dried (Na$_2$SO$_4$), filtered and concentrated to give the phenol (92 mg, 85%) as a light yellow solid: $^1$H NMR (300 MHz, CDCl$_3$) δ 11.95 (br s, 1H), 10.61 (s, 1H), 8.10-8.07 (m, 2H), 7.65-7.55 (m, 3H), 7.37 (dd, J=8.4, 3.0 Hz, 1H), 7.03 (dd, J=8.4, 3.0 Hz, 1H), 3.98 (s, 3H); $^{19}$F NMR (282 MHz, CDCl$_3$) δ −115.50; MS (ESI+) m/z 290 (M+H).

Step E: A mixture of the amide from Step D (90 mg, 0.31 mmol), p-toluenesulfonic acid monohydrate (89 mg, 0.47 mmol) and toluene (4 mL) was heated at reflex under nitrogen for 1 h. The reaction mixture was then cooled to room temperature, diluted with ethyl acetate, washed with a saturated solution of sodium bicarbonate and brine, dried over sodium sulfate, filtered and concentrated to afford the benzoxazole (69 mg, 84%) as a light yellow solid: $^1$H NMR (300 MHz, CDCl$_3$) δ 8.34-8.30 (m, 2H), 7.78 (dd, J=8.4, 3.0 Hz, 1H), 7.56-7.50 (m, 4H), 4.07 (s, 3H); $^{19}$F NMR (282 MHz, CDCl$_3$) δ −114.95; MS (ESI+) m/z 272 (M+H).

Step F: A mixture of the ester from Step E (68 mg, 0.25 mmol), 2 N NaOH (1.0 mL, 2.0 mmol), methanol (2 mL) and THF (2 mL) was stirred at room temperature under nitrogen overnight. The reaction mixture was acidified with 1 N HCl, extracted with methylene chloride, washed with brine, dried over sodium sulfate, filtered and concentrated to afford the acid (60 mg, 93%) as a light yellow solid: $^1$H NMR (300 MHz, CDCl$_3$) δ 11.50 (br s, 1H), 8.30-8.26 (m, 2H), 7.90 (dd, J=9.6, 2.4 Hz, 1H), 7.64-7.55 (m, 4H); $^{19}$F NMR (282 MHz, CDCl$_3$) δ −111.75; MS (ESI+) m/z 258 (M+H).

Step G: A mixture of the carboxylic acid from Step F (30 mg, 0.12 mmol), (S)-3-aminoquinuclidine dihydrochloride (28 mg, 0.14 mmol), 1-ethyl-3-(3-dimethylaminopropyl)carbodiimide hydrochloride (46 mg, 0.24 mmol) and 1-hydroxybenzotriazole (32 mg, 0.24 mmol) in DMF (5 mL) was stirred under nitrogen at room temperature for 10 min, and then triethylamine (0.10 mL, 0.72 mmol) was added. The resulting reaction mixture was stirred at room temperature overnight, and then was quenched with a saturated solution of sodium bicarbonate, extracted with methylene chloride. The combined organic layers were dried (Na$_2$SO$_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-6-fluoro-2-phenylbenzoxazole-4-carboxamide (38 mg, 88%) as a light yellow solid: $^1$H NMR (500 MHz, CDCl$_3$) δ 9.50 (d, J=7.0 Hz, 1H), 8.21-8.19 (m, 2H), 7.93 (dd, J=10.5, 2.5 Hz, 1H), 7.63-7.55 (m, 3H), 7.45 (dd, J=7.0, 2.5 Hz, 1H), 4.32-4.28 (m, 1H), 3.52 (ddd, J=14.0, 9.5, 2.0 Hz, 1H), 3.10-2.81 (m, 5H), 2.17-2.06 (m, 2H), 1.80-1.62 (m, 3H); $^{19}$F NMR (282 MHz, CDCl$_3$) δ −113.64; MS (ESI+) m/z 366 (M+H); HPLC>99% (AUC), t$_R$=12.17 min.

Example 102

Preparation of N-(9-Methyl-9-azabicyclo[3.3.1]non-3-yl)-6-fluoro-2-phenyl)benzoxazole-4-carboxamide

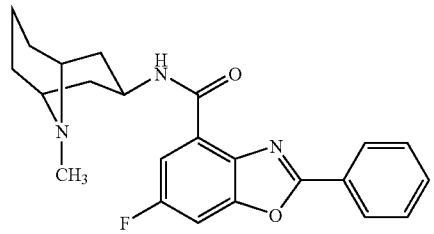

A mixture of 6-fluoro-2-phenylbenzo[d]oxazole-4-carboxylic acid (30 mg, 0.12 mmol), 3-amino-9-methyl-9-azabicyclo[3.3.1]nonane dihydrochloride (32 mg, 0.14 mmol), 1-ethyl-3-(3-dimethylaminopropyl)carbodiimide hydrochloride (46 mg, 0.24 mmol) and 1-hydroxybenzotriazole (32 mg, 0.24 mmol) in DMF (5 mL) was stirred under nitrogen at room temperature for 10 min, and then triethylamine (0.10 mL, 0.72 mmol) was added. The resulting reaction mixture was stirred at room temperature overnight, and then was quenched with a saturated solution of sodium bicarbonate, extracted with methylene chloride. The combined organic layers were washed with brine, dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-6-fluoro-2-phenyl)benzoxazole-4-carboxamide (42 mg, 91%) as a light yellow solid: $^1$H NMR (500 MHz, CDCl$_3$) δ 8.96 (d, J=7.5 Hz, 1H), 8.23-8.22 (m, 2H), 7.96 (d, J=10.5 Hz, 1H), 7.63-7.55 (m, 3H), 7.42 (d, J=7.0 Hz, 1H), 4.62-4.53 (m, 1H), 3.13-3.11 (m, 2H), 2.67-2.60 (m, 2H), 2.54 (s, 3H), 2.15-1.98 (m, 3H), 1.62-1.46 (m, 3H), 1.18-1.13 (m, 2H); $^{19}$F NMR (282 MHz, CDCl$_3$) δ −113.93; MS (ESI+) m/z 394 (M+H); HPLC>99% (AUC), t$_R$=12.78 min.

Example 103

Preparation of (S)-N-(1-Azabicyclo[2.2.2]oct-3-yl)-6-fluoro-2-(2-methoxyphenyl)benzoxazole-4-carboxamide Hydrochloride

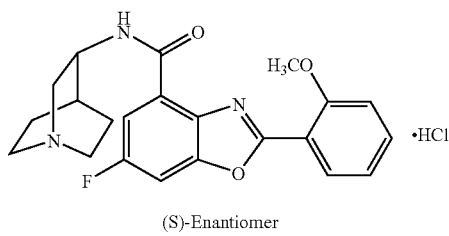

(S)-Enantiomer

Step A: Iodine (3.6 g, 14.2 mmol) was added to a mixture of methyl 2-amino-5-fluorobenzoate (2.4 g, 14.2 mmol), silver sulfate (4.42 g, 14.2 mmol) and ethanol (30 mL) at room temperature. The mixture was stirred under nitrogen for 1 h, and then quenched with a saturated solution of sodium bicarbonate, extracted with ethyl acetate. The combined organic layers were washed with brine, dried (Na$_2$SO$_4$), filtered and concentrated. The crude material was purified by column chromatography (silica gel, 90:10 hexanes/ethyl acetate) to afford iodide (3.9 g, 93%) as a light yellow solid: $^1$H NMR (300 MHz, CDCl$_3$) δ 7.66-7.58 (m, 2H), 6.21 (br s, 2H), 3.89 (s, 3H); $^{19}$F NMR (282 MHz, CDCl$_3$) δ −127.87; MS (ESI+) m/z 296 (M+H).

Step B: A mixture of the iodide from Step A (500 mg, 1.69 mmol), bis(pinacolato)diboron (515 mg, 2.03 mmol), potassium acetate (497 mg, 5.07 mmol), and toluene (10 mL) was degassed with nitrogen for 15 min. PdCl$_2$(dppf) (277 mg, 0.34 mmol) was added. The mixture was heated at 100° C. under nitrogen for 24 h and then cooled to room temperature, quenched with a saturated solution of sodium bicarbonate, extracted with ethyl acetate. The combined organic layers were washed with brine, dried (Na$_2$SO$_4$), filtered and concentrated. The crude material was purified by column chromatography (silica gel, 90:10 hexanes/ethyl acetate) to afford borate (264 mg, 53%) as a light yellow solid: $^1$H NMR (300 MHz, CDCl$_3$) δ 7.64 (dd, J=9.6, 3.3 Hz, 1H), 7.52 (dd, J=8.1, 3.3 Hz, 1H), 6.88 (br s, 2H), 3.85 (s, 3H), 1.35 (s, 12H); $^9$F NMR (282 MHz, CDCl$_3$) δ −131.16; MS (ESI+) m/z 296 (M+H).

Step C: 2-Anisoyl chloride (0.16 mL, 1.06 mmol) was added to a solution of the amine from Step B (260 mg, 0.88 mmol) in methylene chloride (4 mL) at room temperature, followed by triethylamine (0.24 mL, 1.76 mmol). The mixture was stirred under nitrogen overnight and then quenched with a saturated solution of sodium bicarbonate, extracted with methylene chloride. The combined organic layers were washed with brine, dried (Na$_2$SO$_4$), filtered and concentrated. The crude material was purified by column chromatography (silica gel, 50:50 hexanes/ethyl acetate) to afford amide (350 mg, 93%) as a white solid: $^1$H NMR (300 MHz, CDCl$_3$) δ 13.74 (br s, 1H), 8.34 (dd, J=8.1, 2.1 Hz, 1H), 7.67 (d, J=8.7 Hz, 2H), 7.19-6.85 (m, 3H), 4.18 (s, 3H), 3.96 (s, 3H), 1.39 (s, 12H); $^{19}$F NMR (282 MHz, CDCl$_3$) δ −115.91; MS (ESI+) m/z 430 (M+H).

Step D: To a solution of sodium hydroxide (49 mg, 1.2 mmol) and sodium bicarbonate (274 mg, 3.26 mmol) in water (10 mL) at 0° C., was added oxone (750 mg, 1.22 mmol), followed by the borate from Step C (350 mg, 0.816 mmol) in acetone (20 mL). The mixture was allowed to warm to room temperature and stirred for 4 h, and then quenched with water, extracted with methylene chloride. The combined organic layers were washed with brine, dried (Na$_2$SO$_4$), filtered and concentrated. The crude material was purified by Combi-flash chromatography (silica gel, 80:20 hexanes/ethyl acetate) to afford amide (213 mg, 82%) as a white solid: $^1$H NMR (300 MHz, CDCl$_3$) δ 12.18 (br s, 1H), 9.63 (s, 1H), 8.27 (dd, J=8.1, 1.8 Hz, 1H), 7.60-7.52 (m, 1H), 7.30 (dd, J=8.4, 3.0 Hz, 1H), 7.14-7.00 (m, 3H), 4.11 (s, 3H), 3.91 (s, 3H); $^{19}$F NMR (282 MHz, CDCl$_3$) δ −115.40; MS (ESI+) m/z 320 (M+H).

Step E: A mixture of the amide from Step D (213 mg, 0.668 mmol), p-toluenesulfonic acid monohydrate (127 mg, 0.668 mmol) and toluene (10 mL) was heated at reflux under nitrogen for 2 h. The reaction mixture was then cooled to room temperature, diluted with ethyl acetate, washed with a saturated solution of sodium bicarbonate and brine, dried over sodium sulfate, filtered and concentrated. The crude material was purified by Combi-flash chromatography (silica gel, 70:30 hexanes/ethyl acetate) to afford benzoxazole (85 mg, 42%) as a white solid: $^1$H NMR (300 MHz, CDCl$_3$) δ 8.21 (dd, J=8.1, 1.8 Hz, 1H), 7.77 (dd, J=8.4, 3.0 Hz, 1H), 7.56-7.50 (m, 2H), 7.13-7.07 (m, 2H), 4.06 (s, 3H), 4.02 (s, 3H); $^{19}$F NMR (282 MHz, CDCl$_3$) δ −114.92; MS (ESI+) m/z 302 (M+H).

Step F: A mixture of the ester from Step E (85 mg, 0.28 mmol), 2 N NaOH (1.0 mL, 2.0 mmol), methanol (2 mL) and THF (2 mL) was stirred at room temperature under nitrogen overnight. The reaction mixture was acidified with 1 N HCl, extracted with methylene chloride, washed with brine, dried over sodium sulfate, filtered and concentrated to afford the acid (80 mg, 99%) as a white solid: $^1$H NMR (300 MHz, CDCl$_3$) δ 11.90 (br s, 1H), 8.17 (dd, J=8.1, 1.8 Hz, 1H), 7.87 (dd, J=8.4, 3.0 Hz, 1H), 7.63-7.50 (m, 2H), 7.17-7.07 (m, 2H), 4.03 (s, 3H); $^{19}$F NMR (282 MHz, CDCl$_3$) δ −112.37; MS (ESI+) m/z 288 (M+H).

Step G: A mixture of the carboxylic acid from Step F (40 mg, 0.14 mmol), (S)-3-aminoquinuclidine dihydrochloride (34 mg, 0.17 mmol), 1-ethyl-3-(3-dimethylaminopropyl)carbodiimide hydrochloride (54 mg, 0.28 mmol) and 1-hydroxybenzotriazole (38 mg, 0.28 mmol) in DMF (4 mL) was stirred under nitrogen at room temperature for 10 min, and then triethylamine (0.12 mL, 0.84 mmol) was added. The resulting reaction mixture was stirred at room temperature overnight, and then was quenched with a saturated solution of sodium bicarbonate, extracted with methylene chloride. The combined organic layers were dried (Na$_2$SO$_4$), filtered and concentrated. The crude material was purified by Combi-flash chromatography (silica gel, 90:9:1 ethyl acetate/methanol/concentrated ammonium hydroxide) to afford the desired amide (33 mg, 60%) as a light yellow solid: $^1$H NMR (300 MHz, CDCl$_3$) δ 9.60 (d, J=7.0 Hz, 1H), 8.11 (dd, J=8.1, 1.8 Hz, 1H), 7.91 (dd, J=10.2, 2.7 Hz, 1H), 7.60-7.54 (m, 1H), 7.44 (dd, J=7.2, 2.7 Hz, 1H), 7.16-7.11 (m, 2H), 4.32-4.22 (m, 1H), 4.01 (s, 3H), 3.52 (ddd, J=14.0, 9.5, 2.0 Hz, 1H), 3.10-2.78 (m, 5H), 2.19-1.96 (m, 2H), 1.80-1.52 (m, 3H); $^{19}$F NMR (282 MHz, CDCl$_3$) δ −113.94; MS (ESI+) m/z 396 (M+H).

Step H: Hydrogen chloride in diethyl ether (1.0 M, 0.17 mL, 0.17 mmol) was added dropwise to a solution of the amide from Step G (33 mg, 0.083 mmol) in methanol (1 mL) at room temperature. The mixture was stirred for 5 min, and then diethyl ether (20 mL) was added. The resulting solid was filtered, washed with diethyl ether, and dried under vacuum overnight to afford (S)-N-(1-azabicyclo[2.2.2]oct-3-yl)-6-fluoro-2-(2-methoxyphenyl)benzoxazole-4-carboxamide hydrochloride (28 mg, 78%) as a white solid: $^1$H NMR (300 MHz, DMSO-$d_6$) δ 10.12 (br s, 1H), 9.41 (d, J=6.3 Hz, 1H), 8.11-8.08 (m, 2H), 7.73-7.66 (m, 2H), 7.36 (d, J=8.4 Hz, 1H), 7.21 (t, J=7.2 Hz, 1H), 4.45-4.38 (m, 1H), 3.96 (s, 3H), 3.77 (t, J=14.0 Hz, 1H), 3.45-3.20 (m, 5H), 2.46-2.18 (m, 2H), 2.04-1.92 (m, 3H); $^{19}$F NMR (282 MHz, DMSO-$d_6$) δ −113.91; MS (ESI+) m/z 396 (M+H); HPLC>99% (AUC), $t_R$=12.54 min.

Example 104

Preparation of N-(9-Methyl-9-azabicyclo[3.3.1]non-3-yl)-6-fluoro-2-(2-methoxyphenyl)benzoxazole-4-carboxamide Hydrochloride

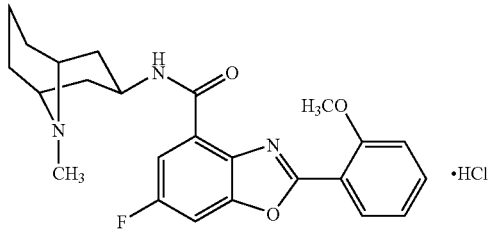

Step A: A mixture of 6-fluoro-2-(2-methoxyphenyl)benzo[d]oxazole-4-carboxylic acid (40 mg, 0.14 mmol), 3-amino-9-methyl-9-azabicyclo[3.3.1]nonane dihydrochloride (39 mg, 0.17 mmol), 1-ethyl-3-(3-dimethylaminopropyl)carbodiimide hydrochloride (54 mg, 0.28 mmol) and 1-hydroxybenzotriazole (38 mg, 0.28 mmol) in DMF (4 mL) was stirred under nitrogen at room temperature for 10 min, and then triethylamine (0.12 mL, 0.84 mmol) was added. The resulting reaction mixture was stirred at room temperature overnight, and then was quenched with a saturated solution of sodium bicarbonate, extracted with methylene chloride. The combined organic layers were washed with brine, dried ($Na_2SO_4$), filtered and concentrated. The crude material was purified by Combi-flash chromatography (silica gel, 90:9:1 ethyl acetate/methanol/concentrated ammonium hydroxide) to afford amide (41 mg, 69%) as a light yellow solid: $^1$H NMR (300 MHz, CDCl$_3$) δ 9.20 (d, J=7.2 Hz, 1H), 8.12 (dd, J=8.1, 1.8 Hz, 1H), 7.92 (dd, J=10.2, 2.7 Hz, 1H), 7.60-7.54 (m, 1H), 7.42 (dd, J=7.2, 2.7 Hz, 1H), 7.16-7.11 (m, 2H), 4.67-4.53 (m, 1H), 4.03 (s, 3H), 3.23-3.15 (m, 2H), 2.72-2.60 (m, 2H), 2.58 (s, 3H), 2.15-1.98 (m, 3H), 1.62-1.53 (m, 3H), 1.21-1.15 (m, 2H); $^{19}$F NMR (282 MHz, CDCl$_3$) δ −113.78; MS (ESI+) m/z 424 (M+H).

Step B: Hydrogen chloride in diethyl ether (1.0 M, 0.19 mL, 0.19 mmol) was added dropwise to a solution of the amide from Step A (41 mg, 0.097 mmol) in methanol (3 mL) at room temperature. The mixture was stirred for 5 min, and then diethyl ether (30 mL) was added. The resulting solid was filtered, washed with diethyl ether, and dried under vacuum overnight to afford N-(9-methyl-9-azabicyclo[3.3.1]non-3-yl)-6-fluoro-2-(2-methoxyphenyl)benzoxazole-4-carboxamide hydrochloride (25 mg, 57%) as a white solid: $^1$H NMR (300 MHz, DMSO-$d_6$) δ 10.25 (br s, 0.3H), 9.51 (br s, 0.7H), 9.31 (d, J=7.2 Hz, 0.3H), 9.08 (d, J=7.2 Hz, 0.7H), 8.13-8.06 (m, 2H), 7.74-7.66 (m, 2H), 7.35 (d, J=8.4 Hz, 1H), 7.21 (t, J=7.2 Hz, 1H), 4.73-4.45 (m, 1H), 3.98 (s, 2.1H), 3.96 (s, 0.9H), 3.73-3.55 (m, 2H), 2.82-2.60 (m, 2H), 2.50 (s, 3H), 2.15-2.05 (m, 3H), 1.90-1.80 (m, 3H), 1.60-1.50 (m, 2H); $^{19}$F NMR (282 MHz, DMSO-$d_6$) δ −114.00; MS (ESI+) m/z 424 (M+H); HPLC>99% (AUC), $t_R$=12.52 min.

Example 105

Preparation of N-(9-Methyl-9-azabicyclo[3.3.1]non-3-yl)-2-pyridin-4-ylbenzoxazole-4-carboxamide

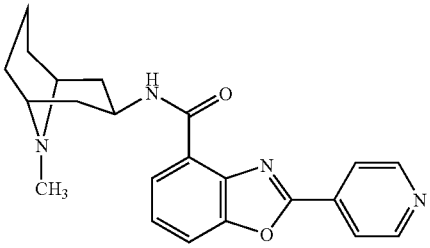

Step A: To a suspension of 2-amino-3-hydroxybenzoic acid hydrobromide (152 mg, 0.65 mmol) in dichloromethane (15 mL) was added pyridine (0.42 ml, 5.2 mmol) followed by isonicotinoyl chloride hydrochloride (347 mg, 1.95 mmol). The resulting reaction mixture was stirred at room temperature for 15 min and DMAP (16 mg, 0.13 mmol) was added, then the reaction mixture was stirred at room temperature overnight. Water (10 mL) was added and the reaction was stirred at room temperature for 10 min. The aqueous layer was extracted with ethyl acetate. The organic layers were washed with brine, dried over $Na_2SO_4$, filtered and concentrated. The product was dissolved in toluene (5 mL) and the solution was treated with p-toluenesulfonic acid monohydrate (127 mg, 0.67 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to an orange solid. The crude product was purified by column chromatography (silica gel, 9:1 to 2:1 ethyl acetate/methanol) to afford the desired product (56 mg, 46%): $^1$H NMR (500 MHz, CD$_3$OD) δ 8.77-8.76 (m, 2H), 8.29-8.27 (m, 2H), 7.87 (d, J=7.5 Hz, 1H), 7.77 (d, J=8.5 Hz, 1H), 7.49 (t, J=8.0 Hz, 1H); MS (ESI+) m/z 241 (M+H).

Step B: A mixture of 2-pyridin-4-ylbenzoxazole-4-carboxylic acid from Step A (28 mg, 0.11 mmol), 3-amino-9-methyl-9-azabicyclo[3.3.1]nonane dihydrochloride (30 mg, 0.13 mmol), 1-ethyl-3-(3-dimethylaminopropyl)carbodiimide hydrochloride (30 mg, 0.16 mmol) and 1-hydroxybenzotriazole (42 mg, 0.31 mmol) in DMF (5 mL) was stirred for 10 min at room temperature, then DIPEA (0.09 mL, 0.55 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by semi-preparative HPLC to afford N-(9-methyl-9-azabicyclo[3.3.1]non-3-yl)-2-pyridin-4-ylbenzoxazole-4-carboxamide (15 mg, 36%) as a white solid: $^1$H NMR (500 MHz, CDCl$_3$) δ 8.91-8.89 (m, 2H), 8.82 (d, J=7.0 Hz, 1H), 8.28 (dd, J=7.5, 1.0 Hz, 1H), 8.09-8.08 (m, 2H), 7.76 (dd, J=8.0, 0.5 Hz, 1H), 7.55 (t, J=8.0 Hz, 2H), 4.65-4.56 (m, 1H), 3.14 (d, J=10.5 Hz, 2H), 2.69-2.62 (m, 1H), 2.55 (s, 3H), 2.19-2.00 (m, 3H), 1.66-1.58 (m, 1H), 1.52-1.47 (m, 2H), 1.17 (d, J=11.5 Hz, 2H); MS (ESI+) m/z 377 (M+H); HPLC>99% (AUC), $t_R$=14.65 min.

Example 106

Preparation of (S)-N-(1-Azabicyclo[2.2.2]oct-3-yl)-2-furan-2-ylbenzoxazole-4-carboxamide

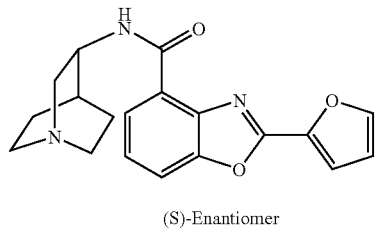

(S)-Enantiomer

Step A: To a suspension of 2-amino-3-hydroxybenzoic acid hydrobromide (304 mg, 1.30 mmol) in dichloromethane (20 mL) was added pyridine (0.84 mL, 10.4 mmol) followed by 2-furoyl chloride (0.39 ml, 3.9 mmol). The resulting reaction mixture was stirred at room temperature for 15 min, then DMAP (32 mg, 0.26 mmol) was added and the reaction mixture was stirred at room temperature overnight. Water (10 mL) was added and the reaction was stirred for 10 min. The reaction was quenched with aqueous 1 N HCl (20 mL) until the solution reached pH 1. The solution was stirred for 30 min. The aqueous layer was extracted with ethyl acetate. The organic layers were washed with brine and dried over $Na_2SO_4$, filtered and concentrated to a pale yellow solid. The product was directly re-dissolved in toluene (10 mL) and the solution was treated with p-toluenesulfonic acid monohydrate (462 mg, 2.43 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (102 mg, 28%) as a pale orange solid: $^1H$ NMR (500 MHz, $CD_3OD$) δ 7.95 (d, J=9.0 Hz, 1H), 7.65 (d, J=10.0 Hz, 1H), 7.45-7.37 (m, 2H), 7.31-7.27 (m, 1H), 6.42 (s, 1H); MS (ESI+) m/z 230 (M+H).

Step B: A mixture of 2-furan-2-ylbenzoxazole-4-carboxylic acid from Step A (51 mg, 0.22 mmol), (S)-3-aminoquinuclidine dihydrochloride (52 mg, 0.26 mmol), 1-ethyl-3-(3-dimethylaminopropyl)carbodiimide hydrochloride (59 mg, 0.31 mmol) and 1-hydroxybenzotriazole (84 mg, 0.62 mmol) in DMF (5 mL) was stirred for 10 min at room temperature, then triethylamine (0.14 mL, 1.1 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-furan-2-ylbenzoxazole-4-carboxamide (42 mg, 56%) as a white solid: $^1H$ NMR (500 MHz, $CDCl_3$) δ 9.51 (d, J=7.5 Hz, 1H), 8.19 (dd, J=8.0, 1.0 Hz, 1H), 7.73 (m, 1H), 7.70 (dd, J=8.0, 1.0 Hz, 1H), 7.47 (t, J=8.0 Hz, 1H), 7.33 (dd, J=3.5, 0.5 Hz, 1H), 6.68-6.65 (m, 1H), 4.34-4.28 (m, 1H), 3.53-3.47 (m, 1H), 3.14-2.98 (m, 2H), 2.93-2.89 (m, 3H), 2.16-2.04 (m, 1H), 1.81-1.58 (m, 4H); MS (ESI+) m/z 338 (M+H); HPLC>99% (AUC), $t_R$=11.59 min.

Example 107

Preparation of N-(9-Methyl-9-azabicyclo[3.3.1]non-3-yl)-2-furan-2-ylbenzoxazole-4-carboxamide

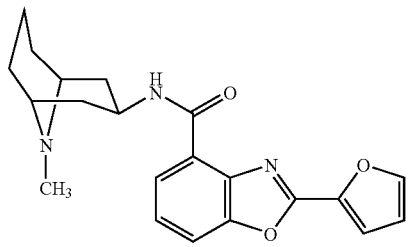

A mixture of 2-furan-2-ylbenzoxazole-4-carboxylic acid (51 mg, 0.22 mmol), 3-amino-9-methyl-9-azabicyclo[3.3.1]nonane dihydrochloride (59 mg, 0.26 mmol), 1-ethyl-3-(3-dimethylaminopropyl)carbodiimide hydrochloride (59 mg, 0.31 mmol) and 1-hydroxybenzotriazole (84 mg, 0.62 mmol) in DMF (5 mL) was stirred for 10 min at room temperature, then triethylamine (0.14 mL, 1.1 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-2-furan-2-ylbenzoxazole-4-carboxamide (49 mg, 61%) as an off-white solid: $^1H$ NMR (500 MHz, $CDCl_3$) δ 8.94 (d, J=6.0 Hz, 1H), 8.22 (dd, J=7.5, 1.0 Hz, 1H), 7.74 (d, J=1.5 Hz, 1H), 7.68 (dd, J=8.0, 1.0 Hz, 1H), 7.46 (t, J=4.0 Hz, 1H), 7.35 (d, J=4.0 Hz, 1H), 6.79-6.66 (m, 1H), 4.58-4.53 (m, 1H), 3.12 (d, J=10.0 Hz, 2H), 2.66-2.59 (m, 2H), 2.55 (s, 3H), 2.18-1.98 (m, 3H), 1.68-1.49 (m, 3H), 1.22-1.17 (m, 2H); MS (ESI+) m/z 366 (M+H); HPLC>99% (AUC), $t_R$=12.12 mm.

Example 108

Preparation of (S)-N-(1-Azabicyclo[2.2.2]oct-3-yl)-2-thiophen-2-ylbenzoxazole-4-carboxamide

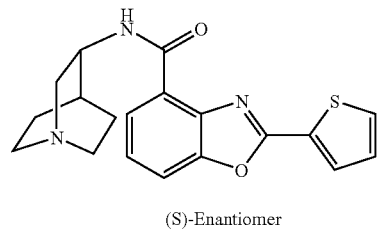

(S)-Enantiomer

Step A: To a suspension of 2-amino-3-hydroxybenzoic acid hydrobromide (152 mg, 0.65 mmol) in dichloromethane (15 mL) was added pyridine (0.42 mL, 5.2 mmol) followed by 2-thiophenecarbonyl chloride (0.21 ml, 1.95 mmol). The resulting reaction mixture was stirred at room temperature for 15 min, then DMAP (16 mg, 0.13 mmol) was added and the reaction mixture was stirred at room temperature overnight. Water (10 mL) was added and the reaction stirred for 10 min. The reaction was quenched with aqueous 1 N HCl (30 mL) until the solution reached pH 1. The solution was stirred for 30 min. The aqueous layer was extracted with ethyl acetate. The organic layers were washed with brine and dried over $Na_2SO_4$, filtered and concentrated to a yellow solid. The product was directly re-dissolved in toluene (10 mL) and the solution was treated with p-toluenesulfonic acid monohydrate (262 mg, 1.38 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (147 mg, 65%) as a pale orange solid: MS (ESI+) m/z 246 (M+H).

Step B: A mixture of 2-thiophen-2-ylbenzoxazole-4-carboxylic acid from Step A (64 mg, 0.26 mmol), (S)-3-aminoquinuclidine dihydrochloride (62 mg, 0.31 mmol), 1-ethyl-3-(3-dimethylaminopropyl)carbodiimide hydrochloride (70 mg, 0.37 mmol) and 1-hydroxybenzotriazole (99 mg, 0.73 mmol) in DMF (5 mL) was stirred for 10 min at room temperature, then triethylamine (0.17 mL, 1.30 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-thiophen-2-ylbenzoxazole-4-carboxamide (58 mg, 63%) as a white solid: $^1$H NMR (500 MHz, CDCl$_3$) δ 9.53 (d, J=7.5 Hz, 1H), 8.18 (d, J=8.0 Hz, 1H), 7.94 (d, J=4.0 Hz, 1H), 7.68 (d, J=8.0 Hz, 1H), 7.64 (d, J=5.0 Hz, 1H), 7.45 (t, J=8.0 Hz, 1H), 7.24 (t, J=4.0 Hz, 1H), 4.33-4.30 (m, 1H), 3.52-3.47 (m, 1H), 3.16-2.99 (m, 2H), 2.95-2.77 (m, 3H), 2.15-2.09 (m, 2H), 1.79-1.60 (m, 3H); MS (ESI+) m/z 354 (M+H); HPLC>99% (AUC), $t_R$=24.25 min.

Example 109

Preparation of N-(9-Methyl-9-azabicyclo[3.3.1]non-3-yl)-2-thiophen-2-ylbenzoxazole-4-carboxamide

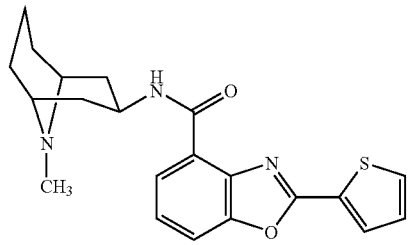

A mixture of 2-thiophen-2-ylbenzoxazole-4-carboxylic acid (64 mg, 0.26 mmol), 3-amino-9-methyl-9-azabicyclo[3.3.1]nonane dihydrochloride (70 mg, 0.37 mmol), 1-ethyl-3-(3-dimethylaminopropyl)carbodiimide hydrochloride (99 mg, 0.52 mmol) and 1-hydroxybenzotriazole (99 mg, 0.74 mmol) in DMF (5 mL) was stirred for 10 min at room temperature, then triethylamine (0.17 mL, 1.3 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) and then recrystallized from acetonitrile to afford N-(9-methyl-9-azabicyclo[3.3.1]non-3-yl)-2-thiophen-2-ylbenzoxazole-4-carboxamide (55 mg, 56%) as an off-white solid: $^1$H NMR (500 MHz, CDCl$_3$) δ 8.99 (d, J=7.0 Hz, 1H), 8.20 (dd, J=7.5, 0.5 Hz, 1H), 7.95 (dd, J=4.0, 1.0 Hz, 1H), 7.67-7.63 (m, 2H), 7.45 (t, J=4.0 Hz, 1H), 7.27-7.23 (m, 1H), 4.62-4.56 (m, 1H), 3.15-3.09 (m, 2H), 2.67-2.59 (m, 2H) 2.54 (s, 3H), 2.18-1.88 (m, 3H), 1.65-1.57 (m, 5H); MS (ESI+) m/z 382 (M+H); HPLC>99% (AUC), $t_R$=24.24 min.

Example 110

Preparation of N-(9-Methyl-9-azabicyclo[3.3.1]non-3-yl)-6-chloro-2-thiophen-2-ylbenzoxazole-4-carboxamide

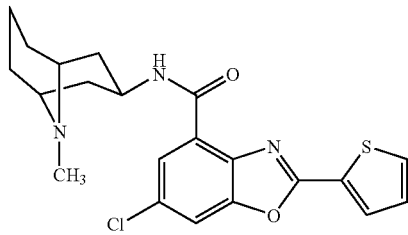

Step A: To a mixture of 2-amino-3-hydroxy-5-chlorobenzoic acid (0.27 g, 1.44 mmol) and 2-thiophenecarbonyl chloride (0.15 mL, 1.44 mmol) in dichloromethane (10 mL) was added triethylamine (0.81 mL, 5.76 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (10 mL) and the solution was treated with p-toluenesulfonic acid monohydrate (249 mg, 1.31 mmol). The reaction mixture was then heated to reflux overnight. The reaction was cooled down to room temperature, poured into water and extracted with ethyl acetate. The organic layer was separated then washed with water, brine, dried ($Na_2SO_4$), filtered and concentrated. The crude product was purified by column chromatography (silica gel, 9:1 to 3:1 ethyl acetate/methanol) to afford the desired product (0.16 g, 44%) as a brown solid: $^1$H NMR (500 MHz, DMSO-d$_6$) δ 8.02 (d, J=3.0 Hz, 1H), 7.98 (dd, J=5.0, 1.0 Hz, 1H), 7.92 (d, J=2.0 Hz, 1H), 7.72 (s, 1H), 7.31 (dd, J=4.5, 4.0 Hz, 1H); MS (ESI+) m/z 279 (M+H).

Step B: A mixture of benzoxazole carboxylic acid from Step A (70 mg, 0.25 mmol), 3-amino-9-methyl-9-azabicyclo

[3.3.1]nonane dihydrochloride (57 mg, 0.25 mmol), 1-ethyl-3-(3-dimethylaminopropyl)carbodiimide hydrochloride (96 mg, 0.57 mmol) and 1-hydroxybenzotriazole (68 mg, 0.50 mmol) in DMF (2 mL) was stirred at room temperature for 5 min, then triethylamine (0.13 mL, 1.0 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) followed by recrystallization from ethyl acetate to afford N-(9-methyl-9-azabicyclo[3.3.1]non-3-yl)-6-chloro-2-thiophen-2-ylbenzoxazole-4-carboxamide (40 mg, 38%) as an off-white solid: $^1$H NMR (500 MHz, CDCl$_3$) δ 8.84 (d, J=6.5 Hz, 1H), 8.18 (d, J=2.0 Hz, 1H), 7.95 (dd, J=3.5, 1.0 Hz, 1H), 7.67-7.64 (m, 2H), 7.26-7.23 (m, 1H), 4.58-4.52 (m, 1H), 3.12 (d, J=10.5 Hz, 2H), 2.65-2.58 (m, 2H), 2.53 (s, 3H), 2.15-1.95 (m, 3H), 1.60-1.52 (m, 1H), 1.48 (t, J=11.0 Hz, 2H), 1.18 (d, J=12.0 Hz, 2H); MS (ESI+) m/z 416 (M+H); HPLC>99% (AUC), $t_R$=13.84 min.

Example 111

Preparation of (S)-N-(1-Azabicyclo[2.2.2]oct-3-yl)-6-chloro-2-thiophen-2-ylbenzoxazole-4-carboxamide

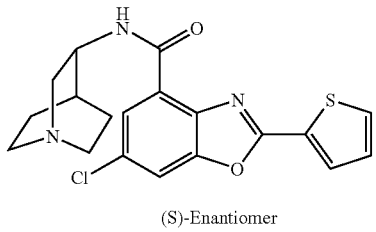

(S)-Enantiomer

A mixture of 6-chloro-2-(thiophen-2-yl)benzo[d]oxazole-4-carboxylic acid (70 mg, 0.25 mmol), (S)-(−)-3-aminoquinuclidine dihydrochloride (50 mg, 0.25 mmol), 1-ethyl-3-(3-dimethylaminopropyl)carbodiimide hydrochloride (96 mg, 0.50 mmol) and 1-hydroxybenzotriazole (68 mg, 0.50 mmol) in DMF (2 mL) was stirred at room temperature for 5 min, then triethylamine (0.13 mL, 1.00 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford (S)-N-(1-azabicyclo[2.2.2]oct-3-yl)-6-chloro-2-thiophen-2-ylbenzoxazole-4-carboxamide (30 mg, 31%) as a white solid: $^1$H NMR (500 MHz, CDCl$_3$) δ 9.40 (d, J=7.5 Hz, 1H), 8.16 (d, J=2.0 Hz, 1H), 7.94 (dd, J=4.0, 1.5 Hz, 1H), 7.67-7.65 (m, 2H), 7.26-7.23 (m, 1H), 4.30-4.26 (m, 1H), 3.49 (ddd, J=11.5, 9.5, 2.0 Hz, 1H), 3.15-2.85 (m, 4H), 2.77 (dd, J=14.5, 3.5 Hz, 1H), 2.15-2.05 (m, 2H), 1.78-1.70 (m, 2H), 1.65-1.53 (m, 1H); MS (ESI+) m/z 388 (M+H); HPLC>99% (AUC), $t_R$=13.84 min.

Example 112

Preparation of (S)-N-(1-Azabicyclo[2.2.2]oct-3-yl)-2-thiophen-3-ylbenzoxazole-4-carboxamide

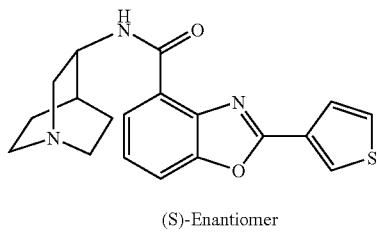

(S)-Enantiomer

Step A: To a suspension of 2-amino-3-hydroxybenzoic acid hydrobromide (152 mg, 0.65 mmol) in dichloromethane (15 mL) was added pyridine (0.42 mL, 11.8 mmol) followed by 3-thiophenecarbonyl chloride (286 mg, 1.95 mmol). The resulting reaction mixture was stirred at room temperature for 15 min then DMAP (40 mg, 0.33 mmol) was added and the reaction mixture was stirred at room temperature overnight. Water (10 mL) was added and the reaction stirred for 10 min. The reaction was quenched with aqueous 1 N HCl (30 mL) until the solution reached pH 1. The solution was stirred for 30 min. The aqueous layer was extracted with ethyl acetate. The organic layers were washed with water and brine, dried over Na$_2$SO$_4$, filtered and concentrated to a pale orange solid. The amide product was directly re-dissolved in toluene (10 mL) and the solution was treated with p-toluenesulfonic acid monohydrate (243 mg, 1.28 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to an orange solid. The crude product was purified by column chromatography (silica gel, 9:1 to 2:1 ethyl acetate/methanol) to afford the desired product (154 mg, quantitative) as a white solid: MS (ESI+) m/z 246 (M+H).

Step B: A mixture of 2-thiophen-3-ylbenzoxazole-4-carboxylic acid from Step A (78 mg, 0.32 mmol), (S)-3-aminoquinuclidine dihydrochloride (76 mg, 0.38 mmol), 1-ethyl-3-(3-dimethylaminopropyl)carbodiimide hydrochloride (86 mg, 0.45 mmol) and 1-hydroxybenzotriazole (122 mg, 0.90 mmol) in DMF (5 mL) was stirred for 10 min at room temperature, then DIPEA (0.26 mL, 1.60 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) and then recrystallized from acetonitrile to afford (S)-N-(1-azabicyclo[2.2.2]oct-3-yl)-2-thiophen-3-ylbenzoxazole-4-carboxamide (92 mg, 82%) as an off-white solid: $^1$H NMR (500 MHz, CDCl$_3$) δ 9.54 (d, J=7.0 Hz, 1H), 8.23 (dd, J=3.0, 1.0 Hz, 1H), 8.19 (dd, J=8.0, 1.0 Hz, 1H), 7.75 (dd, J=6.5, 1.0 Hz, 1H), 7.69 (dd, J=9.0, 1.0 Hz, 1H), 7.51 (dd, J=8.0, 3.0 Hz, 1H), 7.46 (t, J=8.0 Hz, 1H), 4.32-4.28 (m, 1H), 3.53-3.48 (m, 1H), 3.11-2.99 (m, 2H), 2.92-2.85 (m, 2H), 2.80 (dd, J=14.0, 4.0 Hz, 1H), 2.14-2.12 (m, 1H), 2.09-2.05 (m, 2H), 1.78-1.74 (m, 2H); MS (ESI+) m/z 354 (M+H); HPLC>99% (AUC), $t_R$=12.89 min.

Example 113

Preparation of N-(9-Methyl-9-azabicyclo[3.3.1]non-3-yl)-2-thiophen-3-ylbenzoxazole-4-carboxamide

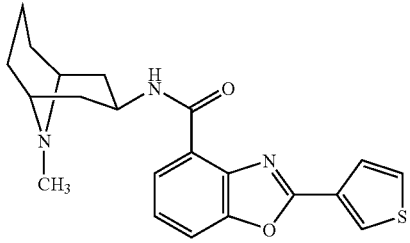

A mixture of 2-thiophen-3-ylbenzoxazole-4-carboxylic acid (78 mg, 0.32 mmol), 3-amino-9-methyl-9-azabicyclo[3.3.1]nonane dihydrochloride (86 mg, 0.38 mmol), 1-ethyl-3-(3-dimethylaminopropyl)carbodiimide hydrochloride (86 mg, 0.45 mmol) and 1-hydroxybenzotriazole (122 mg, 0.90 mmol) in DMF (5 mL) was stirred for 10 min at room temperature, then DIPEA (0.26 mL, 1.6 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) and then recrystallized from acetonitrile to afford N-(9-methyl-9-azabicyclo[3.3.1]non-3-yl)-2-thiophen-3-ylbenzoxazole-4-carboxamide (51 mg, 41%) as an off-white solid: $^1$H NMR (500 MHz, CDCl$_3$) δ 8.99 (d, J=7.0 Hz, 1H), 8.24 (d, J=1.5 Hz, 1H), 8.20 (d, J=7.5 Hz, 1H), 7.78 (d, J=5.0 Hz, 1H), 7.77 (d, J=7.5 Hz, 1H), 7.52-7.51 (m, 1H), 7.44 (t, J=7.5 Hz, 1H), 4.61-4.51 (m, 1H), 3.19-3.01 (m, 2H), 2.72-2.61 (m, 2H), 2.54 (s, 3H), 2.22-1.98 (m, 2H), 1.60-1.47 (m, 4H), 1.26-1.13 (m, 2H); MS (ESI+) m/z 382 (M+H); HPLC>99% (AUC), $t_R$=13.40 min.

Example 114

Preparation of N-(9-Methyl-3-oxa-9-azabicyclo[3.3.1]non-7-yl)-6-chloro-2-thiophen-3-ylbenzoxazole-4-carboxamide

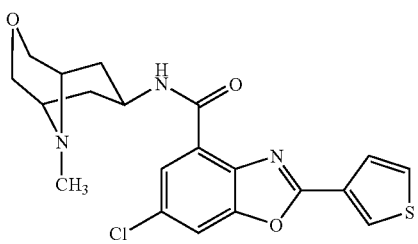

Step A: To a mixture of 2-amino-5-chloro-3-hydroxybenzoic acid hydrobromide (0.40 g, 1.49 mmol) and 3-thiophenecarbonyl chloride (219 mg, 1.49 mmol) in dichloromethane (10 mL) was added triethylamine (0.84 mL, 5.96 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried (Na$_2$SO$_4$), filtered and concentrated. The crude product was dissolved in toluene (10 mL) and the solution was treated with p-toluenesulfonic acid monohydrate (230 mg, 1.21 mmol). The reaction mixture was then heated to reflux for 2 h. The reaction was cooled down to room temperature, poured into water and extracted with ethyl acetate. The organic layer was separated then washed with water, brine, dried (Na$_2$SO$_4$), filtered and concentrated. The crude product was purified by column chromatography (silica gel, 9:1 to 3:1 ethyl acetate/methanol) to afford the desired product (0.28 g, 67%) as a yellow solid: $^1$H NMR (500 MHz, DMSO-d$_6$) δ 8.53 (s, 1H), 7.94 (s, 1H), 7.82 (dd, J=5.0, 3.0 Hz, 1H), 7.78 (d, J=5.0 Hz, 1H), 7.74 (s, 1H); MS (ESI+) m/z 279 (M+H).

Step B: A mixture of benzoxazole carboxylic acid from Step A (70 mg, 0.25 mmol), 9-methyl-3-oxa-9-azabicyclo[3.3.1]non-7-ylamine dihydrochloride (57 mg, 0.25 mmol), 1-ethyl-3-(3-dimethylaminopropyl)carbodiimide hydrochloride (96 mg, 0.50 mmol) and 1-hydroxybenzotriazole (68 mg, 0.50 mmol) in DMF (2 mL) was stirred at room temperature for 5 min, then triethylamine (0.13 mL, 1.0 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) followed by recrystallization from ethyl acetate to afford N-(9-methyl-3-oxa-9-azabicyclo[3.3.1]non-7-yl)-6-chloro-2-thiophen-3-ylbenzoxazole-4-carboxamide (25 mg, 24%) as an off-white solid: $^1$H NMR (500 MHz, CDCl$_3$) δ 10.18 (d, J=9.5 Hz, 1H), 8.31 (dd, J=3.0, 1.0 Hz, 1H), 8.17 (d, J=3.0 Hz, 1H), 7.84 (dd, J=5.0, 1.0 Hz, 1H), 7.64 (d, J=2.0 Hz, 1H), 7.48 (dd, J=5.0, 3.0 Hz, 1H), 4.94-4.88 (m, 1H), 4.08 (d, J=11.0 Hz, 2H), 3.93 (d, J=11.0 Hz, 2H), 2.72 (s, 2H), 2.61-2.54 (m, 5H), 1.58 (s, 2H); MS (ESI+) m/z 418 (M+H); HPLC 98.1% (AUC), $t_R$=13.22 min.

Example 115

Preparation of N-(9-Methyl-9-azabicyclo[3.3.1]non-3-yl)-6-chloro-2-thiophen-3-ylbenzoxazole-4-carboxamide

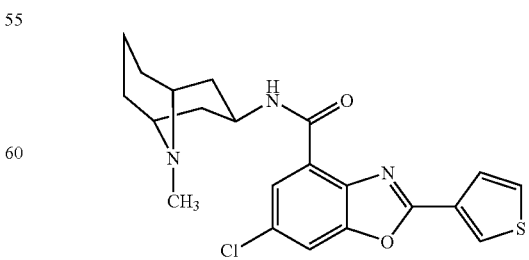

A mixture of 6-chloro-2-(thiophen-3-yl)benzo[d]oxazole-4-carboxylic acid (70 mg, 0.25 mmol), 3-amino-9-methyl- 9-azabicyclo[3.3.1]nonane dihydrochloride (57 mg, 0.25 mmol), 1-ethyl-3-(3-dimethylaminopropyl)carbodiimide hydrochloride (96 mg, 0.50 mmol) and 1-hydroxybenzotriazole (68 mg, 0.50 mmol) in DMF (2 mL) was stirred at room temperature for 5 min, then triethylamine (0.13 mL, 1.0 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) followed by recrystallization from acetonitrile to afford N-(9-methyl-9-azabicyclo[3.3.1]non-3-yl)-6-chloro-2-thiophen-3-ylbenzoxazole-4-carboxamide (30 mg, 29%) as a white solid: $^1$H NMR (500 MHz, $CDCl_3$) δ 8.85 (d, J=7.5 Hz, 1H), 8.25 (dd, J=3.0, 1.5 Hz, 1H), 8.19 (d, J=2.0 Hz, 1H), 7.75 (dd, J=5.0, 1.5 Hz, 1H), 7.66 (d, J=2.0 Hz, 1H), 7.52 (dd, J=5.5, 3.0 Hz, 1H), 4.60-4.53 (m, 1H), 3.12 (d, J=10.5 Hz, 2H), 2.65-2.58 (m, 2H), 2.53 (s, 3H), 2.12-1.95 (m, 3H), 1.60-1.52 (m, 1H), 1.49-1.43 (m, 2H), 1.14 (d, J=12.5 Hz, 2H); MS (ESI+) m/z 416 (M+H); HPLC 98.2% (AUC), $t_R$=12.82 min.

Example 116

Preparation of (S)-N-(1-Azabicyclo[2.2.2]oct-3-yl)-6-chloro-2-thiophen-3-ylbenzoxazole-4-carboxamide

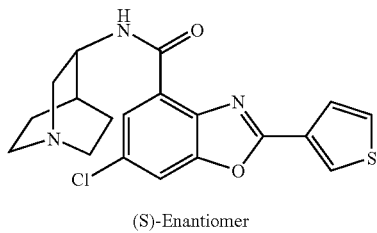

(S)-Enantiomer

A mixture of 6-chloro-2-(thiophen-3-yl)benzo[d]oxazole-4-carboxylic acid (70 mg, 0.25 mmol), (S)-(−)-3-aminoquinuclidine dihydrochloride (50 mg, 0.25 mmol), 1-ethyl-3-(3-dimethylaminopropyl)carbodiimide hydrochloride (96 mg, 0.50 mmol) and 1-hydroxybenzotriazole (68 mg, 0.50 mmol) in DMF (2 mL) was stirred at room temperature for 5 min, then triethylamine (0.13 mL, 1.0 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×20 mL). The combined organics were dried ($Na_2SO_4$), filtered and concentrated. The crude material was purified by column chromatography (silica gel, 89:10:1 dichloromethane/methanol/concentrated ammonium hydroxide) followed by recrystallization from acetonitrile to afford (S)-N-(1-azabicyclo[2.2.2]oct-3-yl)-6-chloro-2-thiophen-3-ylbenzoxazole-4-carboxamide (17 mg, 18%) as a colorless crystal: $^1$H NMR (500 MHz, $CDCl_3$) δ 9.41 (d, J=7.5 Hz, 1H), 8.23 (dd, J=3.0, 1.5 Hz, 1H), 8.16 (d, J=2.0 Hz, 1H), 7.73 (dd, J=5.0, 1.0 Hz, 1H), 7.68 (d, J=2.0 Hz, 1H), 7.52 (dd, J=5.0, 3.0 Hz, 1H), 4.29-4.25 (m, 1H), 3.49 (ddd, J=11.5, 9.5, 2.0 Hz, 1H), 3.10-2.83 (m, 4H), 2.77 (dd, J=14.0, 4.5 Hz, 1H), 2.15-2.11 (m, 1H), 2.04-1.98 (m, 1H), 1.78-1.70 (m, 2H), 1.60-1.51 (m, 1H); MS (ESI+) m/z 388 (M+H); HPLC>99% (AUC), $t_R$=12.45 min.

Example 117

Preparation of (S)-N-(1-Azabicyclo[2.2.2]oct-3-yl)-2-benzo[b]thiophen-2-ylbenzoxazole-4-carboxamide

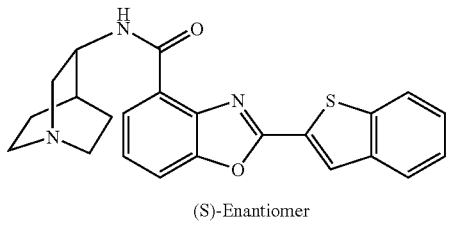

(S)-Enantiomer

Step A: To a suspension of 2-amino-3-hydroxybenzoic acid hydrobromide (152 mg, 0.65 mmol) in dichloromethane (15 mL) was added pyridine (0.42 mL, 5.2 mmol) followed by thianaphthene-2-carbonyl chloride (384 mg, 1.95 mmol). The resulting reaction mixture was stirred at room temperature for 15 min, then DMAP (16 mg, 0.13 mmol) was added and the reaction mixture was stirred at room temperature overnight. Water (10 mL) was added and the reaction was stirred for 10 min. The reaction was quenched with aqueous 1 N HCl (20 mL) until the solution reached pH 1. The solution was stirred for 30 min. The aqueous layer was extracted with ethyl acetate. The organic layers were washed with brine and dried over $Na_2SO_4$, filtered and concentrated to a yellow solid. The product was directly re-dissolved in toluene (10 mL) and the solution was treated with p-toluenesulfonic acid monohydrate (234 mg, 1.23 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (256 mg, quantitative) as a pale yellow solid: $^1$H NMR (300 MHz, DMSO-$d_6$) δ 8.42 (s, 1H), 8.13-8.02 (m, 1H), 7.87-7.74 (m, 2H), 7.57-7.46 (m, 2H), 7.40 (t, J=15.0 Hz, 1H), 7.32-7.28 (m, 1H); MS (ESI+) m/z 296 (M+H).

Step B: A mixture of 2-benzo[b]thiophen-2-ylbenzoxazole-4-carboxylic acid from Step A (128 mg, 0.43 mmol), (S)-3-aminoquinuclidine dihydrochloride (104 mg, 0.52 mmol), 1-ethyl-3-(3-dimethylaminopropyl)carbodiimide hydrochloride (164 mg, 0.86 mmol) and 1-hydroxybenzotriazole (116 mg, 0.86 mmol) in DMF (5 mL) was stirred for 10 min at room temperature, then triethylamine (0.63 mL, 2.2 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-benzo[b]thiophen-2-ylbenzoxazole-4-carboxamide (42 mg, 24%) as a white solid: $^1$H NMR (500 MHz, $CDCl_3$) δ 9.52 (d, J=7.5 Hz, 1H), 8.26-8.18 (m, 2H), 7.95-7.92 (m, 2H), 7.72 (dd, J=7.0, 1.0

Hz, 1H), 7.52-7.45 (m, 3H), 7.44 (t, J=8.0 Hz, 1H), 4.34-4.29 (m, 1H), 3.55-3.49 (m, 1H), 3.21-3.04 (m, 2H), 2.96-2.82 (m, 3H), 2.18-2.12 (m, 2H), 1.81-1.63 (m, 2H); MS (ESI+) m/z 404 (M+H); HPLC>99% (AUC), $t_R$=13.10 min.

Example 118

Preparation of N-(9-Methyl-9-azabicyclo[3.3.1]non-3-yl)-2-benzo[b]thiophen-2-yl benzoxazole-4-carboxamide

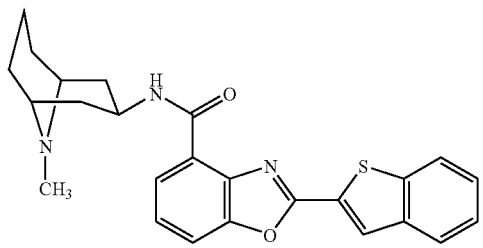

A mixture of 2-benzo[b]thiophen-2-ylbenzoxazole-4-carboxylic acid (128 mg, 0.43 mmol), 3-amino-9-methyl-9-azabicyclo[3.3.1]nonane dihydrochloride (118 mg, 0.52 mmol), 1-ethyl-3-(3-dimethylaminopropyl)carbodiimide hydrochloride (164 mg, 0.86 mmol) and 1-hydroxybenzotriazole (116 mg, 0.86 mmol) in DMF (5 mL) was stirred for 10 min at room temperature, then triethylamine (0.63 mL, 2.2 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-2-benzo[b]thiophen-2-yl benzoxazole-4-carboxamide (49 mg, 61%) as an off-white solid: $^1$H NMR (500 MHz, CDCl$_3$) δ 8.97 (d, J=7.0 Hz, 1H), 8.38-8.19 (m, 2H), 7.95 (dd, J=7.5, 1.5 Hz, 2H), 7.71 (dd, J=8.0, 1.0 Hz, 1H), 7.51-7.46 (m, 3H), 4.63-4.55 (m, 1H), 3.14 (d, J=10.0 Hz, 2H), 2.70-2.62 (m, 2H), 2.56 (s, 3H), 2.08-2.00 (m, 2H), 1.66-1.52 (m, 4H), 1.28-1.22 (m, 2H); MS (ESI+) m/z 432 (M+H); HPLC>99% (AUC), $t_R$=14.59 min.

Example 119

Preparation of (S)-N-(1-Azabicyclo[2.2.2]oct-3-yl)-2-benzofuran-2-ylbenzoxazole-4-carboxamide ( )

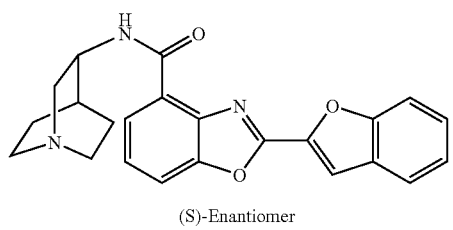

(S)-Enantiomer

Step A: To a suspension of 2-amino-3-hydroxybenzoic acid hydrobromide (152 mg, 0.65 mmol) in dichloromethane (15 mL) was added pyridine (0.42 mL, 5.2 mmol) followed by benzofuran-2-carbonyl chloride (352 mg, 1.95 mmol). The resulting reaction mixture was stirred at room temperature for 15 min, then DMAP (16 mg, 0.13 mmol) was added and the reaction mixture was stirred at room temperature overnight. Water (10 mL) was added and the reaction was stirred for 10 min. The reaction was quenched with aqueous 1 N HCl (20 mL) until the solution reached pH 1. The solution was stirred for 30 min. The aqueous layer was extracted with ethyl acetate. The organic layers were washed with brine and dried over $Na_2SO_4$, filtered and concentrated to a yellow solid. The product was directly re-dissolved in toluene (10 mL) and the solution was treated with p-toluenesulfonic acid monohydrate (240 mg, 1.26 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (337 mg, quantitative) as a yellow solid: $^1$H NMR (500 MHz, DMSO-d$_6$) δ 8.09-8.03 (m, 1H), 7.89-7.84 (m, 1H), 7.63-7.59 (m, 1H), 7.55-7.44 (m, 2H), 7.33-7.27 (m, 1H), 7.23-7.17 (m, 1H), 7.05 (s, 1H); MS (ESI+) m/z 280 (M+H).

Step B: A mixture of 2-benzofuran-2-ylbenzoxazole-4-carboxylic acid from Step A (168 mg, 0.60 mmol), (S)-3-aminoquinuclidine dihydrochloride (143 mg, 0.72 mmol), 1-ethyl-3-(3-dimethylaminopropyl)carbodiimide hydrochloride (229 mg, 1.20 mmol) and 1-hydroxybenzotriazole (162 mg, 1.20 mmol) in DMF (5 mL) was stirred for 10 min at room temperature, then triethylamine (0.39 mL, 3.0 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried ($Na_2SO_4$), filtered and concentrated. The crude material was purified by column chromatography (silica gel, 90:9:1 ethyl acetate/methanol/concentrated ammonium hydroxide) to afford the desired product (157 mg, 68%) as an off-white solid which was purified again by semi-preparative HPLC and recrystallization from ethyl acetate to give (S)-N-(1-azabicyclo[2.2.2]oct-3-yl)-2-benzofuran-2-ylbenzoxazole-4-carboxamide: $^1$H NMR (500 MHz, CDCl$_3$) δ 9.52 (d, J=7.0 Hz, 1H), 8.24 (dd, J=8.0, 1.0 Hz, 1H), 7.76 (dd, J=8.0, 1.5 Hz, 2H), 7.69-7.64 (m, 2H), 7.55-7.48 (m, 2H), 7.39-7.35 (m, 1H), 4.35-4.29 (m, 1H), 3.55-3.49 (m, 1H), 3.20-3.03 (m, 2H), 2.97-2.84 (m, 3H), 2.19-2.10 (m, 2H), 1.81-1.63 (m, 3H); MS (ESI+) m/z 388 (M+H); HPLC>99% (AUC), $t_R$=12.90 min.

Example 120

Preparation of N-(9-Methyl-9-azabicyclo[3.3.1]non-3-yl)-2-benzofuran-2-ylbenzoxazole-4-carboxamide

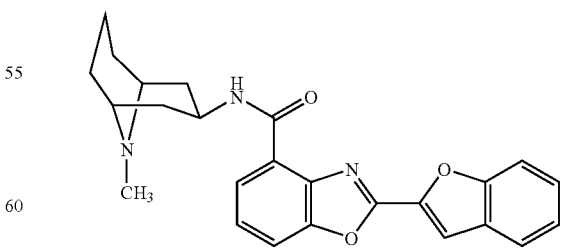

A mixture of 2-benzofuran-2-ylbenzoxazole-4-carboxylic acid (168 mg, 0.60 mmol), 3-amino-9-methyl-9-azabicyclo [3.3.1]nonane dihydrochloride (163 mg, 0.72 mmol), 1-ethyl-3-(3-dimethylaminopropyl)carbodiimide hydrochloride (229 mg, 1.20 mmol) and 1-hydroxybenzotriazole (162 mg, 1.20 mmol) in DMF (5 mL) was stirred for 10 min at room temperature, then triethylamine (0.39 mL, 3.0 mmol) was added. The resulting reaction mixture was stirred at room temperature overnight. The mixture was diluted with ethyl acetate (20 mL), and then washed with a saturated solution of sodium bicarbonate. The aqueous layer was further extracted with ethyl acetate (2×50 mL). The combined organics were dried (Na$_2$SO$_4$), filtered and concentrated. The crude material was purified by semi-preparative HPLC to afford N-(9-methyl-9-azabicyclo[3.3.1]non-3-yl)-2-benzofuran-2-ylbenzoxazole-4-carboxamide (22 mg, 9%) as an off-white solid: $^1$H NMR (500 MHz, CDCl$_3$) δ 9.00-8.95 (m, 1H), 8.26 (dd, J=7.5, 1.0 Hz, 1H), 7.78-7.66 (m, 4H), 7.53-7.47 (m, 2H), 7.38 (t, J=7.5 Hz, 1H), 4.65-4.58 (m, 1H), 3.23-3.12 (m, 2H), 2.71-2.63 (m, 2H), 2.58 (s, 3H), 2.21-2.00 (m, 3H), 1.68-1.52 (m, 3H), 1.32-1.22 (m, 2H); MS (ESI+) m/z 416 (M+H); HPLC>99% (AUC), t$_R$=13.43 min.

Example 121

Preparation of (S)-N-(1-Azabicyclo[2.2.2]oct-3-yl)-2-(3-methylthiophen-2-yl)benzoxazole-4-carboxamide

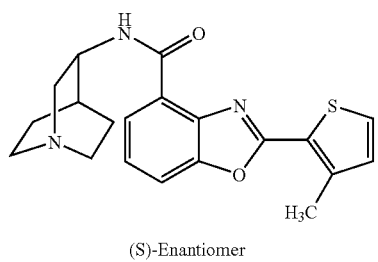

(S)-Enantiomer

Step A: To a suspension of 2-amino-3-hydroxybenzoic-acid hydrobromide (314 mg, 1.34 mmol) in dichloromethane (10 mL) was added 3-methylthiophene-2-carbonyl chloride (215 mg, 1.34 mmol). The resulting reaction mixture was stirred at room temperature for 10 min, then triethylamine (0.70 mL, 5.40 mmol) was added and the reaction mixture was stirred at room temperature overnight. The reaction was quenched with aqueous 1 N HCl (25 mL) until the solution reached pH 1. The solution was stirred for 30 min. The aqueous layer was extracted with ethyl acetate. The organic layers were washed with water and brine, dried over Na$_2$SO$_4$, filtered and concentrated to an orange solid. The amide product was directly re-dissolved in toluene (10 mL) and the solution was treated with p-toluenesulfonic acid monohydrate (336 mg, 1.77 mmol). The reaction mixture was then heated to reflux overnight. The reaction was cooled down to room temperature, poured into water and extracted with ethyl acetate. The organic layer was separated then washed with water, brine, dried over Na$_2$SO$_4$, filtered and concentrated to an orange solid. The crude product was purified by column chromatography (silica gel, 9:1 to 3:1 ethyl acetate/methanol) to afford the desired product (200 mg, 65%) as an orange solid: $^1$H NMR (500 MHz, CD$_3$OD) δ 7.94 (dd, J=8.0, 1.0 Hz, 1H), 7.81 (dd, J=8.5, 1.0 Hz, 1H), 7.65 (d, J=5.0 Hz, 1H), 7.44 (t, J=8.0 Hz, 1H), 7.08 (d, J=5.0 Hz, 1H), 2.74 (s, 3H); MS (ESI+) m/z 260 (M+H).

Step B: A mixture of 2-(3-methylthiophen-2-yl)benzoxazole-4-carboxylic acid from Step A (87 mg, 0.34 mmol), (S)-3-aminoquinuclidine dihydrochloride (82 mg, 0.41 mmol), 1-ethyl-3-(3-dimethylaminopropyl)carbodiimide hydrochloride (130 mg, 0.68 mmol) and 1-hydroxybenzotriazole (92 mg, 0.68 mmol) in DMF (5 mL) was stirred at room temperature for 10 min, then triethylamine (0.24 mL, 1.70 mmol) was added. The resulting reaction mixture was stirred at room temperature overnight. The mixture was diluted with dichloromethane (20 mL), and then washed with a saturated solution of sodium bicarbonate. The aqueous layer was further extracted with dichloromethane (2×50 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-(3-methylthiophen-2-yl)benzoxazole-4-carboxamide (87 mg, 70%) as a white solid: $^1$H NMR (500 MHz, CDCl$_3$) δ 9.41 (d, J=7.0 Hz, 1H), 8.18 (dd, J=7.5, 1.0 Hz, 1H), 7.68 (dd, J=8.0, 1.0 Hz, 1H), 7.51 (d, J=5.0 Hz, 1H), 7.44 (t, J=8.0 Hz, 1H), 7.05 (d, J=5.0 Hz, 1H), 4.34-4.27 (m, 1H), 3.08-2.88 (m, 4H), 2.79-2.76 (m, 4H), 2.15-2.11 (m, 1H), 1.79-1.55 (m, 5H); MS (ESI+) m/z 368 (M+H); HPLC>99% (AUC), t$_R$=12.33 min.

Example 122

Preparation of N-(9-Methyl-9-azabicyclo[3.3.1]non-3-yl)-2-(3-methylthiophen-2-yl)benzoxazole-4-carboxamide

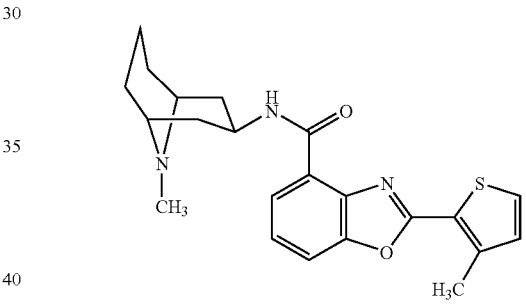

A mixture of 2-(3-methylthiophen-2-yl)benzoxazole-4-carboxylic acid (87 mg, 0.34 mmol), 3-amino-9-methyl-9-azabicyclo[3.3.1]nonane dihydrochloride (93 mg, 0.41 mmol), 1-ethyl-3-(3-dimethylaminopropyl)carbodiimide hydrochloride (130 mg, 0.68 mmol) and 1-hydroxybenzotriazole (92 mg, 0.68 mmol) in DMF (5 mL) was stirred at room temperature for 10 min, then triethylamine (0.24 mL, 1.7 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) to afford N-(9-methyl-9-azabicyclo[3.3.1]non-3-yl)-2-(3-methylthiophen-2-yl)benzoxazole-4-carboxamide (92 mg, 69%) as an off-white solid: $^1$H NMR (500 MHz, CDCl$_3$) δ 8.99 (d, J=7.0 Hz, 1H), 8.19 (dd, J=8.0, 1.0 Hz, 1H), 7.66 (dd, J=8.5, 1.0 Hz, 1H), 7.51 (d, J=5.0 Hz, 1H), 7.43 (t, J=7.5 Hz, 1H), 7.06 (d, J=5.0 Hz, 1H), 4.55-4.51 (m, 1H), 3.18-3.09 (m, 2H), 2.79 (s, 3H), 2.68-2.60 (m, 2H), 2.55 (s, 3H), 2.08-1.98 (m, 3H), 1.65-1.42 (m, 3H), 1.16-1.11 (m, 2H); MS (ESI+) m/z 396 (M+H); HPLC=98.4% (AUC), t$_R$=12.84 min.

Example 123

Preparation of N-(9-Methyl-9-azabicyclo[3.3.1]non-3-yl)-6-chloro-2-(3'-methylthiophen-2-yl)benzoxazole-4-carboxamide

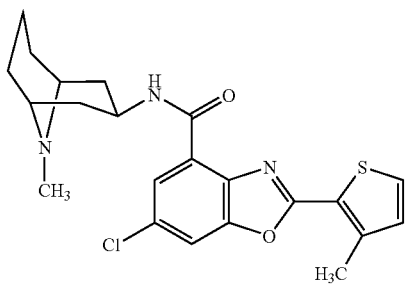

Step A: To a suspension of 2-amino-3-hydroxybenzoic acid hydrobromide (359 mg, 1.34 mmol) in dichloromethane (10 mL) was added 3-methylthiophene-2-carbonyl chloride (215 mg, 1.34 mmol). The resulting reaction mixture was stirred at room temperature for 10 min then triethylamine (0.70 mL, 5.40 mmol) was added and the reaction mixture was stirred at room temperature overnight. The reaction was quenched with aqueous 1 N HCl (25 mL) until the solution reached pH 1. The solution was stirred for 30 min. The aqueous layer was extracted with ethyl acetate. The organic layers were washed with water and brine, dried over $Na_2SO_4$, filtered and concentrated to a yellow solid. The amide product was directly re-dissolved in toluene (10 mL) and the solution was treated with p-toluenesulfonic acid monohydrate (382 mg, 2.01 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to an orange solid. The crude product was purified by column chromatography (silica gel, 9:1 to 2:1 ethyl acetate/methanol) to afford the desired product (243 mg, 62%) as an orange solid: $^1$H NMR (300 MHz, DMSO-$d_6$) δ 7.90 (d, J=1.5 Hz, 1H), 7.84 (d, J=5.1 Hz, 1H), 7.62 (s, 1H), 7.16 (d, J=5.1 Hz, 1H), 2.68 (s, 3H); MS (ESI+) m/z 293 (M+H).

Step B: A mixture of 6-chloro-2-(3-methylthiophen-2-yl)benzoxazole-4-carboxylic acid from step A (89 mg, 0.31 mmol), 3-amino-9-methyl-9-azabicyclo[3.3.1]nonane dihydrochloride (84 mg, 0.37 mmol), 1-ethyl-3-(3-dimethylaminopropyl)carbodiimide hydrochloride (118 mg, 0.62 mmol) and 1-hydroxybenzotriazole (84 mg, 0.62 mmol) in DMF (3 mL) was stirred at room temperature for 10 min, then triethylamine (0.22 mL, 1.6 mmol) was added. The resulting reaction mixture was stirred at room temperature overnight. The mixture was diluted with dichloromethane (100 mL), and then washed with a saturated solution of sodium bicarbonate. The aqueous layer was further extracted with dichloromethane (2×100 mL). The combined organics were dried ($Na_2SO_4$), filtered and concentrated. The crude material was purified by column chromatography (silica gel, 90:9:1 ethyl acetate/methanol/concentrated ammonium hydroxide) and semi-preparative HPLC to afford N-(9-methyl-9-azabicyclo[3.3.1]non-3-yl)-6-chloro-2-(3-methylthiophen-2-yl)benzoxazole-4-carboxamide (18 mg, 14%) as a white solid: $^1$H NMR (500 MHz, CDCl$_3$) δ 8.94 (d, J=6.5 Hz, 1H), 8.17 (d, J=2.0 Hz, 1H), 7.66 (d, J=2.0 Hz, 1H), 7.53 (d, J=5.0 Hz, 1H), 7.06 (d, J=5.0 Hz, 1H), 4.62-4.54 (m, 1H), 3.17-3.13 (m, 2H), 2.77 (s, 3H), 2.68-2.59 (m, 2H), 2.55 (s, 3H), 2.07-1.99 (m, 3H), 1.60-1.43 (m, 3H), 1.17-1.11 (m, 2H); MS (ESI+) m/z 430 (M+H); HPLC>99.0% (AUC), $t_R$=13.50 min.

Example 124

Preparation of (S)-N-(1-Azabicyclo[2.2.2]oct-3-yl)-2-(3-chlorothiophen-2-yl)benzoxazole-4-carboxamide

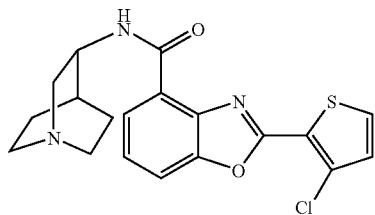

(S)-Enantiomer

Step A: To an ice-cold solution of 3-chlorothiophene-2-carboxylic acid (218 mg, 1.34 mmol) in dichloromethane (10 mL) was added oxalyl chloride (0.11 mL, 1.34 mmol) dropwise. The ice bath was removed and stirring continued for 1 h. 2-Amino-3-hydroxybenzoic acid hydrobromide (314 mg, 1.34 mmol) was added followed by triethylamine (0.75 mL, 5.4 mmol). The resulting reaction mixture was stirred at room temperature overnight. The reaction was quenched with aqueous 1 N HCl (25 mL) until the solution reached pH 1 and stirred for 30 min. The aqueous layer was extracted with ethyl acetate. The organic layers were washed with brine and dried over $Na_2SO_4$, filtered and concentrated to a yellow solid. The product was directly re-dissolved in toluene (10 mL) and the solution was treated with p-toluenesulfonic acid monohydrate (447 mg, 2.36 mmol). The reaction mixture was then heated to reflux overnight. The reaction was cooled down to room temperature, poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (108 mg, 25%) as a yellow solid: $^1$H NMR (500 MHz, DMSO-$d_6$) δ 8.05 (d, J=5.0 Hz, 1H), 7.83 (d, J=8.0 Hz, 1H), 7.79 (d, J=7.5 Hz, 1H), 7.42 (t, J=7.5 Hz, 1H), 7.34 (d, J=5.5 Hz, 1H); MS (ESI+) m/z 280 (M+H).

Step B: A mixture of 2-(3-chlorothiophen-2-yl)benzoxazole-4-carboxylic acid from Step A (59 mg, 0.21 mmol), (S)-3-aminoquinuclidine dihydrochloride (50 mg, 0.251 mmol), 1-ethyl-3-(3-dimethylaminopropyl)carbodiimide hydrochloride (80 mg, 0.42 mmol) and 1-hydroxybenzotriazole (57 mg, 0.42 mmol) in DMF (2 mL) was stirred at room temperature for 10 min, then triethylamine (0.15 mL, 1.05 mmol) was added. The resulting reaction mixture was stirred at room temperature overnight. The mixture was diluted with dichoromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and semi-preparative HPLC to afford (S)-N-(1-azabicyclo[2.2.2]oct-3-yl)-2-(3-chlorothiophen-2-yl)benzoxazole-4-carboxamide (21 mg, 26%) as a white solid: $^1$H NMR (500 MHz, CDCl$_3$) δ 9.45 (d, J=7.0 Hz, 1H), 8.21 (dd, J=8.0, 1.0 Hz, 1H), 7.73 (dd, J=8.0, 1.0 Hz, 1H), 7.59 (d, J=5.5 Hz, 1H), 7.50 (t, J=8.0 Hz, 1H), 7.16 (d, J=5.0 Hz, 1H), 4.37-4.30 (m, 1H), 3.57-3.49 (m, 1H), 3.14-3.06 (m, 1H), 3.04-2.89 (m, 3H), 2.86-

2.80 (m, 1H), 2.19-2.05 (m, 2H), 1.83-1.75 (m, 2H) 1.63-1.45 (m, 1H); MS (ESI+) m/z 388 (M+H); HPLC 96.5% (AUC), $t_R$=12.57 min.

Example 125

Preparation of N-(9-Methyl-9-azabicyclo[3.3.1]non-3-yl)-2-(3-chlorothiophen-2-yl)benzoxazole-4-carboxamide

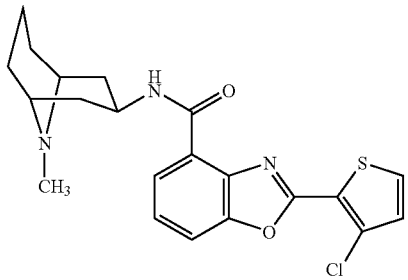

A mixture of 2-(3-chlorothiophen-2-yl)benzoxazole-4-carboxylic acid (59 mg, 0.21 mmol), 3-amino-9-methyl-9-azabicyclo[3.3.1]nonane dihydrochloride (57 mg, 0.25 mmol), 1-ethyl-3-(3-dimethylaminopropyl)carbodiimide hydrochloride (80 mg, 0.42 mmol) and 1-hydroxybenzotriazole (57 mg, 0.42 mmol) in DMF (2 mL) was stirred at room temperature for 10 min, then triethylamine (0.15 mL, 1.05 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) and semi-preparative HPLC to afford N-(9-methyl-9-azabicyclo[3.3.1]non-3-yl)-2-(3-chlorothiophen-2-yl)benzoxazole-4-carboxamide (45 mg, 51%) as a white solid: $^1$H NMR (500 MHz, CDCl$_3$) δ 9.11 (d, J=7.0 Hz, 1H), 8.22 (dd, J=8.0, 1.0 Hz, 1H), 7.69 (dd, J=8.0, 1.0 Hz, 1H), 7.59 (d, J=5.5 Hz, 1H), 7.48 (t, J=8.0 Hz, 1H), 7.16 (d, J=5.5 Hz, 1H), 4.65-4.55 (m, 1H), 3.18-3.09 (m, 2H), 2.68-2.60 (m, 2H) 2.56 (s, 3H), 2.12-1.95 (m, 3H), 1.62-1.44 (m, 4H), 1.21-1.10 (m, 1H); MS (ESI+) m/z 416 (M+H); HPLC>99% (AUC), $t_R$=12.97 min.

Example 126

Preparation of (S)-N-(1-Azabicyclo[2.2.2]oct-3-yl)-2-(3-bromothiophen-2-yl)benzoxazole-4-carboxamide

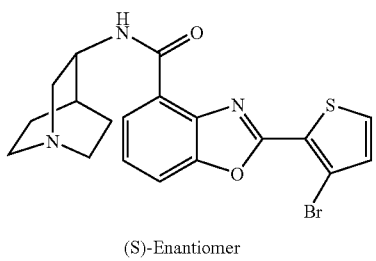

(S)-Enantiomer

Step A: To a suspension of 3-bromothiophene-2-carboxylic acid (500 mg, 2.42 mmol) dichloromethane (10 mL) was added oxalyl chloride (0.42 mL, 4.84 mmol) dropwise, followed by 2 drops of DMF. The reaction was stirred at room temperature for 3 h. The solvent was evaporated and the solid directly redissolved in dichloromethane (10 mL). 2-Amino-3-hydroxybenzoic acid hydrobromide (565 mg, 2.42 mmol) was added to the reaction mixture followed by triethylamine (1.35 mL, 9.68 mmol). The reaction mixture was stirred at room temperature overnight. The reaction was quenched with aqueous 1 N HCl (20 mL) until the solution reached pH 1. The solution was stirred for 30 min. The aqueous layer was extracted with ethyl acetate. The organic layers were washed with brine and dried over Na$_2$SO$_4$, filtered and concentrated to an orange solid. The product was directly re-dissolved in toluene (10 mL) and the solution was treated with p-toluenesulfonic acid monohydrate (670 mg, 3.53 mmol). The reaction mixture was then heated to reflux for 6 h. The reaction was cooled down to room temperature, poured into water and extracted with ethyl acetate. The organic layer was separated then washed with water, brine, dried over Na$_2$SO$_4$, filtered and concentrated to an orange solid. The crude product was purified by column chromatography (silica gel, 9:1 to 2:1 ethyl acetate/methanol) to afford the desired product (488 mg, 64%) as a pale yellow solid: $^1$H NMR (500 MHz, DMSO-d$_6$) δ 8.00 (d, J=5.5 Hz, 1H), 7.78 (d, J=8.0 Hz, 1H), 7.74 (d, J=7.5 Hz, 1H), 7.40 (t, J=8.0 Hz, 1H), 7.37 (d, J=5.0 Hz, 1H); MS (ESI+) m/z 324 (M+H).

Step B: A mixture of 2-(3-bromothiophen-2-yl)benzoxazole-4-carboxylic acid from Step A (302 mg, 0.93 mmol), (S)-3-aminoquinuclidine dihydrochloride (223 mg, 1.12 mmol), 1-ethyl-3-(3-dimethylaminopropyl)carbodiimide hydrochloride (355 mg, 1.86 mmol) and 1-hydroxybenzotriazole (251 mg, 1.86 mmol) in DMF (5 mL) was stirred at room temperature for 10 min, then triethylamine (0.65 mL, 4.65 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried (Na$_2$SO$_4$), filtered and concentrated. The crude material was purified by column chromatography (silica gel, 90:9:1 ethyl acetate/methanol/concentrated ammonium hydroxide) and semi-preparative HPLC to afford (S)-N-(1-azabicyclo[2.2.2]oct-3-yl)-2-(3-bromothiophen-2-yl)benzoxazole-4-carboxamide (39 mg, 10%) as a white solid: $^1$H NMR (500 MHz, CDCl$_3$) δ 9.39 (d, J=7.0 Hz, 1H), 8.22 (dd, J=7.5, 1.0 Hz, 1H), 7.73 (dd, J=8.0, 1.0 Hz, 1H), 7.57 (d, J=8.0 Hz, 1H), 7.50 (t, J=8.0 Hz, 1H), 7.23 (d, J=5.0 Hz, 1H), 4.37-4.30 (m, 1H), 3.57-3.50 (m, 1H), 3.14-3.06 (m, 1H), 3.02-2.83 (m, 4H), 2.19-2.15 (m, 1H), 2.13-2.05 (m, 1H), 1.82-1.73 (m, 2H), 1.62-1.54 (m, 1H); MS (ESI+) m/z 432 (M+H); HPLC>99% (AUC), $t_R$=12.42 min.

Example 127

Preparation of N-(9-Methyl-9-azabicyclo[3.3.1]non-3-yl)-2-(3-bromothiophen-2-yl)benzoxazole-4-carboxamide

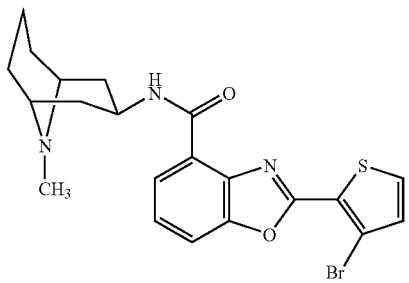

A mixture of 2-(3-bromothiophen-2-yl)benzoxazole-4-carboxylic acid (188 mg, 0.58 mmol), 3-amino-9-methyl-9- azabicyclo[3.3.1]nonane dihydrochloride (159 mg, 0.70 mmol), 1-ethyl-3-(3-dimethylaminopropyl)carbodiimide hydrochloride (222 mg, 1.16 mmol) and 1-hydroxybenzotriazole (157 mg, 1.16 mmol) in DMF (3 mL) was stirred at room temperature for 10 min, then triethylamine (0.40 mL, 2.9 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and recrystallized from acetonitrile to afford N-(9-methyl-9-azabicyclo[3.3.1]non-3-yl)-2-(3-bromothiophen-2-yl)benzoxazole-4-carboxamide (199 mg, 75%) as a white solid: $^1$H NMR (500 MHz, $CDCl_3$) δ 9.11 (d, J=6.5 Hz, 1H), 8.22 (dd, J=7.5, 1.0 Hz, 1H), 7.70 (d, J=8.0 Hz, 1H), 7.58 (d, J=5.5 Hz, 1H), 7.48 (t, J=8.0 Hz, 1H), 7.24 (d, J=5.5 Hz, 1H), 4.68-4.59 (m, 1H), 3.22-3.13 (m, 2H), 2.70-2.55 (m, 5H), 2.13-1.98 (m, 3H), 1.63-1.49 (m, 3H), 1.26-1.12 (m, 2H); MS (ESI+) m/z 460 (M+H); HPLC>99% (AUC), $t_R$=13.09 min.

Example 128

Preparation of (S)-N-(1-Azabicyclo[2.2.2]oct-3-yl)-6-chloro-2-(3-chlorothiophen-2-yl)benzoxazole-4-carboxamide

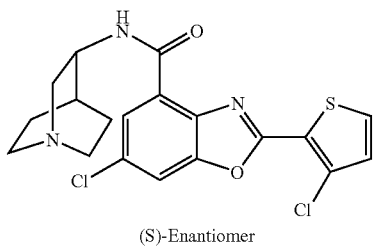

(S)-Enantiomer

Step A: To a suspension of 3-chlorothiophene-2-carboxylic acid (218 mg, 1.34 mmol) in dichloromethane (8 mL) was added oxalyl chloride (0.23 mL, 2.68 mmol) dropwise, followed by 2 drops of DMF. The reaction was stirred at room temperature for 2 h. The solvent was evaporated and the solid directly redissolved in dichloromethane (8 mL). 2-Amino-5-chloro-3-hydroxybenzoic acid hydrobromide (359 mg, 1.34 mmol) was added to the reaction mixture followed by triethylamine (0.75 mL, 5.40 mmol). The reaction mixture was stirred at room temperature overnight. The reaction was quenched with aqueous 1 N HCl (20 mL) until the solution reached pH 1. The solution was stirred for 30 min. The aqueous layer was extracted with ethyl acetate. The organic layers were washed with brine and dried over $Na_2SO_4$, filtered and concentrated to a yellow solid. The product was directly re-dissolved in toluene (10 mL) and the solution was treated with p-toluenesulfonic acid monohydrate (384 mg, 2.02 mmol). The reaction mixture was then heated to reflux for 6 h. The reaction was cooled down to room temperature and the solvent was evaporated. The reaction mixture was poured into water and extracted with ethyl acetate. The organic layer was separated then washed with water, brine, dried over $Na_2SO_4$, filtered and concentrated to a yellow solid. The crude product was purified by column chromatography (silica gel, 9:1 to 2:1 ethyl acetate/methanol) to afford the desired product (135 mg, 32%) as a yellow solid: $^1$H NMR (500 MHz, DMSO-$d_6$) δ 8.05 (d, J=5.0 Hz, 1H), 7.96 (d, J=1.5 Hz, 1H), 7.73-7.67 (m, 1H), 7.34 (d, J=5.5 Hz, 1H); MS (ESI+) m/z 314 (M+H).

Step B: A mixture of 6-chloro-2-(3-chlorothiophen-2-yl)benzoxazole-4-carboxylic acid from Step A (67 mg, 0.21 mmol), (S)-3-aminoquinuclidine dihydrochloride (50 mg, 0.25 mmol), 1-ethyl-3-(3-dimethylaminopropyl)carbodiimide hydrochloride (80 mg, 0.42 mmol) and 1-hydroxybenzotriazole (57 mg, 0.42 mmol) in DMF (2 mL) was stirred at room temperature, then triethylamine (0.15 mL, 1.05 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and recrystallized from acetonitrile to afford (S)-N-(1-azabicyclo[2.2.2]oct-3-yl)-6-chloro-2-(3-chlorothiophen-2-yl)benzoxazole-4-carboxamide (32 mg, 36%) as a white solid: $^1$H NMR (500 MHz, $CDCl_3$) δ 9.32 (d, J=7.0 Hz, 1H), 8.19 (d, J=2.0 Hz, 1H), 7.72 (d, J=2.0 Hz, 1H), 7.61 (d, J=5.0 Hz, 1H), 7.16 (d, J=5.0 Hz, 1H), 4.34-4.28 (m, 1H), 3.55-3.48 (m, 2H), 3.11-3.05 (m, 1H), 3.02-2.88 (m, 3H), 2.83-2.76 (m, 1H), 2.16-2.12 (m, 1H), 2.09-2.01 (m, 1H), 1.81-1.75 (m, 1H), 1.62-1.55 (m, 1H); MS (ESI+) m/z 422 (M+H); HPLC>99% (AUC), $t_R$=12.85 min.

Example 129

Preparation of N-(9-Methyl-9-azabicyclo[3.3.1]non-3-yl)-6-chloro-2-(3-chlorothiophen-2-yl)benzoxazole-4-carboxamide

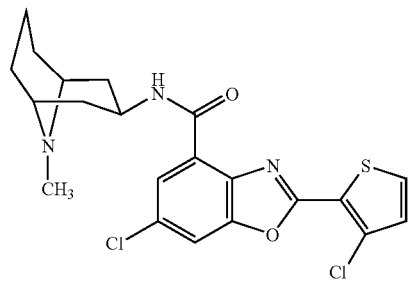

A mixture of 6-chloro-2-(3-chlorothiophen-2-yl)benzoxazole-4-carboxylic acid (67 mg, 0.21 mmol), 3-amino-9-methyl-9-azabicyclo[3.3.1]nonane dihydrochloride (57 mg, 0.25 mmol), 1-ethyl-3-(3-dimethylaminopropyl)carbodiimide hydrochloride (80 mg, 0.42 mmol) and 1-hydroxybenzotriazole (57 mg, 0.42 mmol) in DMF (5 mL) was stirred at room temperature, then triethylamine (0.15 mL, 1.05 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and recrystallized from acetonitrile to afford N-(9-methyl-9-azabicyclo[3.3.1]non-3-yl)-6-chloro-2-(3-chlorothiophen-2-yl)benzoxazole-4-carboxamide (35 mg, 37%) as a white solid: $^1$H NMR (500 MHz, $CDCl_3$) δ 9.01 (d, J=6.0 Hz, 1H), 8.20 (d, J=2.0 Hz, 1H), 7.70 (d, J=1.5 Hz, 1H), 7.61 (d, J=5.5 Hz, 1H), 7.17 (d, J=5.0 Hz, 1H), 4.63-4.53 (m, 1H), 3.24-3.13 (m, 2H), 2.70-2.55 (m, 5H), 2.12-2.00 (m, 3H), 1.64-1.48 (m, 3H), 1.28-1.12 (m, 2H); MS (ESI+) m/z 450 (M+H); HPLC>99% (AUC), $t_R$=13.32 min.

Example 130

Preparation of (S)-N-(1-Azabicyclo[2.2.2]oct-3-yl)-2-(5-methylthiophen-2-yl)benzoxazole-4-carboxamide

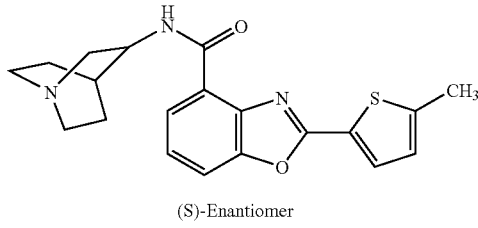

(S)-Enantiomer

Step A: To an ice-cold suspension of 5-methyl-2-thiophenecaboxylic acid (304 mg, 2.14 mmol) in dichloromethane (10 mL) was added oxalyl chloride (0.18 mL, 2.14 mmol) dropwise. Then the ice-water bath was removed and the mixture was stirred for 1 h. To the above solution was added 2-amino-3-hydroxybenzoic acid hydrobromide (0.50 g, 2.14 mmol) followed by triethylamine (1.20 mL, 8.56 mmol). The resulting reaction mixture was stirred at room temperature overnight. The reaction was quenched with water (50 mL). The reaction mixture was extracted with dichloromethane. The aqueous layer was extracted with dichloromethane (2×50 mL). The combined organic layers were dried over $Na_2SO_4$, filtered and concentrated to afford a yellow solid. The crude was dissolved in toluene (5 mL) and the solution was treated with p-toluenesulfonic acid monohydrate (464 mg, 2.44 mmol). The reaction mixture was then heated at 95° C. under nitrogen for 5 h. The reaction was cooled down to room temperature, poured into water and extracted with dichloromethane. The organic layer was separated, washed with water, brine, dried over $Na_2SO_4$, filtered and concentrated to a yellow solid. The crude material was purified by recrystallization from methanol to afford the desired product (111 mg, 26%) as an off-white solid: $^1H$ NMR (500 MHz, DMSO-$d_6$) δ 7.83-7.80 (m, 1H), 7.75-7.70 (m, 2H), 7.58-7.55 (m, 1H), 7.37-7.32 (m, 1H); MS (ESI+) m/z 260 (M+H).

Step B: A mixture of 2-(5-methylthiophen-2-yl)benzoxazole-4-carboxylic acid (106 mg, 0.41 mmol), 1-ethyl-3-(3-dimethylaminopropyl)carbodiimide hydrochloride (156 mg, 0.82 mmol), 1-hydroxybenzotriazole (110 mg, 0.82 mmol) and (S)-(−)-3-aminoquinuclidine dihydrochloride (101 mg, 0.51 mmol) in DMF (3 mL) was stirred at room temperature for 10 min, then triethylamine (0.23 mL, 1.64 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford (S)-N-(1-azabicyclo[2.2.2]oct-3-yl)-2-(5-methylthiophen-2-yl)benzoxazole-4-carboxamide (19 mg, 13%) as a light yellow solid: $^1H$ NMR (500 MHz, CDCl$_3$) δ 9.55 (d, J=7.4 Hz, 1H), 8.15 (dd, J=7.8, 0.9 Hz, 1H), 7.74 (d, J=3.7 Hz, 1H), 7.65 (dd, J=7.2, 1.0 Hz, 1H), 7.42 (t, J=7.9 Hz, 1H), 6.89 (dd, J=3.7, 1.0 Hz, 1H), 4.35-4.30 (m, 1H), 3.55-3.48 (m, 1H), 3.16-3.07 (m, 2H), 2.96-2.91 (m, 2H), 2.86-2.82 (m, 1H), 2.60 (s, 3H), 2.18-2.12 (m, 2H), 1.80-1.75 (m, 2H), 1.71-1.65 (m, 1H); MS (ESI+) m/z 368 (M+H); HPLC 98.0% (AUC), $t_R$=12.40 min.

Example 131

Preparation of (S)-N-(1-Azabicyclo[2.2.2]oct-3-yl)-2-(5-chloro-thiophen-2-yl)benzoxazole-4-carboxamide

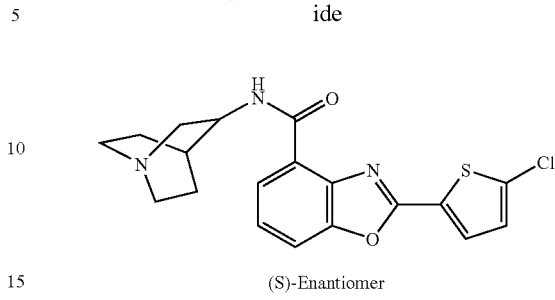

(S)-Enantiomer

Step A: To an ice-cold suspension of 5-chlorothiophene-2-caboxylic acid (347 mg, 2.14 mmol) in dichloromethane (15 mL) was added oxalyl chloride (0.18 mL, 2.14 mmol) dropwise. Then the ice-water bath was removed and the mixture was stirred for 1 h. To the above solution was added 2-amino-3-hydroxybenzoic acid hydrobromide (0.50 g, 2.14 mmol) followed by the addition of triethylamine (1.19 mL, 8.56 mmol). The resulting reaction mixture was stirred at room temperature overnight. The reaction was quenched with water (50 mL). The reaction mixture was extracted with dichloromethane. The aqueous layer was extracted with dichloromethane (2×50 mL). The combined organic layers were dried over $Na_2SO_4$, filtered and concentrated to afford a yellow solid. The crude was dissolved in toluene (10 mL) and the solution was treated with p-toluenesulfonic acid monohydrate (258 mg, 1.36 mmol). The reaction mixture was then heated at 95° C. under nitrogen for 6 h. The reaction was cooled down to room temperature, poured into water and extracted with dichloromethane. The organic layer was separated, washed with water, brine, dried over $Na_2SO_4$, filtered and concentrated to a yellow solid. The crude material was purified by column chromatography (silica gel, 90:9:1 ethyl acetate/methanol/concentrated ammonium hydroxide) to afford the desired product (225 mg, 38%) as an off-white solid: $^1H$ NMR (500 MHz, DMSO-$d_6$) δ 8.01 (dd, J=8.2, 0.9 Hz, 1H), 7.93-7.90 (m, 2H), 7.52 (t, J=4.0 Hz, 1H), 7.39 (d, J=4.0 Hz, 1H); MS (ESI+) m/z 280 (M+H).

Step B: A mixture of 2-(5-chlorothiophen-2-yl)benzoxazole-4-carboxylic acid (110 mg, 0.39 mmol), 1-ethyl-3-(3-dimethylaminopropyl)carbodiimide hydrochloride (149 mg, 0.78 mmol), 1-hydroxybenzotriazole (106 mg, 0.78 mmol) and (S)-(−)-3-aminoquinuclidine dihydrochloride (135 mg, 0.49 mmol) in DMF (3 mL) was stirred at room temperature for 10 min, then triethylamine (0.22 mL, 1.4 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (50 mL), dried ($Na_2SO_4$), filtered and concentrated. The crude material was purified by column chromatography (silica gel, 90:9:1 dichloromethane/methanol/concentrated ammonium hydroxide) to afford (S)-N-(1-azabicyclo[2.2.2]oct-3-yl)-2-(5-chloro-thiophen-2-yl)benzoxazole-4-carboxamide (22 mg, 17%) as a white solid: $^1H$ NMR (500 MHz, CDCl$_3$) δ 9.41 (d, J=7.3 Hz, 1H), 8.17 (dd, J=7.8, 1.0 Hz, 1H), 7.73 (d, J=4.1 Hz, 1H), 7.69 (dd, J=8.2, 1.0 Hz, 1H), 7.48 (t, J=8.0 Hz, 1H), 7.06 (d, J=4.0 Hz, 1H), 4.50-4.45 (m, 1H), 3.65-3.60 (m, 1H), 3.30-3.20 (m, 2H), 3.15-3.05 (m, 2H), 3.02-2.95 (m, 1H), 2.30-2.55 (m, 2H), 1.95-1.78 (m, 3H); MS (ESI+) m/z 388 (M+H); HPLC>99% (AUC), $t_R$=12.59 min.

Example 132

Preparation of N-(9-Methyl-9-azabicyclo[3.3.1]non-3-yl)-2-(5-chlorothiophene-2-yl)benzoxazole-4-carboxamide

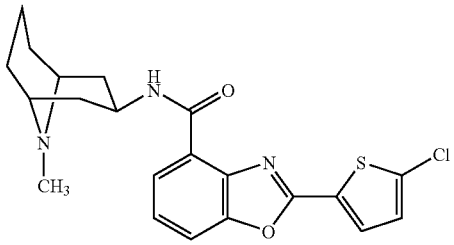

A mixture of 2-(5-chlorothiophen-2-yl)benzoxazole-4-carboxylic acid (110 mg, 0.39 mmol), 1-ethyl-3-(3-dimethylaminopropyl)carbodiimide hydrochloride (149 mg, 0.78 mmol), 1-hydroxybenzotriazole (106 mg, 0.78 mmol) and 3-amino-9-methyl-9-azabicyclo[3.3.1]nonane dihydrochloride (111 mg, 0.48 mmol) in DMF (5 mL) was stirred at room temperature for 10 min, then triethylamine (0.22 mL, 1.56 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with water (2×50 mL), brine (2×50 mL), dried (Na$_2$SO$_4$), filtered and concentrated. The crude material was purified by column chromatography (silica gel, 90:9:1 dichloromethane/methanol/concentrated ammonium hydroxide) and recrystallization from acetonitrile to afford N-(9-methyl-9-azabicyclo[3.3.1]non-3-yl)-2-(5-chlorothiophene-2-yl)benzoxazole-4-carboxamide (19 mg, 12%) as a light brown solid: $^1$H NMR (500 MHz, CDCl$_3$) δ 8.85 (d, J=6.3 Hz, 1H), 8.20 (dd, J=7.8, 1.0 Hz, 1H), 7.73 (d, J=4.0 Hz, 1H), 7.65 (dd, J=8.1, 1.0 Hz, 1H), 7.45 (t, J=7.9 Hz, 1H), 7.06 (d, J=4.1 Hz, 1H), 4.60-4.54 (m, 1H), 3.20-3.10 (m, 2H), 2.67-2.58 (m, 2H), 2.56 (s, 3H), 2.20-2.00 (m, 3H), 1.60-1.45 (m, 3H), 1.25-1.15 (m, 2H); MS (ESI+) m/z 416 (M+H); HPLC>99% (AUC), t$_R$=13.02 min.

Example 133

Preparation of (S)-N-(1-Azabicyclo[2.2.2]oct-3-yl)-2-(5-bromothiophen-2-yl)benzoxazole-4-carboxamide

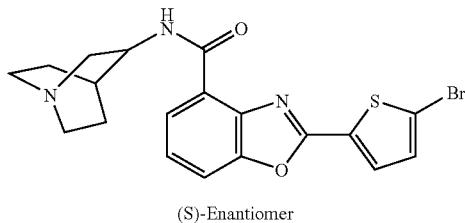

(S)-Enantiomer

Step A: To an ice-cold suspension of 5-bromothiophene-2-caboxylic acid (2.07 g, 10.0 mmol) in dichloromethane (20 mL) was added oxalyl chloride (0.18 mL, 2.14 mmol) dropwise. Then the ice-water bath was removed and the mixture was stirred for 1 h. To the above solution was added 2-amino-3-hydroxybenzoic acid hydrobromide (2.34 g, 10.0 mmol) followed by the addition of triethylamine (5.57 mL, 40.0 mmol). The resulting reaction mixture was stirred at room temperature overnight. The reaction was quenched with 1 N HCl (50 mL), and the reaction mixture was extracted with dichloromethane. The aqueous layer was extracted with dichloromethane (2×100 mL). The combined organic layers were dried over Na$_2$SO$_4$, filtered and concentrated to afford a yellow solid. The crude was dissolved in toluene (15 mL) and the solution was treated with p-toluenesulfonic acid monohydrate (0.87 g, 4.59 mmol). The reaction mixture was then heated to reflux under nitrogen for 6 h. The reaction was cooled down to room temperature, poured into water and extracted with dichloromethane. The organic layer was separated, washed with water, brine, dried over Na$_2$SO$_4$, filtered and concentrated to a yellow solid. The crude material was purified by recrystallization from dichloromethane and ethyl acetate to afford the desired product (356 mg, 25%) as an off-white solid: $^1$H NMR (500 MHz, DMSO-d$_6$) δ 13.17 (s, 1H), 8.01 (dd, J=8.2, 1.0 Hz, 1H), 8.91 (dd, J=7.8, 1.0 Hz, 1H), 7.86 (d, J=4.3 Hz, 1H), 7.52 (t, J=8.2 Hz, 1H), 7.48 (d, J=4.0 Hz, 1H); MS (ESI+) m/z 324 (M+H).

Step B: A mixture of 2-(5-bromo-2-thiophene)benzoxazole-4-carboxylic acid (64 mg, 0.20 mmol), 1-ethyl-3-(3-dimethylaminopropyl)carbodiimide hydrochloride (76 mg, 0.40 mmol), 1-hydroxybenzotriazole (54 mg, 0.40 mmol) and (S)-(−)-3-aminoquinuclidine dihydrochloride (50 mg, 0.25 mmol) in DMF (4 mL) was stirred 10 min at room temperature, then triethylamine (0.10 mL, 0.80 mmol) was added. The resulting reaction mixture was stirred at room temperature overnight. The mixture was diluted with dichloromethane and then washed with a saturated solution of sodium bicarbonate. The aqueous layer was further extracted with dichloromethane (2×50 mL). The combined organic layers were washed with brine (2×50 mL), dried (Na$_2$SO$_4$), filtered and concentrated. The crude material was purified by column chromatography (silica gel, 90:9:1 dichloromethane/methanol/concentrated ammonium hydroxide) to afford (S)-N-(1-azabicyclo[2.2.2]oct-3-yl)-2-(5-bromothiophene-2-yl)benzoxazole-4-carboxamide (76 mg, 88%) as a light yellow solid: $^1$H NMR (500 MHz, CDCl$_3$) δ 9.38 (d, J=7.4 Hz, 1H), 8.19 (dd, J=7.8, 1.0 Hz, 1H), 7.69-7.65 (m, 2H), 7.48 (t, J=7.9 Hz, 1H), 7.19 (d, J=4.0 Hz, 1H), 4.35-4.25 (m, 1H), 3.55-3.48 (m, 1H), 3.15-3.03 (m, 2H), 2.95-2.90 (m, 2H), 2.85-2.76 (m, 1H), 2.15-2.05 (m, 2H), 1.80-1.62 (m, 3H); MS (ESI+) m/z 432 (M+H); HPLC>99% (AUC), t$_R$=12.79 min.

Example 134

Preparation of N-(9-Methyl-9-azabicyclo[3.3.1]non-3-yl)-2-(5-bromothiophene-2-yl)benzoxazole-4-carboxamide

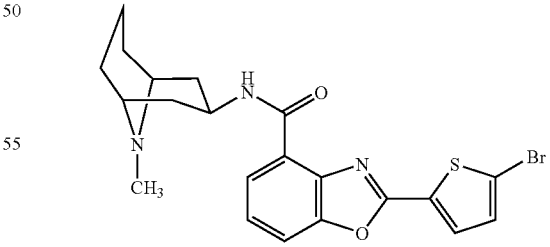

A mixture of 2-(5-bromothiophene)benzoxazole-4-carboxylic acid (64 mg, 0.20 mmol), 1-ethyl-3-(3-dimethylaminopropyl)carbodiimide hydrochloride (76 mg, 0.40 mmol), 1-hydroxybenzotriazole (54 mg, 0.40 mmol) and 3-amino-9-methyl-9-azabicyclo[3.3.1]nonane dihydrochloride (69 mg, 0.25 mmol) in DMF (4 mL) was stirred at room temperature for 10 min, then triethylamine (0.11 mL, 0.80 mmol) was added. The resulting reaction mixture was stirred at room temperature overnight. The mixture was diluted with dichloromethane and then washed with a saturated solution of sodium bicarbonate. The aqueous layer was further extracted with ethyl acetate (2×100 mL). The combined organic layers were washed with water (2×100 mL), brine (2×100 mL), dried ($Na_2SO_4$), filtered and concentrated. The crude material was purified by column chromatography (silica gel, 90:9:1 dichloromethane/methanol/concentrated ammonium hydroxide) and recrystallizations to afford N-(9-methyl-9-azabicyclo[3.3.1]non-3-yl)-2-(5-bromothiophene-2-yl)benzoxazole-4-carboxamide (39 mg, 42%) as a light yellow solid: $^1$H NMR (500 MHz, $CDCl_3$) δ 8.84 (d, J=6.2 Hz, 1H), 8.20 (dd, J=7.8, 1.0 Hz, 1H), 7.69 (d, J=3.9 Hz, 1H), 7.65 (dd, J=8.1, 1.0 Hz, 1H), 7.45 (t, J=7.9 Hz, 1H), 7.20 (d, J=4.1 Hz, 1H), 4.60-4.54 (m, 1H), 3.20-3.10 (m, 2H), 2.67-2.60 (m, 2H), 2.56 (s, 3H), 2.20-2.00 (m, 3H), 1.62-1.47 (m, 3H), 1.26-1.17 (m, 2H); MS (ESI+) m/z 460 (M+H); HPLC>99% (AUC), $t_R$=13.02 min.

Example 135

Preparation of (S)-N-(1-Azabicyclo[2.2.2]oct-3-yl)-6-chloro-2-(5-methylthiophen-2-yl)benzoxazole-4-carboxamide

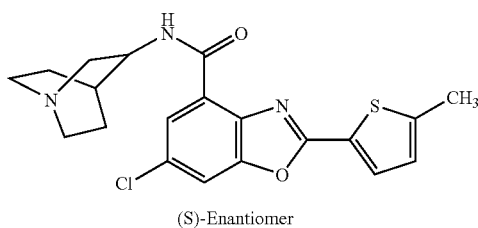

(S)-Enantiomer

Step A: To an ice-cold suspension of 5-methyl-2-thiophenecarboxyl acid (400 mg, 2.14 mmol) in dichloromethane (20 mL) was added oxalyl chloride (0.21 mL, 2.14 mmol) dropwise followed by a few drops of DMF. Then the ice-water bath was removed and the reaction mixture was stirred for 1 h. To the above solution was added 2-amino-3-hydroxybenzoic acid hydrobromide (0.50 g, 2.14 mmol) followed by triethylamine (1.19 mL, 8.56 mmol). The resulting reaction mixture was stirred at room temperature overnight. The reaction was quenched with 1 N HCl (20 mL). The reaction mixture was extracted with dichloromethane. The aqueous layer was extracted with dichloromethane (2×50 mL). The combined organic layers were dried over $Na_2SO_4$, filtered and concentrated to afford a yellow solid. The crude was dissolved in toluene (5 mL) and the solution was treated with p-toluenesulfonic acid monohydrate (619 mg, 3.25 mmol). The reaction mixture was then heated to reflux under nitrogen for 3 h. The reaction was cooled down to room temperature, poured into water and extracted with dichloromethane. The organic layer was separated, washed with water, brine, dried over $Na_2SO_4$, filtered and concentrated to a yellow solid. The crude material was recrystallized from methanol to afford the desired product (198 mg, 48%) as an off-white solid (78 mg, 12%): $^1$H NMR (500 MHz, DMSO-$d_6$) δ 8.20 (d, J=2.1 Hz, 1H), 7.84 (d, J=3.7 Hz, 1H), 7.83 (d, J=2.2 Hz, 1H), 7.06 (dd, J=3.7, 1.1 Hz, 1H), 3.17 (s, 3H), MS (ESI+) m/z 293 (M+H).

Step B: A mixture of 6-chloro-2-(5-methylthiophen-2-yl)benzoxazole-4-carboxylic acid (41 mg, 0.14 mmol), 1-ethyl-3-(3-dimethylaminopropyl)carbodiimide hydrochloride (53 mg, 0.28 mmol), 1-hydroxybenzotriazole (38 mg, 0.28 mmol) and (S)-(−)-3-aminoquinuclidine dihydrochloride (35 mg, 0.17 mmol) in DMF (2 mL) was stirred at room temperature for 10 min, then triethylamine (0.08 mL, 0.56 mmol) was added. The resulting reaction mixture was stirred at room temperature for 4 h. The mixture was diluted with dichloromethane and then washed with a saturated solution of sodium bicarbonate. The aqueous layer was further extracted with dichloromethane (2×50 mL). The combined organic layers were washed with brine (2×25 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford (S)-N-(1-azabicyclo[2.2.2]oct-3-yl)-6-chloro-2-(5-methylthiophen-2-yl)benzoxazole-4-carboxamide (30 mg, 55%) as a white solid: $^1$H NMR (500 MHz, $CDCl_3$) δ 9.43 (d, J=7.4 Hz, 1H), 8.12 (d, J=1.9 Hz, 1H), 7.74 (d, J=3.7 Hz, 1H), 7.64 (d, J=1.9 Hz, 1H), 6.90 (dd, J=3.7, 0.9 Hz, 1H), 4.33-4.29 (m, 1H), 3.54-3.47 (m, 1H), 3.15-3.03 (m, 2H), 2.95-2.90 (m, 2H), 2.85-2.79 (m, 1H), 2.61 (s, 3H), 2.15-2.05 (m, 2H), 1.86-1.76 (m, 2H), 1.75-1.65 (m, 1H); MS (ESI+) m/z 402 (M+H); HPLC>99% (AUC), $t_R$=12.99 min.

Example 136

Preparation of N-(9-Methyl-9-azabicyclo[3.3.1]non-3-yl)-6-chloro-2-(5-methylthiophen-2-yl)benzoxazole-4-carboxamide

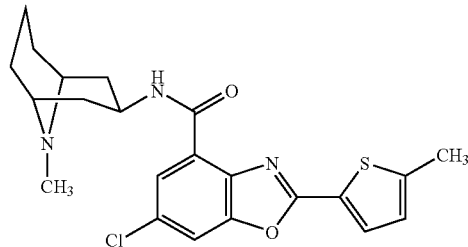

A mixture of 6-chloro-2-(5-methylthiophen-2-yl)benzoxazole-4-carboxylic acid (31 mg, 0.11 mmol), 1-ethyl-3-(3-dimethylaminopropyl)carbodiimide hydrochloride (41 mg, 0.21 mmol), 1-hydroxybenzotriazole (29 mg, 0.21 mmol) and 3-amino-9-methyl-9-azabicyclo[3.3.1]nonane dihydrochloride (30 mg, 0.13 mmol) in DMF (2 mL) was stirred at room temperature for 10 min, then triethylamine (0.059 mL, 0.42 mmol) was added. The resulting reaction mixture was stirred at room temperature for 7 h. The mixture was diluted with dichloromethane and then washed with a saturated solution of sodium bicarbonate. The aqueous layer was further extracted with dichloromethane (2×50 mL). The combined organic layers were washed with water (2×25 mL), brine (2×25 mL), dried ($Na_2SO_4$), filtered and concentrated. The crude material was purified by column chromatography (silica gel, 90:9:1 ethyl acetate/methanol/concentrated ammonium hydroxide) and recrystallization from acetonitrile to afford N-(9-methyl-9-azabicyclo[3.3.1]non-3-yl)-6-chloro-2-(5-methylthiophen-2-yl)benzoxazole-4-carboxamide (21 mg, 47%) as an off-white solid: $^1$H NMR (500 MHz, $CDCl_3$) δ 8.90 (br s, 1H), 8.15 (d, J=2.0 Hz, 1H), 7.75 (d, J=3.7 Hz, 1H), 7.62 (d, J=2.0 Hz, 1H), 6.90 (dd, J=3.7, 1.0 Hz, 1H), 4.60-4.52 (m, 1H), 4.20-4.10 (m, 2H), 2.70-2.65 (m, 1H), 2.61 (s, 3H), 2.58 (s, 3H), 2.40-2.00 (m, 3H), 1.65-1.50 (m, 4H), 1.35-1.15 (m, 2H); MS (ESI+) m/z 430 (M+H); HPLC>99% (AUC), $t_R$=13.48 min.

Example 137

Preparation of (S)-N-(1-Azabicyclo[2.2.2]oct-3-yl)-2-(5,6-dihydro-4H-cyclopenta[b]thiophen-2-yl)benzoxazole-4-carboxamide

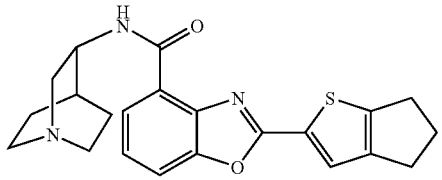

Step A: Oxalyl chloride (0.11 mL, 1.31 mmol) was added to a suspension of 5,6-dihydro-4H-cyclopent[b]thiophene-2-carboxylic acid (200 mg, 1.19 mmol) in methylene chloride (2 mL) at room temperature and the mixture was stirred under nitrogen for 2 h. 3-Hydroxyanthranilic acid hydrobromide (278 mg, 1.19 mmol) was added, followed by triethylamine (0.83 mL, 5.95 mmol) and methylene chloride (3 mL). The resulting mixture was stirred under nitrogen overnight, and then quenched with 1 N HCl. The organic layer was separated and the aqueous layer was extracted with methylene chloride. The combined organic layers were washed with brine, dried over sodium sulfate, filtered and concentrated in vacuo to give the crude product (340 mg, 94%) as a light yellow solid: $^1$H NMR (500 MHz, CDCl$_3$) δ 11.75 (br s, 1H), 10.28 (br s, 1H), 7.73 (dd, J=8.0, 1.5 Hz, 1H), 7.57 (s, 1H), 7.33 (dd, J=8.0, 1.5 Hz, 1H), 7.18 (t, J=8.0 Hz, 1H), 2.98 (t, J=7.5 Hz, 2H), 2.81 (t, J=7.5 Hz, 2H), 2.53-2.47 (m, 2H); MS (ESI+) m/z 304 (M+H).

Step B: A mixture of the amide from Step A (340 mg, 1.12 mmol), p-toluenesulfonic acid monohydrate (213 mg, 1.12 mmol) and toluene (10 mL) was heated at 100° C. under nitrogen overnight. The reaction mixture was cooled to room temperature, quenched with 1 N HCl, extracted with methylene chloride, washed with brine, dried over sodium sulfate, filtered and concentrated. The crude material was purified by column chromatography (silica gel, 70:30 ethyl acetate/methanol) to afford the acid (180 mg, 56%) as a light yellow solid: $^1$H NMR (500 MHz, DMSO-d$_6$) δ 12.95 (br s, 1H), 7.96 (dd, J=8.0, 1.0 Hz, 1H), 7.88 (dd, J=8.0, 1.0 Hz, 1H), 7.77 (s, 1H), 7.46 (t, J=8.0 Hz, 1H), 2.98 (t, J=7.5 Hz, 2H), 2.78 (t, J=7.5 Hz, 2H), 2.48-2.42 (m, 2H); MS (ESI+) m/z 286 (M+H).

Step C: A mixture of the carboxylic acid from Step B (90 mg, 0.32 mmol), (S)-3-aminoquinuclidine dihydrochloride (76 mg, 0.38 mmol), 1-ethyl-3-(3-dimethylaminopropyl)carbodiimide hydrochloride (122 mg, 0.64 mmol) and 1-hydroxybenzotriazole (86 mg, 0.64 mmol) in DMF (5 mL) was stirred under nitrogen at room temperature for 10 min, and then triethylamine (0.27 mL, 1.92 mmol) was added. The resulting reaction mixture was stirred at room temperature overnight, and then was quenched with a saturated solution of sodium bicarbonate, extracted with methylene chloride. The combined organic layers were dried (Na$_2$SO$_4$), filtered and concentrated. The crude material was purified by column chromatography (silica gel, 90:9:1 ethyl acetate/methanol/concentrated ammonium hydroxide) to afford (S)-N-(1-azabicyclo[2.2.2]oct-3-yl)-2-(5,6-dihydro-4H-cyclopenta[b]thiophen-2-yl)benzoxazole-4-carboxamide (82 mg, 66%) as a light yellow solid: $^1$H NMR (500 MHz, CDCl$_3$) δ 9.56 (d, J=7.5 Hz, 1H), 8.14 (dd, J=8.0, 1.0 Hz, 1H), 7.63 (s, 1H), 7.62 (dd, J=8.0, 1.0 Hz, 1H), 7.40 (t, J=8.0 Hz, 1H), 4.32-4.28 (m, 1H), 3.47 (ddd, J=14.0, 9.5, 2.0 Hz, 1H), 3.12-2.98 (m, 4H), 2.92-2.77 (m, 5H), 2.57-2.50 (m, 2H), 2.12-2.07 (m, 2H), 1.76-1.58 (m, 3H); MS (ESI+) m/z 394 (M+H); HPLC>99% (AUC), $t_R$=13.28 min.

Example 138

Preparation of N-(9-Methyl-9-azabicyclo[3.3.1]non-3-yl)-2-(5,6-dihydro-4H-cyclopenta[b]thiophen-2-yl)benzoxazole-4-carboxamide

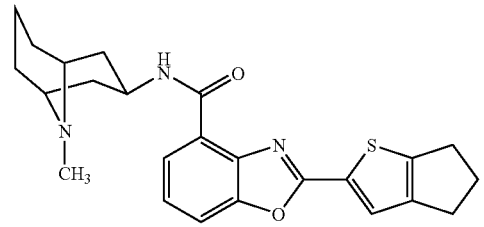

A mixture of 2-(5,6-dihydro-4H-cyclopenta[b]thiophen-2-yl)benzo[d]oxazole-4-carboxylic acid (90 mg, 0.32 mmol), 3-amino-9-methyl-9-azabicyclo[3.3.1]nonane dihydrochloride (86 mg, 0.38 mmol), 1-ethyl-3-(3-dimethylaminopropyl)carbodiimide hydrochloride (122 mg, 0.64 mmol) and 1-hydroxybenzotriazole (86 mg, 0.64 mmol) in DMF (5 mL) was stirred under nitrogen at room temperature for 10 min, and then triethylamine (0.27 mL, 1.92 mmol) was added. The resulting reaction mixture was stirred at room temperature overnight, and then was quenched with a saturated solution of sodium bicarbonate, extracted with methylene chloride. The combined organic layers were washed with brine, dried (Na$_2$SO$_4$), filtered and concentrated. The crude material was purified by column chromatography (silica gel, 90:9:1 ethyl acetate/methanol/concentrated ammonium hydroxide) and semi-preparative HPLC to afford N-(9-methyl-9-azabicyclo[3.3.1]non-3-yl)-2-(5,6-dihydro-4H-cyclopenta[b]thiophen-2-yl)benzoxazole-4-carboxamide (55 mg, 41%) as a light yellow solid: $^1$H NMR (500 MHz, CDCl$_3$) δ 9.01 (d, J=7.5 Hz, 1H), 8.16 (dd, J=8.0, 1.0 Hz, 1H), 7.65 (s, 1H), 7.61 (dd, J=8.0, 1.0 Hz, 1H), 7.39 (t, J=8.0 Hz, 1H), 4.60-4.50 (m, 1H), 3.10 (d, J=10.0 Hz, 2H), 3.03-3.00 (m, 2H), 2.86-2.82 (m, 2H), 2.65-2.52 (m, 4H), 2.54 (s, 3H), 2.18-1.96 (m, 3H), 1.62-1.46 (m, 3H), 1.25-1.18 (m, 2H); MS (ESI+) m/z 422 (M+H); HPLC>99% (AUC), $t_R$=13.28 min.

Example 139

Preparation of (S)-N-(1-Azabicyclo[2.2.2]oct-3-yl)-2-(3,5-dimethylisoxazole-4-yl)benzoxazole-4-carboxamide

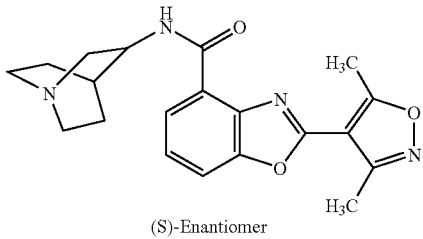

(S)-Enantiomer

Step A: To a suspension of 2-amino-3-hydroxybenzoic acid hydrobromide (500 mg, 2.14 mmol) in dichloromethane (15 mL) was added triethylamine (1.19 mL, 8.56 mmol) followed by 3,5-dimethylisoxazole-4-carbonyl chloride (341 mg, 2.14 mmol) at room temperature. The resulting reaction mixture was stirred at room temperature overnight. The reaction was quenched with aqueous 2 N HCl (50 mL). The reaction mixture was extracted with dichloromethane. The combined organic layers were dried over Na₂SO₄, filtered and concentrated to a brown solid. The crude was dissolved in toluene (10 mL) and the solution was treated with p-toluenesulfonic acid monohydrate (0.581 g, 3.06 mmol). The resulting reaction mixture was then heated to reflux under nitrogen for 4 h. The reaction was cooled down to room temperature, poured into water and extracted with ethyl acetate (400 mL). The organic layer was separated then washed with water, brine, dried over Na₂SO₄, filtered and concentrated to an off-white solid. The crude product was purified by recrystallization from ethyl acetate to afford the desired product (271 mg, 49%) as an off-white solid: $^1$H NMR (500 MHz, DMSO-$d_6$) δ 13.04 (br s, 1H), 8.03 (dd, J=8.1, 0.8 Hz, 1H), 8.16 (dd, J=7.8, 0.9 Hz, 1H), 2.87 (s, 3H), 2.61 (s, 3H); MS (ESI+) m/z 259 (M+H).

Step B: A mixture of 2-(3,5-dimethylisoxazol-4-yl)benzoxazole-4-carboxylic acid (136 mg, 0.53 mmol), 1-ethyl-3-(3-dimethylaminopropyl)carbodiimide hydrochloride (201 mg, 1.05 mmol), 1-hydroxybenzotriazole (142 mg, 1.05 mmol) and (S)-(−)-3-aminoquinuclidine dihydrochloride (131 mg, 0.66 mmol) in DMF (5 mL) was stirred at room temperature for 10 min, then triethylamine (0.56 mL, 4.0 mmol) was added. The resulting reaction mixture was stirred at room temperature overnight. The mixture was diluted with dichloromethane (100 mL), and then washed with a saturated solution of sodium bicarbonate. The aqueous layer was further extracted with dichloromethane (2×50 mL). The combined organics were washed with water (5×25 mL), brine (25 mL), dried (Na₂SO₄), filtered and concentrated. The crude material was purified by column chromatography (silica gel, 90:9:1 methylene chloride/methanol/concentrated ammonium hydroxide) and recrystallization from acetonitrile to afford (S)-N-(1-azabicyclo[2.2.2]oct-3-yl)-2-(3,5-dimethylisoxazole-4-yl)benzoxazole-4-carboxamide (91 mg, 47%) as a white solid: $^1$H NMR (500 MHz, CDCl₃) δ 9.09 (d, J=6.5 Hz, 1H), 8.22 (dd, J=7.8, 1.0 Hz, 1H), 7.72 (dd, J=8.1, 1.0 Hz, 1H), 7.49 (t, J=8.0 Hz, 1H), 4.33-4.29 (m, 1H), 3.58-3.53 (m, 1H), 3.00-2.90 (m, 3H), 2.89 (s, 3H), 2.76-2.71 (m, 1H), 2.69 (s, 3H), 2.15-2.10 (m, 1H), 1.97-1.85 (m, 2H), 1.80-1.70 (m, 2H), 1.61-1.50 (m, 1H); MS (ESI+) m/z 367 (M+H); HPLC>99% (AUC), $t_R$=11.69 min.

Example 140

Preparation of N-(9-Methyl-9-azabicyclo[3.3.1]non-3-yl)-2-(3,5-dimethylisoxazole-4-yl)benzoxazole-4-carboxamide

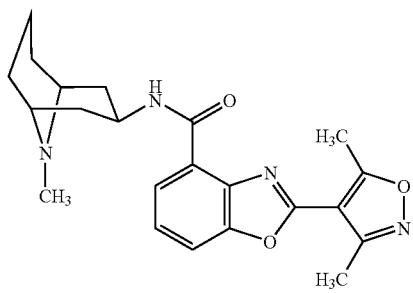

A mixture of 2-(3,5-dimethylisoxazol-4-yl)benzoxazole-4-carboxylic acid (136 mg, 0.53 mmol), 1-ethyl-3-(3-dimethylaminopropyl)carbodiimide hydrochloride (201 mg, 1.05 mmol), 1-hydroxybenzotriazole (142 mg, 1.05 mmol) and 3-amino-9-methyl-9-azabicyclo[3.3.1]nonane dihydrochloride (150 mg, 0.66 mmol) in DMF (5 mL) was stirred at room temperature for 10 min, then triethylamine (0.29 mL, 2.11 mmol) was added. The resulting reaction mixture was stirred at room temperature overnight. The mixture was diluted with ethyl acetate and then washed with a saturated solution of sodium bicarbonate. The aqueous layer was further extracted with ethyl acetate (2×100 mL). The combined organic layers were washed with brine (2×100 mL), dried (Na₂SO₄), filtered and concentrated. The crude material was purified by column chromatography (silica gel, 90:9:1 ethyl acetate/methanol/concentrated ammonium hydroxide) and recrystallization from acetonitrile to afford N-(9-methyl-9-azabicyclo[3.3.1]non-3-yl)-2-(3,5-dimethyl-isoxazole-4-yl)benzoxazole-4-carboxamide (99 mg, 48%) as a white solid: $^1$H NMR (500 MHz, CDCl₃) δ 8.85 (d, J=6.6 Hz, 1H), 8.22 (dd, J=7.7, 1.0 Hz, 1H), 7.69 (dd, J=8.0, 0.9 Hz, 1H), 7.47 (t, J=7.9 Hz, 1H), 4.66-4.60 (m, 1H), 4.22-4.15 (m, 2H), 2.90 (s, 3H), 2.71 (s, 3H), 2.68-2.60 (m, 2H), 2.57 (s, 3H), 2.07-1.96 (m, 3H), 1.90-1.61 (m, 3H), 1.15-1.05 (m, 2H); MS (ESI+) m/z 395 (M+H); HPLC>99% (AUC), $t_R$=12.33 min.

Example 141

Preparation of (S)-N-(1-Azabicyclo[2.2.2]oct-3-yl)-2-(4-methylthiazol-5-yl)benzoxazole-4-carboxamide Hydrochloride

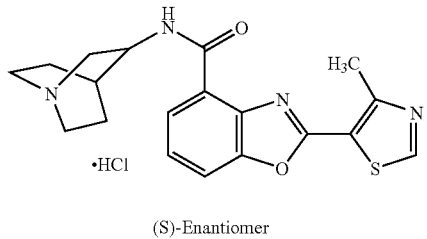

(S)-Enantiomer

Step A: To an ice-cold solution of 4-methyl-5-thiozolcarboxylic acid (306 mg, 2.14 mmol) in dichloromethane (20 mL) was added oxalyl chloride (0.21 mL, 2.14 mmol) dropwise. The ice bath was removed and stirring was continued for 1 h. 2-Amino-3-hydroxybenzoic acid hydrobromide (500 mg, 2.14 mmol) was added, followed by triethylamine (0.90 mL, 6.42 mmol). The resulting reaction mixture was stirred at room temperature overnight. The reaction was quenched with aqueous 1 N HCl (25 mL) until the solution reached pH 1 and stirred for 30 min. The aqueous layer was extracted with dichloromethane. The organic layers were washed with brine, dried over Na₂SO₄, filtered and concentrated. The residue was directly re-dissolved in toluene (10 mL) and the solution was treated with p-toluenesulfonic acid monohydrate (517 mg, 1.85 mmol). The reaction mixture was then heated to reflux for 5 h. The reaction was cooled down to room temperature, poured into water and extracted with ethyl acetate. The organic layer was separated, washed with water and brine, dried over Na₂SO₄, filtered and concentrated to a yellow solid. The crude product was purified by re-crystallization from ethyl acetate to afford the desired product (115 mg, 24%) as a yellow solid: $^1$H NMR (300 MHz, DMSO-$d_6$) δ 13.50 (br s, 1H), 9.31 (s, 1H), 8.05 (dd, J=14.0, 2.0 Hz, 1H), 7.93 (dd, J=7.8, 1.2 Hz, 1H), 7.22 (t, J=7.5 Hz, 1H), 2.91 (s, 3H); MS (ESI+) m/z 261 (M+H).

Step B: A mixture of 2-(4-methylthiazol-5-yl)benzoxazole-4-carboxylic acid (80 mg, 0.31 mmol), 1-ethyl-3-(3-dimethylaminopropyl)carbodiimide hydrochloride (118 mg, 0.62 mmol), 1-hydroxybenzotriazole (84 mg, 0.62 mmol) and (S)-(−)-3-aminoquinuclidine dihydrochloride (73 mg, 0.39 mmol) in DMF (5 mL) was stirred at room temperature for 10 min, then triethylamine (0.18 mL, 4.0 mmol) was added. The resulting reaction mixture was stirred at room temperature overnight. The mixture was diluted with ethyl acetate (50 mL), and then washed with a saturated solution of sodium bicarbonate. The aqueous layer was further extracted with ethyl acetate (2×100 mL). The combined organics were washed with water (2×50 mL) and brine (2×50 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford the desired product (49 mg, 45%) as a yellow solid: $^1$H NMR (500 MHz, $CDCl_3$) δ 9.28 (d, J=7.3 Hz, 1H), 8.90 (s, 1H), 8.22 (dd, J=7.8, 1.0 Hz, 1H), 7.72 (dd, J=8.1, 1.0 Hz, 1H), 7.49 (t, J=8.0 Hz, 1H), 4.40-4.30 (m, 1H), 3.58-3.53 (m, 1H), 3.10-3.03 (m, 2H), 3.00 (s, 3H), 2.98-2.94 (m, 2H), 2.90-2.78 (m, 1H), 2.20-2.15 (m, 1H), 2.10-2.00 (m, 1H), 1.85-1.76 (m, 2H), 1.66-1.63 (m, 1H); MS (ESI+) m/z 369 (M+H).

Step C: To a solution of (S)-N-(1-azabicyclo[2.2.2]oct-3-yl)-2-(4-methylthiazol-5-yl)benzoxazole-4-carboxamide (45 mg, 0.12 mmol) in methanol (2.0 mL) was added a solution of HCl in diethyl ether (1 N, 1.5 mL, 1.5 mmol) at room temperature slowly. The reaction mixture was diluted with diethyl ether. The resulting solid was filtered and washed with diethyl ether to afford (S)-N-(1-azabicyclo[2.2.2]oct-3-yl)-2-(4-methylthiazol-5-yl)benzoxazole-4-carboxamide hydrochloride (40 mg, 74%) as a light yellow solid: $^1$H NMR (500 MHz, DMSO-$d_6$) δ 10.46 (s, 1H), 9.35 (s, 1H), 9.10 (d, J=6.3 Hz, 1H), 8.05 (dd, J=8.2, 0.9 Hz, 1H), 7.94 (dd, J=7.7, 0.9 Hz, 1H), 7.58 (t, J=8.0 Hz, 1H), 4.44-4.40 (m, 1H), 3.64-3.55 (m, 1H), 3.35-3.15 (m, 5H), 2.91(s, 3H), 2.33-2.25 (m, 2H), 2.00-1.95 (m, 3H); MS (ESI+) m/z 369 (M+H); HPLC>99% (AUC), $t_R$=12.05 min.

Example 142

Preparation of N-(9-Methyl-9-azabicyclo[3.3.1]non-3-yl)-2-(4-methylthiazol-5-yl)benzoxazole-4-carboxamide Hydrochloride

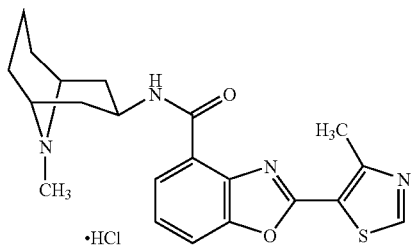

Step A: A mixture of 2-(4-methylthiazol-5-yl)benzoxazole-4-carboxylic acid (60 mg, 0.23 mmol), 1-ethyl-3-(3-dimethylaminopropyl)carbodiimide hydrochloride (88 mg, 0.46 mmol), 1-hydroxybenzotriazole (62 mg, 0.46 mmol) and 3-amino-9-methyl-9-azabicyclo[3.3.1]nonane dihydrochloride (65 mg, 0.29 mmol) in DMF (5 mL) was stirred at room temperature for 10 min, then triethylamine (0.29 mL, 2.11 mmol) was added. The resulting reaction mixture was stirred at room temperature overnight. The mixture was diluted with ethyl acetate and then washed with a saturated solution of sodium bicarbonate. The aqueous layer was further extracted with ethyl acetate (2×100 mL). The combined organic layers were washed with brine (2×100 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford the desired product (57 mg, 63%) as a light yellow solid: $^1$H NMR (300 MHz, $CDCl_3$) δ 8.92 (br s, 1H), 8.90 (s, 1H), 8.22 (dd, J=7.8, 1.0 Hz, 1H), 7.69 (dd, J=8.1, 1.0 Hz, 1H), 7.48 (t, J=8.0 Hz, 1H), 4.70-4.57 (m, 1H), 3.25-3.10 (m, 2H), 3.10 (s, 3H), 2.75-2.60 (m, 2H), 2.57 (s, 3H), 2.15-1.95 (m, 3H), 1.65-1.45 (m, 3H), 1.25-1.10 (m, 2H); MS (ESI+) m/z 397 (M+H).

Step C: To a solution of (S)-N-(1-azabicyclo[2.2.2]oct-3-yl)-2-(4-methylthiazol-5-yl)benzoxazole-4-carboxamide (57 mg, 0.14 mmol) in methanol (2.0 mL) was added a solution of HCl in diethyl ether (1 N, 0.29 mL, 0.29 mmol) at room temperature slowly. The reaction mixture was diluted with diethyl ether. The resulting solid was filtered and washed with diethyl ether to afford N-(9-methyl-9-azabicyclo[3.3.1]non-3-yl)-2-(4-methylthiazol-5-yl)benzoxazole-4-carboxamide hydrochloride (54 mg, 90%) as an off-white solid; $^1$H NMR (500 MHz, DMSO-$d_6$) δ 10.41 (br s, 0.3H), 9.59 (br s, 0.7H), 9.36 (s, 0.7H), 9.34 (s, 0.3H), 8.94 (d, J=7.3 Hz, 0.3H), 8.82 (d, J=7.3 Hz, 0.7H), 8.05-8.02 (m, 1H), 7.99-7.93 (m, 1H), 7.60-7.54 (m, 1H), 4.70-4.60 (m, 1H), 3.70-3.66 (m, 1.3H), 3.62-3.58 (m, 0.7H), 2.94 (s, 2H), 2.91 (s, 1H), 2.88-2.82 (m, 3H), 2.75-2.60 (m, 2H), 2.30-2.20 (m, 1H), 2.18-2.05 (m, 2H), 1.82-1.75 (m, 2H), 1.63-1.55 (m, 1H), 1.52-1.45 (m, 2H); MS (ESI+) m/z 397 (M+H); HPLC>99% (AUC), $t_R$=12.28 min.

Example 143

Preparation of (S)-N-(1-Azabicyclo[2.2.2]oct-3-yl)-2-(thiazole-4-yl)benzoxazole-4-carboxamide Hydrochloride

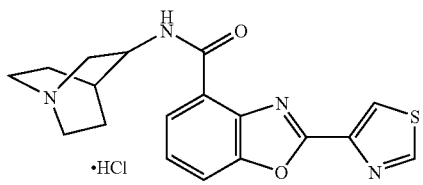

(S)-Enantiomer

Step A: To an ice-cold solution of 1,3-thiozol-4-carboxylic acid (276 mg, 2.14 mmol) in dichloromethane (20 mL) was added oxalyl chloride (0.21 mL, 2.14 mmol) dropwise. The ice bath was removed and stirring was continued for 1 h. 2-Amino-3-hydroxybenzoic acid hydrobromide (500 mg, 2.14 mmol) was added followed by triethylamine (0.90 mL, 6.42 mmol). The resulting reaction mixture was stirred at room temperature overnight. The reaction was quenched with aqueous 1 N HCl (25 mL), until the solution reached pH 1. The reaction mixture was extracted with dichloromethane. The combined organic layers were dried over $Na_2SO_4$, filtered and concentrated to a brown solid. The crude was dissolved in toluene (10 mL) and the solution was treated with p-toluenesulfonic acid monohydrate (458 mg, 2.40 mmol). The reaction mixture was then heated to reflux under nitrogen for 2 h. The reaction was cooled down to room temperature, poured into water and extracted with ethyl acetate (400 mL). The organic layer was separated then washed with water, brine, dried over $Na_2SO_4$, filtered and concentrated to an off-white solid. The crude product was purified by recrystallization from ethyl acetate to afford the desired product (145 mg, 27%) as a light yellow solid: $^1H$ NMR (500 MHz, DMSO-$d_6$) δ 13.25 (br s, 1H), 9.37 (d, J=1.9 Hz, 1H), 8.82 (d, J=1.9 Hz, 1H), 8.06 (dd, J=7.2, 0.9 Hz, 1H), 7.94 (dd, J=7.8, 0.9 Hz, 1H), 2.87 (t, J=7.9 Hz, 1H); MS (ESI+) m/z 247 (M+H).

Step B: A mixture of 2-(thiazol-4-yl)benzoxazole-4-carboxylic acid (80 mg, 0.32 mmol), 1-ethyl-3-(3-dimethylaminopropyl)carbodiimide hydrochloride (122 mg, 0.64 mmol), 1-hydroxybenzotriazole (86 mg, 0.64 mmol) and (S)-(−)-3-aminoquinuclidine dihydrochloride (81 mg, 0.41 mmol) in DMF (5 mL) was stirred at room temperature for 10 min, then triethylamine (0.13 mL, 1.0 mmol) was added. The resulting reaction mixture was stirred at room temperature overnight. The mixture was diluted with dichloromethane (100 mL), and then washed with a saturated solution of sodium bicarbonate. The aqueous layer was further extracted with dichloromethane (2×50 mL). The combined organics were washed with water (5×25 mL), brine (25 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford the desired product (41 mg, 37%) as a light yellow solid: $^1H$ NMR (500 MHz, CDCl$_3$) δ 9.52 (d, J=7.1 Hz, 1H), 9.03 (d, J=2.1 Hz, 1H), 8.35 (d, J=2.1 Hz, 1H), 8.22 (dd, J=7.8, 1.0 Hz, 1H), 7.78 (dd, J=8.1, 1.0 Hz, 1H), 7.53 (t, J=7.9 Hz, 1H), 4.42-4.35 (m, 1H), 3.60-3.53 (m, 1H), 3.25-3.05 (m, 2H), 3.02-2.90 (m, 3H), 2.28-2.10 (m, 2H), 1.87-1.80 (m, 2H), 1.75-1.67 (m, 1H); MS (ESI+) m/z 355 (M+H).

Step C: To a solution of (S)-N-(1-azabicyclo[2.2.2]oct-3-yl)-2-(4-methylthiazol-5-yl)benzoxazole-4-carboxamide (41 mg, 0.12 mmol) in methanol (2.0 mL) was added a solution of HCl in diethyl ether (1 N, 0.32 mL, 0.32 mmol) at room temperature slowly. The reaction mixture was diluted with diethyl ether. The resulting solid was filtered and washed with diethyl ether to afford (S)-N-(1-azabicyclo[2.2.2]oct-3-yl)-2-(thiazole-4-yl)benzoxazole-4-carboxamide hydrochloride (37 mg, 82%) as a light yellow solid: $^1H$ NMR (500 MHz, DMSO-$d_6$) δ 10.20 (s, 1H), 9.41 (d, J=1.8 Hz, 1H), 9.31 (d, J=6.5 Hz, 1H), 8.90 (d, J=2.2 Hz, 1H), 8.07 (dd, J=7.8, 1.0 Hz, 1H), 7.78 (dd, J=8.1, 1.0 Hz, 1H), 7.60 (t, J=8.0 Hz, 1H), 4.56-4.44 (m, 1H), 3.77 (t, J=11.6 Hz, 1H), 3.45-3.20 (m, 5H), 2.28-2.20 (m, 2H), 2.02-1.90 (m, 3H); MS (ESI+) m/z 355 (M+H); HPLC 95.0% (AUC), $t_R$=11.90 min.

Example 144

Preparation of N-(9-Methyl-9-azabicyclo[3.3.1]non-3-yl)-2-(thiazol-4-yl)benzoxazole-4-carboxamide Hydrochloride

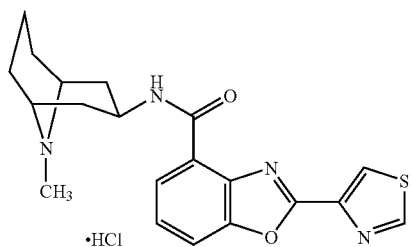

Step A: A mixture of 2-(thiazol-4-yl)benzoxazole-4-carboxylic acid (60 mg, 0.24 mmol), 1-ethyl-3-(3-dimethylaminopropyl)carbodiimide hydrochloride (92 mg, 0.48 mmol), 1-hydroxybenzotriazole (65 mg, 0.48 mmol) and 3-amino-9-methyl-9-azabicyclo[3.3.1]nonane dihydrochloride (68 mg, 0.30 mmol) in DMF (2 mL) was stirred at room temperature for 10 min, then triethylamine (0.10 mL, 0.73 mmol) was added. The resulting reaction mixture was stirred at room temperature overnight. The mixture was diluted with ethyl acetate and then washed with a saturated solution of sodium bicarbonate. The aqueous layer was further extracted with dichloromethane (2×50 mL). The combined organic layers were washed with brine (2×25 mL), dried ($Na_2SO_4$), filtered and concentrated. The crude material was purified by column chromatography (silica gel, 90:9:1 dichloromethane/methanol/concentrated ammonium hydroxide) and recrystallization from acetonitrile to afford the desired product (51 mg, 56%) as a light yellow solid: $^1H$ NMR (500 MHz, CDCl$_3$) δ 9.14 (br s, 1H), 9.03 (d, J=2.0 Hz, 1H), 8.40 (d, J=2.0 Hz, 1H), 8.22 (dd, J=7.8, 1.0 Hz, 1H), 7.76 (dd, J=8.0, 0.9 Hz, 1H), 7.51 (t, J=7.9 Hz, 1H), 4.70-4.61 (m, 1H), 3.35-3.28 (m, 2H), 2.75-2.66 (m, 2H), 2.68 (s, 3H), 2.40-2.30 (m, 1H), 2.24-2.12 (m, 2H), 1.97-1.85 (m, 2H), 1.70-1.61 (m, 1H), 1.50-1.41 (m, 2H); MS (ESI+) m/z 383 (M+H).

Step B: To a solution of (S)-N-(1-azabicyclo[2.2.2]oct-3-yl)-2-(thiazol-4-yl)benzoxazole-4-carboxamide (51 mg, 0.13 mmol) in methanol (2.0 mL) was added a solution of HCl in diethyl ether (1 N, 0.26 mL, 0.26 mmol) at room temperature slowly. The reaction mixture was diluted with diethyl ether. The resulting solid was filtered and washed with diethyl ether to afford N-(9-methyl-9-azabicyclo[3.3.1]non-3-yl)-2-(thiazol-4-yl)benzoxazole-4-carboxamide hydrochloride (32 mg, 59%) as an off-white solid: $^1H$ NMR (500 MHz, DMSO-$d_6$) δ 10.26 (br s, 0.3H), 9.57 (br s, 0.7H), 9.42-9.39 (m, 1H), 9.28 (d, J=6.6 Hz, 0.3H), 8.92-8.90 (m, 1.4H), 8.84-8.81 (m, 0.3H), 8.10-8.05 (m, 1H), 8.00-7.95 (m, 1H), 7.65-7.55 (m, 1H), 4.70-4.60 (m, 0.7H), 4.45-4.35 (m, 0.3H), 3.70-3.65 (m, 1.4H), 3.60-3.55 (m, 0.6H), 3.90-3.80 (m, 3H), 3.75-3.55 (m, 2H), 2.30-2.05 (m, 3H), 1.95-1.85 (m, 3H), 1.65-1.50 (m, 2H); MS (ESI+) m/z 383 (M+H); HPLC 97.6% (AUC), $t_R$=12.47 min.

Example 145

Preparation of (S)-N-(1-Azabicyclo[2.2.2]oct-3-yl)-2-(2-oxo-1,2-dihydropyridin-3-yl)benzoxazole-4-carboxamide

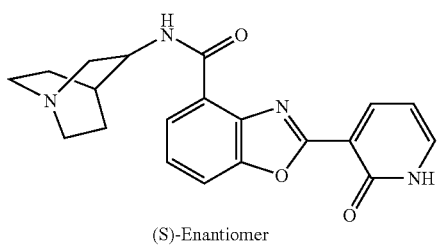

(S)-Enantiomer

Step A: To an ice-cold suspension of 2-methoxynicotinic acid (678 mg, 4.43 mmol) in dichloromethane (10 mL) was added oxalyl chloride (0.42 mL, 4.99 mmol) dropwise. Then the ice-water bath was removed and the reaction mixture was stirred for 2 h. To the above solution was added 2-amino-3-hydroxybenzoic acid hydrobromide (1.0 g, 4.43 mmol) followed by the addition of triethylamine (2.5 mL, 17.7 mmol). The resulting reaction mixture was stirred at room temperature overnight. The reaction was quenched with water (50 mL) and pH was adjusted to 7. The reaction mixture was extracted with dichloromethane. The aqueous layer was extracted with dichloromethane (2×100 mL). The combined organic layers were dried over Na$_2$SO$_4$, filtered and concentrated to afford a yellow solid. The crude was dissolved in toluene (5 mL) and the solution was treated with p-toluenesulfonic acid monohydrate (0.98 g, 4.99 mmol). The reaction mixture was then heated to reflux under nitrogen for 4.5 h. A light yellow solid was precipitated and the solid was separated, washed with dichloromethane to afford the desired product (448 mg, 43%) as a yellow solid: $^1$H NMR (500 MHz, DMSO-d$_6$) 12.55 (br s, 1H), 8.43 (dd, J=5.0, 2.2 Hz, 1H), 8.01 (dd, J=8.1, 1.0 Hz, 1H), 7.90 (dd, J=7.8, 1.0 Hz, 1H), 7.75 (dd, J=6.3, 2.2 Hz, 1H), 7.51-7.48 (m, 1H): MS (ESI+) m/z 256 (M+H).

Step B: A mixture of 2-(2-oxo-1,2-dihydropyridin-3-yl)benzoxazole-4-carboxylic acid (102 mg, 0.40 mmol), 1-ethyl-3-(3-dimethylaminopropyl)carbodiimide hydrochloride (153 mg, 0.80 mmol), 1-hydroxybenzotriazole (108 mg, 0.80 mmol) and (S)-(−)-3-aminoquinuclidine dihydrochloride (99 mg, 0.49 mmol) in DMF (5 mL) was stirred at room temperature for 10 min, then triethylamine (0.22 mL, 1.6 mmol) was added. The resulting reaction mixture was stirred at room temperature overnight. The mixture was diluted with dichloromethane and then washed with a saturated solution of sodium bicarbonate. The aqueous layer was further extracted with dichloromethane (3×100 mL). The combined organic layers were washed with brine (2×50 mL), dried (Na$_2$SO$_4$), filtered and concentrated. The crude material was purified by column chromatography (silica gel, 90:9:1 dichloromethane/methanol/concentrated ammonium hydroxide) and crystallizations from acetonitrile to afford (S)-N-(1-azabicyclo[2.2.2]oct-3-yl)-2-(2-oxo-1,2-dihydropyridin-3-yl)benzoxazole-4-carboxamide (69 mg, 54%) as yellow solid: $^1$H NMR (500 MHz, CDCl$_3$) δ 9.80 (d, J=7.5 Hz, 1H), 8.49 (dd, J=7.3, 2.1 Hz, 1H), 8.18 (dd, J=7.8, 0.9 Hz, 1H), 7.80 (dd, J=6.3, 2.1 Hz, 1H), 7.72 (dd, J=8.2, 0.9 Hz, 1H), 7.48 (t, J=7.9 Hz, 1H), 6.51 (dd, J=7.2, 4.0 Hz, 1H), 4.42-4.36 (m, 1H), 3.57-3.50 (m, 1H), 3.33-3.24 (m, 2H), 3.08-3.01 (m, 1H), 2.99-2.94 (m, 3H), 2.25-2.20 (m, 2H), 1.84-1.80 (m, 2H), 1.65-1.58 (m, 1H); MS (ESI+) m/z 365 (M+H); HPLC>99% (AUC), t$_R$=11.31 min.

Example 146

Preparation of N-(9-Methyl-9-azabicyclo[3.3.1]non-3-yl)-2-(2-oxo-1,2-dihydropyridin-3-yl)benzoxazole-4-carboxamide

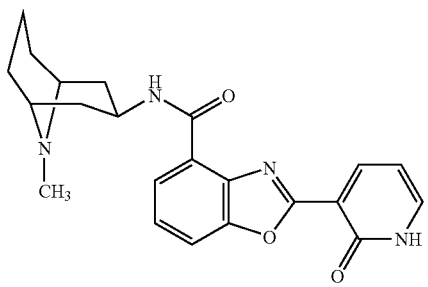

A mixture of 2-(2-oxo-1,2-dihydropyridin-3-yl)benzoxazole-4-carboxylic acid (102 mg, 0.40 mmol), 1-ethyl-3-(3-dimethylaminopropyl)carbodiimide hydrochloride (153 mg, 0.80 mmol), 1-hydroxybenzotriazole (108 mg, 0.80 mmol) and 3-amino-9-methyl-9-azabicyclo[3.3.1]nonane dihydrochloride (135 mg, 0.49 mmol) in DMF (5 mL) was stirred at room temperature for 10 min, then triethylamine (0.22 mL, 1.60 mmol) was added. The resulting reaction mixture was stirred at room temperature overnight. The mixture was diluted with dichloromethane and then washed with a saturated solution of sodium bicarbonate. The aqueous layer was further extracted with dichloromethane (3×100 mL). The combined organic layers were washed with water (2×50 mL), brine (2×50 mL), dried (Na$_2$SO$_4$), filtered and concentrated. The crude material was purified by preparative HPLC to afford N-(9-methyl-9-azabicyclo[3.3.1]non-3-yl)-2-(2-oxo-1,2-dihydropyridin-3-yl)benzoxazole-4-carboxamide (21 mg, 13%) as a yellow solid: $^1$H NMR (500 MHz, CDCl$_3$) δ 8.94 (br s, 1H), 8.53 (dd, J=7.3, 1.7 Hz, 1H), 8.22 (d, J=7.7 Hz, 1H), 7.76-7.69 (m, 2H), 7.48 (t, J=7.9 Hz, 1H), 6.58 (t, J=6.7 Hz, 1H), 4.64-4.55 (m, 1H), 3.15-3.10 (m, 2H), 2.68-2.62 (m, 2H), 2.54 (s, 3H), 2.15-1.95 (m, 3H), 1.60-1.47 (m, 4H), 1.15-1.10 (m, 2H); MS (ESI+) m/z 393(M+H); HPLC>99% (AUC), t$_R$=12.23 min.

Example 147

Preparation of N-(9-Methyl-9-azabicyclo[3.3.1]non-3-yl)-2-(2-morpholinophenyl)benzoxazole-4-carboxamide Maleate

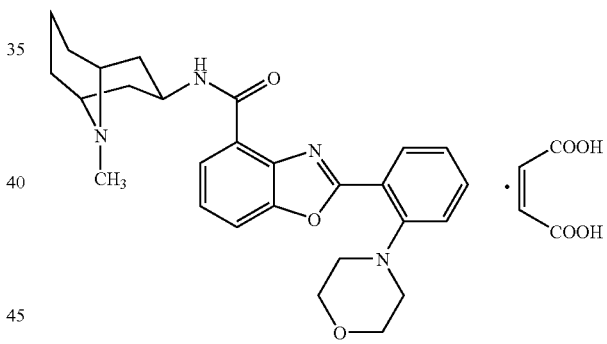

Step A: A dry flask was charged with N-(9-methyl-9-azabicyclo[3.3.1]non-3-yl)-2-(2-bromophenyl)benzoxazole-4-carboxamide (100 mg, 0.22 mmol), morpholine (0.10 mL, 0.66 mmol), Pd(OAc)$_2$ (14 mg, 0.06 mmol), xantphos (46 mg, 0.08 mmol), cesium carbonate (100 mg, 0.31 mmol) and 1,4-dioxane (1.0 mL). The mixture was degassed with argon. The resulting reaction mixture was heated at 100° C. under argon for 12 h. The reaction mixture was cooled to room temperature and extracted with methylene chloride. The combined organic layers were washed with water, brine, dried over sodium sulfate and concentrated to give a yellow solid. The crude was purified by preparative TLC to afford the desired amide (54 mg, 53%) as a light yellow solid: $^1$H NMR (500 MHz, CDCl$_3$) δ 9.05 (br s, 1H), 8.22 (d, J=7.7 Hz, 1H), 8.02 (d, J=7.8 Hz, 1H), 7.72 (d, J=7.8 Hz, 1H), 7.58-7.52 (m, 1H), 7.48 (t, J=8.1 Hz, 1H), 7.21-7.15 (m, 2H), 4.67-4.56 (m, 1H), 3.85 (t, J=4.5 Hz, 4H), 3.30-3.10 (m, 2H), 3.04 (t, J=4.5 Hz, 4H), 2.75-2.50 (m, 5H), 2.25-1.95 (m, 3H), 1.70-1.45 (m, 3H), 1.30-1.10 (m, 2H); MS (ESI+) m/z 461 (M+H).

Step B: To a solution of the benzoxazole carboxamide from step A (31 mg, 0.07 mmol) in methanol (0.5 mL) was added maleic acid (7.4 mg, 0.06 mmol) and acetonitrile (4 mL). The resulting solution was freezed and dried to afford N-(9-methyl-9-azabicyclo[3.3.1]non-3-yl)-2-(2-morpholinophenyl)benzoxazole-4-carboxamide maleate (38 mg, quantitative) as a light green solid: $^1$H NMR (300 MHz, CDCl$_3$) δ 12.07 (br s, 0.4H), 11.49 (br s, 0.6H), 9.56 (d, J=10.0 Hz, 0.4H), 9.42 (d, J=10.0 Hz, 0.6H), 8.24-8.15 (m, 1H), 8.00 (dd, J=12.9, 2.8 Hz, 0.6H), 7.92 (dd, J=12.9, 2.8 Hz, 0.4H), 7.83-7.72 (m, 1H), 7.62-7.45 (m, 3H), 7.14 (t, J=7.8 Hz, 2H), 6.36 (s, 2H), 4.70-4.55 (m, 1H), 3.88-3.80 (m, 4H), 3.75-3.64 (m, 2H), 3.05-3.00 (m, 4H), 2.96-2.90 (m, 5H), 2.87-2.75 (m, 1H), 2.65-2.40 (m, 3H), 2.20-1.65 (m, 4H); MS (ESI+) m/z 461 (M+H); HPLC 97.2% (AUC), $t_R$=12.72 min.

Example 148

Preparation of N-(9-Methyl-9-azabicyclo[3.3.1]non-3-yl)-2-[2-(4-methylpiperazin-1-yl)phenyl]benzoxazole-4-carboxamide Maleate

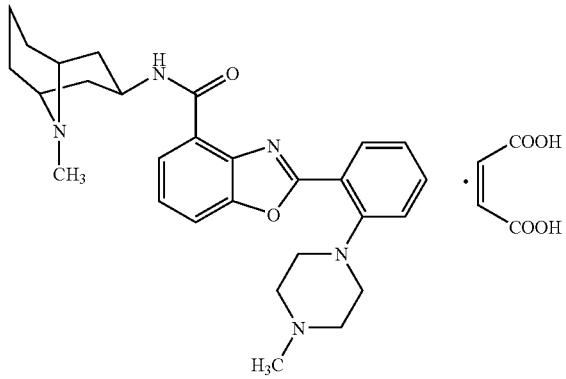

Step A: A dry flask was charged with N-(9-methyl-9-azabicyclo[3.3.1]non-3-yl)-2-(2-bromophenyl)benzoxazole-4-carboxamide (100 mg, 0.22 mmol), 1-methylpiperazine (0.10 mL, 0.88 mmol), Pd(OAc)$_2$ (14 mg, 0.06 mmol), xantphos (46 mg, 0.08 mmol), cesium carbonate (100 mg, 0.31 mmol) and 1,4-dioxane (2.5 mL). The mixture was degassed with argon. The resulting reaction mixture was heated at 100° C. under argon for 12 h. The reaction mixture was then cooled to room temperature and extracted with methylene chloride. The combined organic layers were washed with water and brine, dried over sodium sulfate and concentrated. The crude was purified by preparative TLC to afford the amide (53 mg, 51%) as a yellow solid: $^1$H NMR (500 MHz, CDCl$_3$) δ 9.08 (br s, 1H), 8.22 (d, J=7.7 Hz, 1H), 7.97 (d, J=7.3 Hz, 1H), 7.72 (d, J=8.1 Hz, 1H), 7.55-7.50 (m, 1H), 7.47 (t, J=8.1 Hz, 1H), 7.20-7.16 (m, 2H), 4.67-4.56 (m, 1H), 3.24-3.11 (m, 1H), 3.07 (t, J=4.7 Hz, 4H), 2.70-2.50 (m, 9H), 2.35 (s, 3H), 2.08-1.95 (m, 2H), 1.67-1.45 (m, 5H), 1.20-1.10 (m, 2H); MS (ESI+) m/z 474 (M+H).

Step B: To a solution of the benzoxazole carboxamide (41 mg, 0.09 mmol) in methanol (1.0 mL) was added maleic acid (9 mg, 0.8 mmol) and acetonitrile (4 mL). The resulting solution was freezed and dried to afford N-(9-methyl-9-azabicyclo[3.3.1]non-3-yl)-2-[2-(4-methylpiperazin-1-yl)phenyl]benzoxazole-4-carboxamide maleate (68 mg, quantitative) as a brown solid: $^1$H NMR (300 MHz, CDCl$_3$) δ 11.62 (br s, 0.2H), 10.75 (br s, 0.8H), 9.43 (d, J=10.4 Hz, 0.2H), 9.32 (d, J=10.4 Hz, 0.8H), 8.25-8.15 (m, 1H), 8.07 (dd, J=8.1, 1.6 Hz, 0.8H), 7.92 (dd, J=8.1, 1.6 Hz, 0.2H), 7.83-7.75 (m, 1H), 7.62-7.45 (m, 2H), 7.35-7.28 (m, 2H), 6.36 (s, 3H), 4.90-4.75 (m, 0.8H), 4.65-4.55 (m, 0.2H), 3.80-3.55 (m, 6H), 3.50-3.20 (m, 4H), 3.05-2.90 (m, 6H), 2.75-2.50 (m, 5H), 2.20-1.98 (m, 2H), 1.87-1.65 (m, 3H); MS (ESI+) m/z 474 (M+H); HPLC>99% (AUC), $t_R$=12.17 min.

Example 149

Preparation of N-(9-Methyl-9-azabicyclo[3.3.1]non-3-yl)-2-(2-isopropylphenyl)benzoxazole-4-carboxamide Hydrochloride

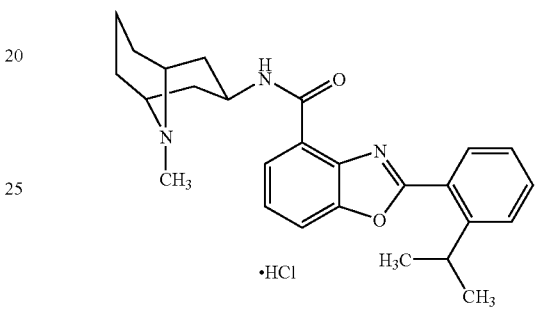

Step A: To a solution of 2-bromoisopropylbenzene (5.00 g, 25.1 mmol) in anhydrous tetrahydrofuran (40 mL) at −78° C., was added n-BuLi (2.5 M solution in hexanes, 25 mL, 62 mmol) dropwise. The reaction mixture was stirred at −78° C. for 2 h and then warmed to 0° C. CO$_2$ was bubbled into the reaction mixture for 40 min and then the reaction was quenched with a saturated solution of sodium carbonate (100 mL). The aqueous layer was separated and washed with diethyl ether (2×150 mL). The aqueous layer was treated with 6 N HCl and extracted with dichloromethane (2×250 mL). The combined organic layers were washed with brine (150 mL), dried over sodium sulfate, filtered and concentrated to afford the desired acid (546 mg, 13%) as a light yellow semi-solid: $^1$H NMR (500 MHz, CDCl$_3$) δ 10.48 (br s, 1H), 7.92 (dd, J=7.9, 1.4 Hz, 1H), 7.52-7.49 (m, 1H), 7.46-7.42 (m, 1H), 7.28-7.20 (m, 1H), 3.95-3.85 (m, 1H), 1.28 (d, J=6.9 Hz, 6H).

Step B: To an ice-cooled suspension of 2-isopropylbenzoic acid (546 mg, 3.33 mmol) in dichloromethane (20 mL) was added oxalyl chloride (0.18 mL, 3.3 mmol) dropwise, followed by few drops of anhydrous DMF. After the ice-water bath was removed, the mixture was stirred for 1 h. To the above solution was added 2-amino-3-hydroxybenzoic acid hydrobromide (0.78 g, 3.3 mmol) followed by triethylamine (1.95 mL, 14.0 mmol). The resulting reaction mixture was stirred at room temperature overnight. The reaction was quenched with 1 N HCl (50 mL) and extracted with dichloromethane. The aqueous layer was further extracted with dichloromethane (2×50 mL). The combined organic layers were dried over Na$_2$SO$_4$, filtrated and concentrated to afford a yellow solid. The crude was dissolved in toluene (5 mL) and the solution was treated with p-toluenesulfonic acid monohydrate (1.06 g, 5.60 mmol). The reaction mixture was then heated to reflux under nitrogen for 6 h. The reaction was cooled down to room temperature, poured into water and extracted with ethyl acetate. The organic layer was separated, washed with water and brine, dried over Na$_2$SO$_4$, filtered and concentrated. The crude product was purified by column chromatography (silica gel, 9:1 to 3:1 ethyl acetate/methanol) to afford the desired acid (310 mg, 33%) as a yellow solid: $^1$H NMR (500 MHz, DMSO-$d_6$) δ 13.06 (br s, 1H), 7.98-7.90 (m, 2H), 7.86 (d, J=7.6 Hz, 1H), 7.63-7.56 (m, 2H), 7.47 (t, J=7.9 Hz, 1H), 7.45-7.35 (m, 1H), 4.00-3.92 (m, 1H), 1.25 (d, J=7.6 Hz, 6H); MS (ESI+) m/z 282 (M+H).

Step C: A mixture of the 2-(2-isopropylphenyl)benzoxazole-4-carboxylic acid from Step B (150 mg, 0.53 mmol), 3-amino-9-methyl-9-azabicyclo[3.3.1]nonane dihydrochloride (150 mg, 0.66 mmol), 1-ethyl-3-(3-dimethylaminopropyl)carbodiimide hydrochloride (202 mg, 1.06 mmol), 1-hydroxybenzotriazole (143 mg, 1.06 mmol) and DMF (5 mL) was stirred under nitrogen at room temperature for 10 min, and then triethylamine (0.30 mL, 2.1 mmol) was added. The resulting reaction mixture was stirred at room temperature overnight, and then quenched with a saturated solution of sodium bicarbonate and extracted with methylene chloride. The combined organic layers were washed with brine, dried ($Na_2SO_4$), filtered and concentrated. The crude material was purified by column chromatography (silica gel, 90:9:1 dichloromethane/methanol/concentrated ammonium hydroxide) to afford the desired amide (201 mg, 90%) as an off-white solid: $^1$H NMR (500 MHz, CDCl$_3$) δ 8.95 (br s, 1H), 8.22 (d, J=7.6 Hz, 1H), 8.12-8.05 (m, 1H), 7.72 (d, J=7.6 Hz, 1H), 7.60-7.54 (m, 2H), 7.48 (t, J=7.8 Hz, 1H), 7.42-7.35 (m, 1H), 4.75-4.60 (m, 1H), 4.35-4.20 (m, 1H), 3.30-3.10 (m, 2H), 2.75-2.50 (m, 5H), 2.20-1.95 (m, 3H), 1.70-1.50 (m, 3H), 1.38 (d, J=6.9 Hz, 6H), 1.20-1.00 (m, 2H); MS (ESI+) m/z 418 (M+H).

Step D: To a solution of the amide from Step C (200 mg, 0.53 mmol) in dichloromethane (2.0 mL) was added a solution of HCl in diethyl ether (1 N, 1.0 mL, 1.0 mmol) at room temperature slowly. The reaction mixture was diluted with diethyl ether. The resulting solid was filtered and washed with diethyl ether to afford N-(9-methyl-9-azabicyclo[3.3.1]non-3-yl)-2-(2-isopropylphenyl)benzoxazole-4-carboxamide hydrochloride (214 mg, quantitative) as a white solid: $^1$H NMR (500 MHz, CDCl$_3$) δ 12.22 (br s, 0.4H), 11.88 (br s, 0.6H), 9.38 (m, 0.6H), 9.28 (d, J=5.8 Hz, 0.4H), 8.22 (d, J=7.8 Hz, 0.4H), 8.17 (d, J=7.8 Hz, 0.6H), 8.01 (d, J=7.7 Hz, 0.6H), 7.97 (d, J=7.7 Hz, 0.4H), 7.79 (d, J=8.1 Hz, 0.4H), 7.75 (d, J=8.1 Hz, 0.6H), 7.62-7.48 (m, 3H), 7.40-7.30 (m, 1H), 4.95-4.80 (m, 0.6H), 4.70-4.60 (m, 0.4H), 4.05-3.90 (m, 1H), 3.70-3.52 (m, 2H), 3.00-2.75 (m, 5H), 2.65-2.50 (m, 2H), 2.20-2.05 (m, 1H), 1.95-1.65 (m, 5H), 1.39 (d, J=6.7 Hz, 3H), 1.35 (d, J=6.7 Hz, 3H); MS (ESI+) m/z 418 (M+H); HPLC>99% (AUC), $t_R$=13.14 min.

Example 150

Preparation of (S)-N-(1-Azabicyclo[2.2.2]oct-3-yl)-2-(2-isopropylphenyl)benzoxazole-4-carboxamide Hydrochloride

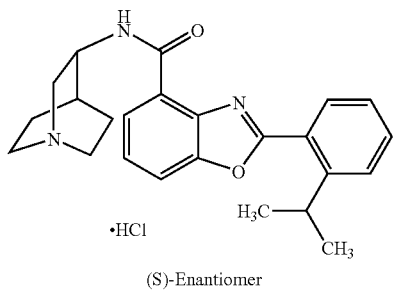

(S)-Enantiomer

Step A: A mixture of 2-(2-isopropylphenyl)benzoxazole-4-carboxylic acid (150 mg, 0.53 mmol), 1-ethyl-3-(3-dimethylaminopropyl)carbodiimide hydrochloride (202 mg, 1.06 mmol), 1-hydroxybenzotriazole (143 mg, 1.06 mmol), (S)-(−)-3-aminoquinuclidine dihydrochloride (130 mg, 0.66 mmol) and DMF (5 mL) was stirred at room temperature for 10 min, then triethylamine (0.30 mL, 0.66 mmol) was added. The resulting reaction mixture was stirred at room temperature for 12 h. The reaction mixture was diluted with ethyl acetate (50 mL), and then treated with a saturated solution of sodium bicarbonate. The organic layer was isolated and the aqueous layer was further extracted with ethyl acetate (2×50 mL). The combined organics were washed with water (2×25 mL) and brine (2×25 mL), dried ($Na_2SO_4$), filtered and concentrated. The crude material was purified by semi-preparative HPLC to afford the desired amide (198 mg, 96%) as an off-white solid: $^1$H NMR (500 MHz, CDCl$_3$) δ 9.24 (d, J=6.4 Hz, 1H), 8.22 (dd, J=7.8, 1.0 Hz, 1H), 8.12 (dd, J=7.9, 1.0 Hz, 1H), 7.74 (dd, J=8.1, 1.0 Hz, 1H), 7.59-7.50 (m, 2H), 7.48 (t, J=7.9 Hz, 1H), 7.41-7.35 (m, 1H), 4.40-4.30 (m, 1H), 4.25-4.15 (m, 1H), 3.60-3.50 (m, 1H), 3.10-2.90 (m, 4H), 2.81 (dd, J=13.8, 4.1 Hz, 1H), 2.20-2.15 (m, 1H), 2.02-1.92 (m, 1H), 1.85-1.75 (m, 2H), 1.65-1.54 (m, 1H), 1.36 (d, J=3.5 Hz, 3H), 1.34 (d, J=3.5 Hz, 3H); MS (ESI+) m/z 390 (M+H).

Step B: To a solution of the benzoxazole carboxamide from Step A (250 mg, 0.49 mmol) in dichloromethane (2.0 mL) was added a solution of HCl in diethyl ether (1 N, 1.0 mL, 1.0 mmol) at 0° C. slowly. The reaction mixture was diluted with diethyl ether. The resulting solid was filtered and washed with diethyl ether to afford (S)-N-(1-azabicyclo[2.2.2]oct-3-yl)-2-(2-isopropylphenyl)benzoxazole-4-carboxamide hydrochloride (209 mg, quantitative) as a white solid: $^1$H NMR (500 MHz, CDCl$_3$) δ 11.93 (br s, 1H), 9.46 (br s, 1H), 8.20 (d, J=7.6 Hz, 1H), 8.05-7.95 (m, 1H), 7.81 (d, J=7.6 Hz, 1H), 7.60-7.50 (m, 3H), 7.45-7.35 (m, 1H), 4.70-4.60 (m, 1H), 4.05-3.85 (m, 2H), 3.55-3.15 (m, 5H), 2.60-2.50 (m, 1H), 2.43-2.00 (m, 4H), 1.32-1.29 (m, 6H); MS (ESI+) m/z 390 (M+H); HPLC>99% (AUC), $t_R$=12.64 min.

Compound Affinity for the 5-HT$_3$ Receptor

In order to evaluate the relative affinity of the various compounds for the 5-HT$_3$ receptor, N1E-155 cell lines were developed to express the target protein. For binding, these cells were homogenized, centrifuged and washed with buffer (20 mM HEPES, 150 mM NaCl, pH 7.4) then suspended in 0.5 mL of buffer and [$^3$H]-GR65630 added at a concentration of $3.5\times10^{-10}$ M. An initial single concentration of $10^{-7}$ M of the test compound was then added. Incubation was carried out at room temperature for 60 minutes at 25° C. then was terminated by rapid removal of the incubation medium. Radioactivity was assessed using liquid scintillation spectrophotometry after exposure to scintillation cocktail for at least three hours. Compounds displaying greater than 75% inhibition of radioligand binding at $10^{-7}$ M were then resubmitted to the above protocol using the following range of test compound concentrations: $10^{-9}$ M, $10^{-8}$ M, $3\times10^{-8}$ M, $10^{-7}$M, $3\times10^{-7}$ M and $10^{-6}$ M. Competition curves were then plotted and IC$_{50}$ determinations made using non-linear regression analysis. Ki values were then calculated from the Cheng-Prusoff equation. In all of the above binding studies the non-specific determinant was MDL-72222 (1.0 μM). Compounds in the examples above all (with the exceptions noted below) exhibited either greater than 30% inhibition at 100 nM or K$_i$ below 300 nM in one or the other of mouse or human 5-HT$_3$ receptor binding. However, compounds in which: (1) Ar is 2-pyridinyl and 3-pyridinyl, except when R$^4$ is methyl azabicyclo[3.3.1]nonane; (2) Ar is phenyl and R$^4$ is 1-azabicyclo[2.2.2]oct-3-yl, and $R^2$ is chloro; and (3) Ar is phenyl or phenyl substituted with halogen, $R^4$ is 1-azabicyclo[2.2.2]oct-3-yl and all of $R^1$, $R^2$ and $R^3$ are H; show binding less than 30% at 100 nM Bezold-Jarisch Assay in vivo. In order to demonstrate functional antagonism of 5-HT3 receptors, certain compounds (Table 1) were evaluated for their ability to inhibit serotonin induced bradycardia in vivo in the mouse [Saxena, P. R. and Lawang, A. A comparison of cardiovascular and smooth muscle effects of 5-hydroxytryptamine and 5-carboxamidotryptamine, a selective agonist of 5-HT1 receptors. Arch. Int. Pharmacodyn. 277: 235-252, 1985]. Test substances and vehicle [2% Tween 80] were each administered orally (30 mg/kg) to a group of 5 male or female CD-1 (Crl.) mice each weighing 24±2 g. A dosing volume of 10 mL/kg was used. Sixty minutes later, 5-HT (0.5 mg/kg IV)-induced bradycardia was recorded in pentobarbital (80 mg/kg IP, given 10 minutes before 5-HT)-anesthetized animals.

TABLE 1

| STRUCTURE | Example number | % Inhibition in vivo |
|---|---|---|
| (structure) | 40 | |
| (structure) | 88 | |
| (structure) | 62 | |

The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. A simple solid line implies nothing about stereochemistry. For example, a solid line is shown in the graphic for example 139 above, but the compound of the example is actually a single enantiomer of the S configuration and could have been accurately depicted as

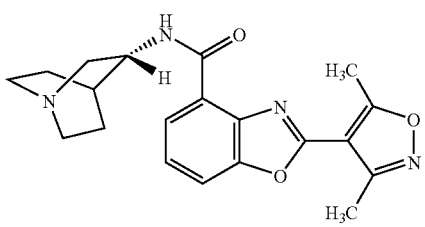

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Preferred unit dosage formulations are those containing an effective dose or an appropriate fraction thereof, of the active ingredient.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

It should be understood that in addition to the ingredients particularly mentioned above, the formulations of this invention may include other agents conventional in the art having regard to the type of formulation in question, for example those suitable for oral administration may include flavoring agents.

Although the foregoing invention has been described in some detail for purposes of illustration, it will be readily apparent to one skilled in the art that changes and modifications may be made without departing from the scope of the invention described herein.

The invention claimed is:

1. A compound of formula

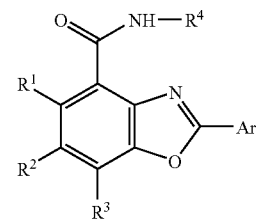

wherein
$R^1$, $R^2$ and $R^3$ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;
$R^4$ is a saturated nitrogen heterocycle or methyl-substituted saturated nitrogen heterocycle, in which said nitrogen is tertiary, said heterocycle containing at least one 5 or 6-membered ring; and
Ar is chosen from the group consisting of
(i) aryl;
(ii) heteroaryl;
(iii) substituted aryl;
(iv) substituted heteroaryl; and
(v) dihydroheteroaryl.

2. A compound according to claim 1 of formula

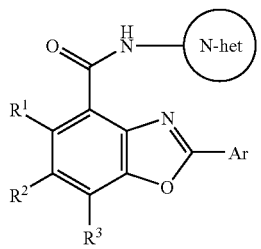

wherein
R¹, R² and R³ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;

represents a saturated nitrogen heterocycle or methyl-substituted saturated nitrogen heterocycle, in which said nitrogen is tertiary, said heterocycle containing at least one 5 or 6-membered ring; and Ar is chosen from the group consisting of:
(i) aryl;
(ii) heteroaryl other than 2-pyridinyl and 3-pyridinyl, provided that when

is methyl azabicyclo[3.3.1]nonane, Ar may additionally be 3-pyridinyl;
(iii) aryl substituted with from one to four substitutents chosen from lower alkoxy, phenoxy, trialkylsilylacetylenyl, anilino, lower alkynyl, lower alkyl, halogen, nitro, cyano, hydroxy, amino, methylenedioxy, alkylamino, dialkylamino, phenyl, heterocyclyl, methylheterocyclyl, methylenedioxy and acylamino;
(iv) heteroaryl substituted with one or two substitutents chosen from oxo, halogen, and alkyl; and
(v) dihydroheteroaryl;
with the proviso that, when Ar is phenyl and

is 1-azabicyclo[2.2.2]oct-3-yl, R² cannot be chloro.

3. A compound of formula

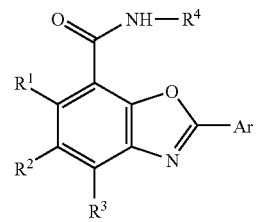

wherein
R¹, R² and R³ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;
R⁴ is a saturated nitrogen heterocycle or methyl-substituted saturated nitrogen heterocycle, in which said nitrogen is tertiary, said heterocycle containing at least one 5 or 6-membered ring; and
Ar is chosen from the group consisting of
(i) aryl;
(ii) heteroaryl;
(iii) substituted aryl;
(iv) substituted heteroaryl; and
(v) dihydroheteroaryl.

4. A compound according to claim 3 of formula

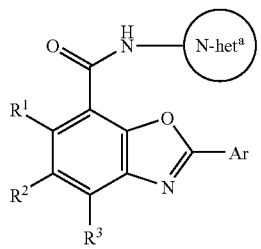

wherein
R¹, R² and R³ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;

represents a saturated nitrogen heterocycle or methyl-substituted saturated nitrogen heterocycle, in which said nitrogen is tertiary, said heterocycle containing at least two 6-membered rings; and
Ar is chosen from the group consisting of
(i) aryl;
(ii) heteroaryl other than 2-pyridinyl and 3-pyridinyl;
(iii) aryl substituted with from one to four substitutents chosen from lower alkoxy, phenoxy, trialkylsilylacetylenyl, anilino, lower alkynyl, lower alkyl, halogen, nitro, cyano, hydroxy, amino, acetylamino, methylenedioxy, alkylamino, dialkylamino, phenyl, heterocyclyl, methylheterocyclyl, methylenedioxy and acylamino;
(iv) heteroaryl substituted with one or two substitutents chosen from oxo, halogen, and alkyl; and
(v) dihydroheteroaryl;
with the proviso that, when

is 1-azabicyclo[2.2.2]oct-3-yl and all of $R^1$, $R^2$ and $R^3$ are H, Ar cannot be phenyl or phenyl substituted with halogen.

5. A compound according to claim 2 wherein

is chosen from:

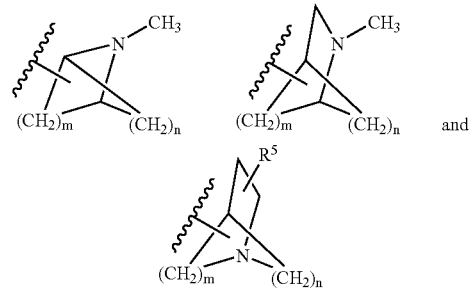

wherein
m=1, 2, 3 or 4;
n=0, 1, 2, 3 or 4; and
$R^5$ is hydrogen or methyl.

6. A compound according to claim 4 wherein

is chosen from:

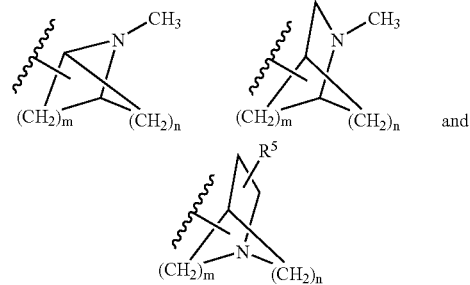

wherein
m=1, 2, 3 or 4;
n=0, 1, 2, 3 or 4; and
$R^5$ is hydrogen or methyl.

7. A compound according to claim 5 wherein

is chosen from quinuclidine, tropane, azabicyclo[3.3.1]nonane and methyl azabicyclo[3.3.1]nonane.

8. A compound according to claim 6 wherein

is chosen from quinuclidine, tropane, azabicyclo[3.3.1]nonane and methyl azabicyclo[3.3.1]nonane.

9. A compound according to claim 1 or 3, wherein $R^1$, $R^2$ and $R^3$ are hydrogen.

10. A compound according to claim 1 or 3, wherein one of $R^1$, $R^2$ and $R^3$ is halogen.

11. A compound according to claim 1 or 3, wherein $R^1$ and $R^3$ are hydrogen and $R^2$ is chosen from amino, halogen, methoxy, hydroxy, acetylamino, and 4-morpholinyl.

12. A compound according to claim 1 or 3 wherein Ar is chosen from the group consisting of phenyl and phenyl substituted with from 1 to 4 groups independently selected from ($C_1$ to $C_4$)alkyl, phenyl, phenoxy, halogen, ($C_1$ to $C_4$)alkoxy, amino, ($C_1$ to $C_4$)alkylamino, di($C_1$ to $C_4$)alkylamino, anilino, heterocyclyl, methylheterocyclyl, methylenedioxy, ($C_1$ to $C_4$)acylamino, ($C_1$ to $C_4$)alkynyl and nitro.

13. A compound according to claim 12 wherein Ar is chosen from the group consisting of phenyl and phenyl substituted with one or two residues chosen independently from ($C_1$ to $C_4$)alkyl, 4-methylpiperazinl-yl, morpholin-4-yl, pyridin-4-yl, phenyl, phenoxy, amino, anilino, halogen, methoxy, dimethylamino, methylenedioxy, acetylamino, propyn-1-yl and nitro.

14. A compound according to claim 1 or 3 wherein Ar is chosen from the group consisting of heteroaryl, dihydroheteroaryl and substituted heteroaryl.

15. A compound according to claim 14 wherein Ar is chosen from thiophene, cyclopenta[b]thiophene, furan, thiazole, isoxazole dihydrobenzofuran, benzofuran, pyridine, benzothiophene, 3-pyridine-2-one, and their methylated and halogenated congeners.

16. A compound according to claim 1 or 3 chosen from the group consisting of:
N-(1-Methylpiperidin-4-yl)-2-phenylbenzoxazole-4-carboxamide,
N-(9-Methyl-9-azabicyclo[3.3.1]non-3-yl)-2-phenylbenzoxazole-4-carboxamide,
N-(8-Methyl-8-azabicyclo[3.2.1]oct-3-yl)-2-phenylbenzoxazole-4-carboxamide,
N-(9-Methyl-9-azabicyclo[3.3.1]non-3-yl)-6-chloro-2-phenylbenzoxazole-4-carboxamide,
N-(Piperidin-4-yl)-2-phenylbenzoxazole-4-carboxamide,
N-(1-Azabicyclo[2.2.2]oct-3-yl)-2-phenylbenzoxazole-4-carboxamide,
N-(1-Methyl-piperidin-4-yl)-6-chloro-2-phenylbenzoxazole-4-carboxamide,
N-(1-Azabicyclo[2.2.2]oct-3-yl)-6-chloro-2-phenylbenzoxazole-4-carboxamide, N-(8-Methyl-8-azabicyclo[3.2.1]oct-3-yl)-6-chloro-2-phenylbenzoxazole-4-carboxamide,
N-(1-Azabicyclo[2.2.2]oct-3-yl)-2-(4-chlorophenyl)benzoxazole-4-carboxamide,
N-(9-Methyl-9-azabicyclo[3.3.1]non-3-yl)-2-(4-chlorophenyl)benzoxazole-4-carboxamide,
N-(1-Azabicyclo[2.2.2]oct-3-yl)-2-(4-methoxyphenyl)benzoxazole-4-carboxamide,
N-(9-Methyl-9-azabicyclo[3.3.1]non-3-yl)-2-(4-methoxyphenyl)benzoxazole-4-carboxamide,
N-(9-Methyl-9-azabicyclo[3.3.1]non-3-yl)-2-(4-fluorophenyl)benzoxazole-4-carboxamide,
N-(1-Azabicyclo[2.2.2]oct-3-yl)-2-(4-fluorophenyl)benzoxazole-4-carboxamide,
N-(9-Methyl-9-azabicyclo[3.3.1]non-3-yl)-2-phenylbenzoxazole-7-carboxamide,
N-(1-Methylpiperidin-4-yl)-2-phenylbenzoxazole-7-carboxamide,
N-(Piperidin-4-yl)-2-phenylbenzoxazole-7-carboxamide,
N-(1-Azabicyclo[2.2.2]oct-3-yl)-2-phenylbenzoxazole-7-carboxamide,
N-(8-Methyl-8-azabicyclo[3.2.1]oct-3-yl)-2-phenylbenzoxazole-7-carboxamide,
N-(1-Azabicyclo[2.2.2]oct-3-yl)-5-chloro-2-phenyl-benzoxazole-7-carboxamide,
N-(9-Methyl-9-azabicyclo[3.3.1]non-3-yl)-5-chloro-2-phenyl-benzoxazole-7-carboxamide,
N-(9-Methyl-9-azabicyclo[3.3.1]non-3-yl)-2-(4-fluorophenyl)benzoxazole-7-carboxamide,
N-(1-Azabicyclo[2.2.2]oct-3-yl)-2-(4-methoxyphenyl)benzoxazole-7-carboxamide,
N-(9-Methyl-9-azabicyclo[3.3.1]non-3-yl)-2-(4-methoxyphenyl)benzoxazole-7-carboxamide,
N-(1-Azabicyclo[2.2.2]oct-3-yl)-2-(4-chlorophenyl)benzoxazole-7-carboxamide,
N-(9-Methyl-9-azabicyclo[3.3.1]non-3-yl)-2-(4-chlorophenyl)benzoxazole-7-carboxamide,
N-(9-Methyl-9-azabicyclo[3.3.1]non-3-yl)-2-phenylbenzothiazole-7-carboxamide,
(S)-N-(1-Azabicyclo[2.2.2]oct-3-yl)-6-chloro-2-phenyl-benzoxazole-4-carboxamide,
N-(9-Methyl-3-oxa-9-azabicyclo[3.3.1]non-7-yl)-2-phenylbenzoxazole-4-carboxamide,
N-(9-Methyl-3-oxa-9-azabicyclo[3.3.1]non-7-yl)-6-chloro-2-phenylbenzoxazole-4-carboxamide,
N-(1-Azabicyclo[2.2.2]oct-3-yl)-2-(2-methoxyphenyl)benzoxazole-4-carboxamide,
N-(9-Methyl-9-azabicyclo[3.3.1]non-3-yl)-2-(2-methoxyphenyl)benzoxazole-4-carboxamide Hydrochloride,
N-(1-Azabicyclo[2.2.2]oct-3-yl)-2-(3-methoxyphenyl)benzoxazole-4-carboxamide,
(S)-N-(1-Azabicyclo[2.2.2]oct-3-yl)-2-(2-hydroxyphenyl)benzoxazole-4-carboxamide, Hydrochloride,
N-(9-Methyl-9-azabicyclo[3.3.1]non-3-yl)-2-(2-hydroxyphenyl)benzoxazole-4-carboxamide Hydrochloride,
N-(9-Methyl-9-azabicyclo[3.3.1]non-3-yl)-2-(2-bromophenyl)benzoxazole-4-carboxamide Hydrochloride,
N-(9-Methyl-9-azabicyclo[3.3.1]non-3-yl)-2-(2-aminophenyl)benzoxazole-4-carboxamide Dihydrochloride,
N-(9-Methyl-9-azabicyclo[3.3.1]non-3-yl)-2-(biphenyl-2-yl)benzoxazole-4-carboxamide Hydrochloride,
N-(9-Methyl-9-azabicyclo[3.3.1]non-3-yl)-2-(2-pyridine-4-yl)phenylbenzoxazole-4-carboxamide Dihydrochloride,
N-(1-Azabicyclo[2.2.2]oct-3-yl)-2-p-tolylbenzoxazole-4-carboxamide,
N-(9-Methyl-9-azabicyclo[3.3.1]non-3-yl)-2-p-tolylbenzoxazole-4-carboxamide,
N-(1-Azabicyclo[2.2.2]oct-3-yl)-2-(4-nitrophenyl)benzoxazole-4-carboxamide,
N-(1-Azabicyclo[2.2.2]oct-3-yl)-2-(4-aminophenyl)benzoxazole-4-carboxamide,
N-(1-Azabicyclo[2.2.2]oct-3-yl)-2-(4-acetylaminophenyl)benzoxazole-4-carboxamide,
N-(1-Azabicyclo[2.2.2]oct-3-yl)-2-(4-dimethylaminophenyl)benzoxazole-4-carboxamide,
N-(9-Methyl-9-azabicyclo[3.3.1]non-3-yl)-2-(4-dimethylaminophenyl)benzoxazole-4-carboxamide,
N-(9-Methyl-9-azabicyclo[3.3.1]non-3-yl)-2-(2-dimethylaminophenyl)benzoxazole-4-carboxamide,
(S)-N-(1-Azabicyclo[2.2.2]oct-3-yl)-2-(2-dimethylaminophenyl)benzoxazole-4-carboxamide,
N-(9-Methyl-9-azabicyclo[3.3.1]non-3-yl)-6-chloro-2-(2-dimethylaminophenyl)benzoxazole-4-carboxamide,
(S)-N-(1-Azabicyclo[2.2.2]oct-3-yl)-6-chloro-2-(2-dimethylaminophenyl)benzoxazole-4-carboxamide,
N-(1-Azabicyclo[2.2.2]oct-3-yl)-2-(4-cyanophenyl)benzoxazole-4-carboxamide,
N-(1-Azabicyclo[2.2.2]oct-3-yl)-2-(4-iodophenyl)benzoxazole-4-carboxamide,
N-(1-Azabicyclo[2.2.2]oct-3-yl)-2-(4-trimethylsilylethynylphenyl)benzoxazole-4-carboxamide,
N-(1-Azabicyclo[2.2.2]oct-3-yl)-2-(4-propyn-1-ylphenyl)benzoxazole-4-carboxamide,
N-(1-Azabicyclo[2.2.2]oct-3-yl)-2-(4-ethynylphenyl)benzoxazole-4-carboxamide,
N-(1-Azabicyclo[2.2.2]oct-3-yl)-2-biphenyl-4-ylbenzoxazole-4-carboxamide,
N-(1-Azabicyclo[2.2.2]oct-3-yl)-2-(4-phenoxyphenyl)benzoxazole-4-carboxamide,
N-(1-Azabicyclo[2.2.2]oct-3-yl)-2-(4-phenylaminophenyl)benzoxazole-4-carboxamide,
N-(9-Methyl-9-azabicyclo[3.3.1]non-3-yl)-2-benzo[1,3]dioxol-5-ylbenzoxazole-4-carboxamide,
(S)-N-(1-Azabicyclo[2.2.2]oct-3-yl)-2-benzo[1,3]dioxol-5-yl-benzoxazole-4-carboxamide,
N-(1-Azabicyclo[2.2.2]oct-3-yl)-2-benzofuran-5-ylbenzoxazole-4-carboxamide,
N-(1-Azabicyclo[2.2.2]oct-3-yl)-2-(2,3-dihydrobenzofuran-5-yl)benzoxazole-4-carboxamide,
N-(9-Methyl-9-azabicyclo[3.3.1]non-3-yl)-2-(2,4-dimethoxyphenyl)benzoxazole-4-carboxamide,
(S)-N-(1-Azabicyclo[2.2.2]oct-3-yl)-2-(2,4-dimethoxyphenyl)benzoxazole-4-carboxamide,
N-(9-Methyl-9-azabicyclo[3.3.1]non-3-yl)-2-(2,4-dichlorophenyl)benzoxazole-4-carboxamide,
(S)-N-(1-Azabicyclo[2.2.2]oct-3-yl)-2-(2,4-dichlorophenyl)benzoxazole-4-carboxamide,
(S)-N-(1-Azabicyclo[2.2.2]oct-3-yl)-2-(4-chloro-2-methoxyphenyl)benzoxazole-4-carboxamide,
N-(9-Methyl-9-azabicyclo[3.3.1]non-3-yl)-2-(4-chloro-2-methoxyphenyl)benzoxazole-4-carboxamide,
(S)-N-(1-Azabicyclo[2.2.2]oct-3-yl)-2-(4-methoxy-2-methylphenyl)benzoxazole-4-carboxamide,
N-(9-Methyl-9-azabicyclo[3.3.1]non-3-yl)-2-(4-methoxy-2-methylphenyl)benzoxazole-4-carboxamide,
(S)-N-(1-Azabicyclo[2.2.2]oct-3-yl)-2-(4-chloro-2-methylphenyl)benzoxazole-4-carboxamide,
N-(9-Methyl-9-azabicyclo[3.3.1]non-3-yl)-2-(4-chloro-2-methylphenyl)benzoxazole-4-carboxamide,
N-(9-Methyl-9-azabicyclo[3.3.1]non-3-yl-2-(2,6-dimethylphenyl)benzoxazole-4-carboxamide, (S)-N-(1-Azabicyclo[2.2.2]oct-3-yl)-2-(2,6-dichlorophenyl)benzoxazole-4-carboxamide,
N-(9-Methyl-9-azabicyclo[3.3.1]non-3-yl)-2-(2,6-dichlorophenyl)benzoxazole-4-carboxamide,
N-(1-Azabicyclo[2.2.2]oct-3-yl)-6-chloro-2-p-tolylbenzoxazole-4-carboxamide,
N-(9-Methyl-9-azabicyclo[3.3.1]non-3-yl)-6-chloro-2-p-tolylbenzoxazole-4-carboxamide,
N-(1-Azabicyclo[2.2.2]oct-3-yl)-6-chloro-2-(4-methoxyphenyl)benzoxazole-4-carboxamide,
N-(9-Methyl-9-azabicyclo[3.3.1]non-3-yl)-6-chloro-2-(4-methoxyphenyl)benzoxazole-4-carboxamide,
N-(1-Azabicyclo[2.2.2]oct-3-yl)-6-bromo-2-phenylbenzoxazole-4-carboxamide,
N-(9-Methyl-9-azabicyclo[3.3.1]non-3-yl)-6-bromo-2-phenylbenzoxazole-4-carboxamide,
N-(1-Azabicyclo[2.2.2]oct-3-yl)-6-bromo-2-p-tolylbenzoxazole-4-carboxamide,
N-(9-Methyl-9-azabicyclo[3.3.1]non-3-yl)-6-bromo-2-p-tolylbenzoxazole-4-carboxamide,
N-(1-Azabicyclo[2.2.2]oct-3-yl)-6-bromo-2-(4-methoxyphenyl)benzoxazole-4-carboxamide,
N-(9-Methyl-9-azabicyclo[3.3.1]non-3-yl)-6-bromo-2-(4-methoxyphenyl)benzoxazole-4-carboxamide,
N-(9-Methyl-9-azabicyclo[3.3.1]non-3-yl)-6-amino-2-phenylbenzoxazole-4-carboxamide Dihydrochloride,
N-(1-Azabicyclo[2.2.2]oct-3-yl)-5-bromo-2-phenylbenzoxazole-4-carboxamide,
N-(9-Methyl-9-azabicyclo[3.3.1]non-3-yl)-5-bromo-2-phenylbenzoxazole-4-carboxamide,
N-(9-Methyl-9-azabicyclo[3.3.1]non-3-yl)-7-bromo-2-phenylbenzoxazole-4-carboxamide,
N-(1-Azabicyclo[2.2.2]oct-3-yl)-7-bromo-2-phenylbenzoxazole-4-carboxamide,
N-(1-Azabicyclo[2.2.2]oct-3-yl)-6-iodo-2-phenylbenzoxazole-4-carboxamide,
N-(9-Methyl-9-azabicyclo[3.3.1]non-3-yl)-6-iodo-2-phenylbenzoxazole-4-carboxamide,
N-(1-Azabicyclo[2.2.2]oct-3-yl)-6-morpholine-2-phenylbenzoxazole-4-carboxamide,
N-(1-Azabicyclo[2.2.2]oct-3-yl)-6-amino-2-phenylbenzoxazole-4-carboxamide,
N-(1-Azabicyclo[2.2.2]oct-3-yl)-6-acetylamino-2-phenylbenzoxazole-4-carboxamide,
(S)-N-(1-Azabicyclo[2.2.2]oct-3-yl)-6-methoxy-2-phenylbenzoxazole-4-carboxamide,
N-(9-Methyl-9-azabicyclo[3.3.1]non-3-yl)-6-methoxy-2-phenylbenzoxazole-4-carboxamide,
(S)-N-(1-Azabicyclo[2.2.2]oct-3-yl)-6-hydroxy-2-phenylbenzoxazole-4-carboxamide,
(S)-N-(1-Azabicyclo[2.2.2]oct-3-yl)-6-fluoro-2-phenylbenzoxazole-4-carboxamide,
N-(9-Methyl-9-azabicyclo[3.3.1]non-3-yl)-6-fluoro-2-phenyl)benzoxazole-4-carboxamide,
(S)-N-(1-Azabicyclo[2.2.2]oct-3-yl)-6-fluoro-2-(2-methoxyphenyl)benzoxazole-4-carboxamide Hydrochloride,
N-(9-Methyl-9-azabicyclo[3.3.1]non-3-yl)-6-fluoro-2-(2-methoxyphenyl)benzoxazole-4-carboxamide, Hydrochloride,
N-(9-Methyl-9-azabicyclo[3.3.1]non-3-yl)-2-pyridin-4-ylbenzoxazole-4-carboxamide,
(S)-N-(1-Azabicyclo[2.2.2]oct-3-yl)-2-furan-2-ylbenzoxazole-4-carboxamide,
N-(9-Methyl-9-azabicyclo[3.3.1]non-3-yl)-2-furan-2-ylbenzoxazole-4-carboxamide,
(S)-N-(1-Azabicyclo[2.2.2]oct-3-yl)-2-thiophen-2-ylbenzoxazole-4-carboxamide,
N-(9-Methyl-9-azabicyclo[3.3.1]non-3-yl)-2-thiophen-2-ylbenzoxazole-4-carboxamide,
N-(9-Methyl-9-azabicyclo[3.3.1]non-3-yl)-6-chloro-2-thiophen-2-ylbenzoxazole-4-carboxamide,
(S)-N-(1-Azabicyclo[2.2.2]oct-3-yl)-6-chloro-2-thiophen-2-ylbenzoxazole-4-carboxamide,
(S)-N-(1-Azabicyclo[2.2.2]oct-3-yl)-2-thiophen-3-ylbenzoxazole-4-carboxamide,
N-(9-Methyl-9-azabicyclo[3.3.1]non-3-yl)-2-thiophen-3-ylbenzoxazole-4-carboxamide,
N-(9-Methyl-3-oxa-9-azabicyclo[3.3.1]non-7-yl)-6-chloro-2-thiophen-3-ylbenzoxazole-4-carboxamide,
N-(9-Methyl-9-azabicyclo[3.3.1]non-3-yl)-6-chloro-2-thiophen-3-ylbenzoxazole-4-carboxamide,
(S)-N-(1-Azabicyclo[2.2.2]oct-3-yl)-6-chloro-2-thiophen-3-ylbenzoxazole-4-carboxamide,
(S)-N-(1-Azabicyclo[2.2.2]oct-3-yl)-2-benzo[b]thiophen-2-ylbenzoxazole-4-carboxamide,
N-(9-Methyl-9-azabicyclo[3.3.1]non-3-yl)-2-benzo[b]thiophen-2-yl benzoxazole-4-carboxamide,
(S)-N-(1-Azabicyclo[2.2.2]oct-3-yl)-2-benzofuran-2-yl-benzoxazole-4-carboxamide,
N-(9-Methyl-9-azabicyclo[3.3.1]non-3-yl)-2-benzofuran-2-ylbenzoxazole-4-carboxamide,
(S)-N-(1-Azabicyclo[2.2.2]oct-3-yl)-2-(3-methylthiophen-2-yl)benzoxazole-4-carboxamide,
N-(9-Methyl-9-azabicyclo[3.3.1]non-3-yl)-2-(3-methylthiophen-2-yl)benzoxazole-4-carboxamide,
N-(9-Methyl-9-azabicyclo[3.3.1]non-3-yl)-6-chloro-2-(3-methylthiophen-2-yl)benzoxazole-4-carboxamide,
(S)-N-(1-Azabicyclo[2.2.2]oct-3-yl)-2-(3-chlorothiophen-2-yl)benzoxazole-4-carboxamide,
N-(9-Methyl-9-azabicyclo[3.3.1]non-3-yl)-2-(3-chlorothiophen-2-yl)benzoxazole-4-carboxamide,
(S)-N-(1-Azabicyclo[2.2.2]oct-3-yl)-2-(3-bromothiophen-2-yl)benzoxazole-4-carboxamide,
N-(9-Methyl-9-azabicyclo[3.3.1]non-3-yl)-2-(3-bromothiophen-2-yl)benzoxazole-4-carboxamide,
(S)-N-(1-Azabicyclo[2.2.2]oct-3-yl)-6-chloro-2-(3-chlorothiophen-2-yl)benzoxazole-4-carboxamide,
N-(9-Methyl-9-azabicyclo[3.3.1]non-3-yl)-6-chloro-2-(3-chlorothiophen-2-yl)benzoxazole-4-carboxamide,
(S)-N-(1-Azabicyclo[2.2.2]oct-3-yl)-2-(5-methylthiophen-2-yl)benzoxazole-4-carboxamide,
(S)-N-(1-Azabicyclo[2.2.2]oct-3-yl)-2-(5-chlorothiophen-2-yl)benzoxazole-4-carboxamide,
N-(9-Methyl-9-azabicyclo[3.3.1]non-3-yl)-2-(5-chlorothiophene-2-yl)benzoxazole-4-carboxamide,
(S)-N-(1-Azabicyclo[2.2.2]oct-3-yl)-2-(5-bromothiophene-2-yl)benzoxazole-4-carboxamide,
N-(9-Methyl-9-azabicyclo[3.3.1]non-3-yl)-2-(5-bromothiophene-2-yl)benzoxazole-4-carboxamide,
(S)-N-(1-Azabicyclo[2.2.2]oct-3-yl)-6-chloro-2-(5-methylthiophen-2-yl)benzoxazole-4-carboxamide,
N-(9-Methyl-9-azabicyclo[3.3.1]non-3-yl)-6-chloro-2-(5-methylthiophen-2-yl)benzoxazole-4-carboxamide,
(S)-N-(1-Azabicyclo[2.2.2]oct-3-yl)-2-(5,6-dihydro-4H-cyclopenta[b]thiophen-2-yl)benzoxazole-4-carboxamide,
N-(9-Methyl-9-azabicyclo[3.3.1]non-3-yl)-2-(5,6-dihydro-4H-cyclopenta[b]thiophen-2-yl)benzoxazole-4-carboxamide, (S)-N-(1-Azabicyclo[2.2.2]oct-3-yl)-2-(3,5-dimethylisoxazole-4-yl)benzoxazole-4-carboxamide,
N-(9-Methyl-9-azabicyclo[3.3.1]non-3-yl)-2-(3,5-dimethylisoxazole-4-yl)benzoxazole-4-carboxamide,
(S)-N-(1-Azabicyclo[2.2.2]oct-3-yl)-2-(4-methylthiazol-5-yl)benzoxazole-4-carboxamide, Hydrochloride,
N-(9-Methyl-9-azabicyclo[3.3.1]non-3-yl)-2-(4-methylthiazol-5-yl)benzoxazole-4-carboxamide Hydrochloride,
(S)-N-(1-Azabicyclo[2.2.2]oct-3-yl)-2-(thiazole-4-yl)benzoxazole-4-carboxamide, Hydrochloride
N-(9-Methyl-9-azabicyclo[3.3.1]non-3-yl)-2-(thiazol-4-yl)benzoxazole-4-carboxamide Hydrochloride,
(S)-N-(1-Azabicyclo[2.2.2]oct-3-yl)-2-(2-oxo-1,2-dihydropyridin-3-yl)benzoxazole-4-carboxamide,
N-(9-Methyl-9-azabicyclo[3.3.1]non-3-yl)-2-(2-oxo-1,2-dihydropyridin-3-yl)benzoxazole-4-carboxamide,
N-(9-Methyl-9-azabicyclo[3.3.1]non-3-yl)-2-(2-morpholinophenyl)benzoxazole-4-carboxamide Maleate,
N-(9-Methyl-9-azabicyclo[3.3.1]non-3-yl)-2-[2-(4-methylpiperazin-1-yl)phenyl]benzoxazole-4-carboxamide Maleate,
N-(9-Methyl-9-azabicyclo[3.3.1]non-3-yl)-2-(2-isopropylphenyl)benzoxazole-4-carboxamide Hydrochloride, and
(S)-N-(1-Azabicyclo[2.2.2]oct-3-yl)-2-(2-isopropylphenyl)benzoxazole-4-carboxamide Hydrochloride.

17. A pharmaceutical composition comprising a pharmaceutically acceptable carrier and a therapeutically effective amount of a compound according to claim 1 or 3.

18. A pharmaceutical composition according to claim 17 additionally comprising a second antiemetic agent.

19. A pharmaceutical composition according to claim 18 wherein said second antiemetic agent is a neurokinin antagonist.

20. A method of treating irritable bowel syndrome or emesis, which comprises administering to a patient in need of such treatment a therapeutically effective amount of a compound according to claim 1 or 3.

21. A method according to claim 20 for treating irritable bowel syndrome.

22. A method according to claim 20 for treating emesis.

* * * * *